US009079879B2

(12) United States Patent
Kadoma et al.

(10) Patent No.: US 9,079,879 B2
(45) Date of Patent: Jul. 14, 2015

(54) HETEROCYCLIC COMPOUND, LIGHT-EMITTING ELEMENT, LIGHT-EMITTING DEVICE, ELECTRONIC DEVICE, AND LIGHTING DEVICE

(75) Inventors: Hiroshi Kadoma, Kanagawa (JP); Nobuharu Ohsawa, Kanagawa (JP); Satoshi Seo, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 539 days.

(21) Appl. No.: 13/031,734

(22) Filed: Feb. 22, 2011

(65) Prior Publication Data

US 2011/0210316 A1 Sep. 1, 2011

(30) Foreign Application Priority Data

Mar. 1, 2010 (JP) ................................ 2010-044720

(51) Int. Cl.

| | |
|---|---|
| ***H01L 51/30*** | (2006.01) |
| ***C07D 409/10*** | (2006.01) |
| ***C07D 403/10*** | (2006.01) |
| ***C07D 405/10*** | (2006.01) |
| ***C09K 11/06*** | (2006.01) |
| ***H01L 51/00*** | (2006.01) |
| ***H05B 33/10*** | (2006.01) |
| *H01L 51/50* | (2006.01) |

(52) U.S. Cl.

CPC ............ *C07D 403/10* (2013.01); *C07D 405/10* (2013.01); *C07D 409/10* (2013.01); *C09K 11/06* (2013.01); *H01L 51/0067* (2013.01); *H01L 51/5048* (2013.01); *H05B 33/10* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *H01L 51/5016* (2013.01)

(58) Field of Classification Search

None

See application file for complete search history.

(56) References Cited

U.S. PATENT DOCUMENTS

| | | | | |
|---|---|---|---|---|
| 6,723,445 | B2 | 4/2004 | Li et al. | |
| 7,355,340 | B2 | 4/2008 | Shitagaki et al. | |
| 7,601,435 | B2 | 10/2009 | Shitagaki et al. | |
| 7,927,720 | B2 | 4/2011 | Nomura et al. | |
| 7,931,974 | B2 | 4/2011 | Egawa et al. | |
| 8,017,252 | B2 | 9/2011 | Iwaki et al. | |
| 8,084,146 | B2 | 12/2011 | Murase et al. | |
| 8,119,259 | B2 | 2/2012 | Kadoma et al. | |
| 8,138,303 | B2 | 3/2012 | Chebotareva et al. | |
| 8,178,216 | B2 | 5/2012 | Nomura et al. | |
| 8,231,984 | B2 | 7/2012 | Shitagaki et al. | |
| 8,252,433 | B2 | 8/2012 | Egawa et al. | |
| 8,252,434 | B2 | 8/2012 | Iwaki et al. | |
| 8,314,101 | B2 | 11/2012 | Kadoma et al. | |
| 8,541,114 | B2 | 9/2013 | Iwaki et al. | |
| 8,758,905 | B2 | 6/2014 | Shitagaki et al. | |
| 8,815,419 | B2 | 8/2014 | Iwaki et al. | |
| 2005/0064237 | A1 | 3/2005 | Kato et al. | |
| 2009/0026922 | A1 | 1/2009 | Iwaki et al. | |
| 2009/0072718 | A1 | 3/2009 | Nomura et al. | |
| 2009/0140641 | A1 | 6/2009 | Nomura et al. | |
| 2009/0140642 | A1 | 6/2009 | Kadoma et al. | |
| 2009/0153041 | A1 | 6/2009 | Kawakami et al. | |
| 2009/0184633 | A1 | 7/2009 | Kadoma et al. | |
| 2009/0203704 | A1 | 8/2009 | Kadoma et al. | |
| 2010/0039024 | A1 | 2/2010 | Wendeborn et al. | |
| 2010/0090588 | A1 | 4/2010 | Yokoyama et al. | |
| 2010/0249349 | A1 | 9/2010 | Chebotareva et al. | |
| 2011/0089407 | A1* | 4/2011 | Schmidhalter et al. | 257/40 |
| 2012/0138907 | A1 | 6/2012 | Murase et al. | |
| 2012/0193613 | A1 | 8/2012 | Kadoma et al. | |
| 2012/0197020 | A1* | 8/2012 | Osaka et al. | 544/343 |
| 2012/0286257 | A1 | 11/2012 | Shitagaki et al. | |
| 2012/0313506 | A1 | 12/2012 | Egawa et al. | |
| 2013/0048971 | A1 | 2/2013 | Kitano et al. | |
| 2013/0060033 | A1 | 3/2013 | Seo et al. | |
| 2013/0075704 | A1 | 3/2013 | Takasu et al. | |
| 2013/0082591 | A1 | 4/2013 | Seo et al. | |
| 2013/0112954 | A1 | 5/2013 | Osaka et al. | |

FOREIGN PATENT DOCUMENTS

| | | | | |
|---|---|---|---|---|
| CN | 101203968 A | | 6/2008 | |
| CN | 101379110 A | | 3/2009 | |
| CN | 101516856 A | | 8/2009 | |
| CN | 101853923 A | | 10/2010 | |
| CN | 101867019 A | | 10/2010 | |
| CN | 101970448 A | | 2/2011 | |
| CN | 102190653 A | | 9/2011 | |
| CN | 103030632 A | | 4/2013 | |
| EP | 1616864 A1 | | 1/2006 | |
| EP | 1748045 A1 | | 1/2007 | |
| EP | 1905768 A1 | | 4/2008 | |
| EP | 1962354 A1 | | 8/2008 | |
| EP | 2055704 A1 | | 5/2009 | |
| EP | 2065378 A1 | | 6/2009 | |
| EP | 2236506 A1 | | 10/2010 | |
| EP | 2 363 398 A1 | | 9/2011 | |
| EP | 2450356 A1 | | 5/2012 | |
| JP | 2006-324850 A | | 11/2006 | |
| JP | 2006324650 A | | 11/2006 | |
| JP | 2007-189001 A | | 7/2007 | |
| JP | 2007189001 A | * | 7/2007 | |
| JP | 2008-021665 A | | 1/2008 | |
| JP | 2008106051 A | | 5/2008 | |
| JP | 2008-239613 A | | 10/2008 | |
| JP | 2009149629 A | | 7/2009 | |
| JP | 2009149631 A | | 7/2009 | |
| JP | 2009149632 A | | 7/2009 | |
| JP | 2009526111 A | | 7/2009 | |
| JP | 2011511821 A | | 4/2011 | |
| KR | 20080005441 A | | 1/2008 | |
| KR | 20100123716 A | | 11/2010 | |
| KR | 20110042004 A | | 4/2011 | |
| TW | 200502352 | | 1/2005 | |
| TW | 200940554 A | | 10/2009 | |
| WO | 03/058667 A1 | | 7/2003 | |
| WO | 2004-043937 A1 | | 5/2004 | |
| WO | WO2004094389 A1 | | 11/2004 | |
| WO | WO2005113531 A1 | | 12/2005 | |
| WO | 2006115232 A1 | | 11/2006 | |
| WO | WO2007069569 A1 | | 6/2007 | |
| WO | 2007/090773 A1 | | 8/2007 | |
| WO | WO2008023628 A1 | | 2/2008 | |
| WO | 2008-031743 A1 | | 3/2008 | |
| WO | 2009/100991 A1 | | 8/2009 | |
| WO | WO 2009/100991 A1 | * | 8/2009 | .............. C07F 15/00 |

OTHER PUBLICATIONS

Machine English translation of JP 2007-189001 A. May 10, 2013.*
Search Report, European Application No. 11155124.8, dated Jun. 24, 2011, 7 pages.
Zhang.M et al., "Highly-efficient solution-processed OLEDs based on new bipolar emitters," Chemical Communications, 2010, vol. 46, pp. 3923-3925 in English.
Onishi et al., "A Method of Measuring an Energy Level," High Molecular El Materials—Development of Light-Emitting High Molecular Compounds, Dec. 25, 2004, pp. 64-67, Kyoritsu Shuppan with Full English Translation.
Goldsmith.C et al., "C—H Bond Activation by a Ferric Methoxide Complex: Modeling the Rate-Determining Step in the Mechanism of Lipoxygenase," J. Am. Chem. Soc. (Journal of the American Chemical Society), 2002, vol. 124, No. 1, pp. 83-96 in English.
Chinese Office Action (CN Application No. 201210579702.0) dated Dec. 26, 2013 with full English translation, 16 pages.
C. Wermuth; "Molecular Variations Based on Isosteric Replacements", The Practice of Medicinal Chemistry; 1996; pp. 204-237.
Chinese Office Action (Application No. 201110052847.0) Dated Jul. 25, 2014.
Taiwanese Office Action (Application No. 101149295) Dated Dec. 23, 2014.

* cited by examiner

*Primary Examiner* — J. L. Yang
(74) *Attorney, Agent, or Firm* — Fish & Richardson P.C.

(57) ABSTRACT

An object is to provide a novel heterocyclic compound which can be used for a light-emitting element, as a host material of a light-emitting layer in which a light-emitting substance is dispersed. Other objects are to provide a light-emitting element having low driving voltage, a light-emitting element having high current efficiency, and a light-emitting element having a long lifetime. Provided are a light-emitting element including a compound in which a dibenzo[f,h]quinoxaline ring and a hole-transport skeleton are bonded through an arylene group, and a light-emitting device, an electronic device, and a lighting device each using this light-emitting element. The heterocyclic compound represented by General Formula (G1) below is provided.

(G1)

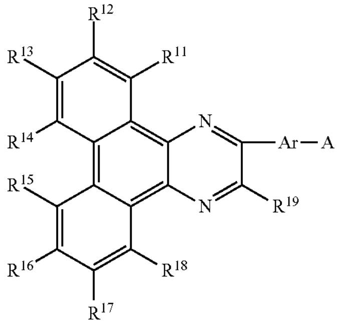

36 Claims, 56 Drawing Sheets

HETEROCYCLIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a heterocyclic compound, a light-emitting element, a light-emitting device, an electronic device, and a lighting device.

2. Description of the Related Art

In recent years, research and development have been extensively conducted on light-emitting elements utilizing electroluminescence (EL). In the basic structure of such a light-emitting element, a layer containing a light-emitting substance is interposed between a pair of electrodes. By voltage application to this element, light emission from the light-emitting substance can be obtained.

Since such light-emitting elements are self-luminous elements, they have advantages over liquid crystal displays in having high pixel visibility and eliminating the need for backlights, for example, thereby being considered as suitable for flat panel display elements. Light-emitting elements are also highly advantageous in that they can be thin and lightweight. Furthermore, very high speed response is one of the features of such elements.

Furthermore, since such light-emitting elements can be formed in a film form, they make it possible to provide planar light emission. Accordingly, elements having a large area can be easily formed. This is a feature difficult to obtain with point light sources typified by incandescent lamps and LEDs or linear light sources typified by fluorescent lamps. Thus, light-emitting elements also have great potential as planar light sources applicable to lightings and the like.

Such light-emitting elements utilizing electroluminescence can be broadly classified according to whether a light-emitting substance is an organic compound or an inorganic compound. In the case of an organic EL element in which a layer containing an organic compound used as a light-emitting substance is provided between a pair of electrodes, application of a voltage to the light-emitting element causes injection of electrons from a cathode and holes from an anode into the layer containing the organic compound having a light-emitting property and thus a current flows. The injected electrons and holes then lead the organic compound having a light-emitting property to its excited state, whereby light emission is obtained from the excited organic compound having a light-emitting property.

The excited state formed by an organic compound can be a singlet excited state or a triplet excited state. Emission from the singlet excited state (S*) is called fluorescence, and emission from the triplet excited state (T*) is called phosphorescence. In addition, the statistical generation ratio thereof in a light-emitting element is considered to be as follows: S*:T*=1:3.

In a compound which converts energy of a singlet excited state into light emission (hereinafter, referred to as a fluorescent compound), at room temperature, emission from the triplet excited state (phosphorescence) is not observed while only emission from the singlet excited state (fluorescence) is observed. Therefore the internal quantum efficiency (the ratio of generated photons to injected carriers) of a light-emitting element using a fluorescent compound is assumed to have a theoretical limit of 25% based on the ratio of S* to T* which is 1:3.

In contrast, in a compound which converts energy of a triplet excited state into light emission (hereinafter, referred to as a phosphorescent compound), emission from the triplet excited state (phosphorescence) is observed. Further, in a phosphorescent compound, since intersystem crossing (i.e. transfer from a singlet excited state to a triplet excited state) easily occurs, the internal quantum efficiency can be increased to 75% to 100% in theory. In other words, the emission efficiency can be three to four times as much as that of a fluorescent compound. For this reason, light-emitting elements using phosphorescent compounds are now under active development in order to realize highly efficient light-emitting elements.

When a light-emitting layer of a light-emitting element is formed using a phosphorescent compound described above, in order to suppress concentration quenching or quenching due to triplet-triplet annihilation in the phosphorescent compound, the light-emitting layer is often formed such that the phosphorescent compound is dispersed in a matrix of another compound. Here, the compound serving as the matrix is called a host material, and the compound dispersed in the matrix, such as a phosphorescent compound, is called a guest material.

In the case where a phosphorescent compound is a guest material, a host material needs to have higher triplet excitation energy (a larger energy difference between a ground state and a triplet excited state) than the phosphorescent compound.

Furthermore, since singlet excitation energy (an energy difference between a ground state and a singlet excited state) is higher than triplet excitation energy, a substance that has high triplet excitation energy also has high singlet excitation energy. Therefore the above substance that has high triplet excitation energy is also effective in a light-emitting element using a fluorescent compound as a light-emitting substance.

Studies have been conducted on compounds having dibenzo[f,h]quinoxaline rings, which are examples of the host material used when a phosphorescent compound is a guest material (e.g., see Patent Documents 1 and 2).

REFERENCES

Patent Document 1: PCT International Publication No. 03/058667

Patent Document 2: Japanese Published Patent Application No. 2007-189001

SUMMARY OF THE INVENTION

However, the above compounds having dibenzo[f,h]quinoxaline rings have a planar structure, and accordingly, these compounds are easily crystallized. A light-emitting element using a compound that is easy to crystallize has a short lifetime. Further, if another skeleton is directly bonded to the dibenzo[f,h]quinoxaline ring so that the compound has a three-dimensionally bulky structure, the conjugated system could possibly extend to cause a decrease in triplet excitation energy.

Further, in order to realize a light-emitting device, an electronic device, and a lighting device each having reduced power consumption and high reliability, a light-emitting element having low driving voltage, a light-emitting element having high current efficiency, or a light-emitting element having a long lifetime have been expected.

Therefore an object of one embodiment of the present invention is to provide a novel heterocyclic compound which can be used for a light-emitting element, as a host material of a light-emitting layer in which a light-emitting substance is dispersed, in particular, a novel heterocyclic compound which can be suitably used as a host material in which a phosphorescent compound is used as a light-emitting substance.

Another object of one embodiment of the present invention is to provide a light-emitting element having low driving voltage. Yet another object of one embodiment of the present invention is to provide a light-emitting element having high current efficiency. Another object of one embodiment of the present invention is to provide a light-emitting element having a long lifetime. Still another object of one embodiment of the present invention is to provide a light-emitting device, an electronic device, and a lighting device each having reduced power consumption by use of any of these light-emitting elements.

A compound with a quinoxaline skeleton has a high electron-transport property, and use of such a compound for a light-emitting element enables the element to have low driving voltage. However, a quinoxaline skeleton has a planar structure. Since a compound having a planar structure is easily crystallized when formed into a film, use of such a compound for light-emitting elements causes the elements to have a short a lifetime. Furthermore, a quinoxaline skeleton is poor at accepting holes. When a compound that cannot easily accept holes is used as a host material of a light-emitting layer, the region of electron-hole recombination concentrates on an interface of the light-emitting layer, leading to a reduction in the lifetime of the light-emitting element. It is likely that these problems will be solved by introduction of a hole-transport skeleton into the molecule. However, if a hole-transport skeleton is directly bonded to a quinoxaline skeleton, the conjugated system extends to cause a decrease in band gap and a decrease in triplet excitation energy.

Nevertheless, the present inventors have found that the above problems can be solved by using, for a light-emitting element, a compound in which a dibenzo[f,h]quinoxaline ring and a hole-transport skeleton are bonded through an arylene group.

One embodiment of the present invention is a light-emitting element including a compound in which a dibenzo[f,h] quinoxaline ring and a hole-transport skeleton are bonded through an arylene group.

A compound applied to one embodiment of the present invention has a hole-transport skeleton in addition to a dibenzo[f,h]quinoxaline ring, making it easy to accept holes. Accordingly, by use of the compound as a host material of a light-emitting layer, electrons and holes recombine in the light-emitting layer, so that it is possible to suppress the decrease in the lifetime of the light-emitting element. Furthermore, the introduction of a hole-transport skeleton enables the compound to have a three-dimensionally bulky structure, and the compound is difficult to crystallize when formed into a film. By the use of the compound for a light-emitting element, the element can have a long lifetime. Moreover, in this compound, since a dibenzo[f,h]quinoxaline ring and a hole-transport skeleton are bonded through an arylene group, decreases in band gap and triplet excitation energy can be prevented as compared with a compound in which a dibenzo[f,h]quinoxaline ring and a hole-transport skeleton are directly bonded. By the use of the compound for a light-emitting element, the element can have high current efficiency.

Thus, the compound described above can be suitably used as a material for an organic device such as a light-emitting element or an organic transistor.

As the hole-transport skeleton, a π-electron rich heteroaromatic ring is preferable. As the π-electron rich heteroaromatic ring, a carbazole ring, a dibenzofuran ring, or a dibenzothiophene ring is preferable. As the arylene group, any of a substituted or unsubstituted phenylene group and a substituted or unsubstituted biphenyldiyl group is preferable.

Since a light-emitting element of one embodiment of the present invention which is obtained as above has low driving voltage, high current efficiency, and a long lifetime, a light-emitting device (such as an image display device) using this light-emitting element can have reduced power consumption. Thus, one embodiment of the present invention is a light-emitting device including any of the above light-emitting elements. One embodiment of the present invention also includes an electronic device using the light-emitting device in its display portion and a lighting device using the light-emitting device in its light-emitting portion.

The light-emitting device in this specification covers an image display device using a light-emitting element and also the following devices: a module including a light-emitting element to which a connector such as an anisotropic conductive film, a TAB (tape automated bonding) tape, or a TCP (tape carrier package) is attached; a module in which the top of a TAB tape or a TCP is provided with a printed wiring board; a module in which an IC (integrated circuit) is directly mounted on a light-emitting element by a COG (chip on glass) technique; and further a light-emitting device used for a lighting device and the like.

As the compound in which a dibenzo[f,h]quinoxaline ring and a hole-transport skeleton are bonded through an arylene group, a heterocyclic compound below can be given.

One embodiment of the present invention is a heterocyclic compound represented by General Formula (G1) below.

[Chemical Formula 1]

(G1)

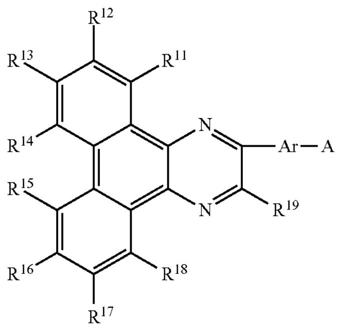

In General Formula (G1), A represents any of a substituted or unsubstituted carbazolyl group, a substituted or unsubstituted dibenzothiophenyl group, and a substituted or unsubstituted dibenzofuranyl group, $R^{11}$ to $R^{19}$ separately represent any of hydrogen, an alkyl group having 1 to 4 carbon atoms, and a substituted or unsubstituted aryl group having 6 to 13 carbon atoms, and Ar represents an arylene group having 6 to 13 carbon atoms. The arylene group may have one or more substituents, and the substituents may be bonded to form a ring.

Another embodiment of the present invention is a heterocyclic compound represented by General Formula (G2-1) below.

[Chemical Formula 2]

(G2-1)

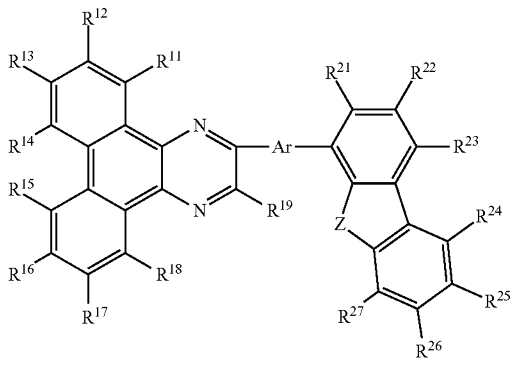

In General Formula (G2-1), Z represents oxygen or sulfur, $R^{11}$ to $R^{19}$ and $R^{21}$ to $R^{27}$ separately represent hydrogen, an alkyl group having 1 to 4 carbon atoms, or a substituted or unsubstituted aryl group having 6 to 13 carbon atoms, and Ar represents an arylene group having 6 to 13 carbon atoms. The arylene group may have one or more substituents, and the substituents may be bonded to form a ring.

Another embodiment of the present invention is a heterocyclic compound represented by General Formula (G2-2) below.

[Chemical Formula 3]

(G2-2)

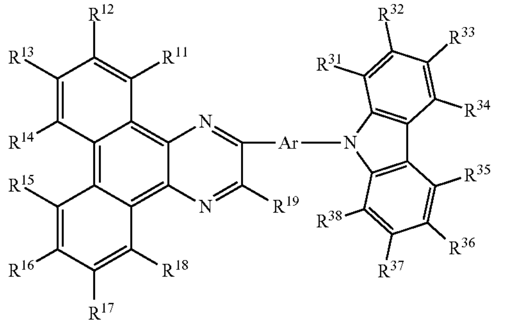

In General Formula (G2-2), $R^{11}$ to $R^{19}$ and $R^{31}$ to $R^{38}$ separately represent hydrogen, an alkyl group having 1 to 4 carbon atoms, or a substituted or unsubstituted aryl group having 6 to 13 carbon atoms, and Ar represents an arylene group having 6 to 13 carbon atoms. The arylene group may have one or more substituents, and the substituents may be bonded to form a ring.

In General Formulae (G2-1) and (G2-2), Ar is preferably any of a substituted or unsubstituted phenylene group and a substituted or unsubstituted biphenyldiyl group, particularly a substituted or unsubstituted phenylene group. Furthermore, Ar is much preferably a substituted or unsubstituted m-phenylene group so as to have a high triplet excited energy level (T1 level).

Another embodiment of the present invention is a heterocyclic compound represented by General Formula (G3-1) below.

[Chemical Formula 4]

(G3-1)

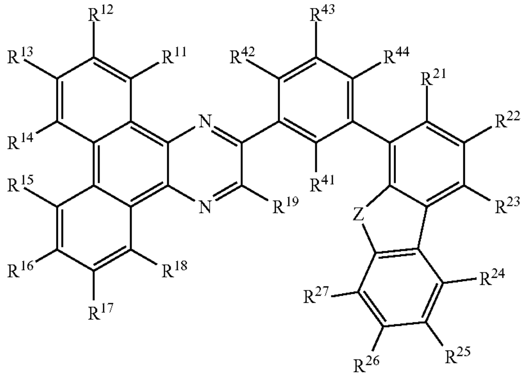

In General Formula (G3-1), Z represents oxygen or sulfur, $R^{11}$ to $R^{19}$, $R^{21}$ to $R^{27}$, and $R^{41}$ to $R^{44}$ separately represent hydrogen, an alkyl group having 1 to 4 carbon atoms, or a substituted or unsubstituted aryl group having 6 to 13 carbon atoms.

Yet another embodiment of the present invention is a heterocyclic compound represented by General Formula (G3-2) below.

[Chemical Formula 5]

(G3-2)

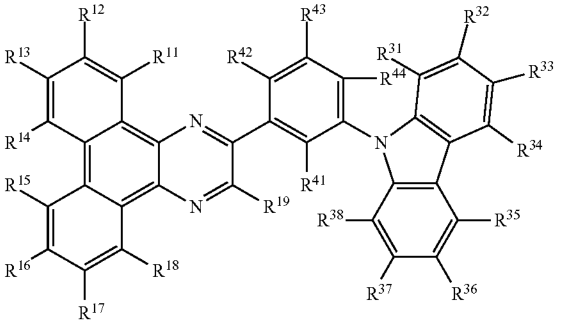

In General Formula (G3-2), $R^{11}$ to $R^{19}$, $R^{31}$ to $R^{38}$, and $R^{41}$ to $R^{44}$ separately represent hydrogen, an alkyl group having 1 to 4 carbon atoms, or a substituted or unsubstituted aryl group having 6 to 13 carbon atoms.

The above heterocyclic compounds are also categorized as the already described compound in which a dibenzo[f,h]quinoxaline ring and a hole-transport skeleton are bonded through an arylene group. Hence, one embodiment of the present invention further covers a light-emitting element including any of the above heterocyclic compounds. Also, one embodiment of the present invention covers a light-emitting device, an electronic device, and a lighting device each including the light-emitting element.

One embodiment of the present invention can provide a novel heterocyclic compound which can be used for a light-emitting element, as a host material of a light-emitting layer in which a light-emitting substance is dispersed. Another embodiment of the present invention can provide a light-emitting element having low driving voltage. Yet another embodiment of the present invention can provide a light-emitting element having high current efficiency. Still another embodiment of the present invention can provide a light-emitting element having a long lifetime. By using the light-emitting element, another embodiment of the present invention can provide a light-emitting device, an electronic device, and a lighting device each having reduced power consumption.

DETAILED DESCRIPTION OF THE INVENTION

Figure 1A:
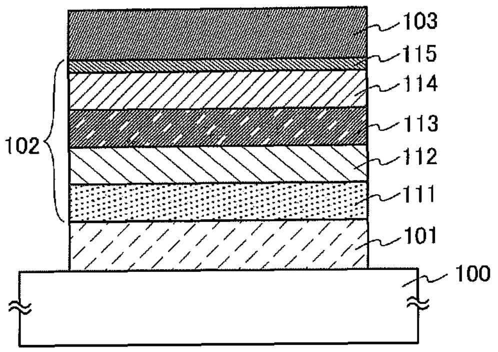
FIGS. 1A and 1B each illustrate a light-emitting element of one embodiment of the present invention.

Embodiments of the present invention will now be described with reference to the accompanying drawings. Note that the invention is not limited to the description below, and it will be easily understood by those skilled in the art that various changes and modifications can be made without departing from the spirit and scope of the invention. Therefore, the invention should not be construed as being limited to the description in the following Embodiments.

Embodiment 1

In Embodiment 1, a heterocyclic compound of one embodiment of the present invention will be described.

One embodiment of the present invention is the heterocyclic compound represented by General Formula (G1).

[Chemical Formula 6]

(G1)

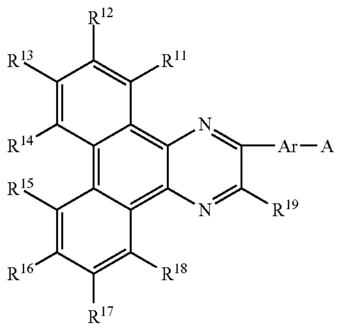

In General Formula (G1), A represents any of a substituted or unsubstituted carbazolyl group, a substituted or unsubstituted dibenzothiophenyl group, and a substituted or unsubstituted dibenzofuranyl group, $R^{11}$ to $R^{19}$ separately represent any of hydrogen, an alkyl group having 1 to 4 carbon atoms, and a substituted or unsubstituted aryl group having 6 to 13 carbon atoms, and Ar represents an arylene group having 6 to 13 carbon atoms. The arylene group may have one or more substituents, and the substituents may be bonded to form a ring.

Another embodiment of the present invention is the heterocyclic compound represented by General Formula (G2-1) below.

[Chemical Formula 7]

(G2-1)

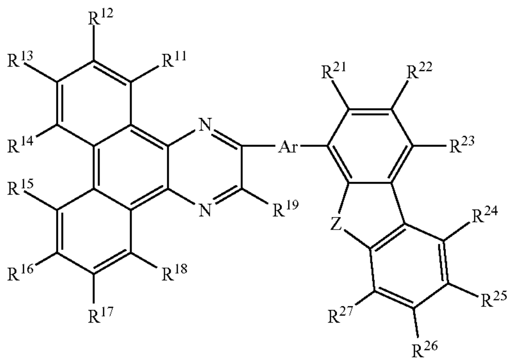

In General Formula (G2-1), Z represents oxygen or sulfur, $R^{11}$ to $R^{19}$ and $R^{21}$ to $R^{27}$ separately represent hydrogen, an alkyl group having 1 to 4 carbon atoms, or a substituted or unsubstituted aryl group having 6 to 13 carbon atoms, and Ar represents an arylene group having 6 to 13 carbon atoms. The arylene group may have one or more substituents, and the substituents may be bonded to form a ring.

Another embodiment of the present invention is the heterocyclic compound represented by General Formula (G2-2) below.

[Chemical Formula 8]

(G2-2)

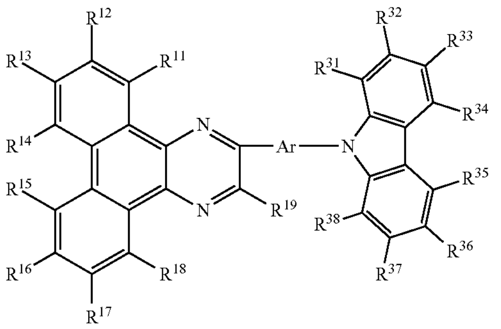

In General Formula (G2-2), $R^{11}$ to $R^{19}$ and $R^{31}$ to $R^{38}$ separately represent hydrogen, an alkyl group having 1 to 4 carbon atoms, or a substituted or unsubstituted aryl group having 6 to 13 carbon atoms, and Ar represents an arylene group having 6 to 13 carbon atoms. The arylene group may have one or more substituents, and the substituents may be bonded to form a ring.

In General Formulae (G2-1) and (G2-2), Ar is preferably any of a substituted or unsubstituted phenylene group and a substituted or unsubstituted biphenyldiyl group, particularly a substituted or unsubstituted phenylene group. Furthermore, Ar is much preferably a substituted or unsubstituted m-phenylene group so as to have a high triplet excited energy level (T1 level).

Another embodiment of the present invention is the heterocyclic compound represented by General Formula (G3-1) below.

[Chemical Formula 9]

(G3-1)

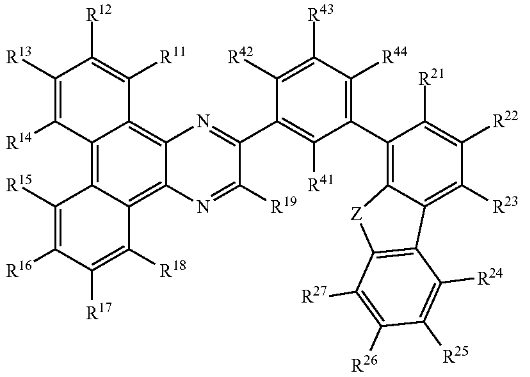

In General Formula (G3-1), Z represents oxygen or sulfur, $R^{11}$ to $R^{19}$, $R^{21}$ to $R^{27}$, and $R^{41}$ to $R^{44}$ separately represent hydrogen, an alkyl group having 1 to 4 carbon atoms, or a substituted or unsubstituted aryl group having 6 to 13 carbon atoms.

Yet another embodiment of the present invention is the heterocyclic compound represented by General Formula (G3-2) below.

[Chemical Formula 10]

(G3-2)

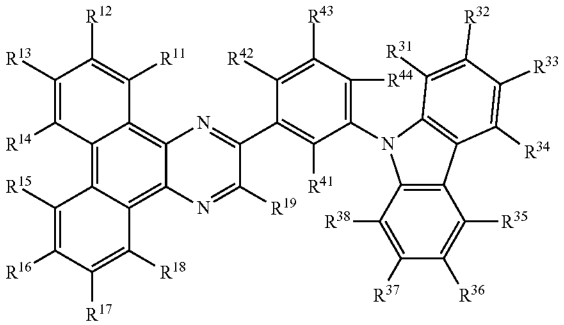

In General Formula (G3-2), to $R^{19}$, $R^{31}$ to $R^{38}$, and $R^{41}$ to $R^{44}$ separately represent hydrogen, an alkyl group having 1 to 4 carbon atoms, or a substituted or unsubstituted aryl group having 6 to 13 carbon atoms.

Examples of the specific structures of Ar in General Formulae (G1), (G2-1), and (G2-2) include substituents represented by Structural Formulae (I-1) to (1-15).

[Chemical Formula 11]

(1-1)

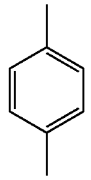

(1-2)

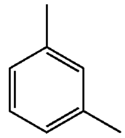

(1-3)

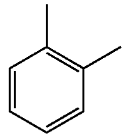

(1-4)

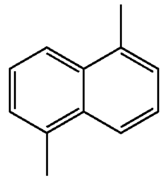

(1-5)

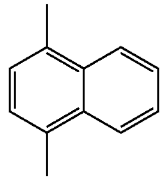

-continued
(1-6)
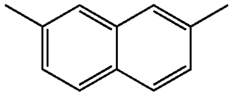
(1-7)
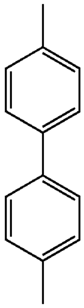
(1-8)
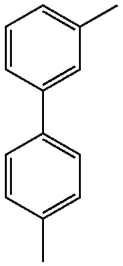
(1-9)
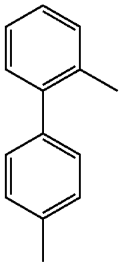
(1-10)
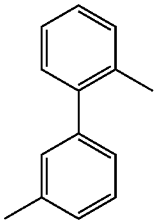
(1-11)
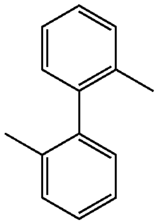
(1-12)
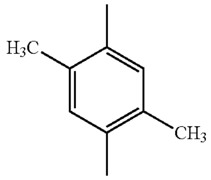
-continued
(1-13)
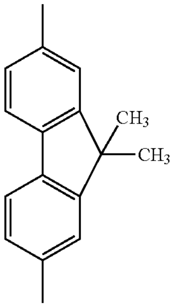
(1-14)
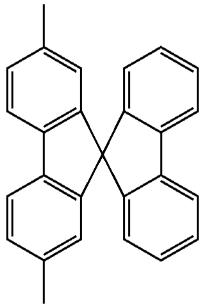
(1-15)
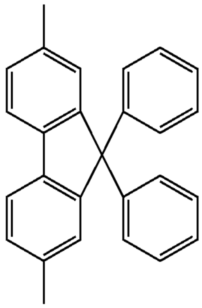
Examples of the specific structures of $R^{11}$ to $R^{19}$, $R^{21}$ to $R^{27}$, $R^{31}$ to $R^{38}$, and $R^{41}$ to $R^{44}$ in General Formulae (G1), (G2-1), (G2-2), (G3-1), and (G3-2) include substituents represented by Structural Formulae (2-1) to (2-23).
[Chemical Formula 12]
(2-1)
(2-2)
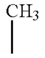
(2-3)
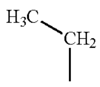
(2-4)
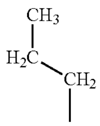
(2-5)
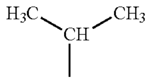

-continued
(2-6)
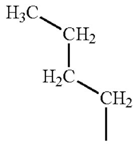
(2-7)
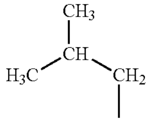
(2-8)
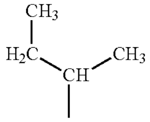
(2-9)
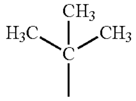
(2-10)
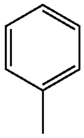
(2-11)
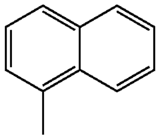
(2-12)
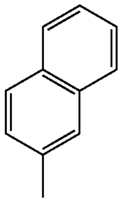
(2-13)
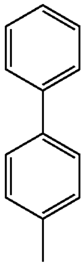
(2-14)
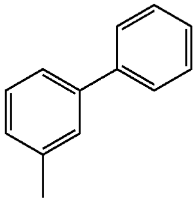
-continued
(2-15)
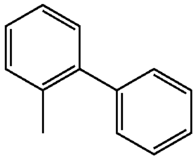
(2-16)
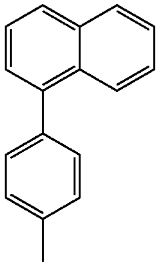
(2-17)
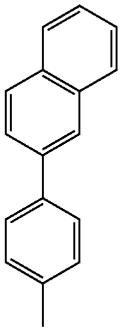
(2-18)
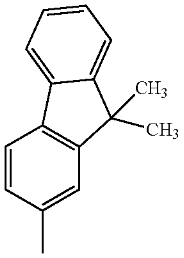
(2-19)
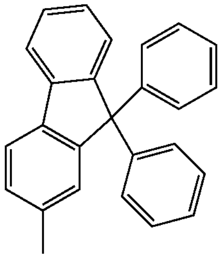
(2-20)
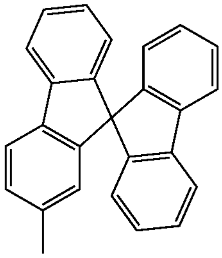

-continued
(2-21)
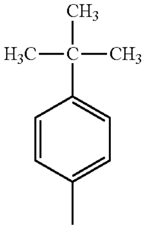
(2-22)
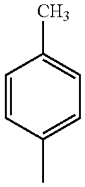
-continued
(2-23)
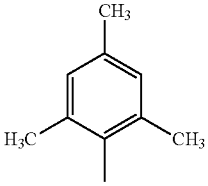
Specific examples of the heterocyclic compound represented by General Formula (G1) include, but are not limited to, heterocyclic compounds represented by Structural Formulae (100) to (174), (200) to (274), (300) to (374), (400) to (487), (500) to (574), and (600) to (674).
[Chemical Formula 13]
(100)
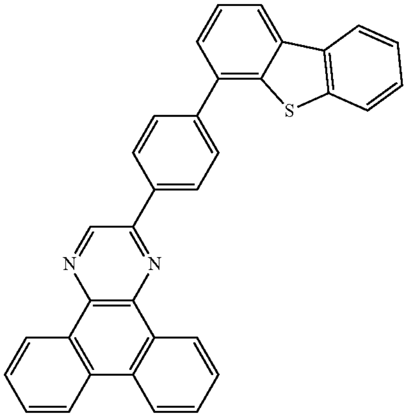
(101)
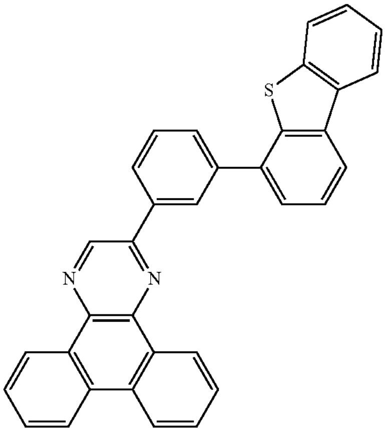
(102)
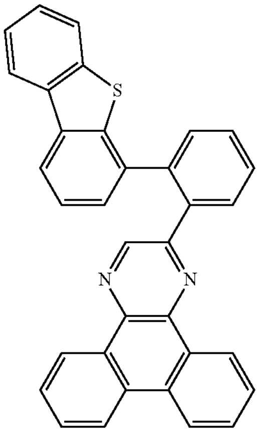
(103)
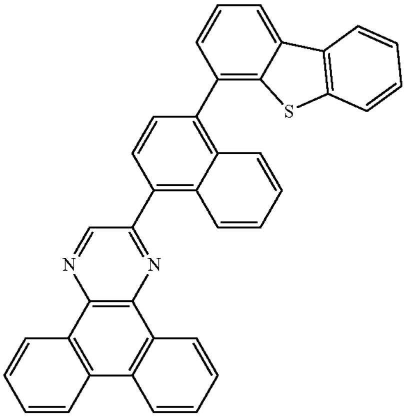

-continued
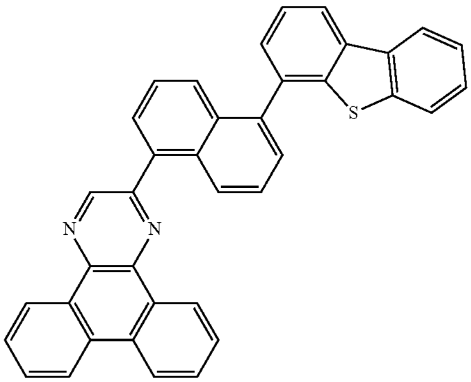
(104)
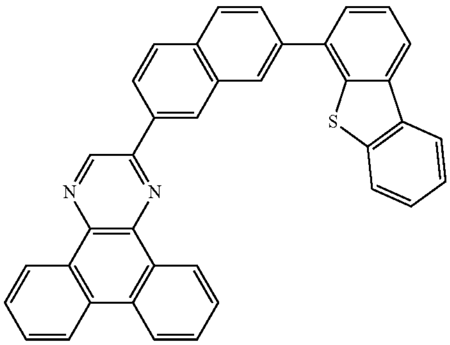
(105)
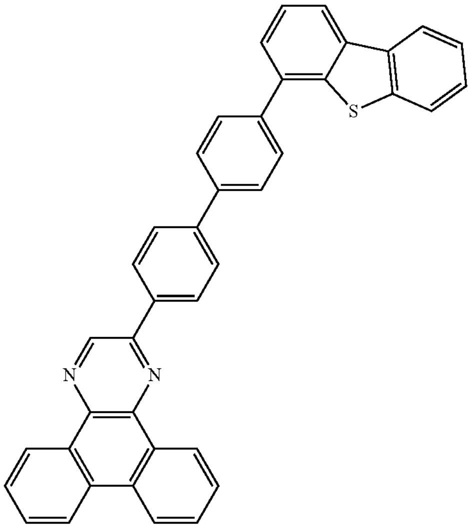
(106)
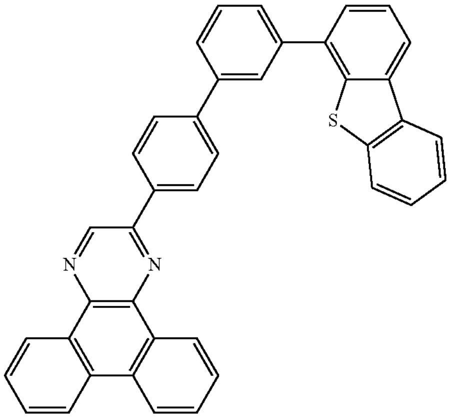
(107)
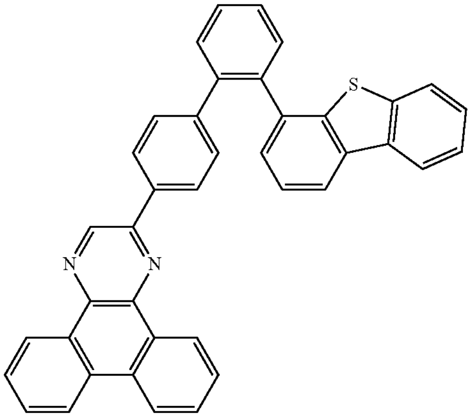
(108)

-continued
[Chemical Formula 14]
(109)
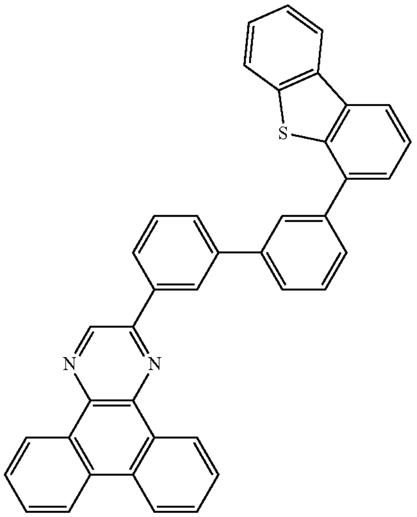
(110)
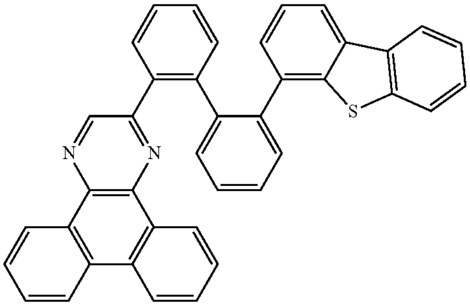
(111)
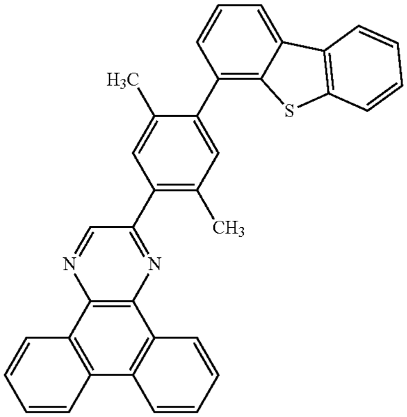
(112)
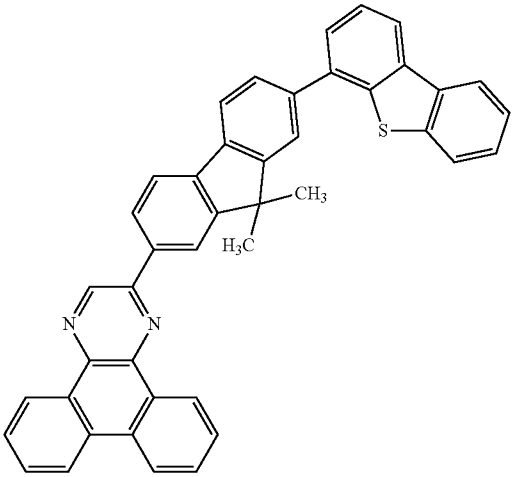
(113)
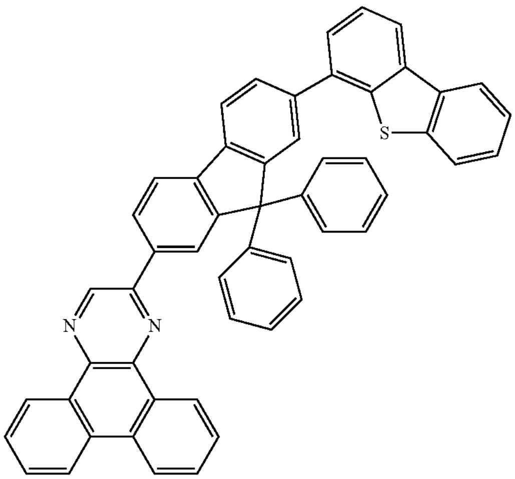
(114)
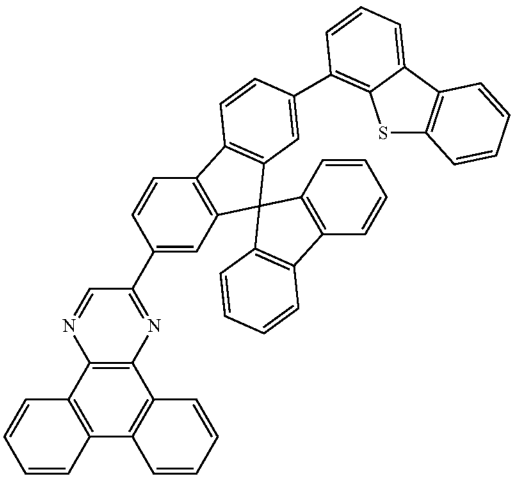

-continued
[Chemical Formula 15]
(115)
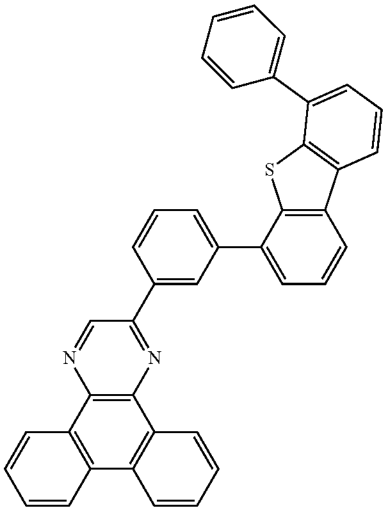
(116)
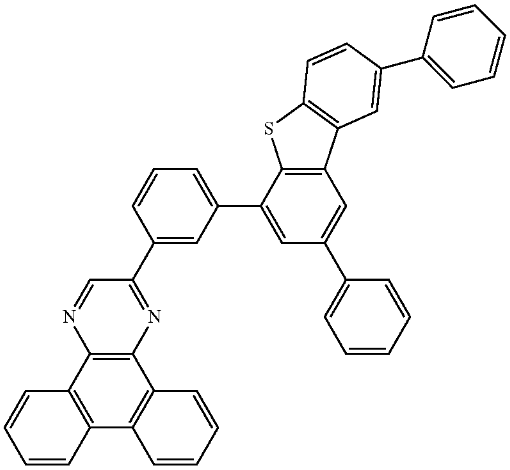
(117)
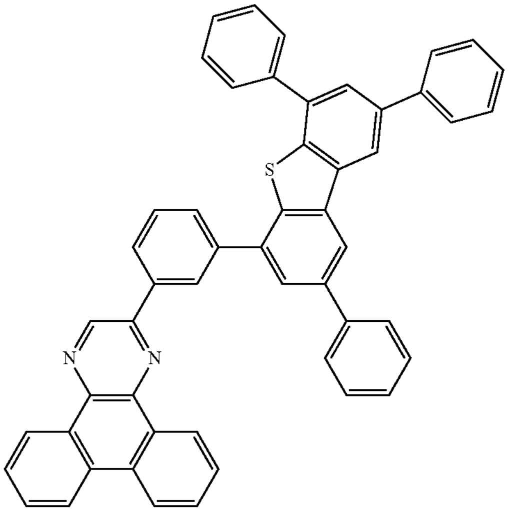
(118)
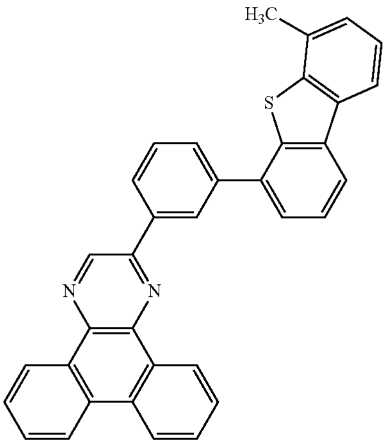
(119)
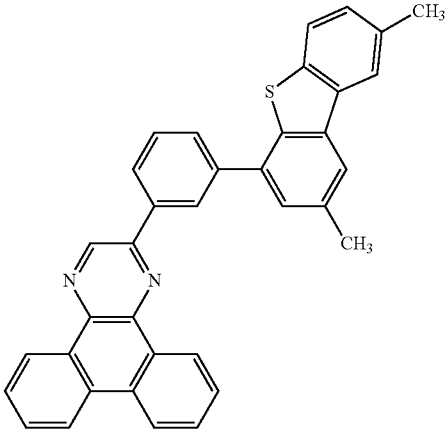
(120)
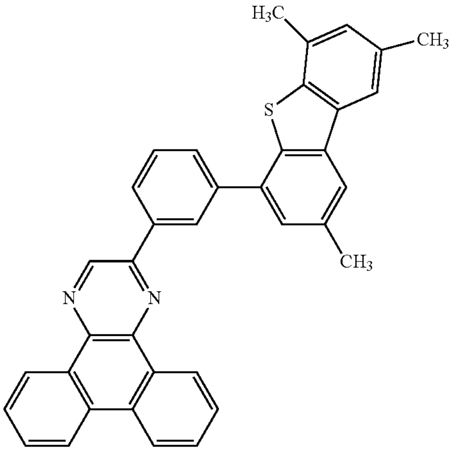

-continued
(121)
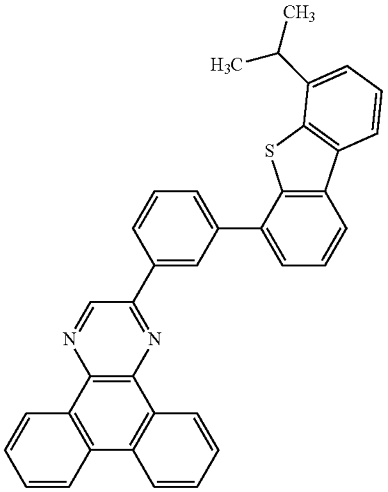
(122)
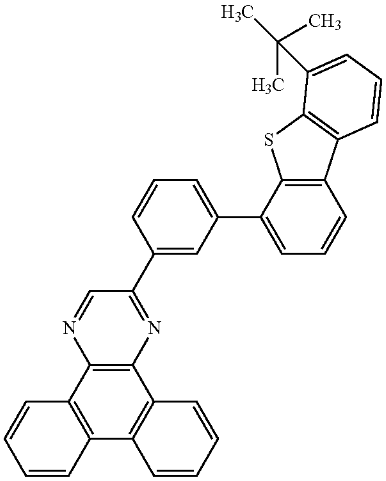
(123)
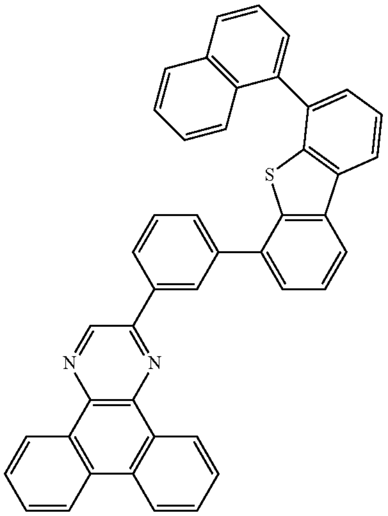
[Chemical Formula 16]
(124)
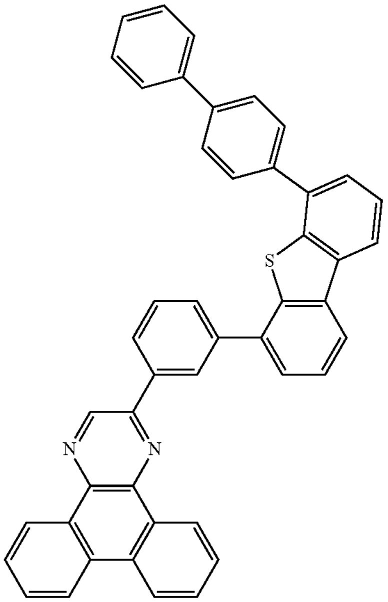
(125)
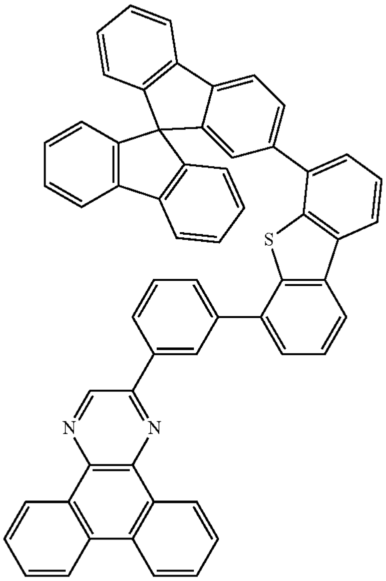

-continued
(126)
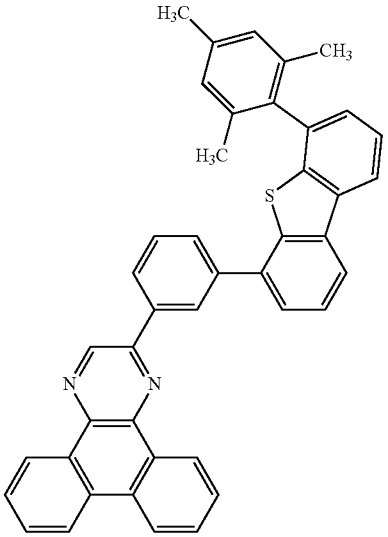
(127)
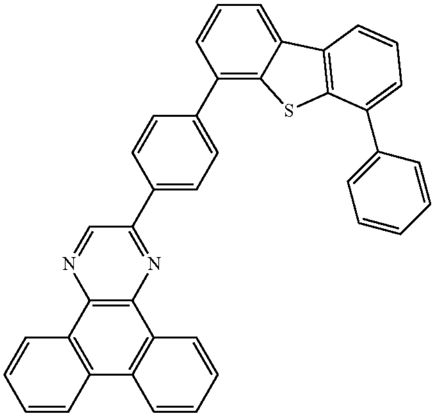
(128)
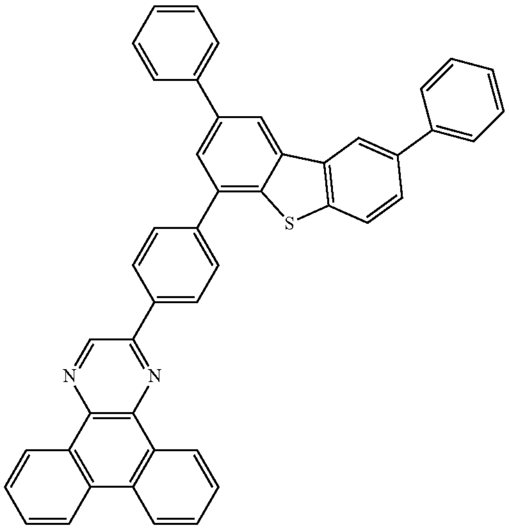
(129)
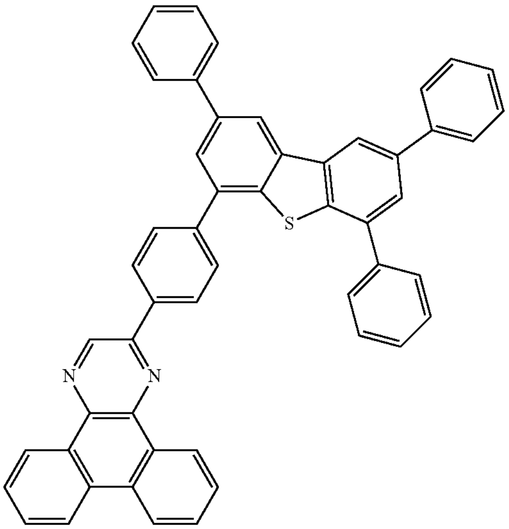
(130)
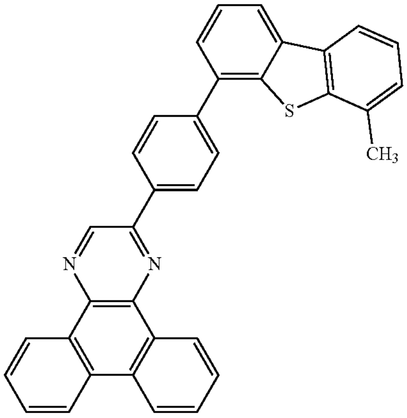
(131)
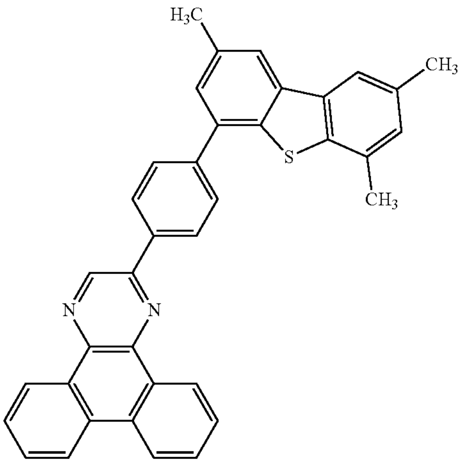

-continued
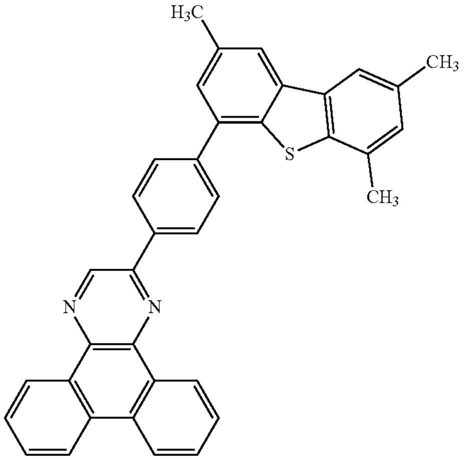
(132)
[Chemical Formula 17]
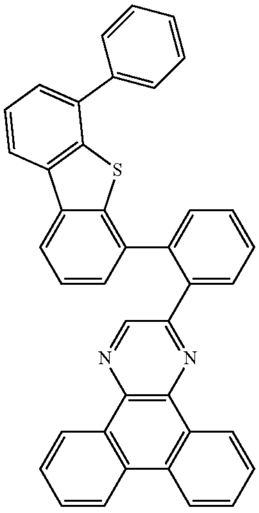
(133)
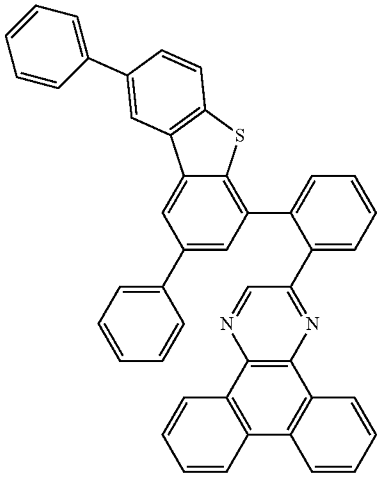
(134)
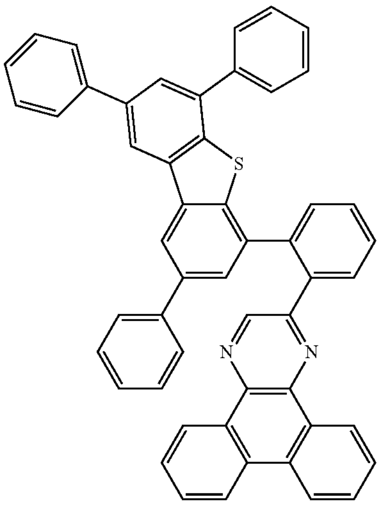
(135)
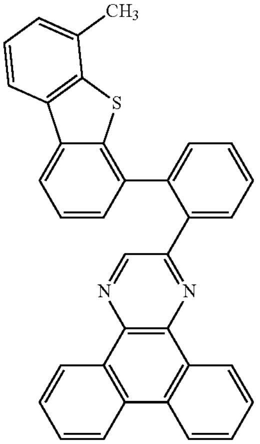
(136)

-continued
(137)
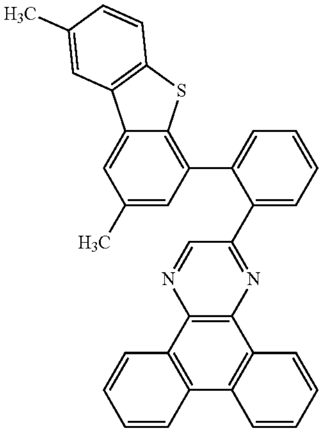
(138)
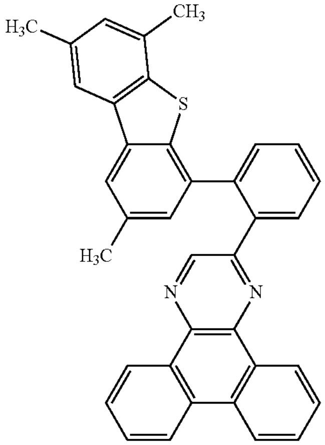
(139)
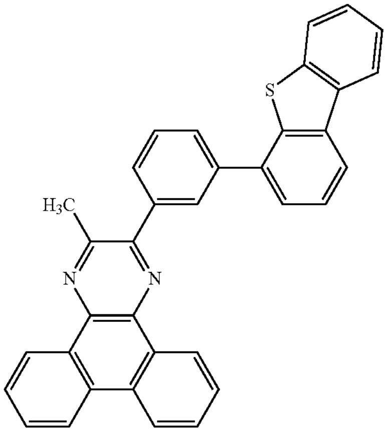
(140)
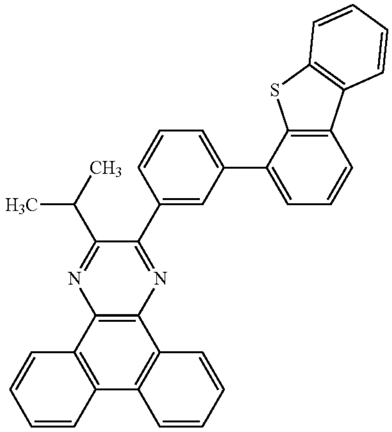
(141)
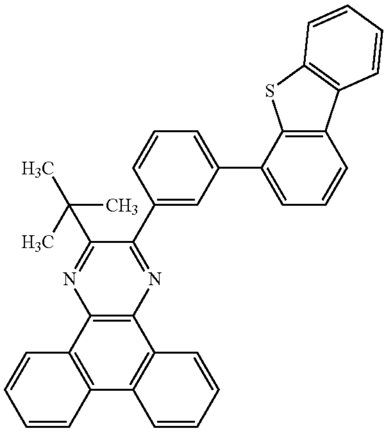

-continued
[Chemical Formula 18]
(142)
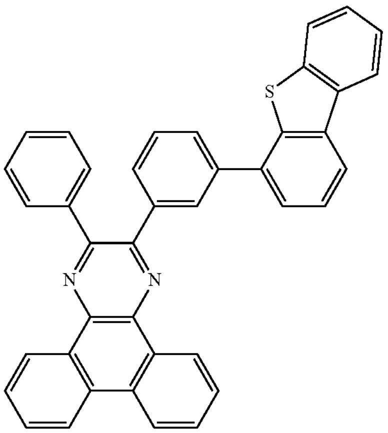
(143)
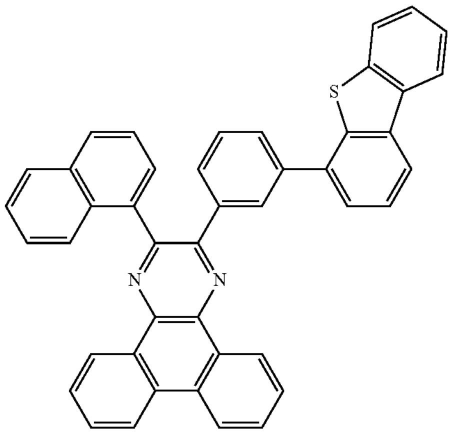
(144)
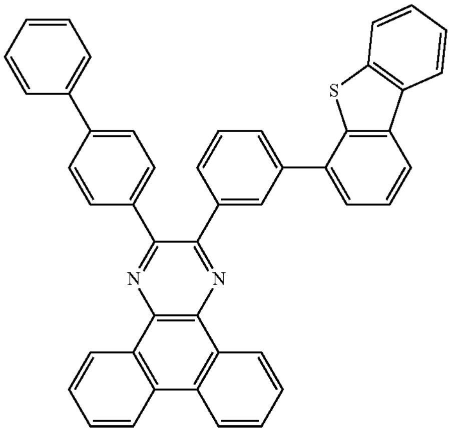
(145)
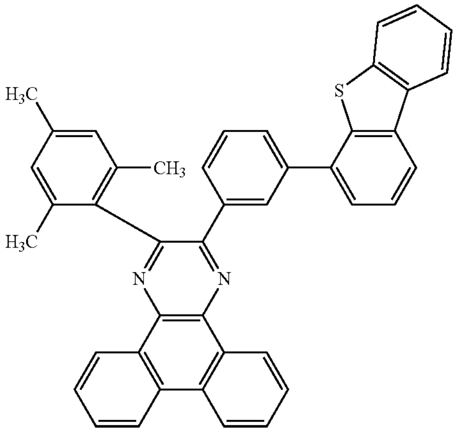
(146)
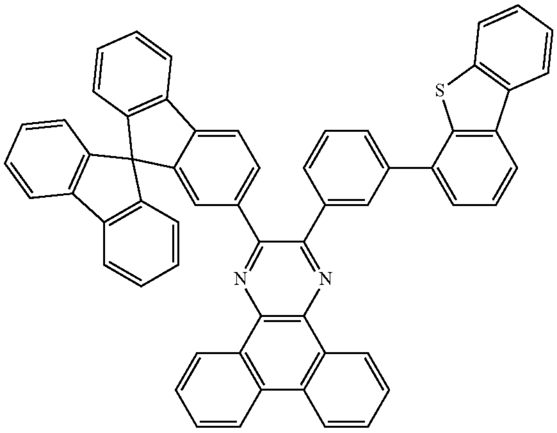
(147)
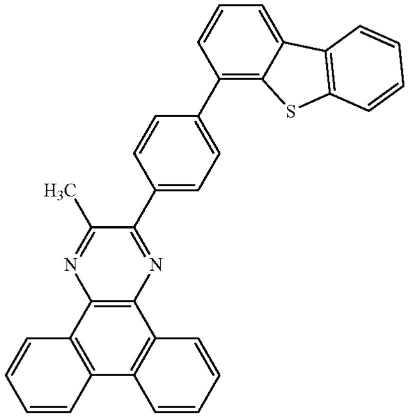

-continued
(148)
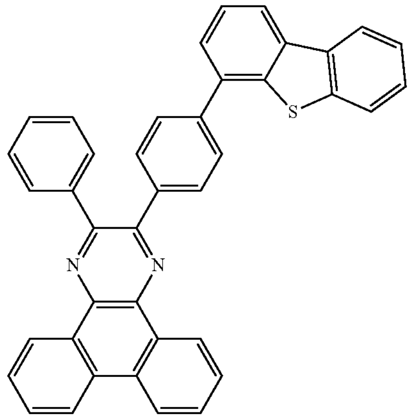
(149)
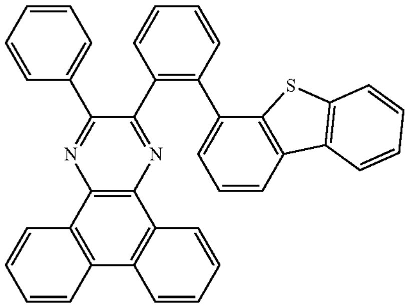
(150)
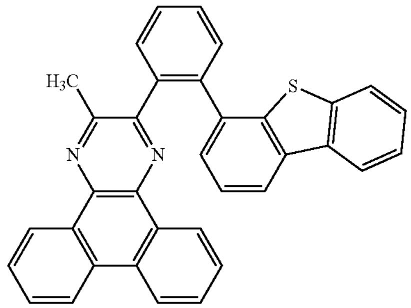
[Chemical Formula 19]
(151)
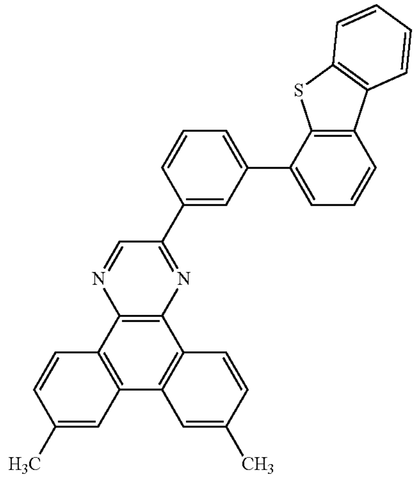
(152)
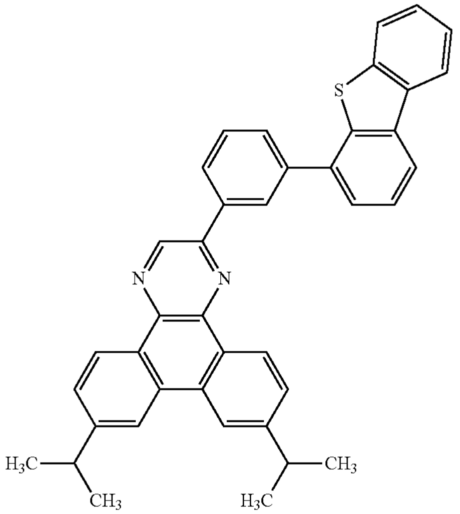

-continued
(153)
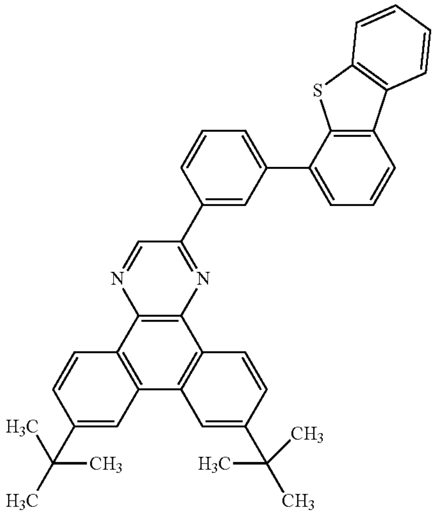
(154)
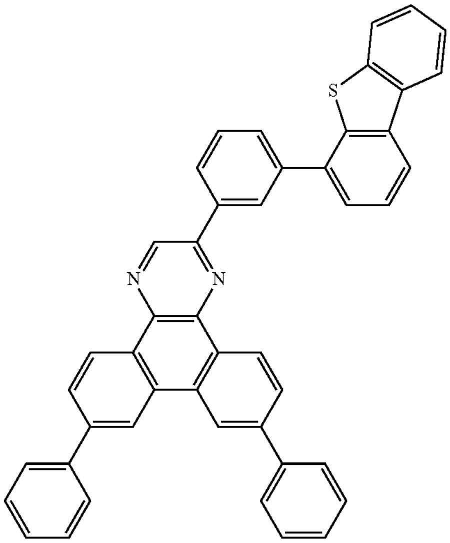
(155)
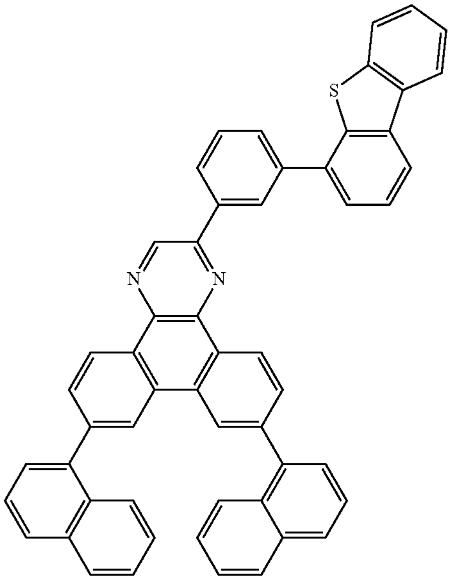
(156)
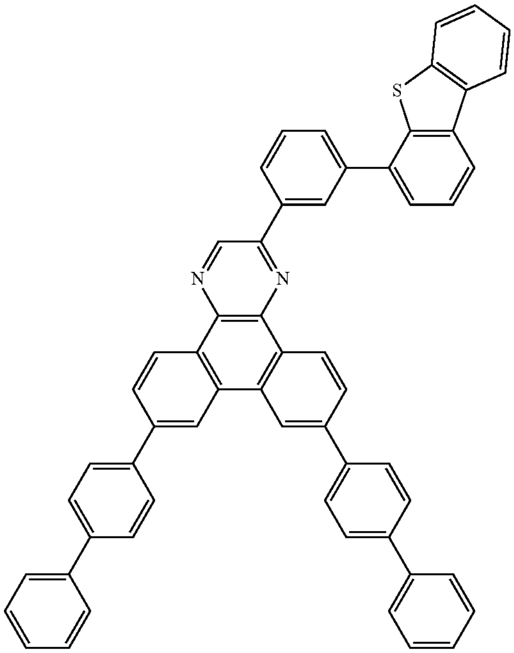

-continued
(157)
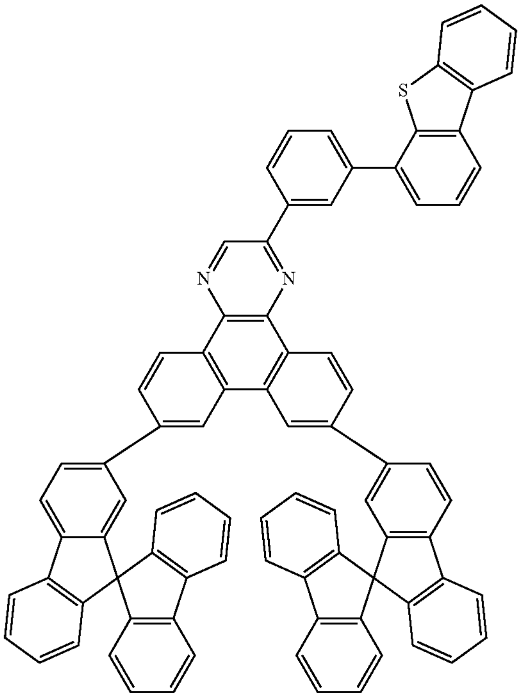
(158)
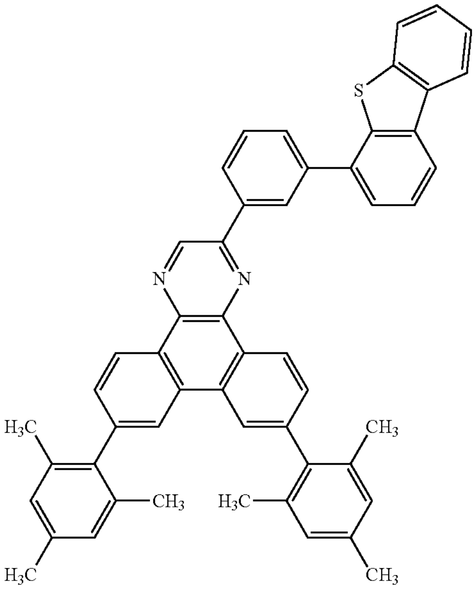
[Chemical Formula 20]
(159)
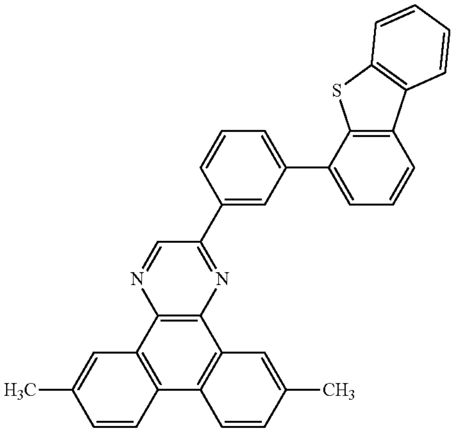
(160)
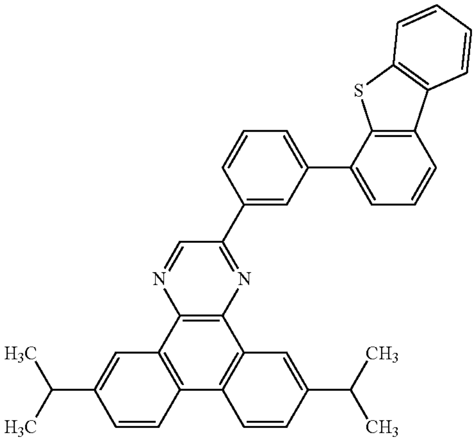
(161)
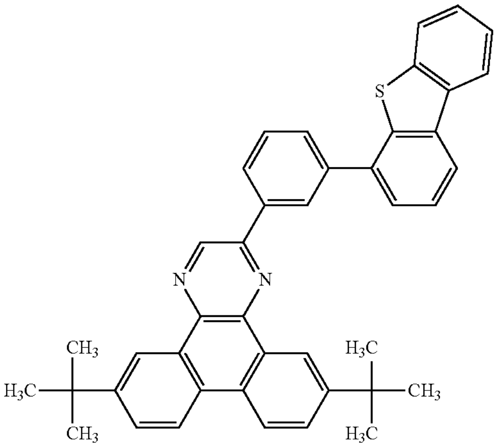
(162)
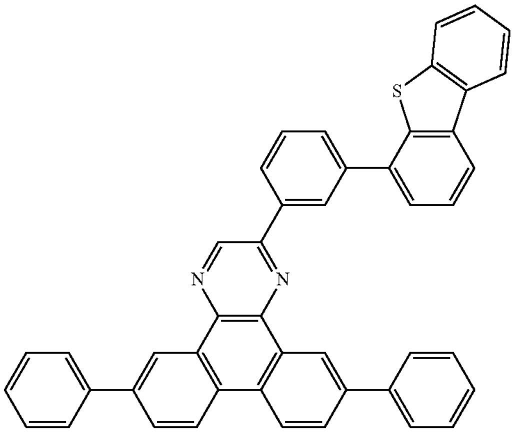

-continued
(163)
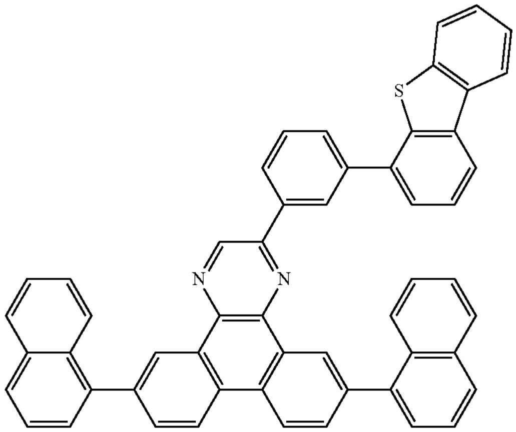
(164)
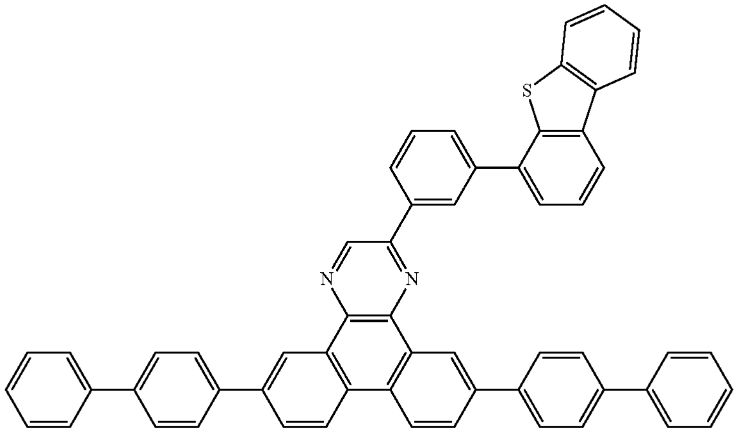
(165)
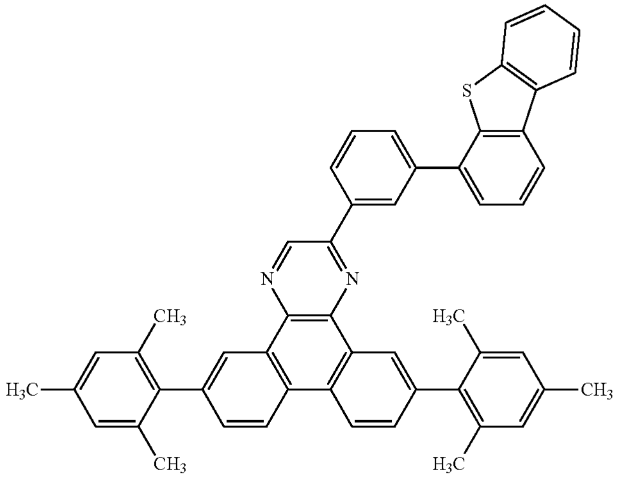

-continued
(166)
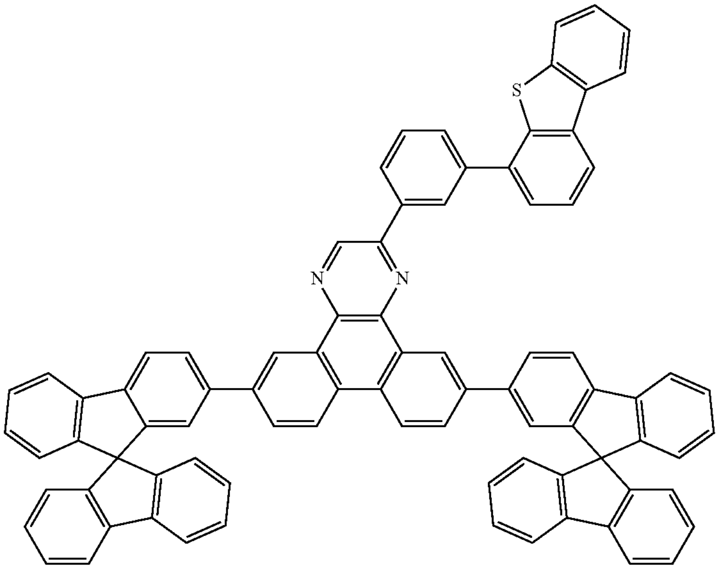
[Chemical Formula 21]
(167)
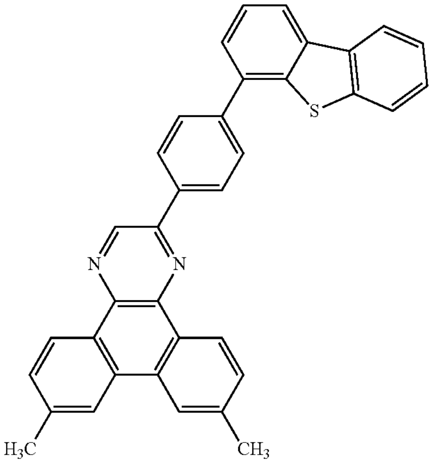
(168)
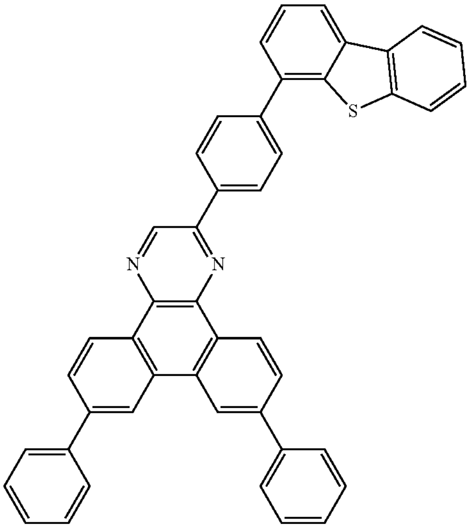
(169)
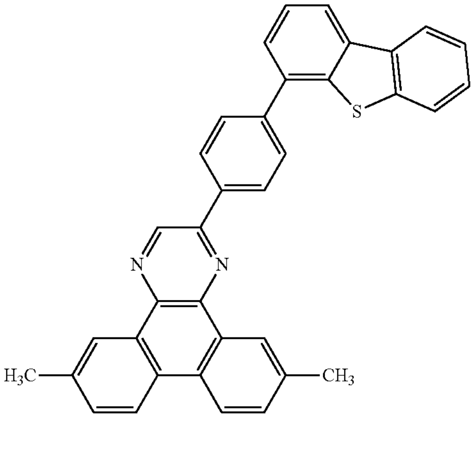
(170)
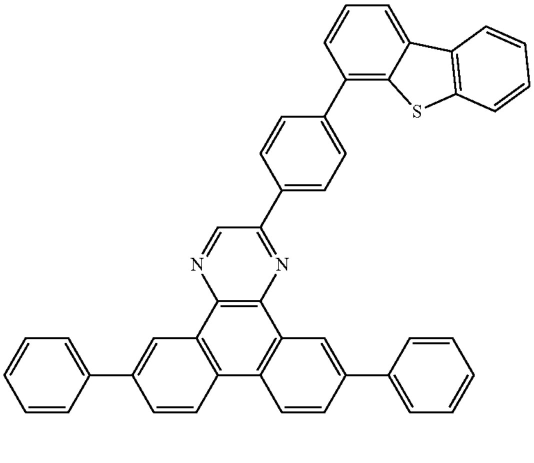

-continued
(171)
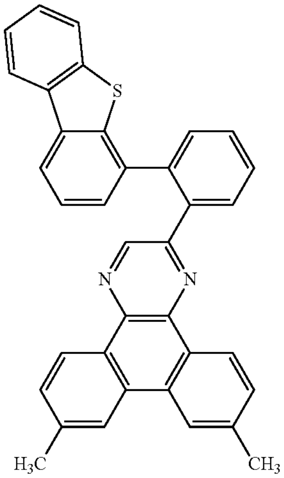
(172)
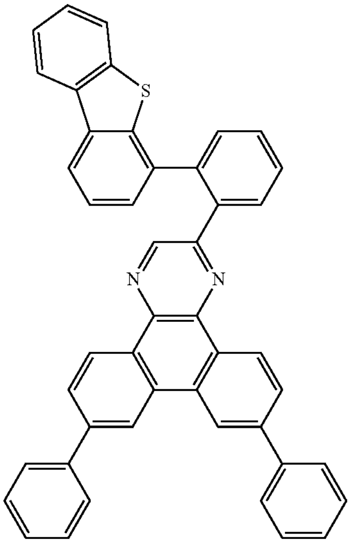
(173)
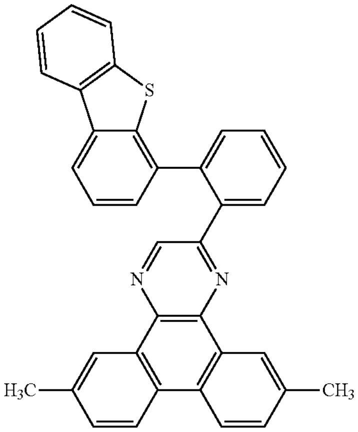
(174)
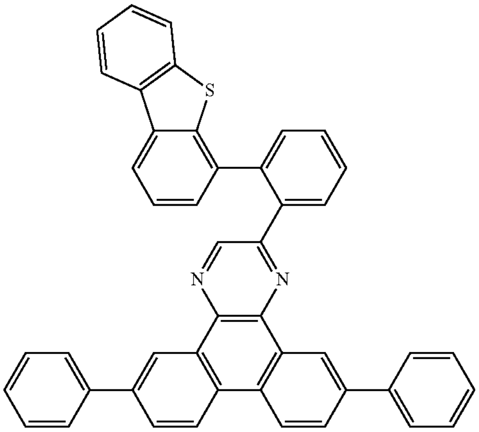
[Chemical Formula 22]
(200)
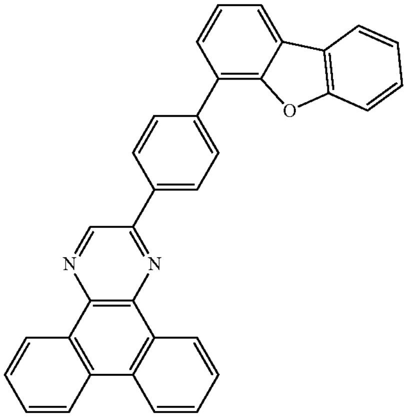
(201)
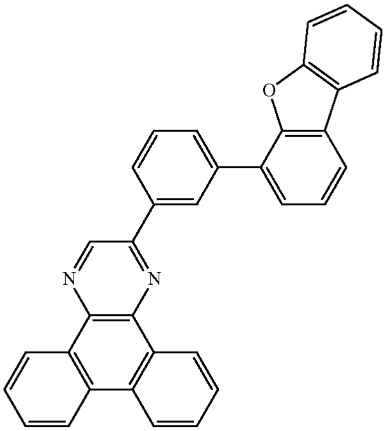

-continued
(202)
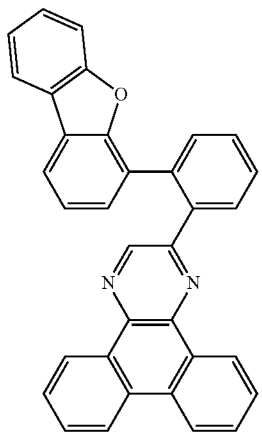
(203)
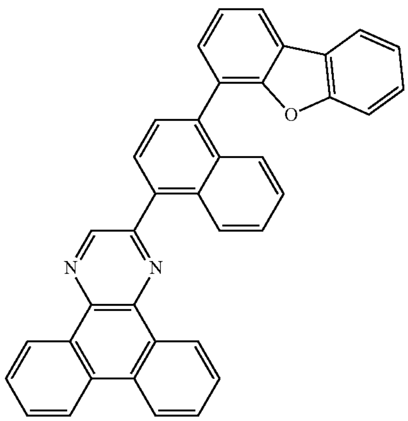
(204)
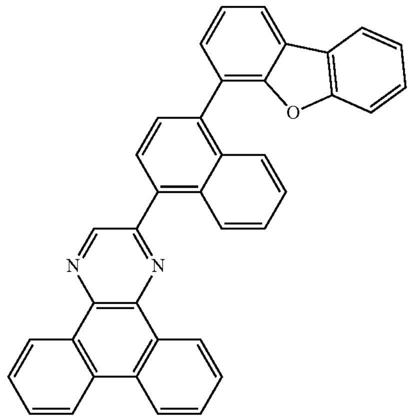
(205)
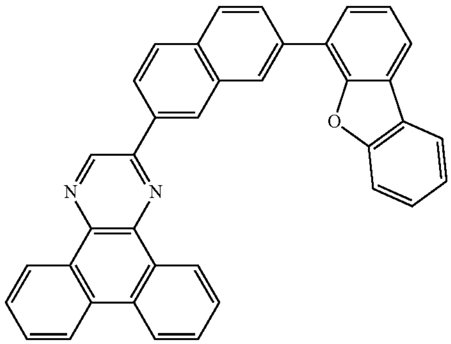
(206)
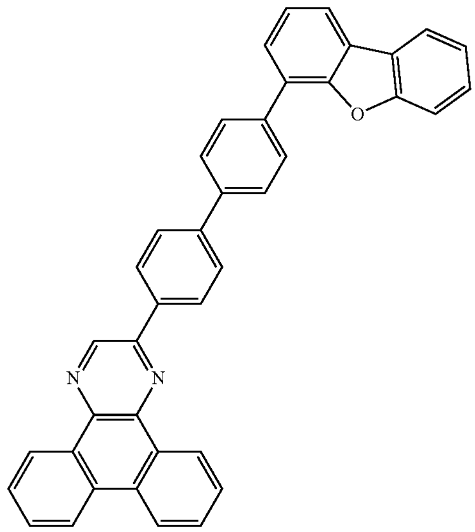
(207)
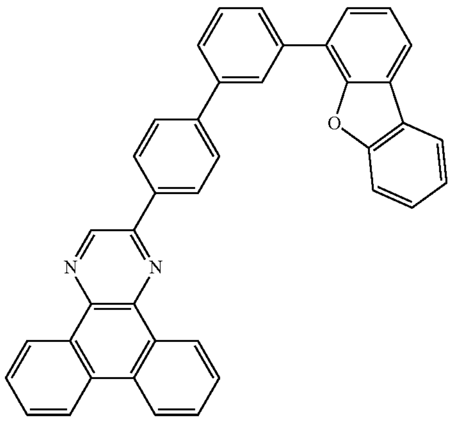

-continued
(208)
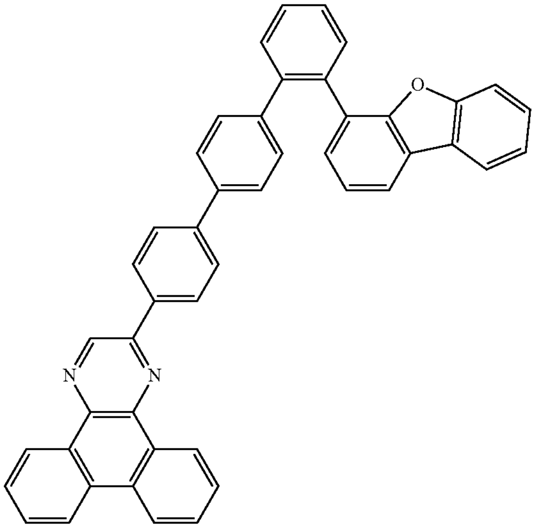
[Chemical Formula 23]
(209)
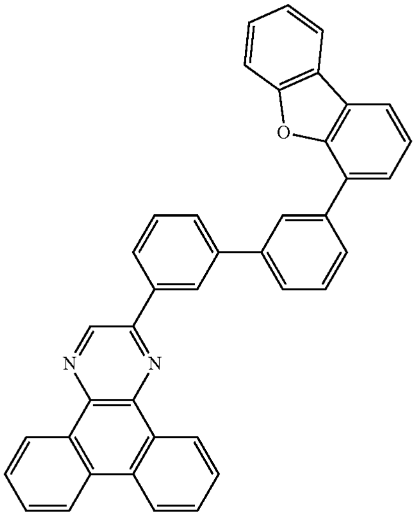
(210)
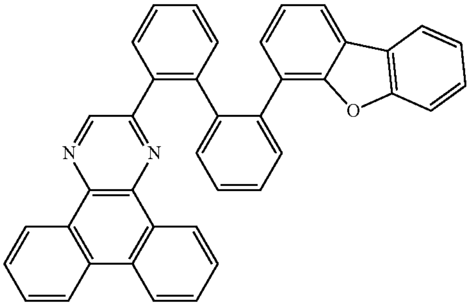
(211)
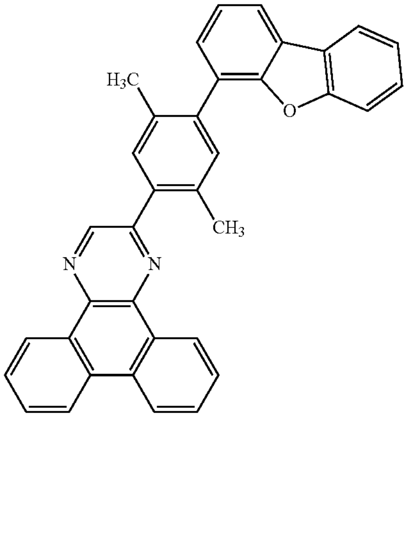
(212)
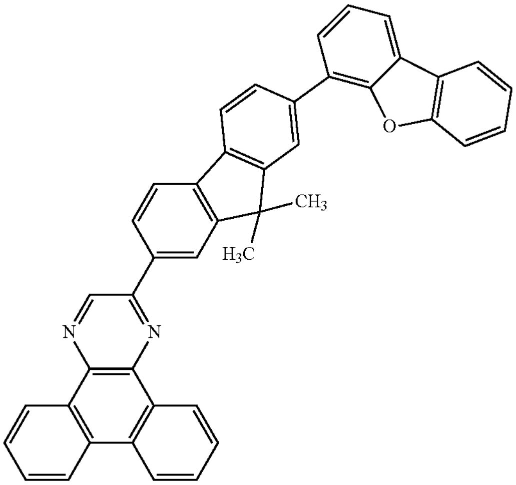

-continued
(213)
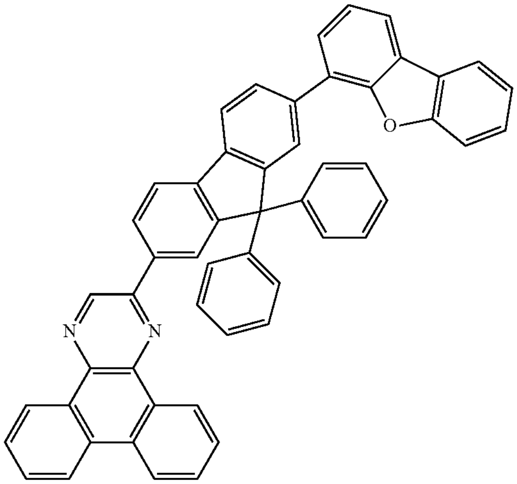
(214)
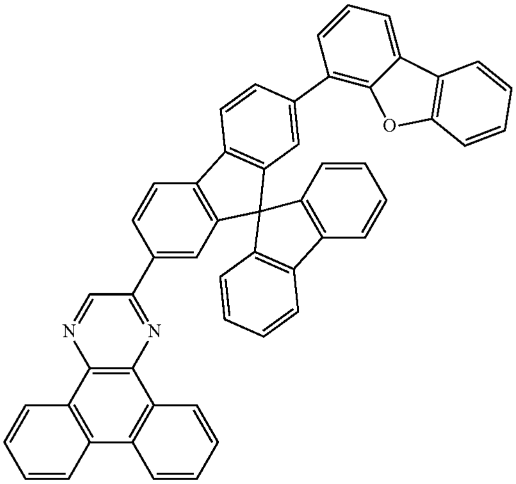
Chemical Formula 24]
(215)
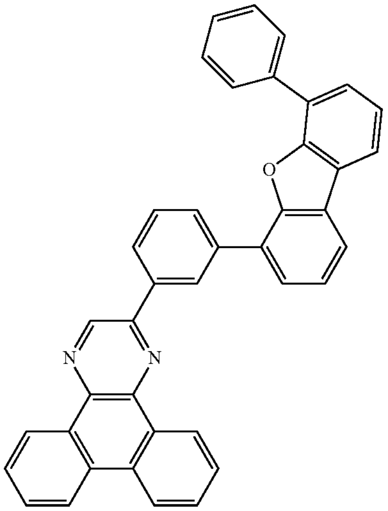
(216)
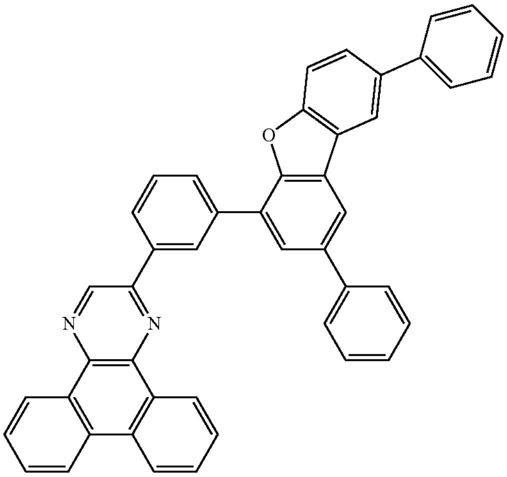
(217)
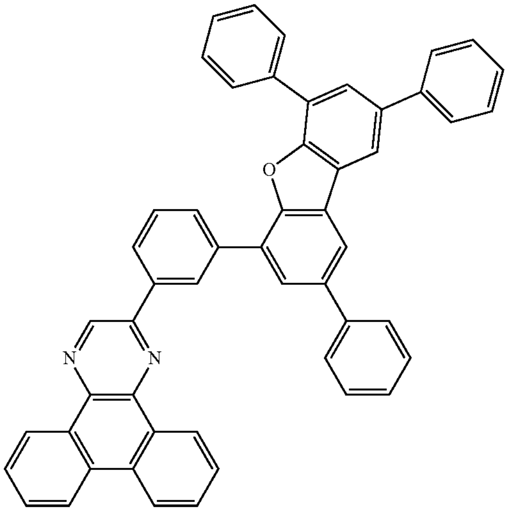
(218)
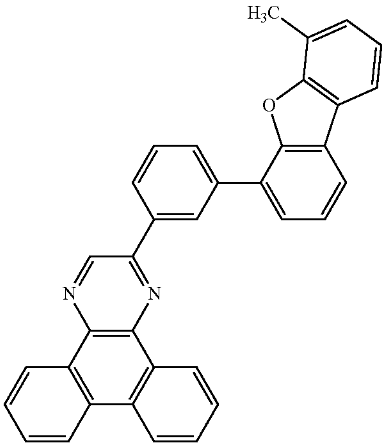

-continued
(219)
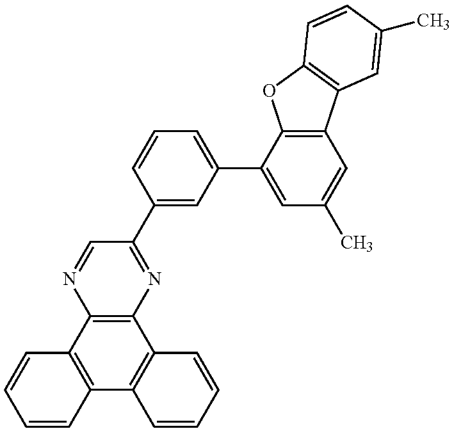
(220)
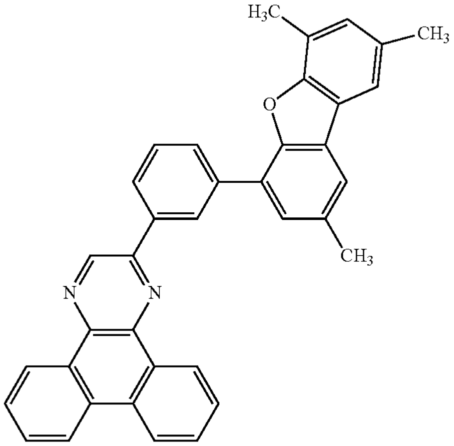
(221)
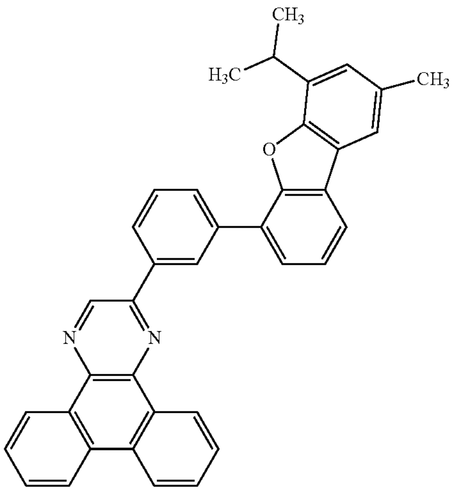
(222)
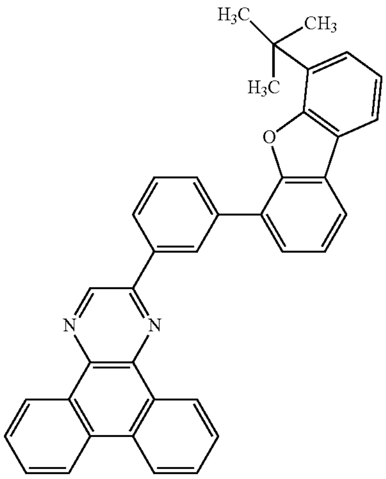
(223)
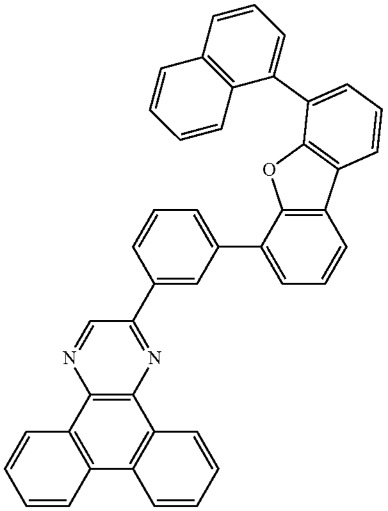

-continued
[Chemical Formula 25]
(224)
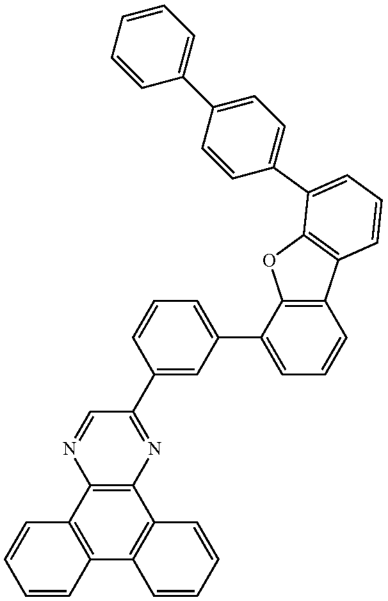
(225)
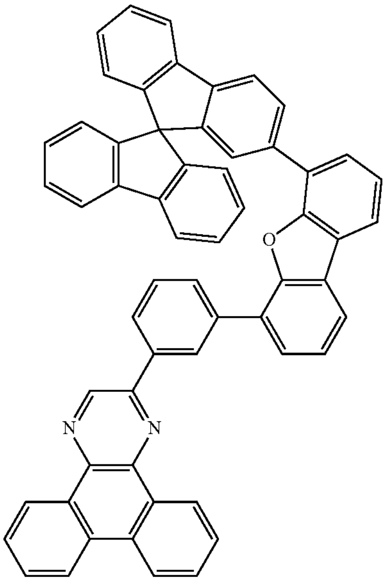
(226)
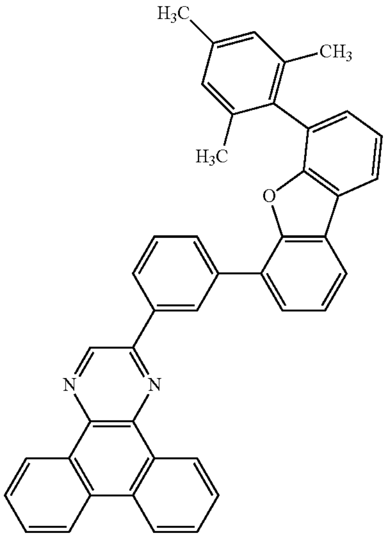
(227)
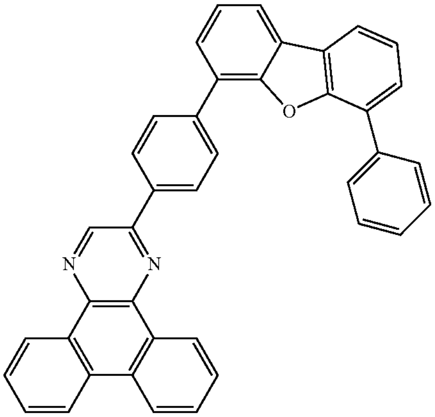

-continued
(228)
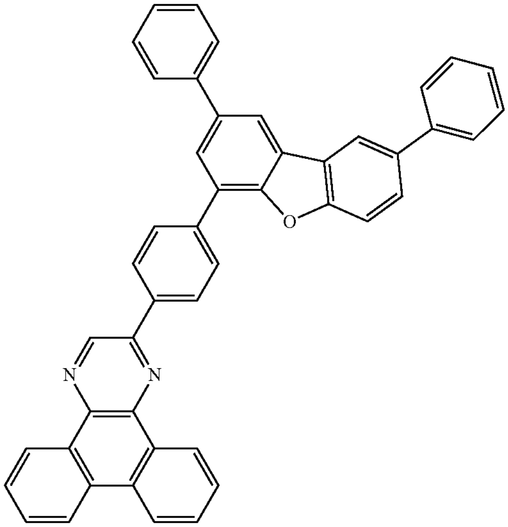
(229)
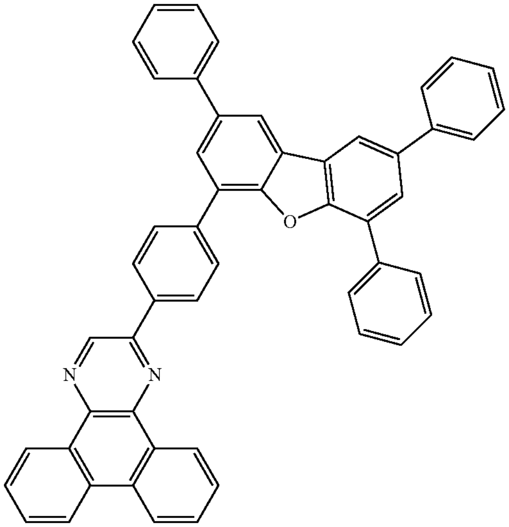
(230)
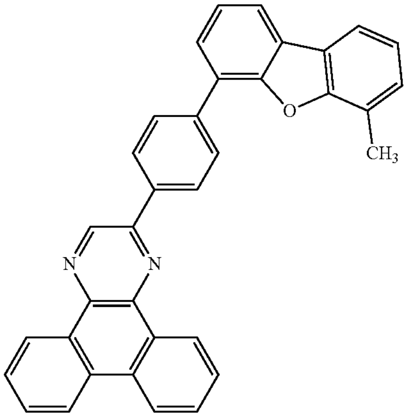
(231)
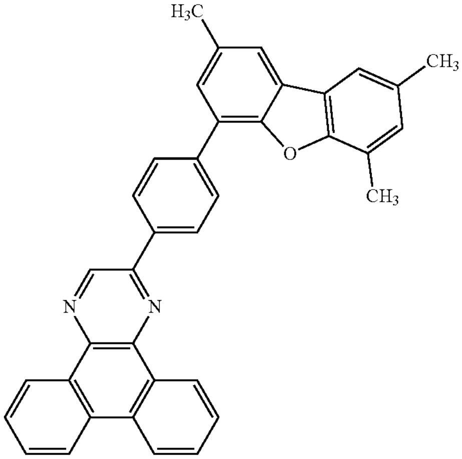
(232)
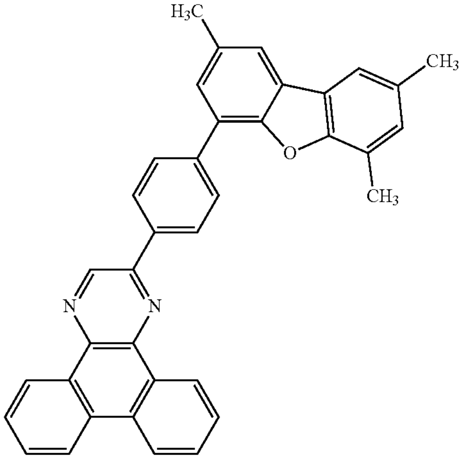

-continued
[Chemical Formula 26]
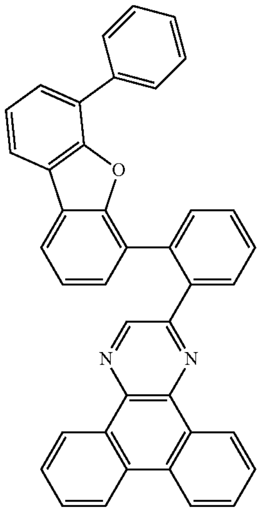
(233)
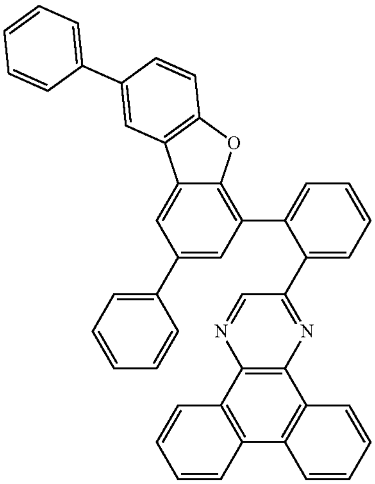
(234)
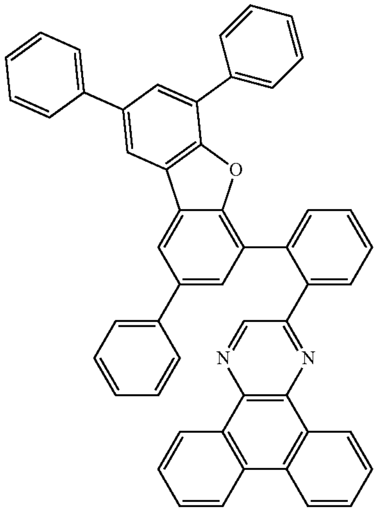
(235)
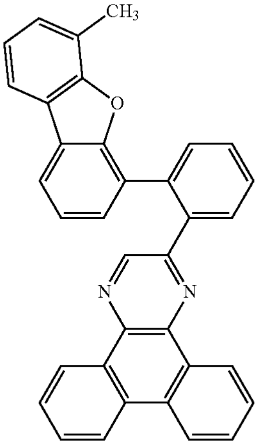
(236)
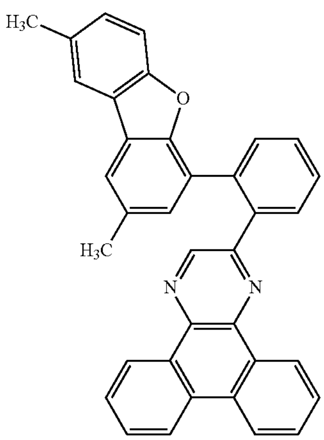
(237)
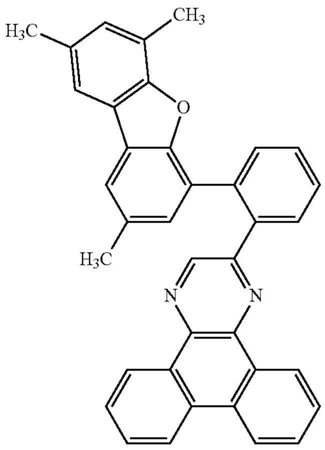
(238)

-continued
(239)
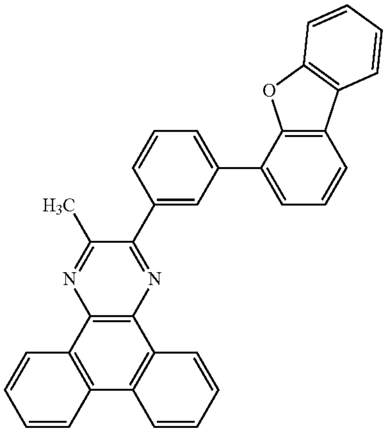
(240)
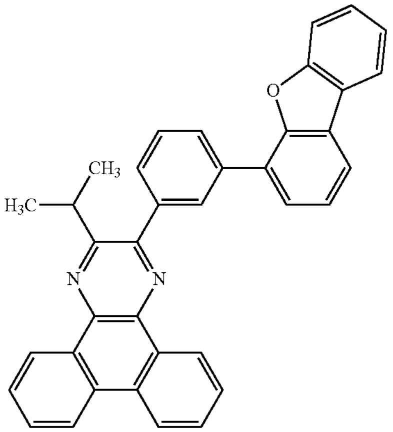
(241)
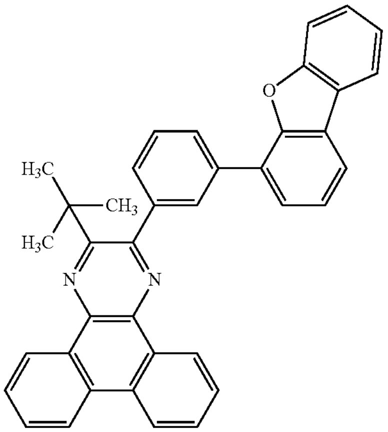
[Chemical Formula 27]
(242)
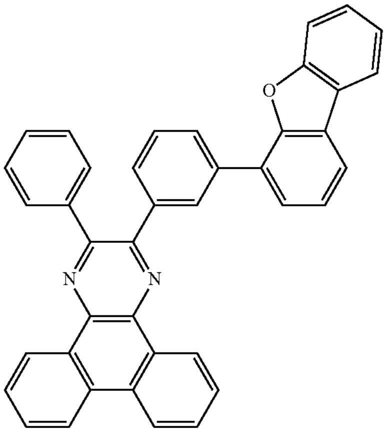
(243)
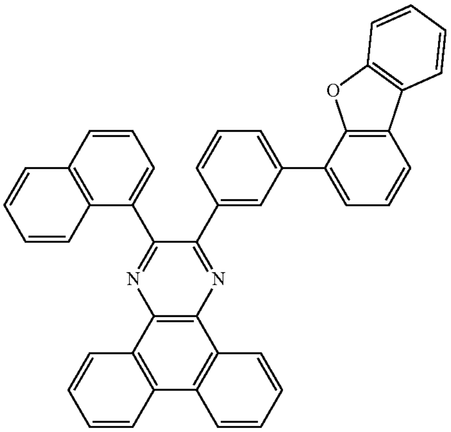

-continued
(244)
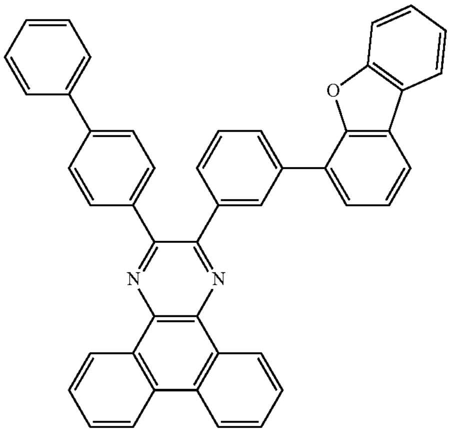
(245)
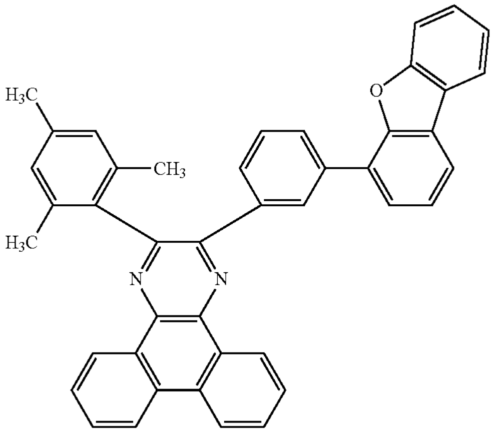
(246)
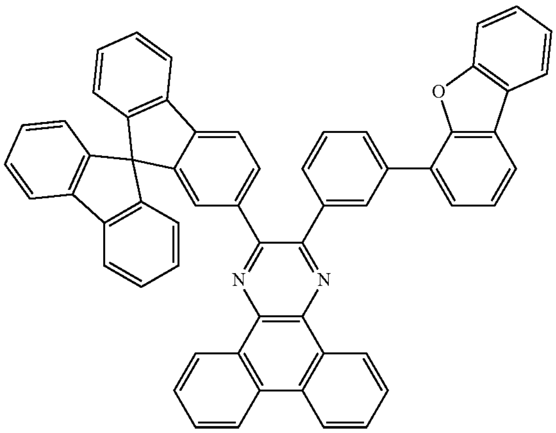
(247)
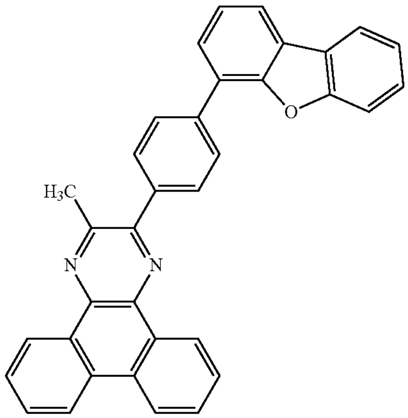
(248)
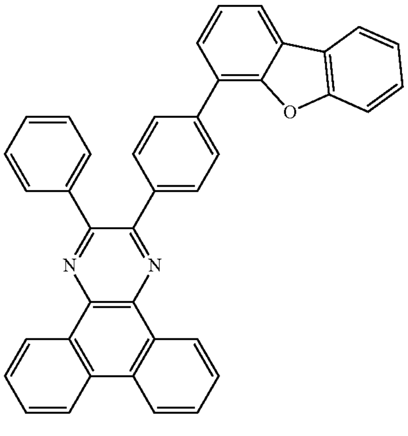
(249)
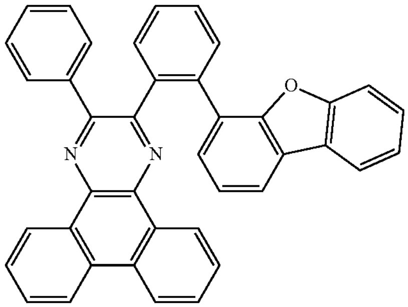
(250)
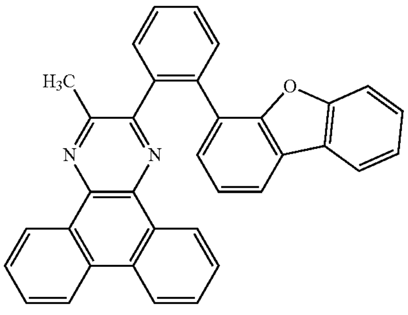

-continued
[Chemical Formula 28]
(251)
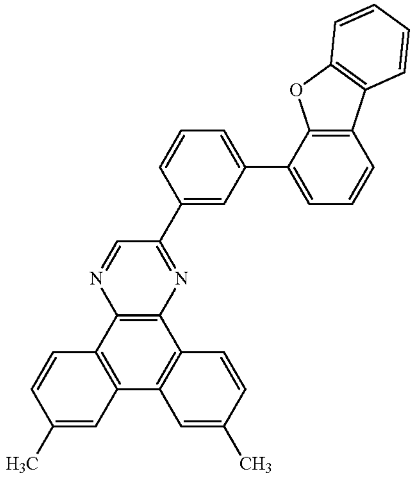
(252)
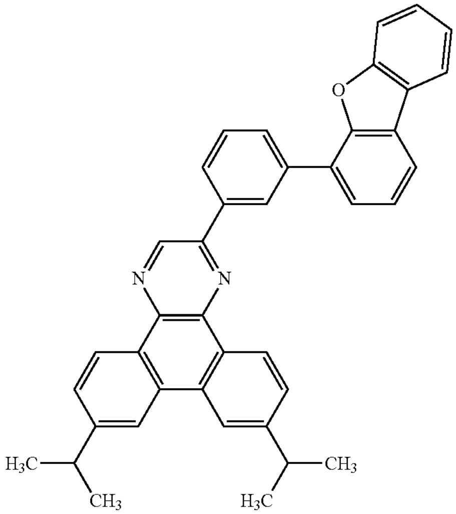
(253)
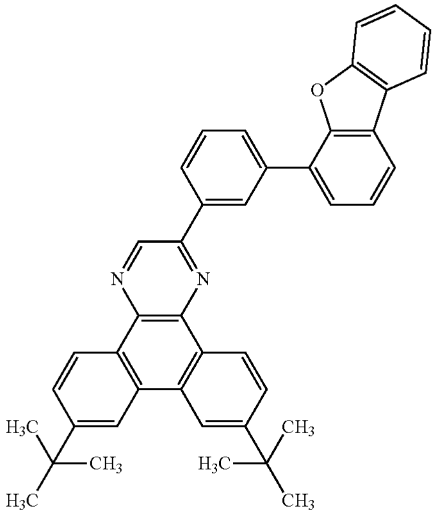
(254)
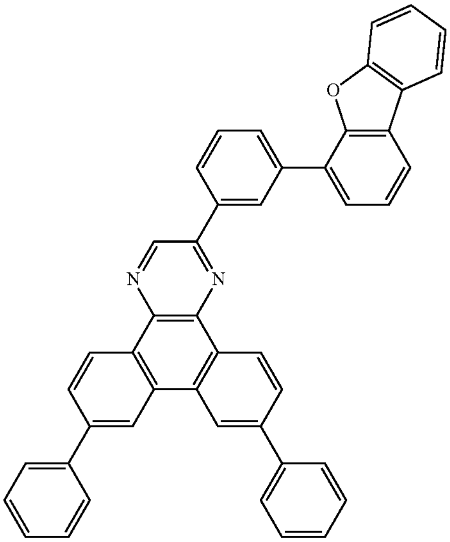

-continued
(255)
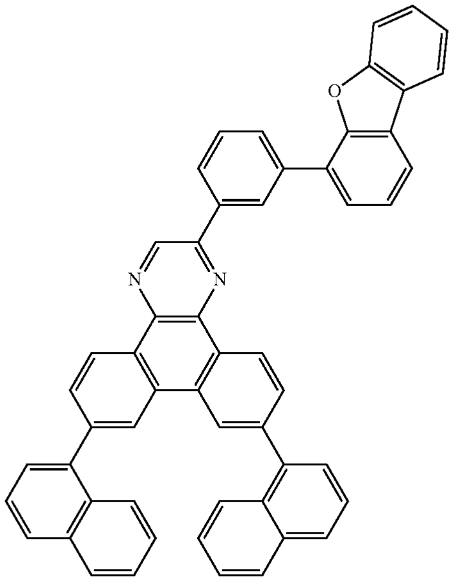
(256)
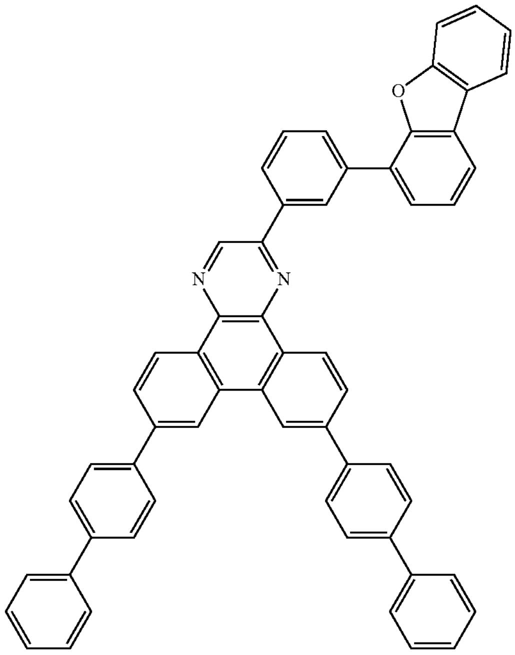
(257)
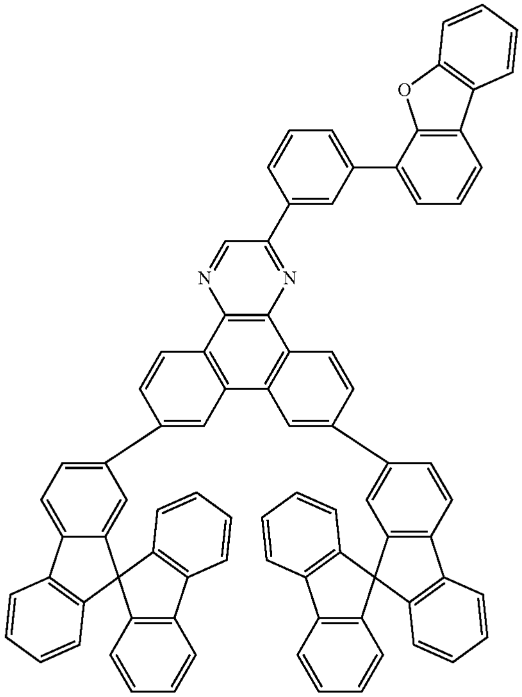
(258)
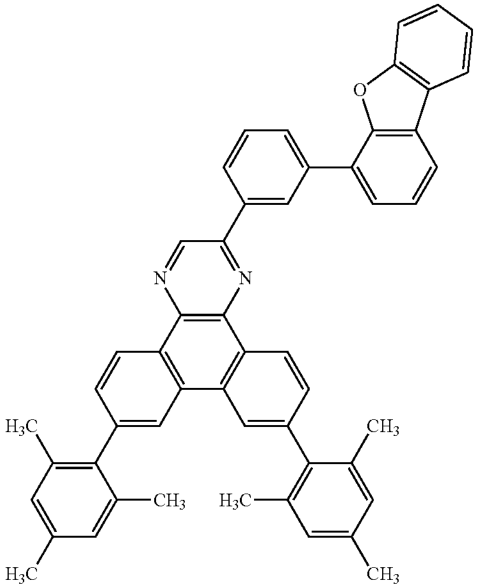

-continued
[Chemical Formula 29]
(259)
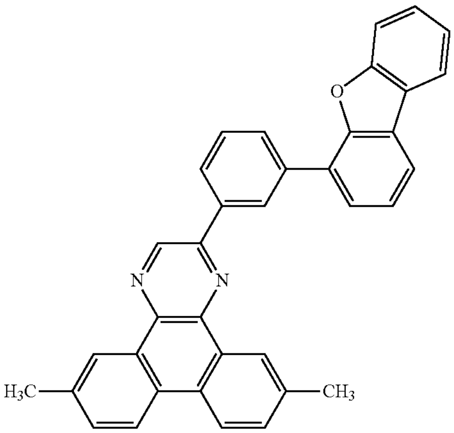
(260)
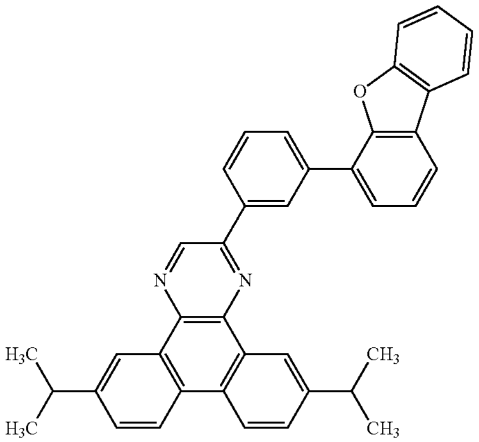
(261)
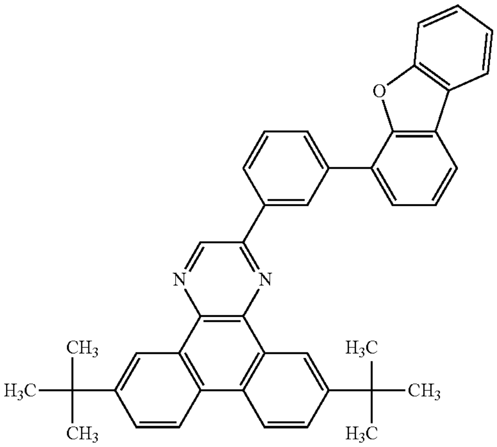
(262)
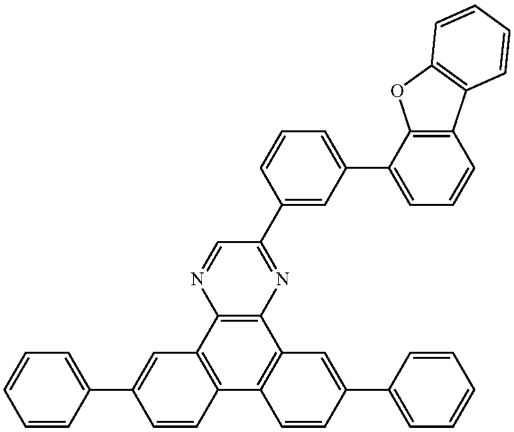
(263)
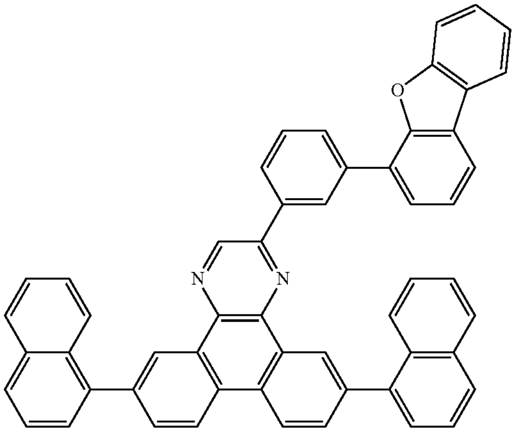

-continued
(264)
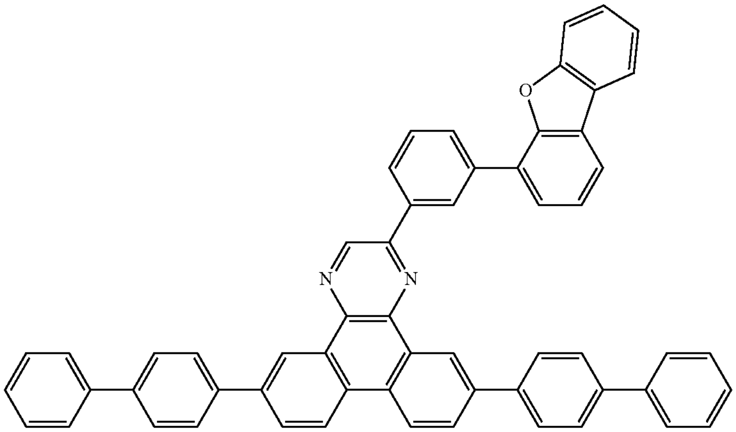
(265)
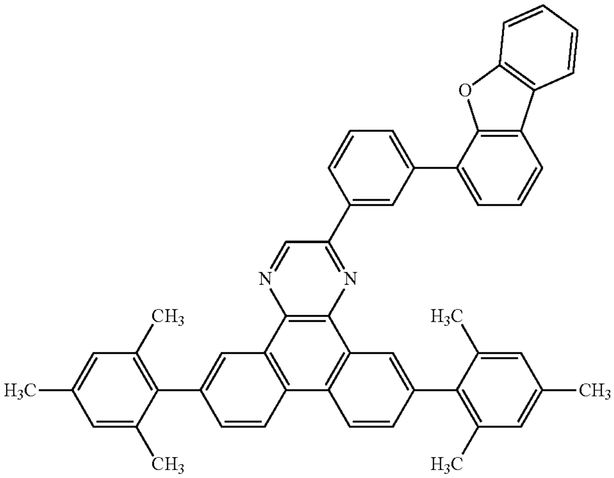
(266)
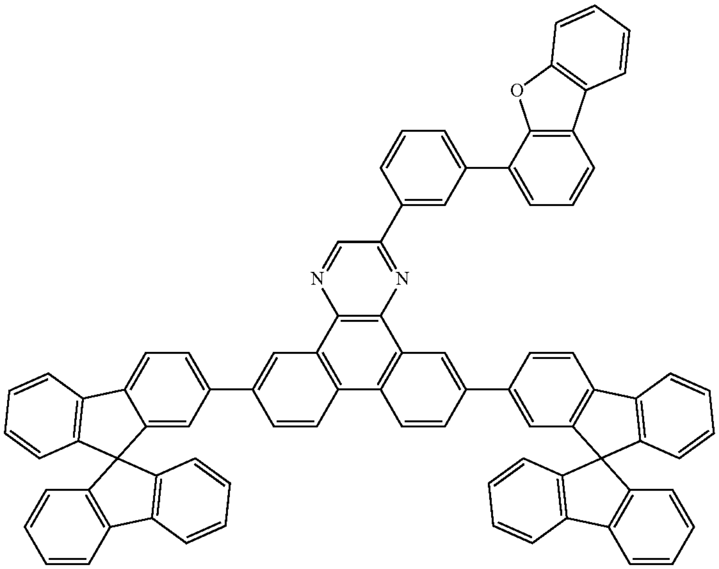

-continued
[Chemical Formula 30]
(267)
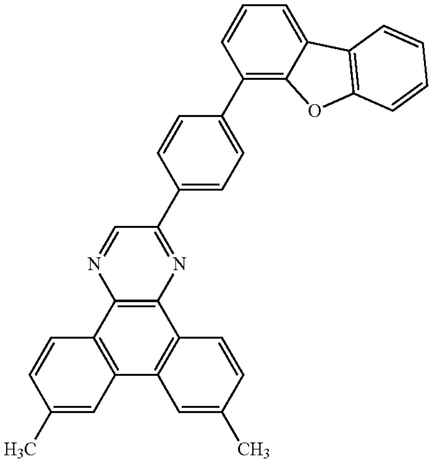
(268)
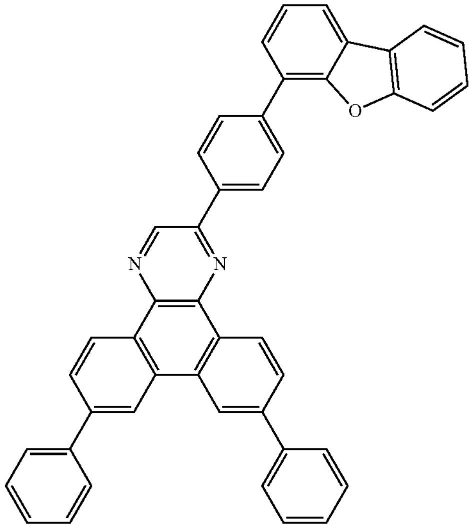
(269)
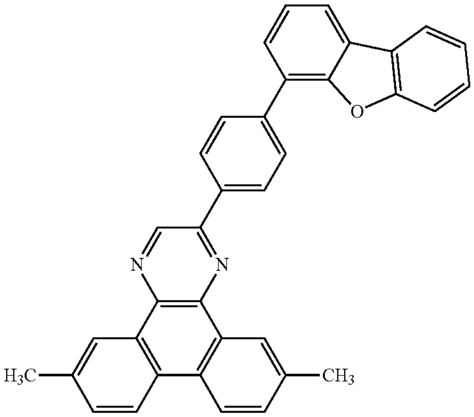
(270)
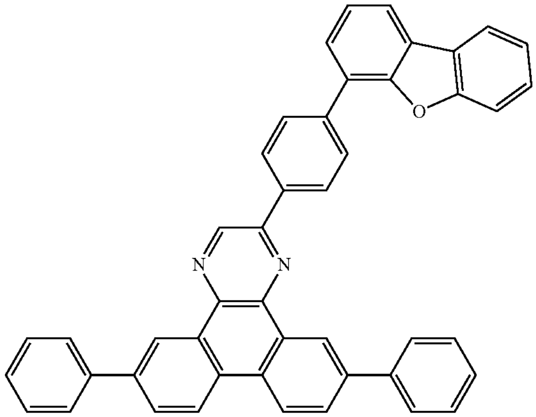
(271)
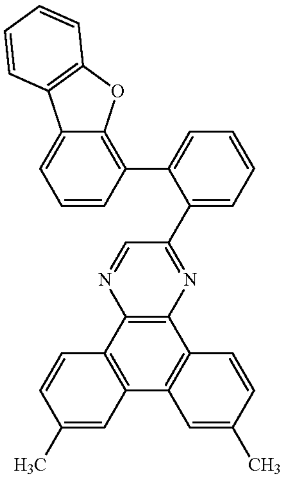
(272)
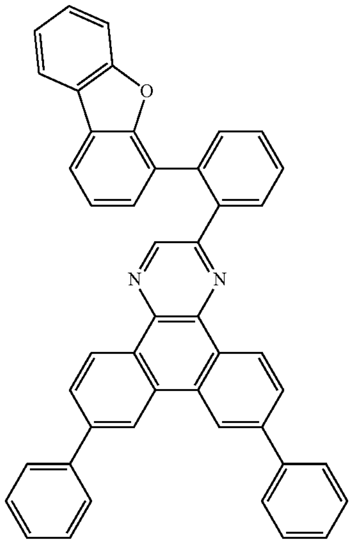

-continued
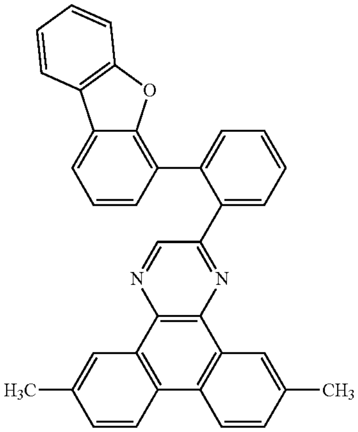
(273)
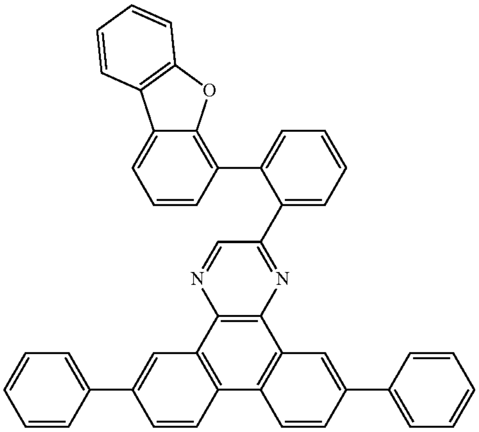
(274)
[Chemical Formula 31]
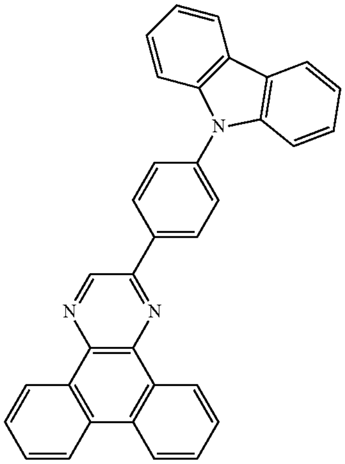
(300)
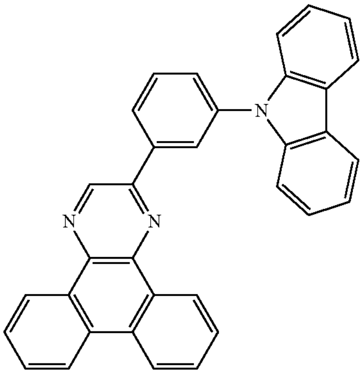
(301)
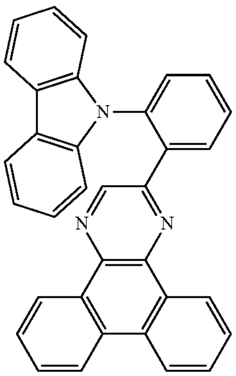
(302)
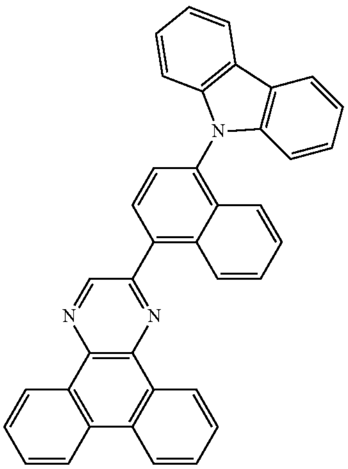
(303)

-continued
(304)
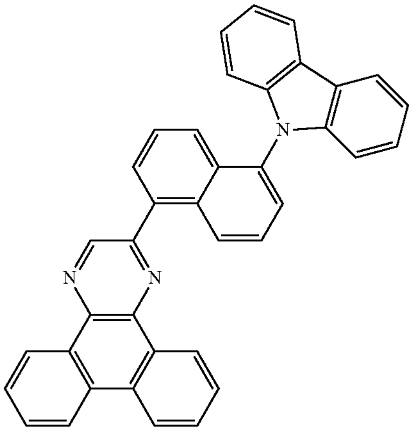
(305)
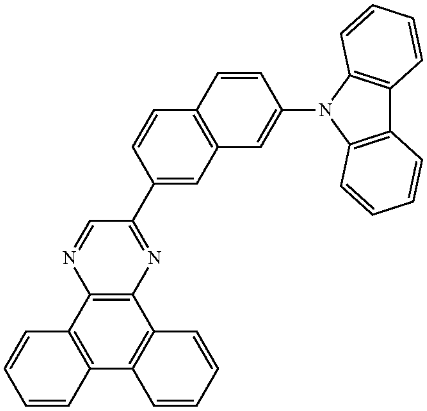
(306)
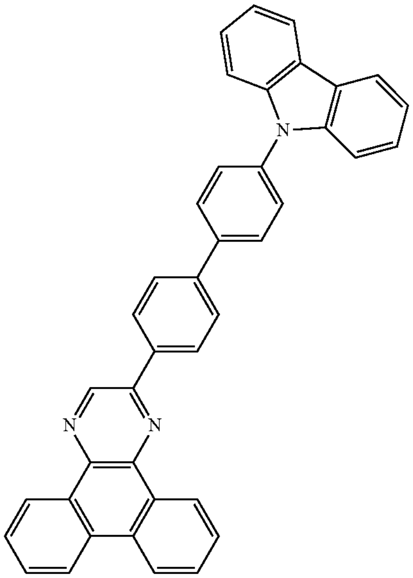
(307)
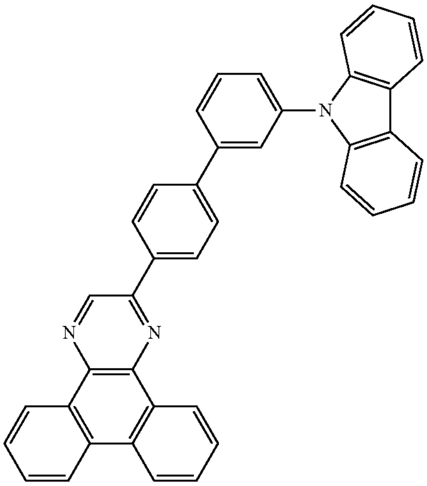
(308)
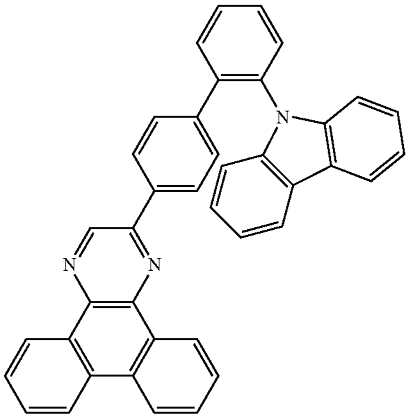

-continued
[Chemical Formula 32]
(309)
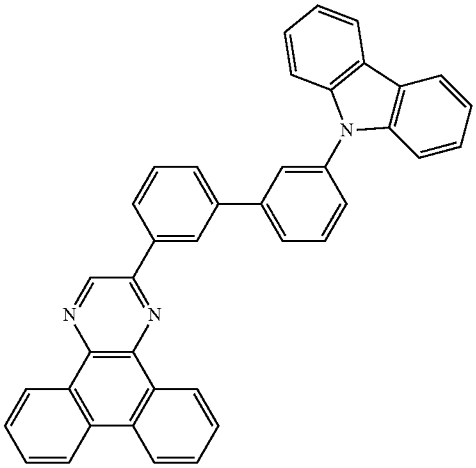
(310)
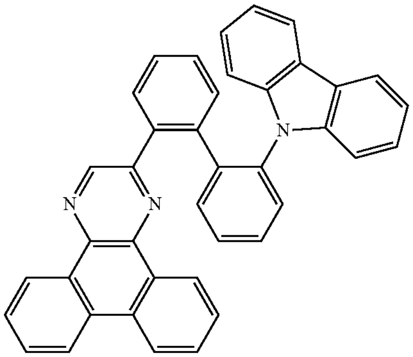
(311)
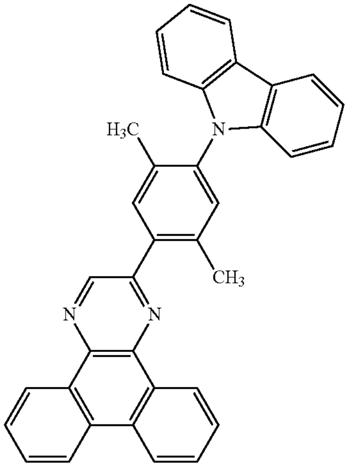
(312)
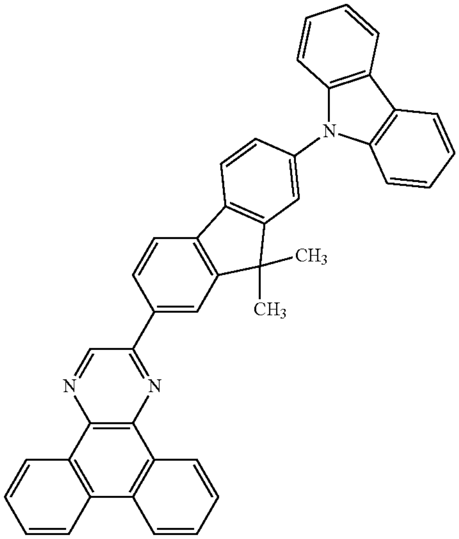
(313)
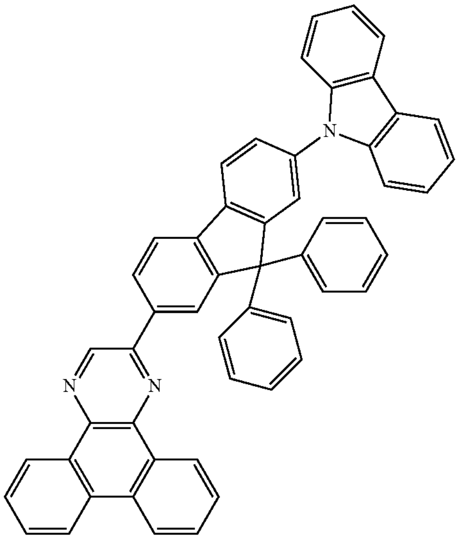
(314)
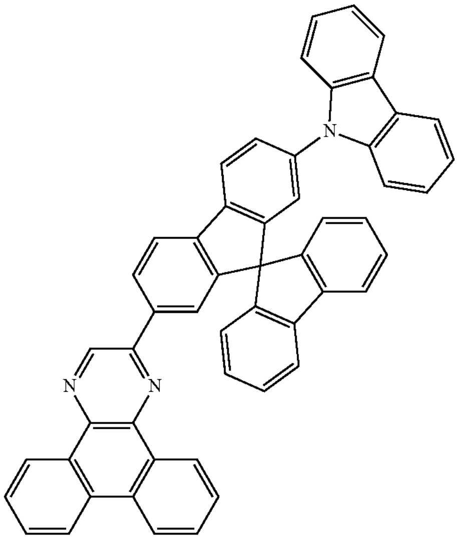

-continued
[Chemical Formula 33]
(315)
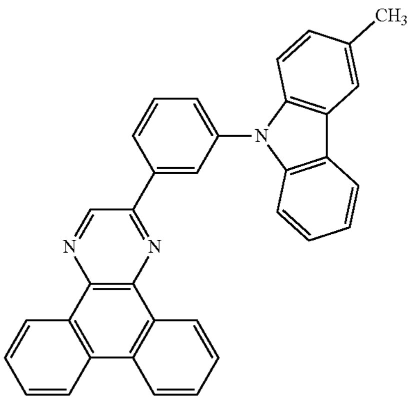
(316)
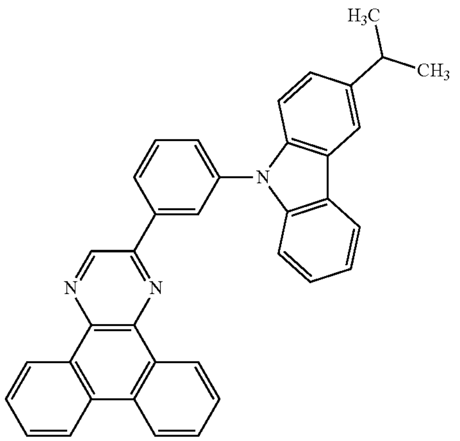
(317)
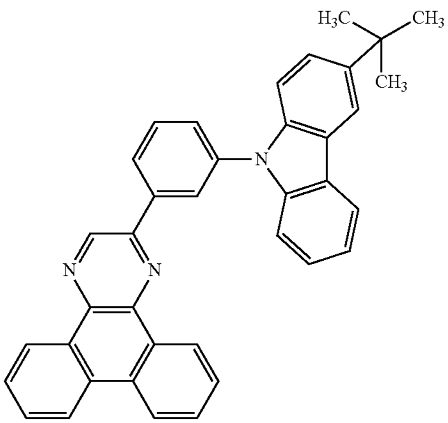
(318)
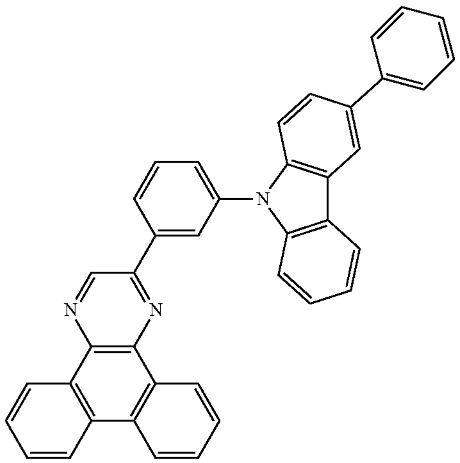
(319)
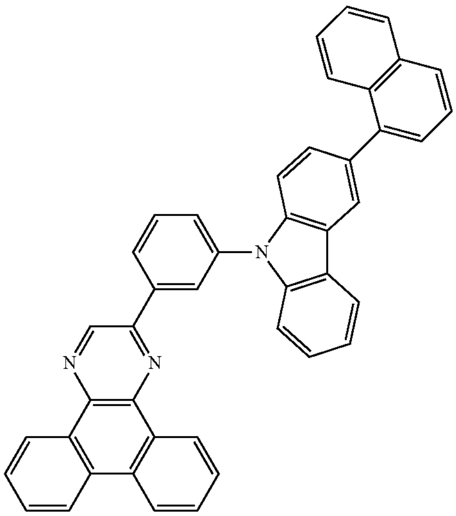
(320)
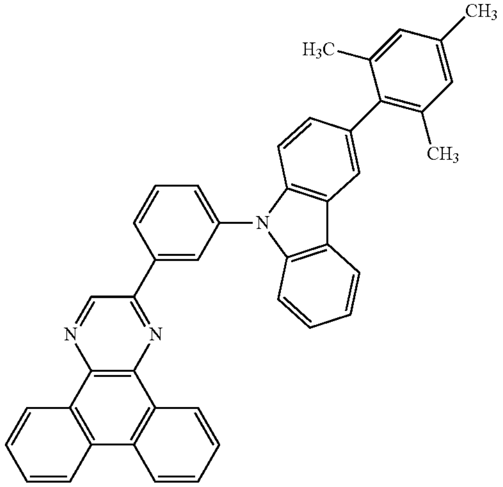

-continued
(321)
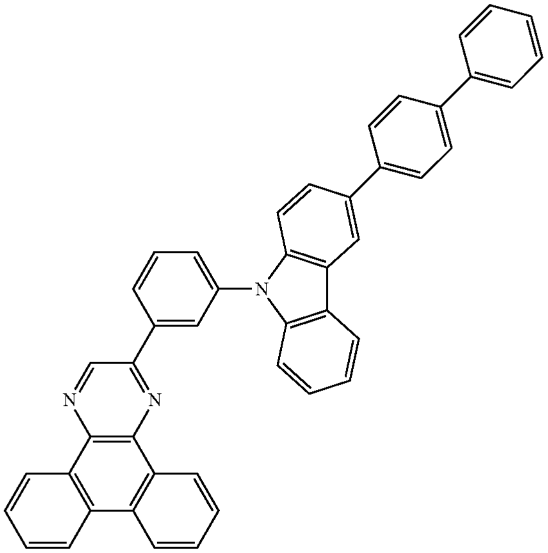
(322)
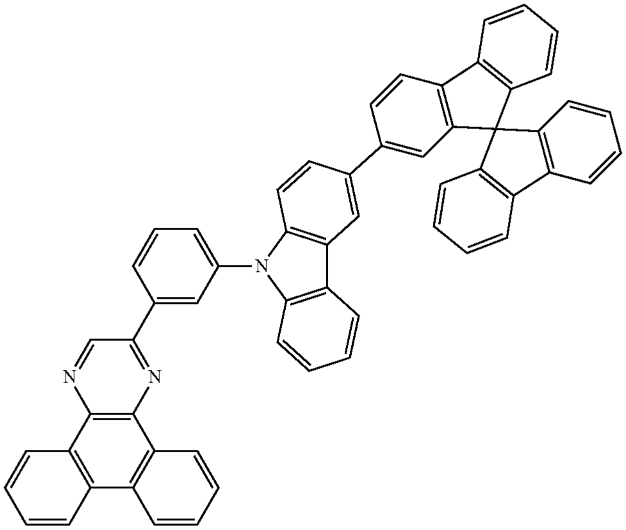
[Chemical Formula 34]
(323)
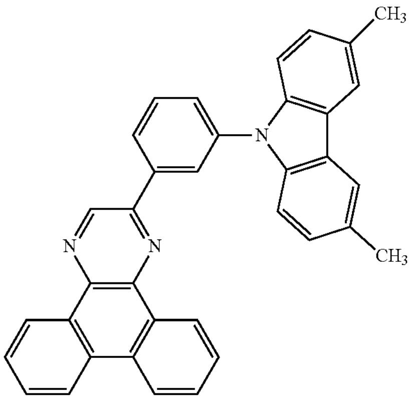
(324)
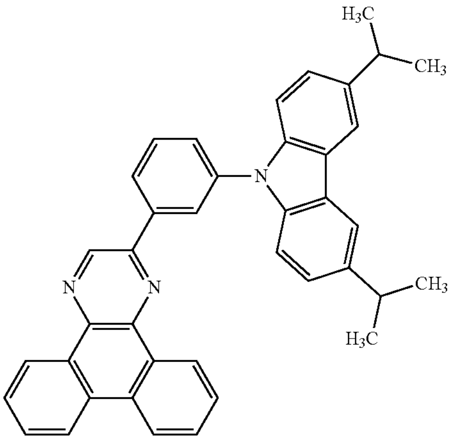

-continued
(325)
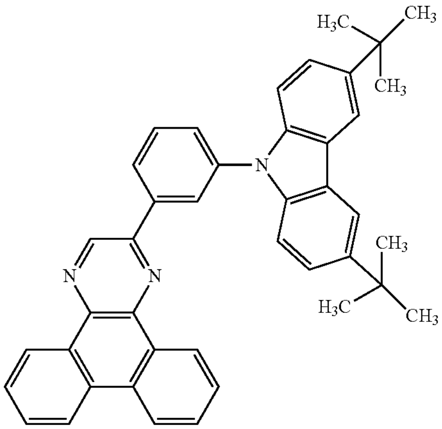
(326)
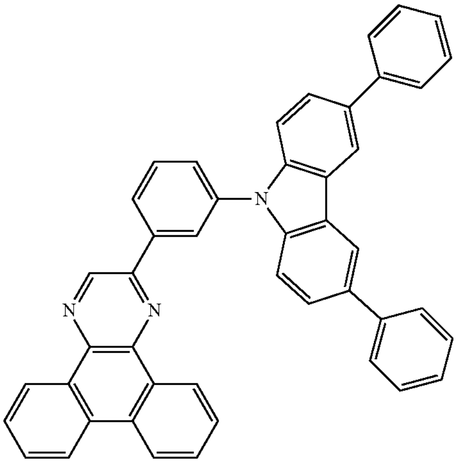
(327)
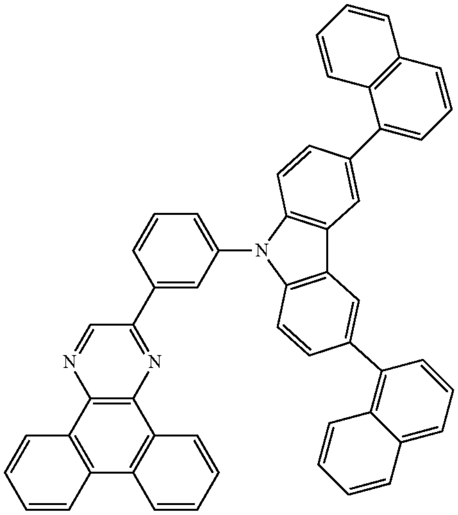
(328)
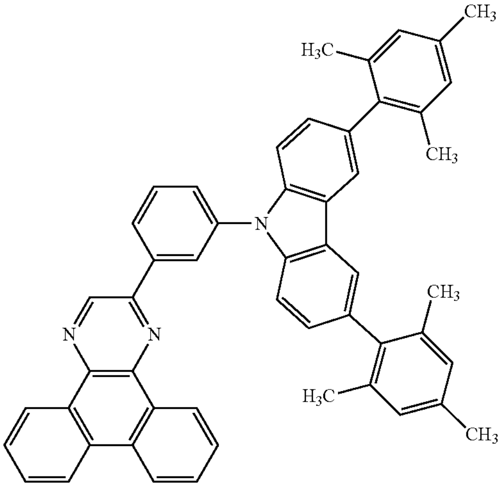
(329)
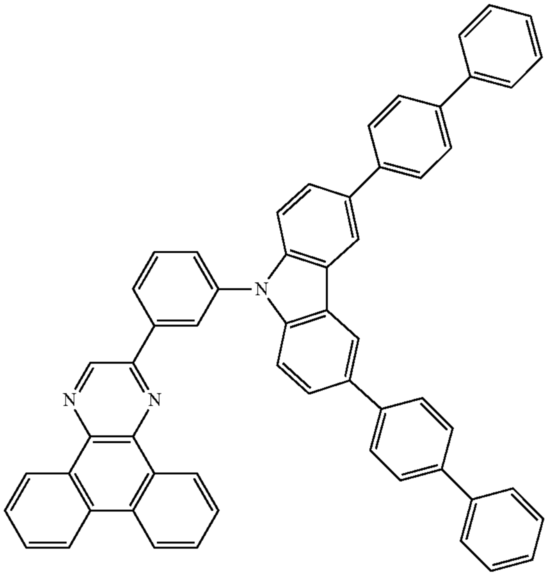

-continued
(330)
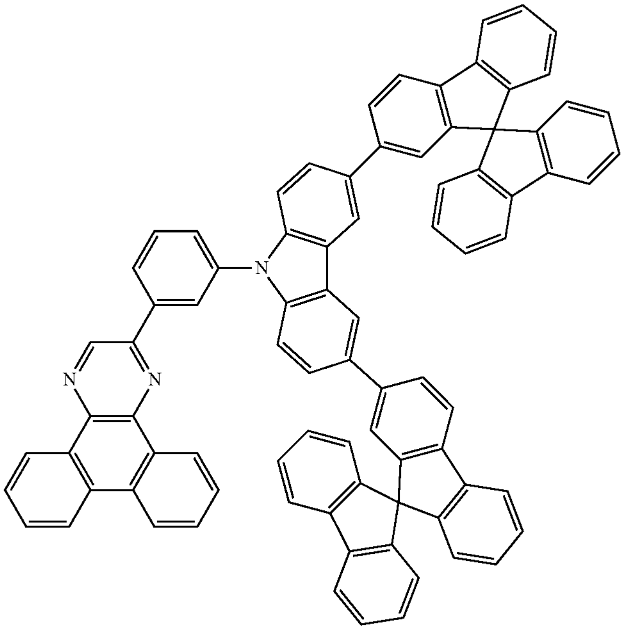
[Chemical Formula 35]
(331)
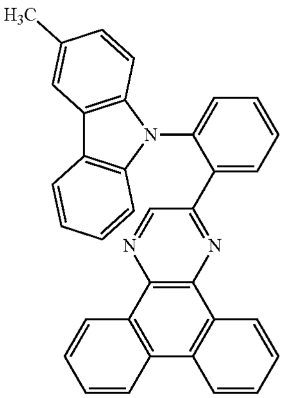
(332)
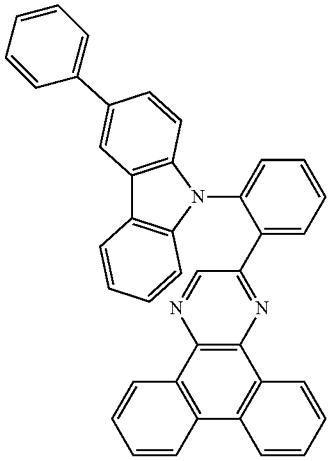
(333)
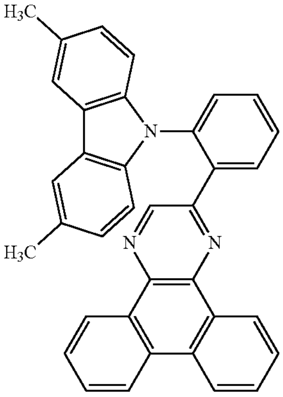
(334)
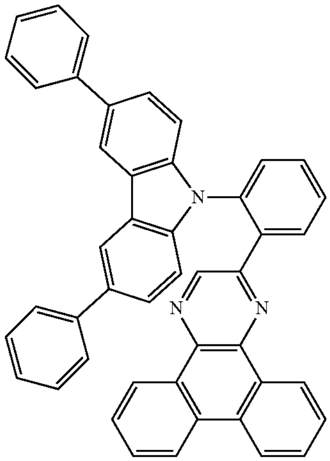

-continued
(335)
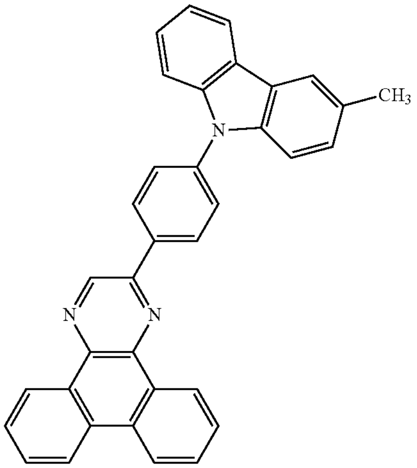
(336)
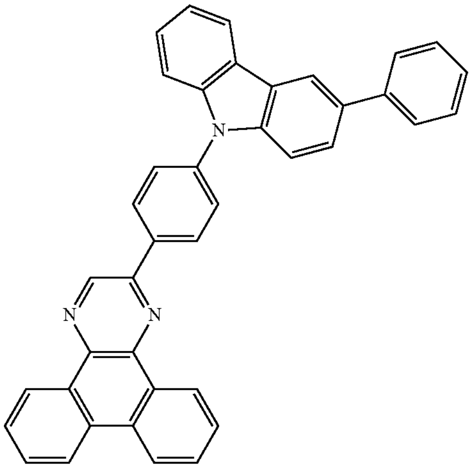
(337)
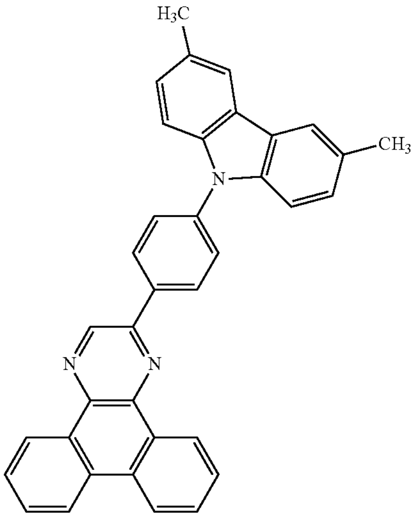
(338)
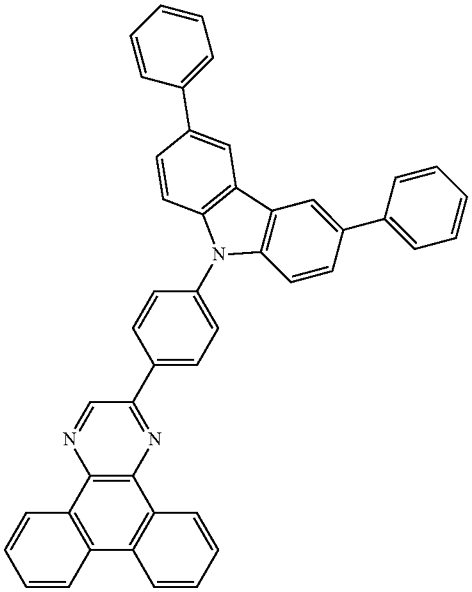
[Chemical Formula 36]
(339)
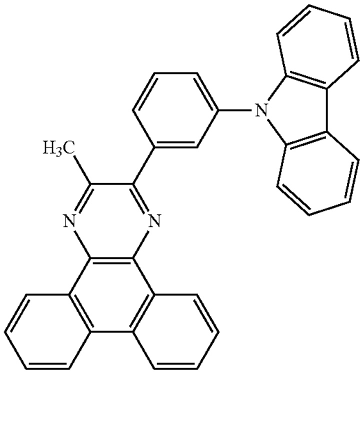
(340)
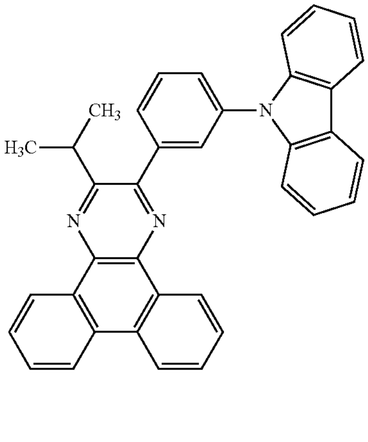

-continued
(341)
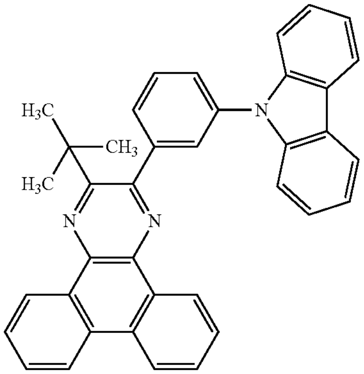
(342)
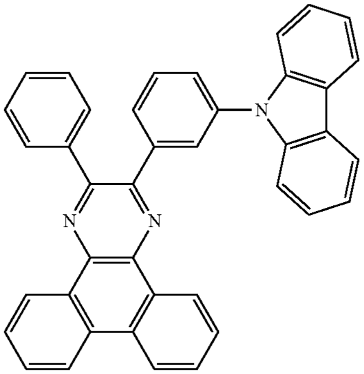
(343)
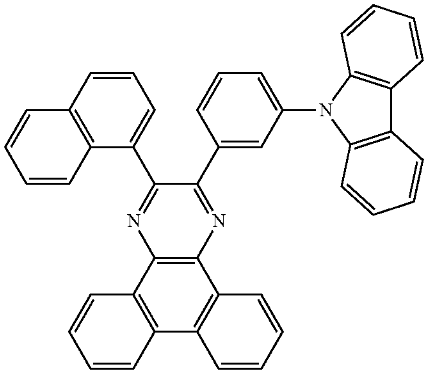
(344)
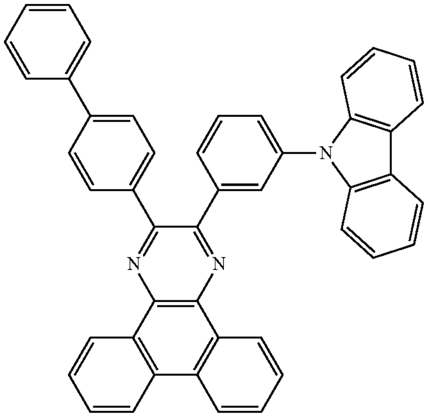
(345)
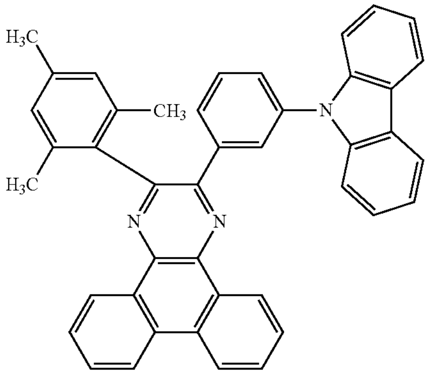
(346)
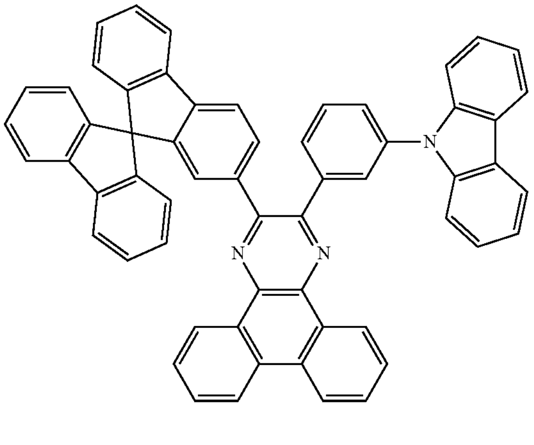

-continued
(347)
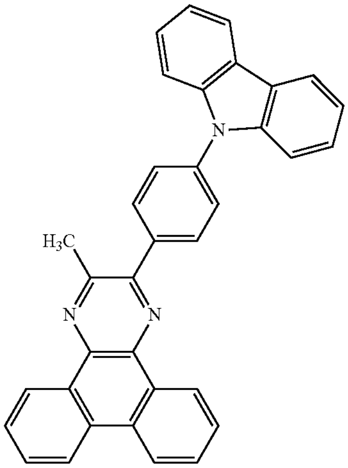
(348)
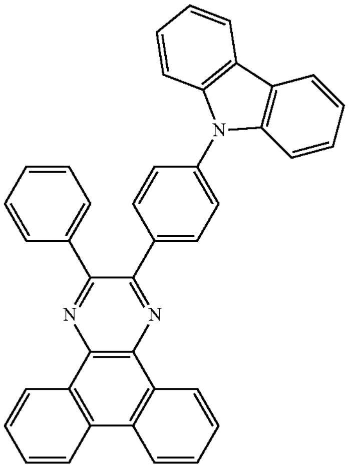
(349)
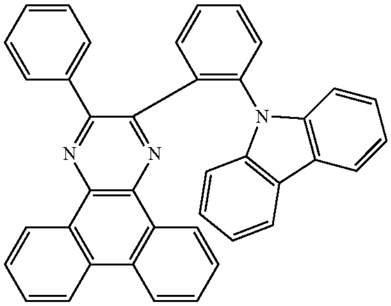
(350)
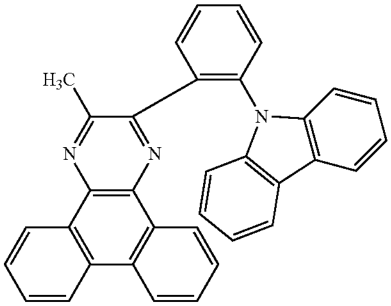
(351)
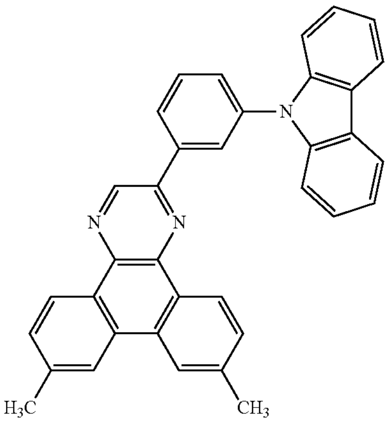
(352)
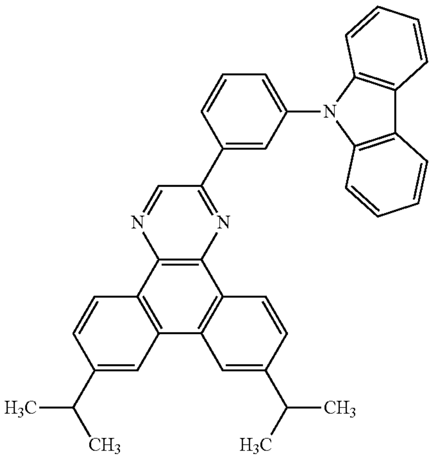

-continued
(353)
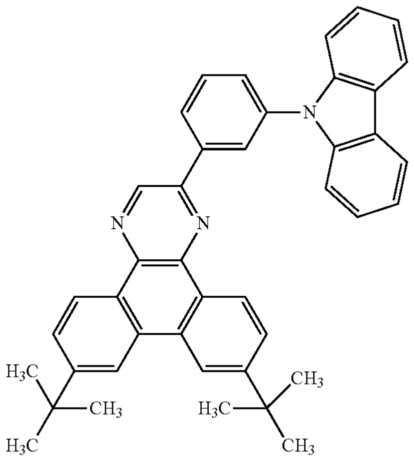
(354)
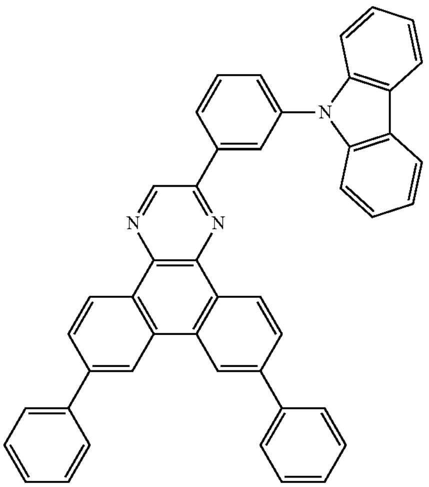
(355)
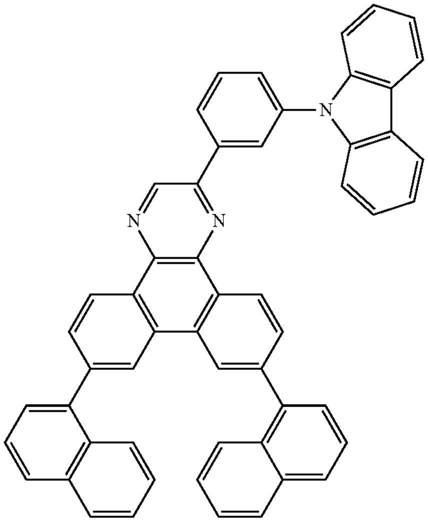
(356)
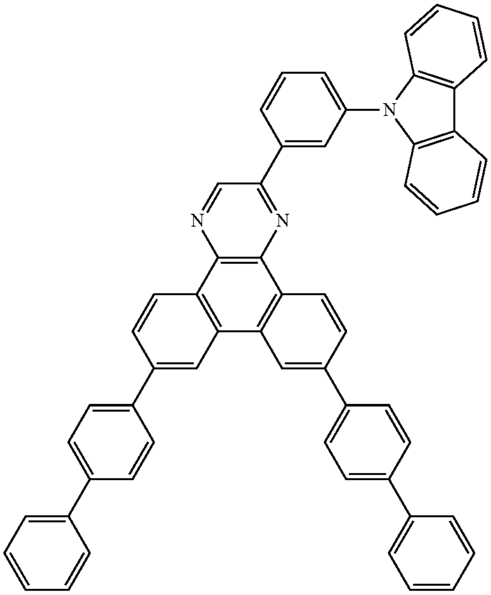

-continued
(357)
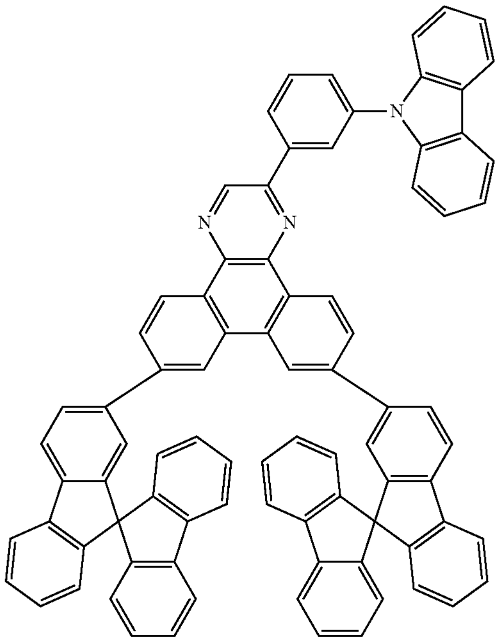
(358)
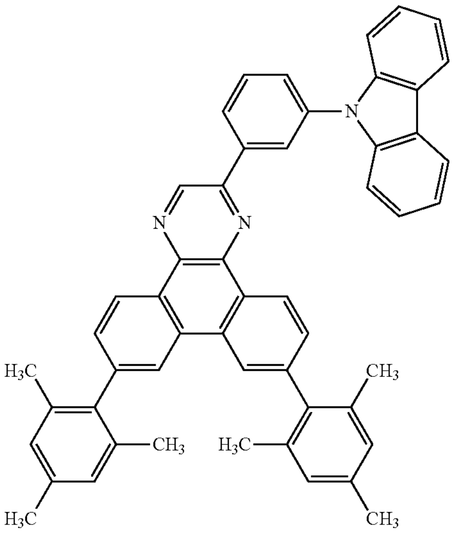
[Chemical Formula 38]
(359)
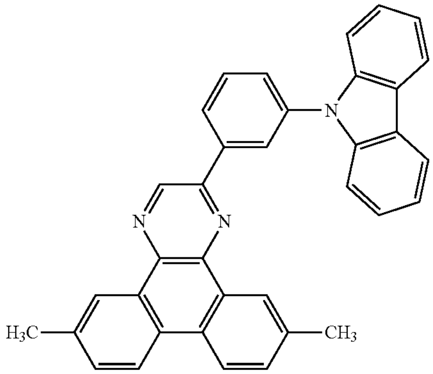
(360)
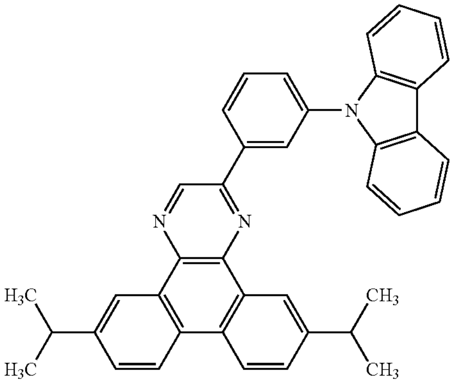
(361)
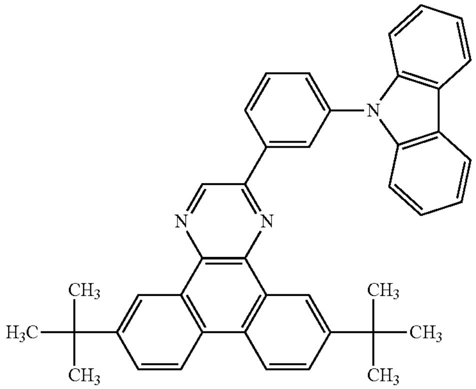
(362)
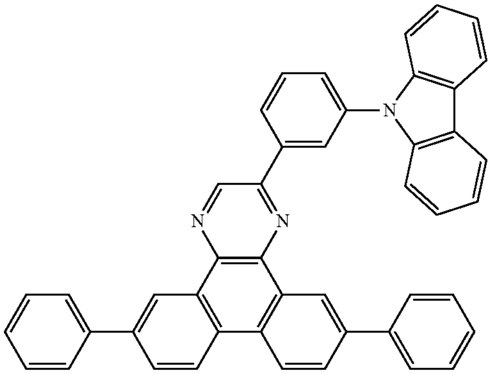

-continued
(363)
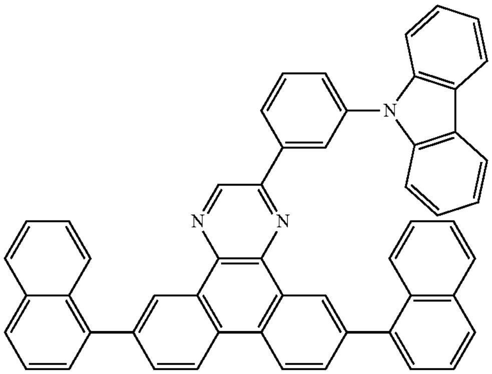
(364)
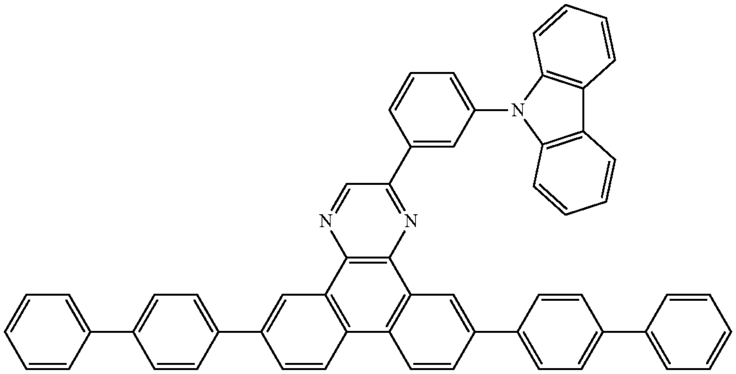
(365)
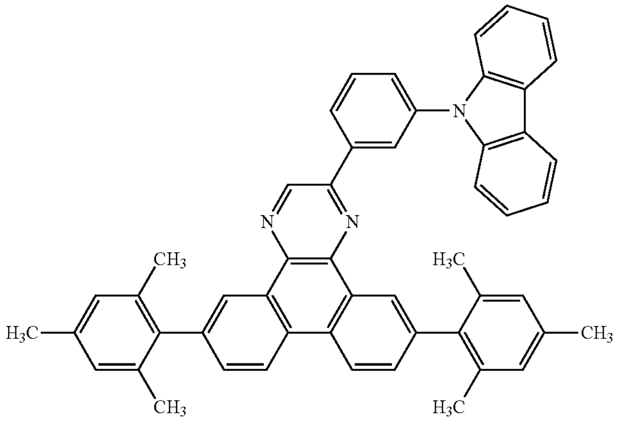

-continued
(366)
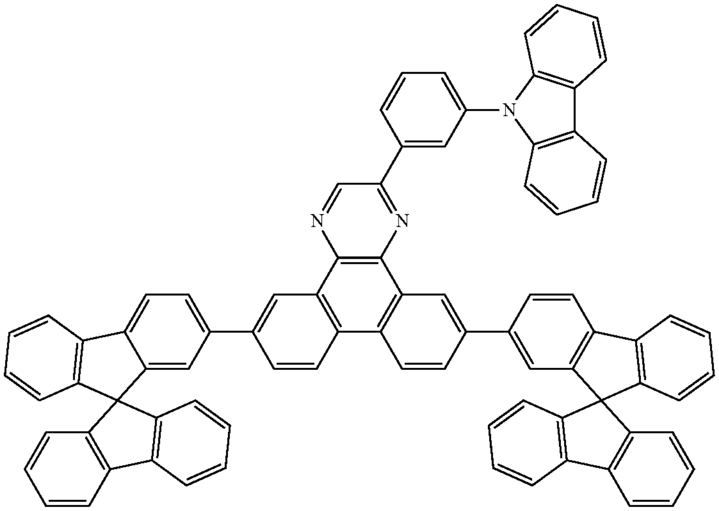
[Chemical Formula 39]
(367)
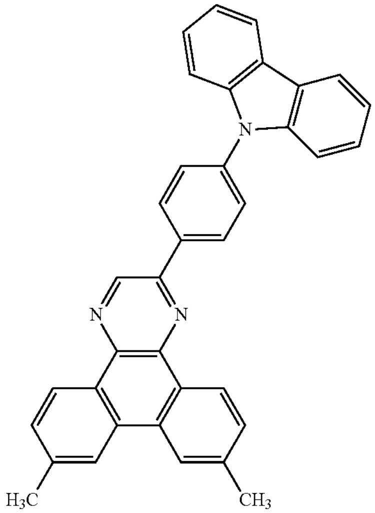
(368)
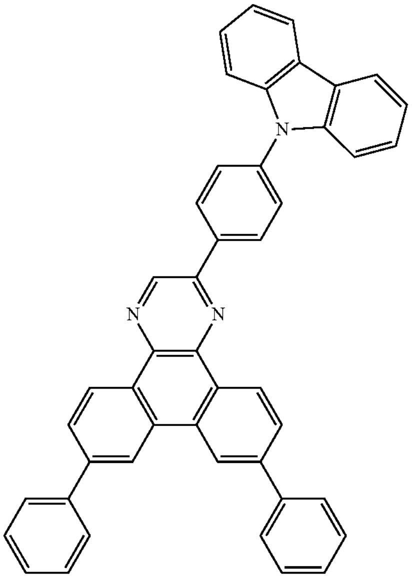
(369)
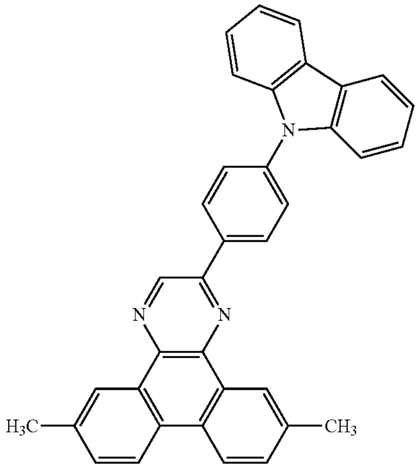
(370)
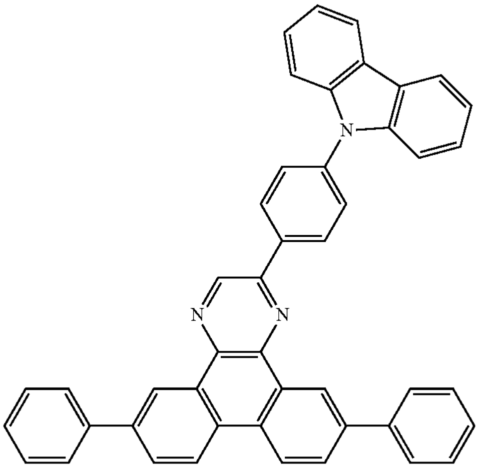

-continued
(371)
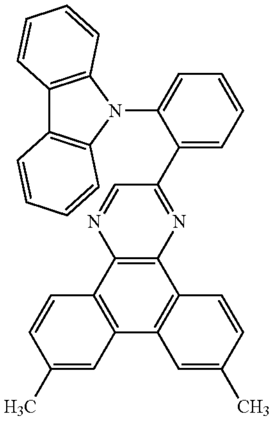
(372)
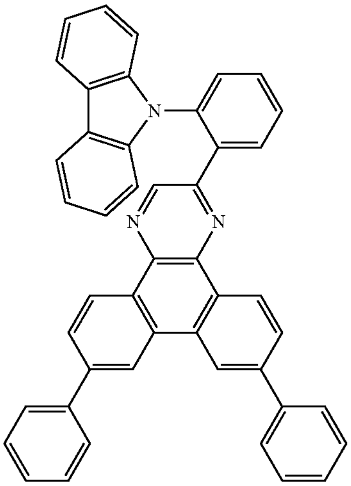
(373)
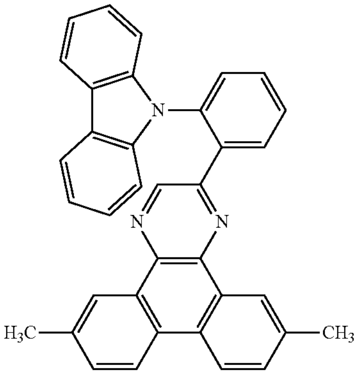
(374)
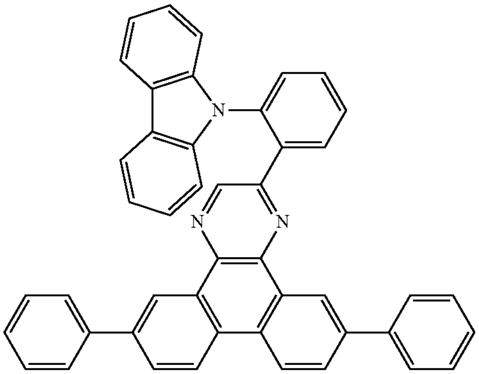
[Chemical Formula 40]
(400)
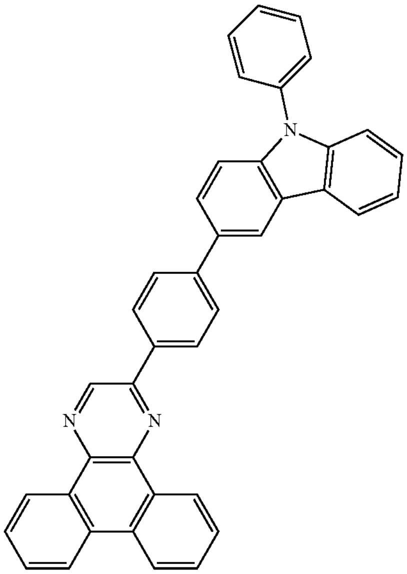
(401)
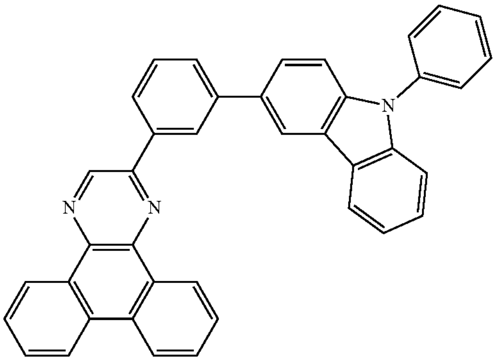

-continued
(402)
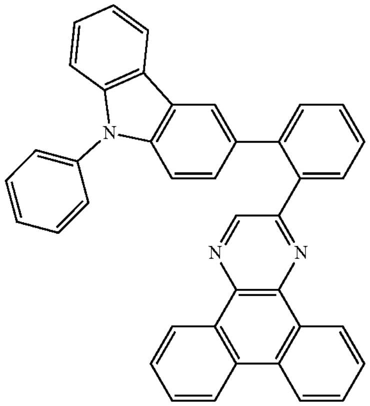
(403)
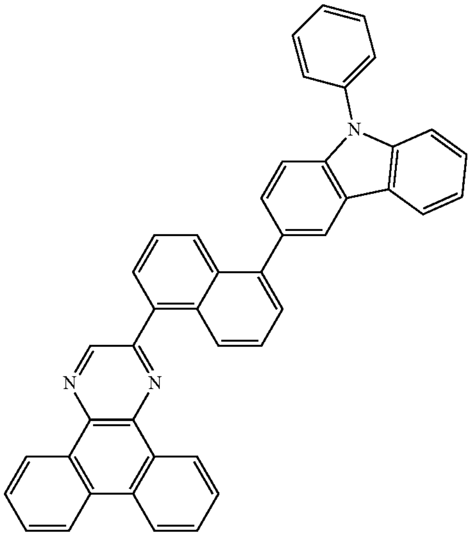
(404)
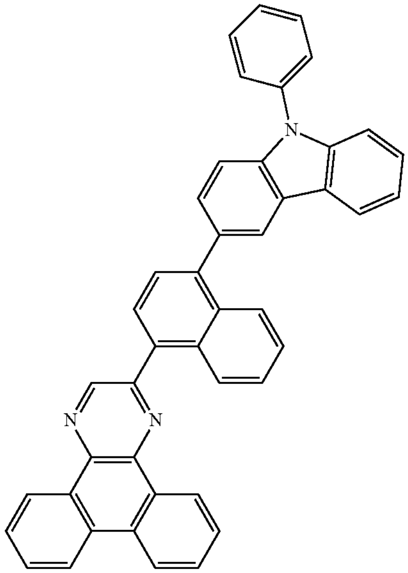
(405)
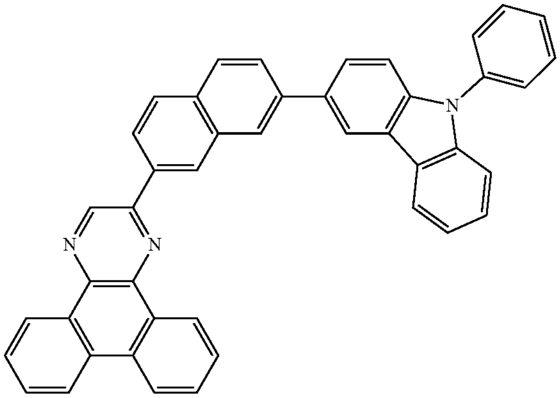
(406)
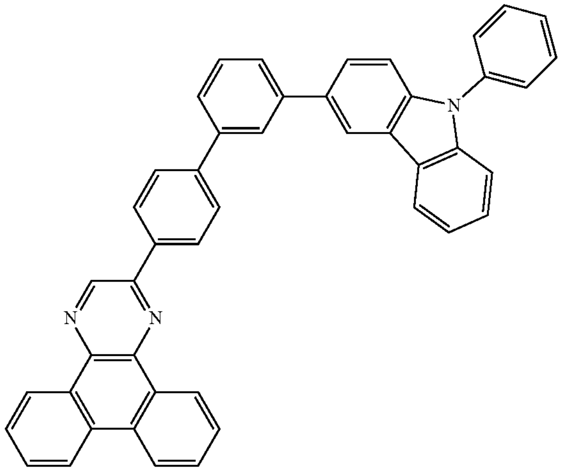

-continued
[Chemical Formula 41]
(407)
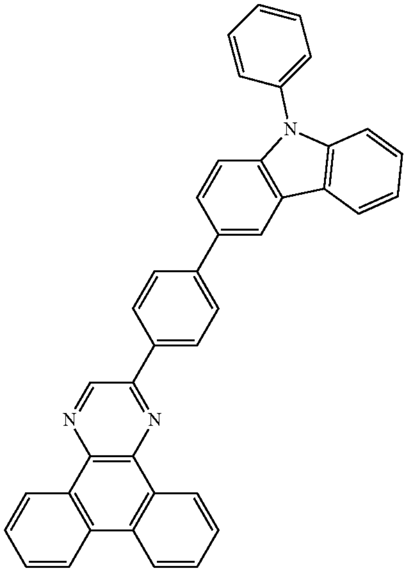
(408)
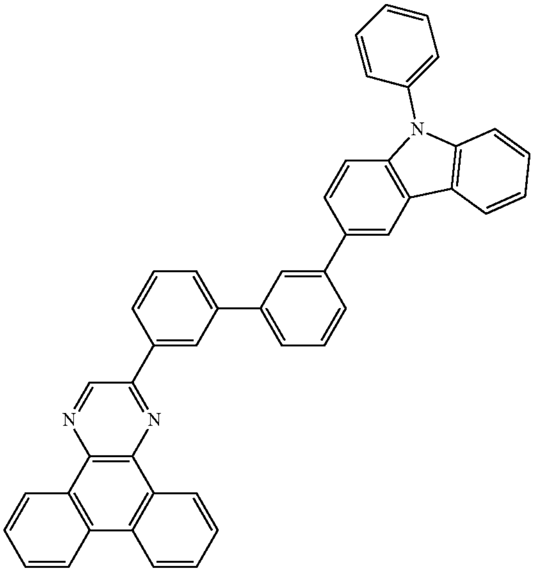
(409)
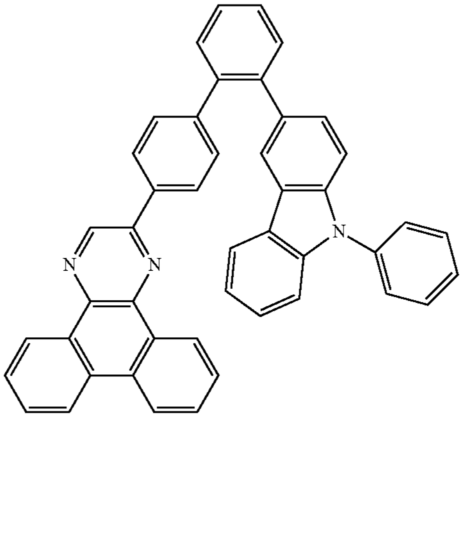
(410)
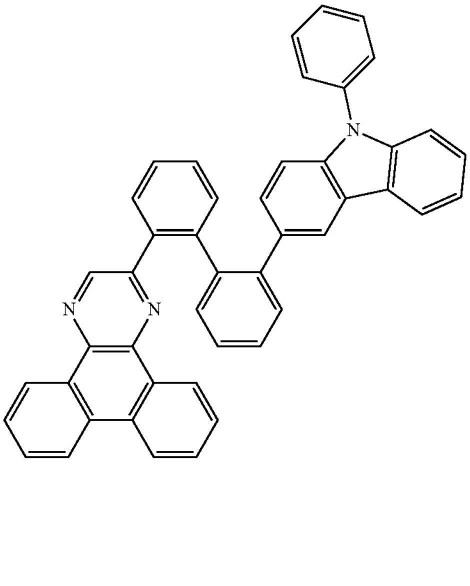

-continued
(411)
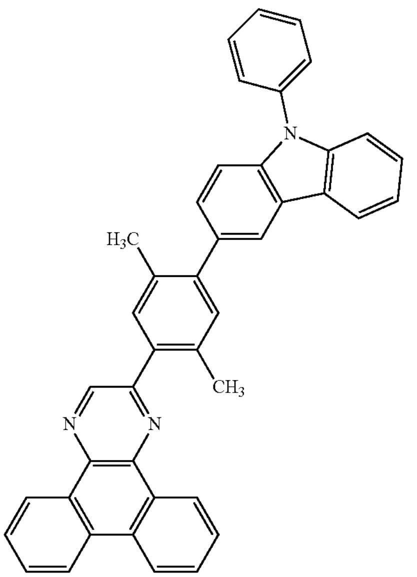
(412)
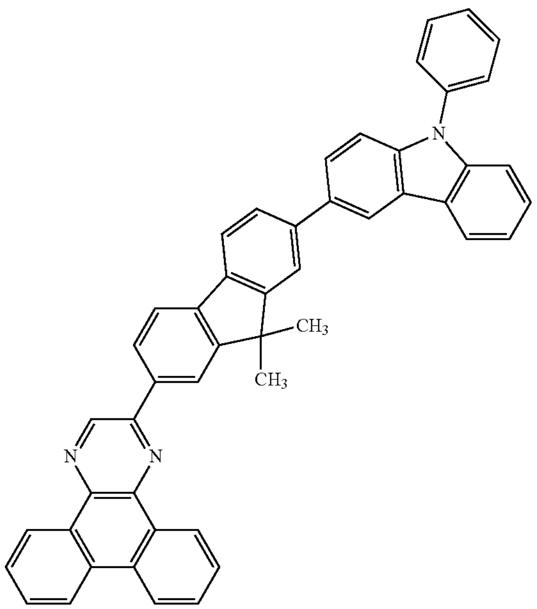
[Chemical Formula 42]
(413)
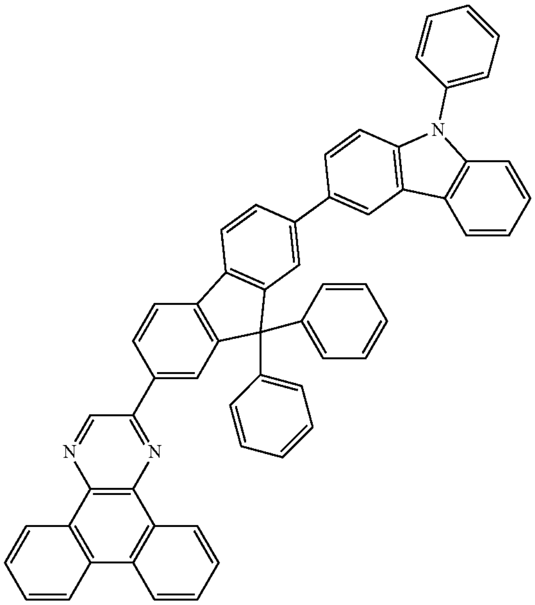
(414)
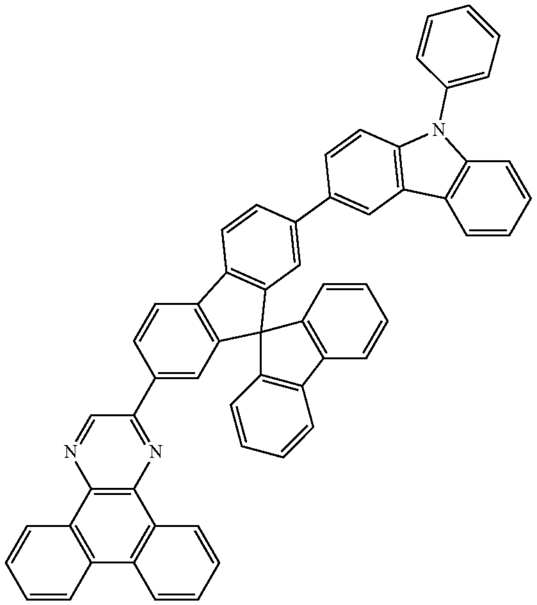
(415)
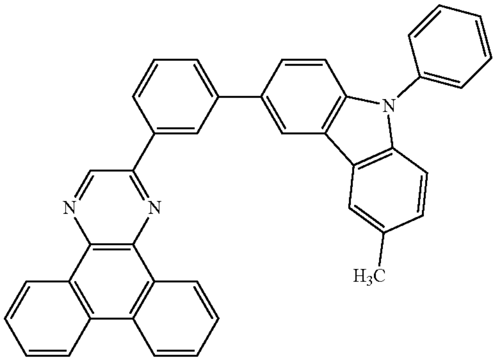
(416)
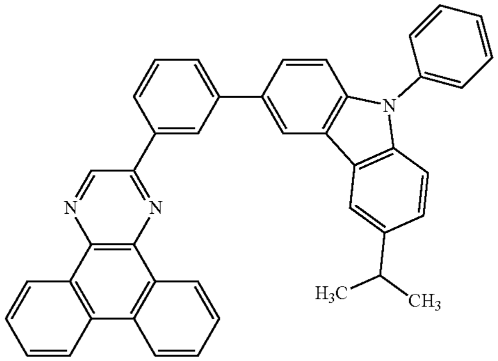

-continued
(417)
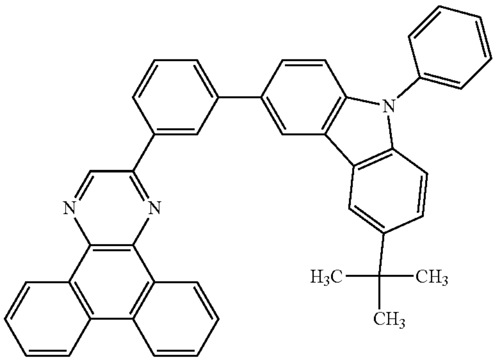
(418)
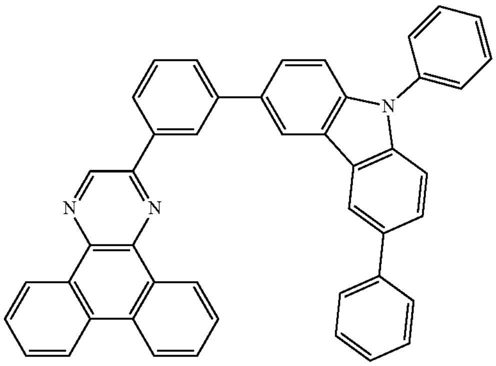
[Chemical Formula 43]
(419)
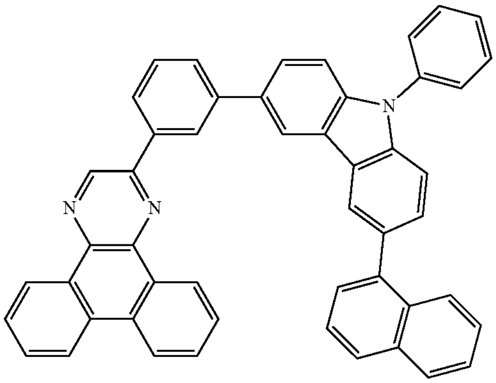
(420)
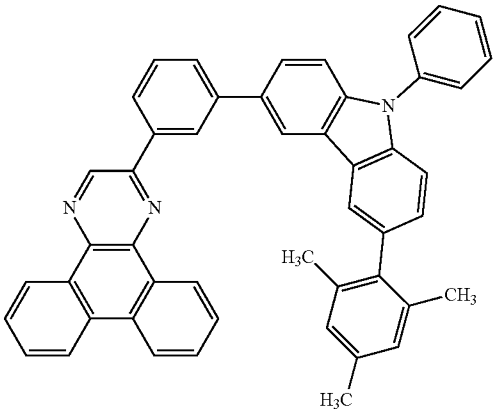
(421)
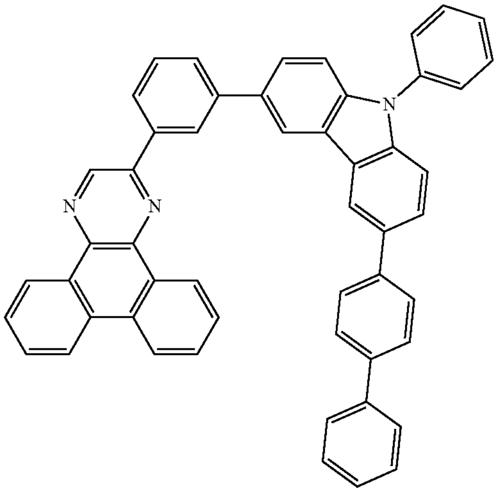
(422)
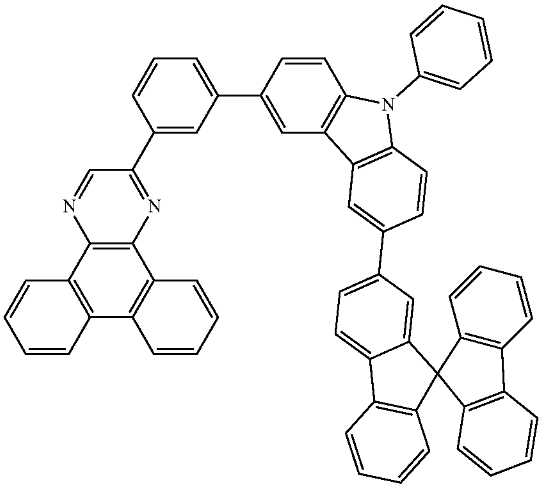

-continued
(423)
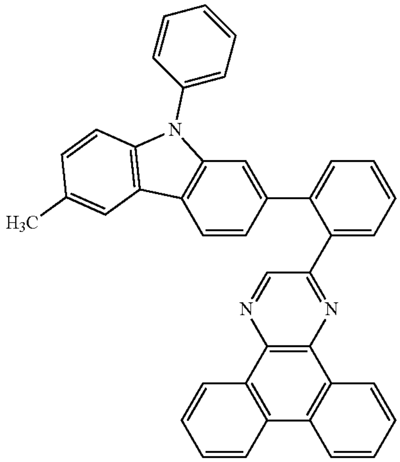
(424)
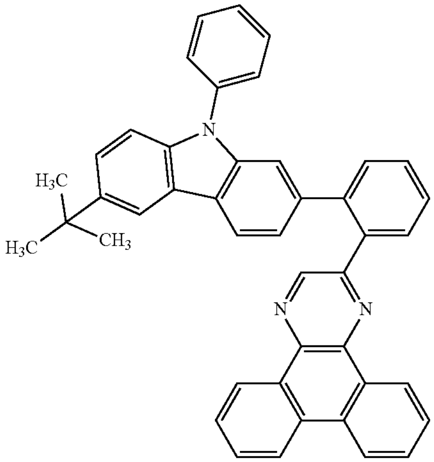
[Chemical Formula 44]
(425)
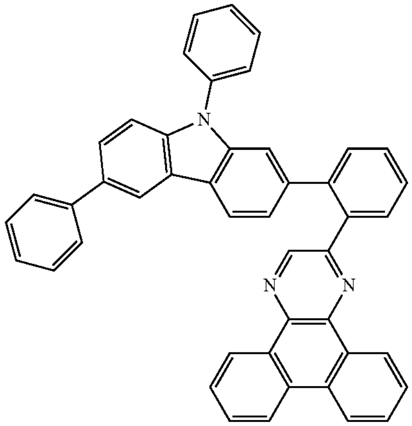
(426)
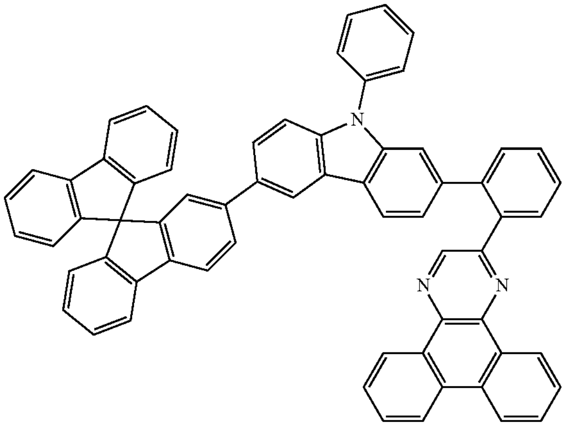
(427)
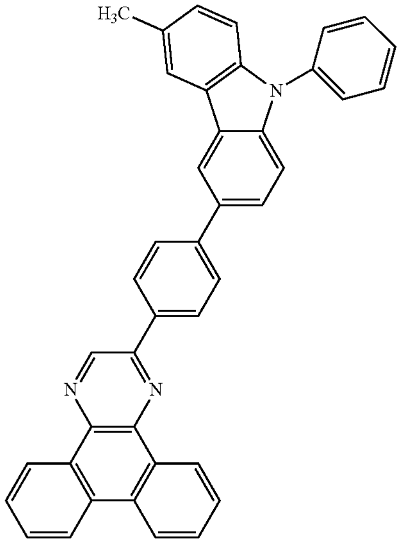
(428)
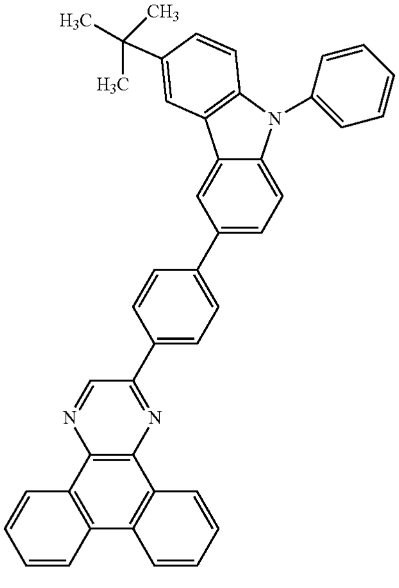

-continued
(429)
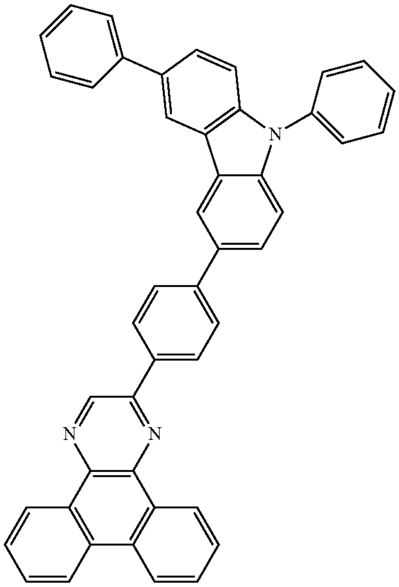
(430)
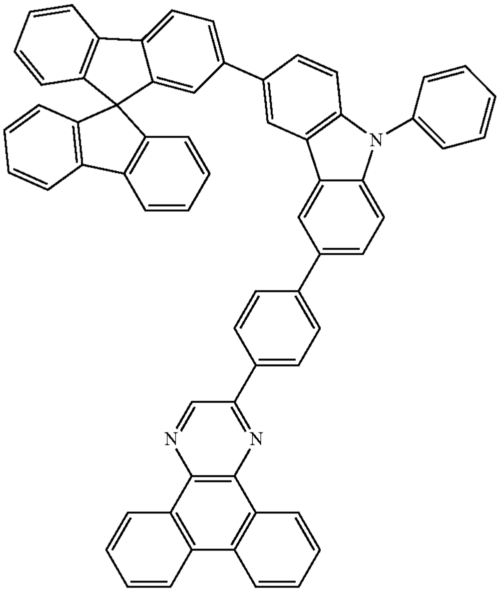
[Chemical Formula 45]
(431)
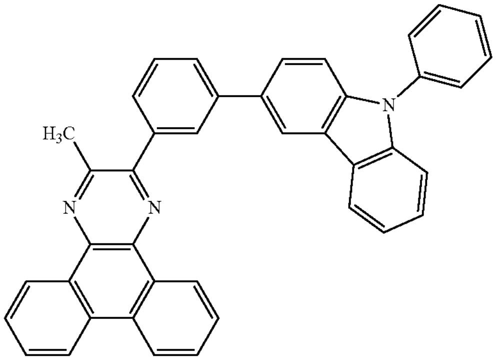
(432)
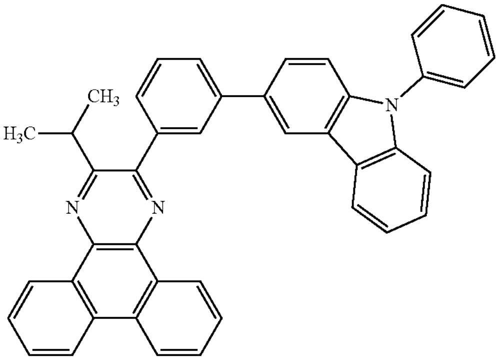
(433)
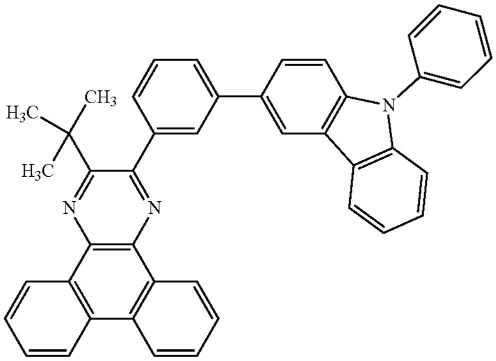
(434)
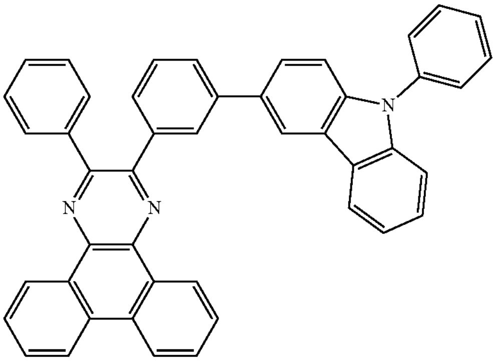

-continued
(435)
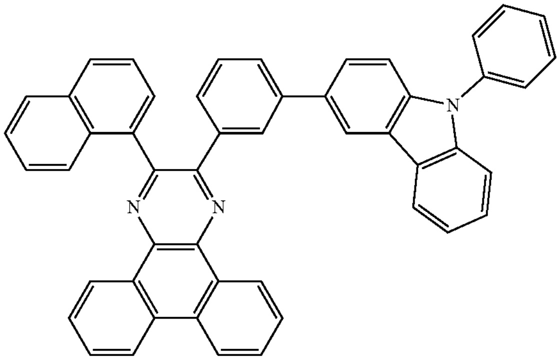
(436)
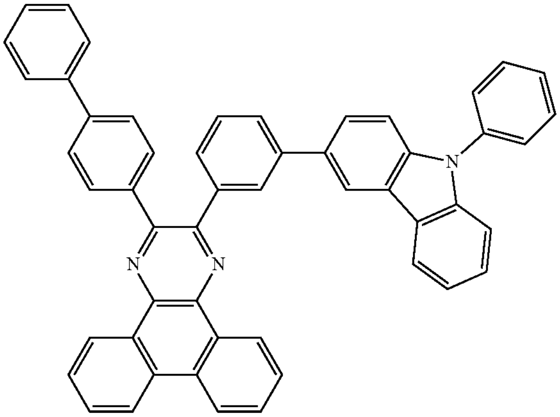
(438)
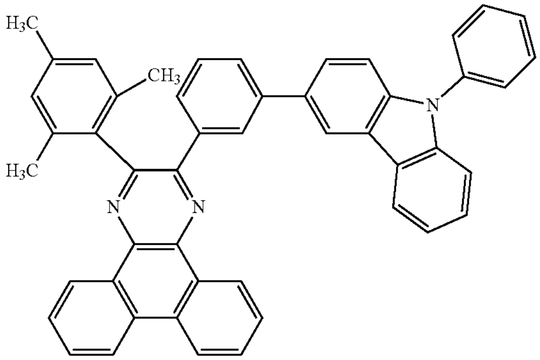
(437)
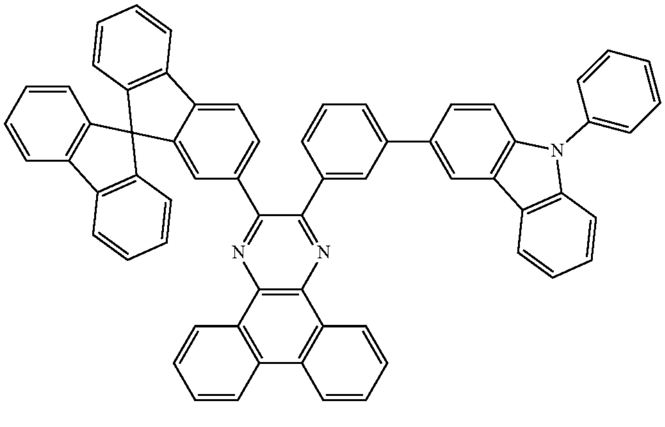

-continued
[Chemical Formula 46]
(439)
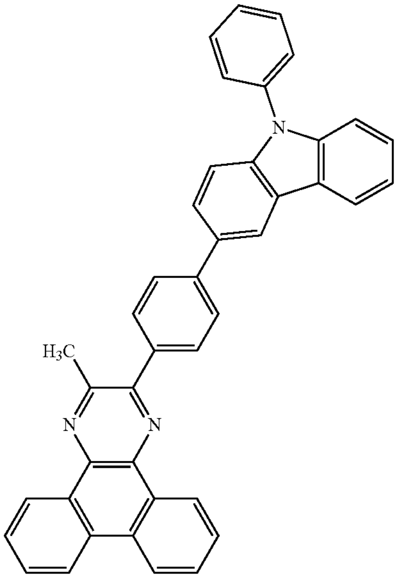
(440)
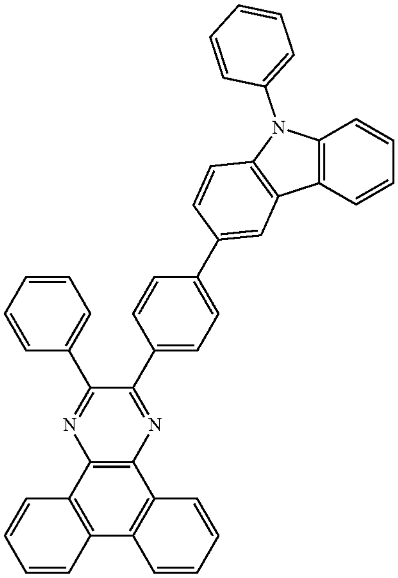
(441)
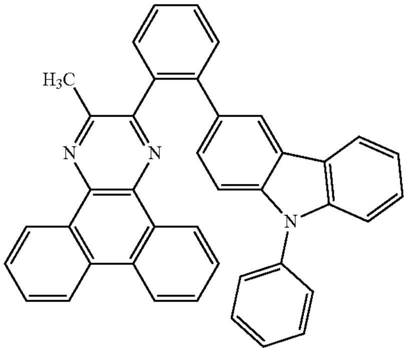
(442)
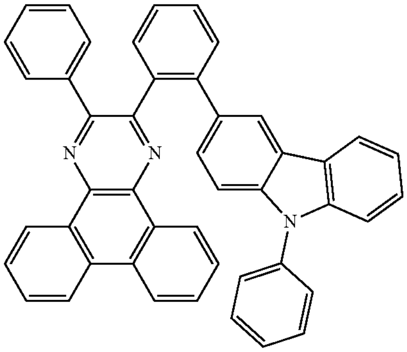
(443)
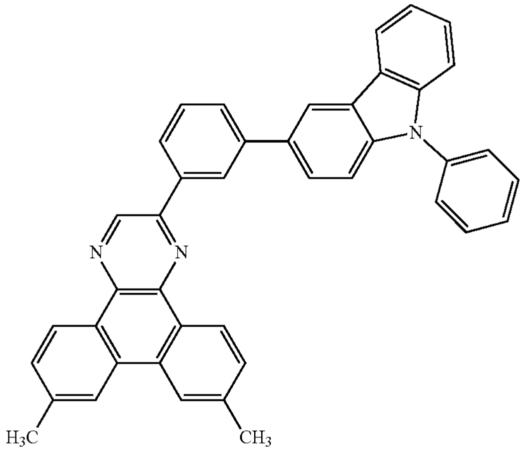
(444)
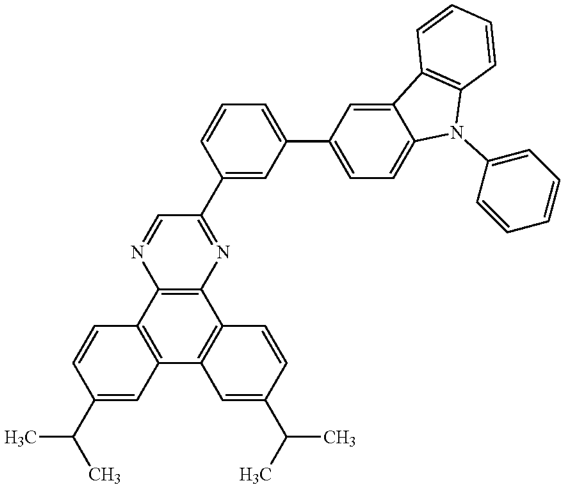

-continued
(445)
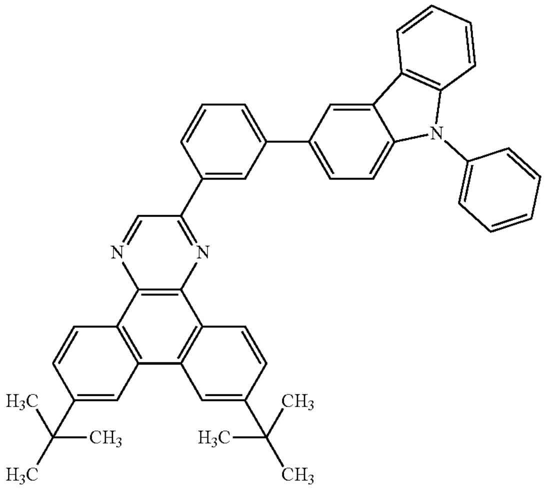
[Chemical Formula 47]
(446)
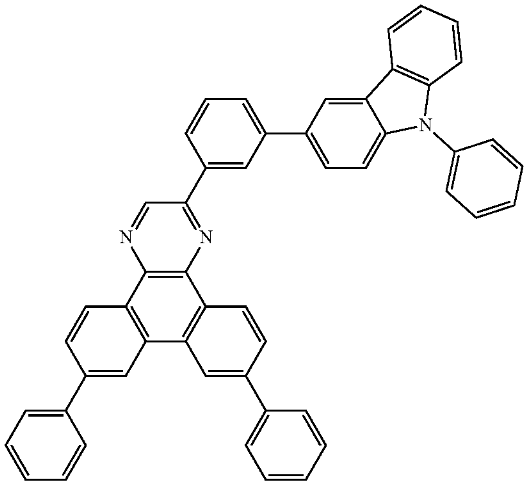
(447)
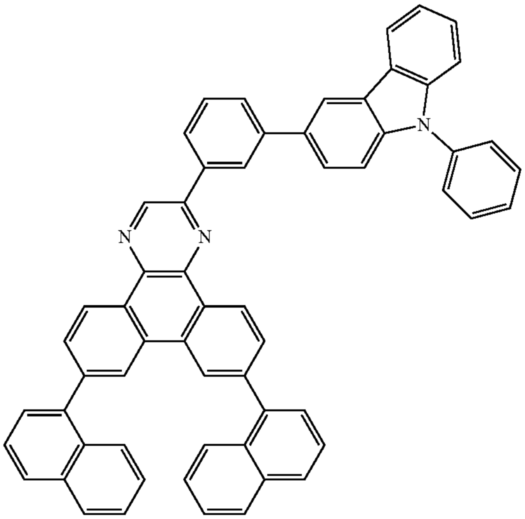

-continued
(448)
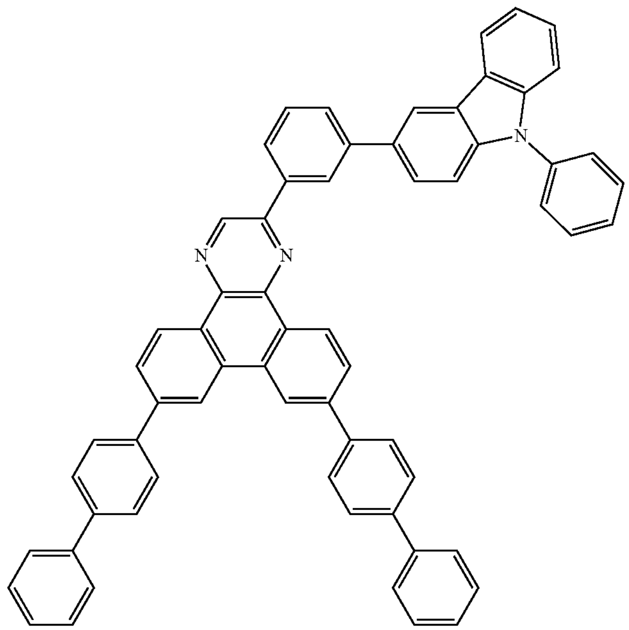
(449)
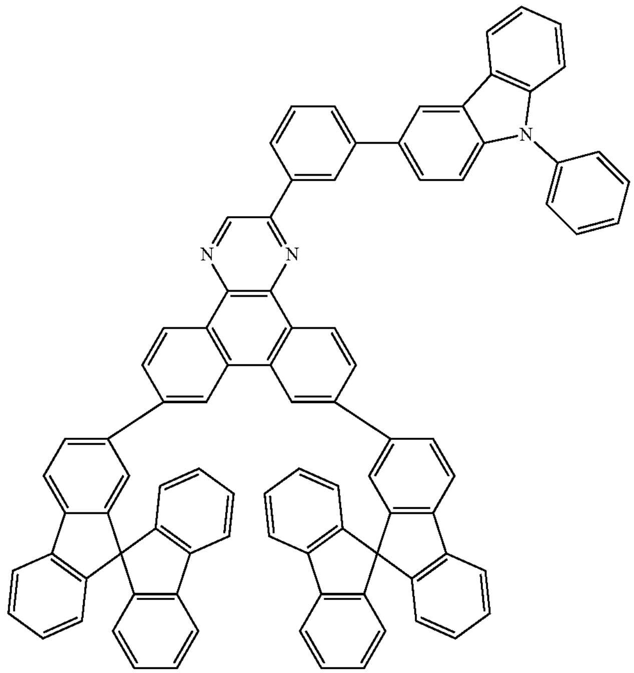

-continued
(450)
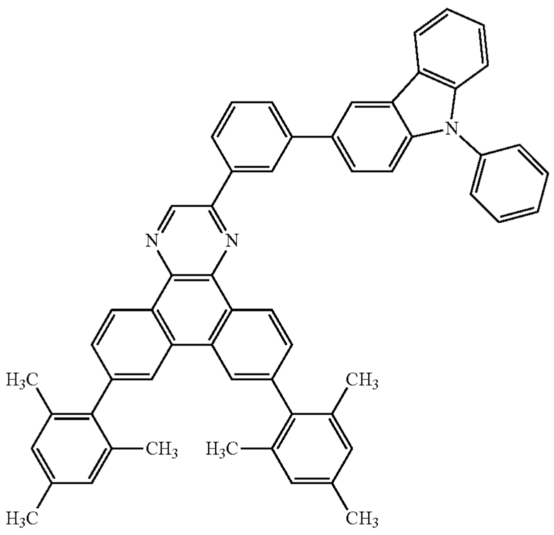
(451)
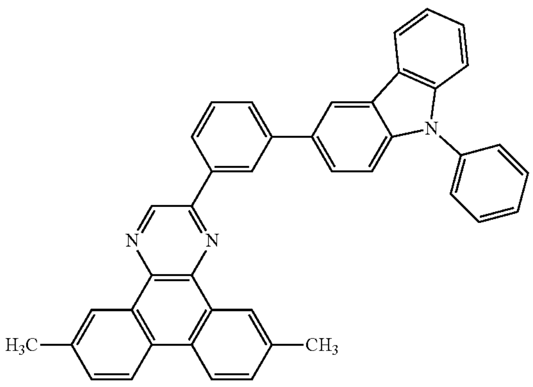
[Chemical Formula 48]
(452)
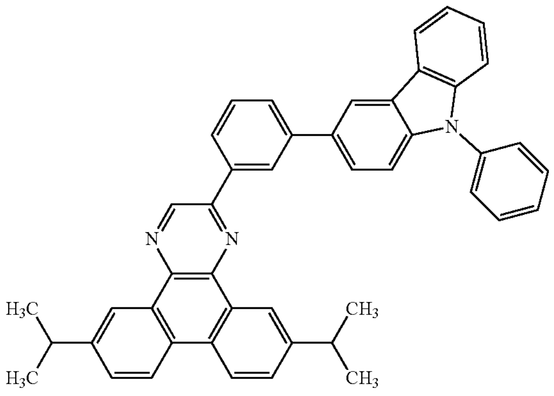
(453)
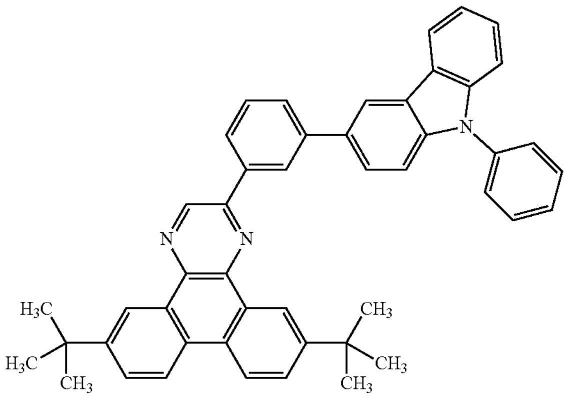
(454)
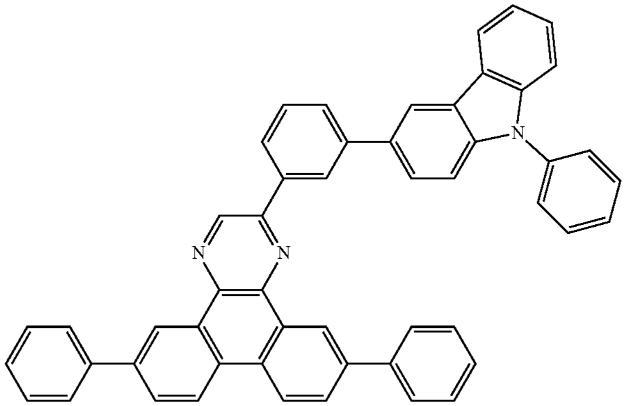

-continued
(455)
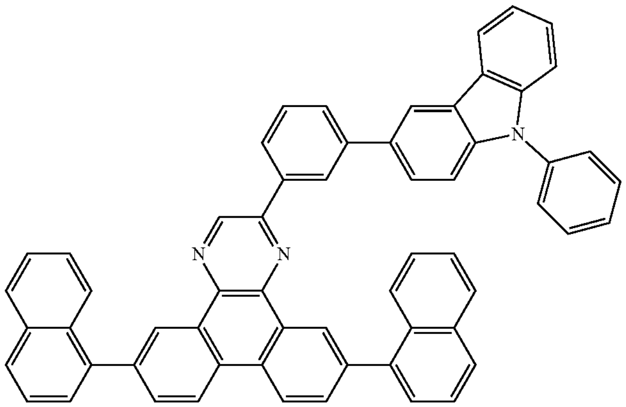
(456)
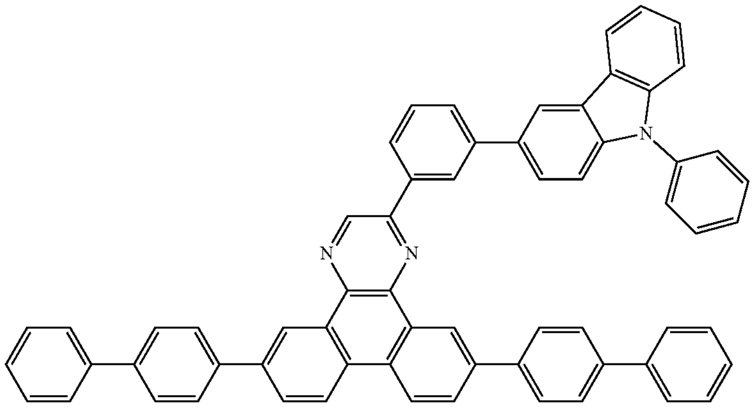
[Chemical Formula 49]
(457)
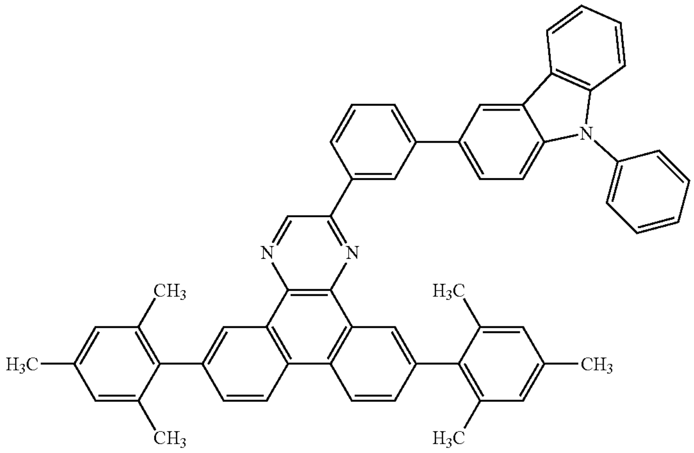

-continued
(458)
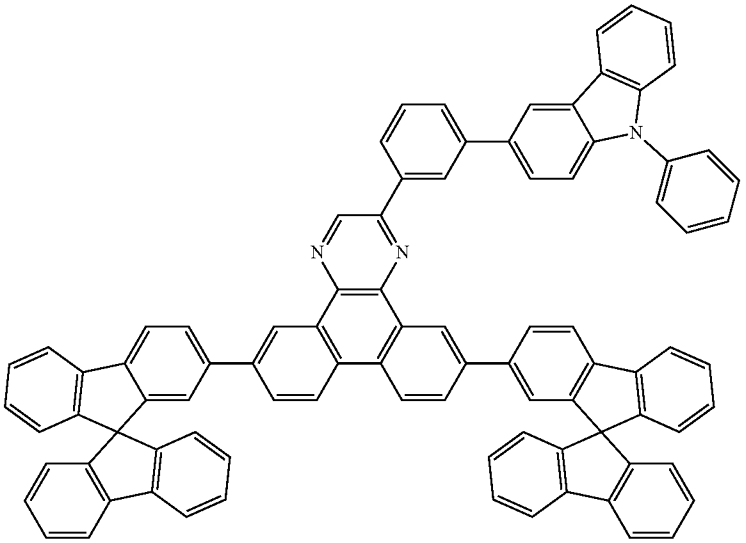
(459)
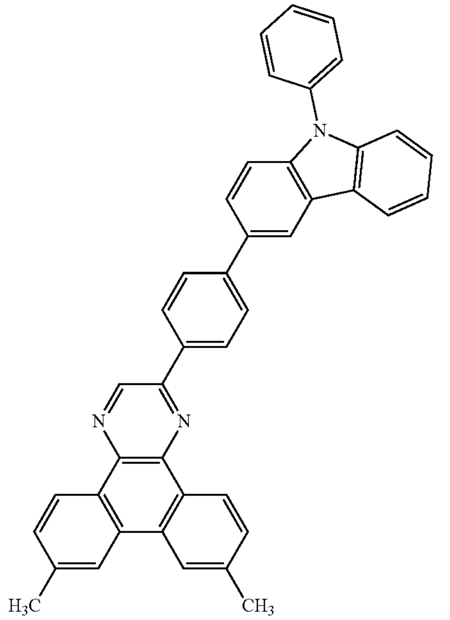
(460)
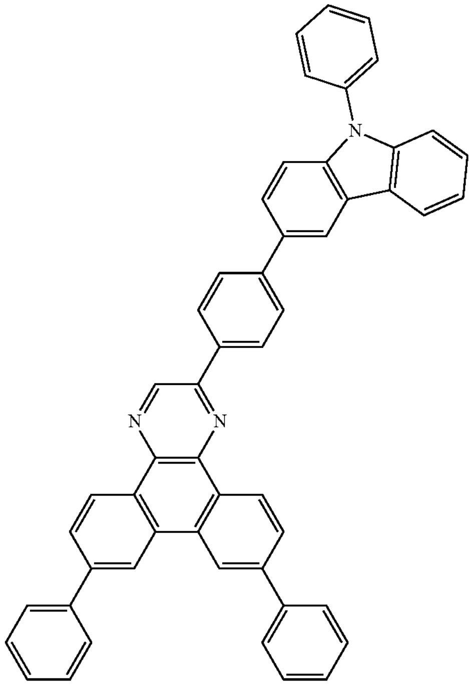

-continued
[Chemical Formula 50]
(461)
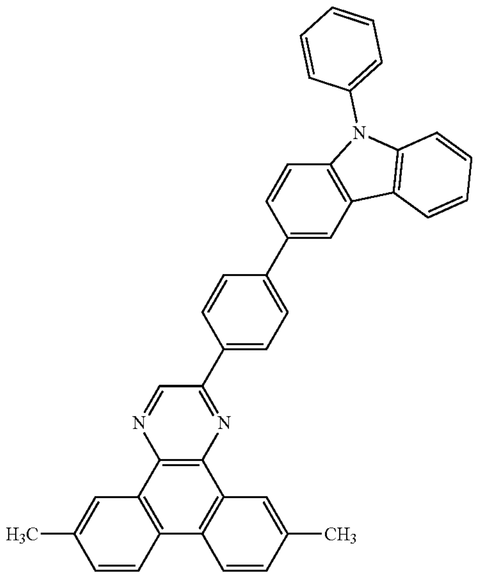
(462)
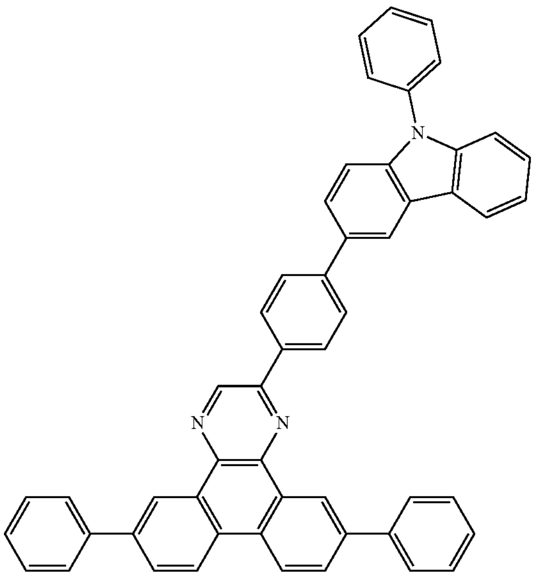
(463)
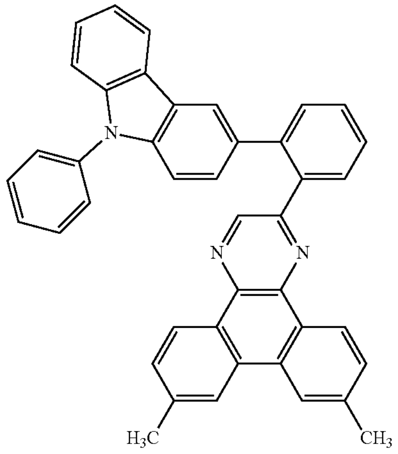
(464)
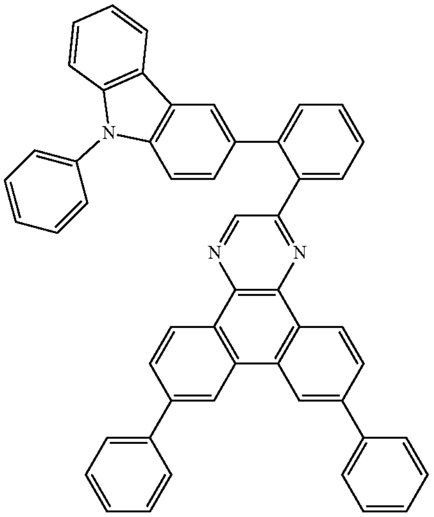
(465)
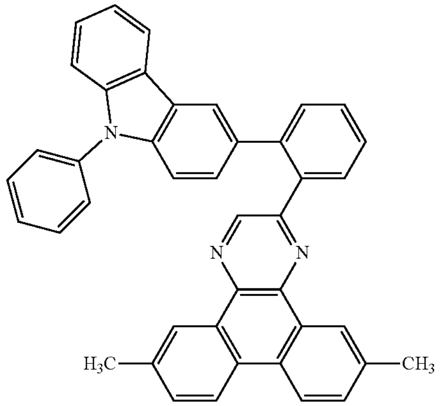
(466)
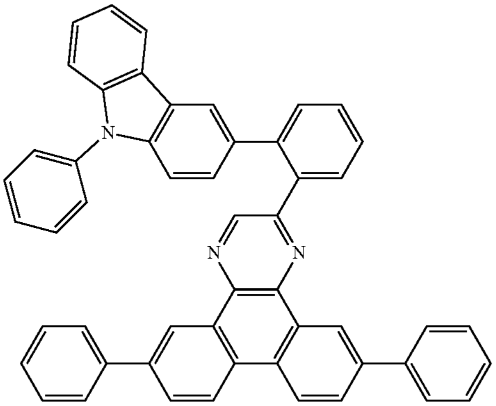

-continued
[Chemical Formula 51]
(467)
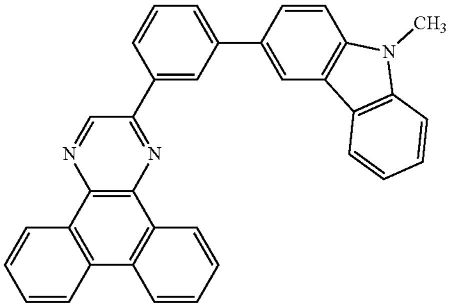
468
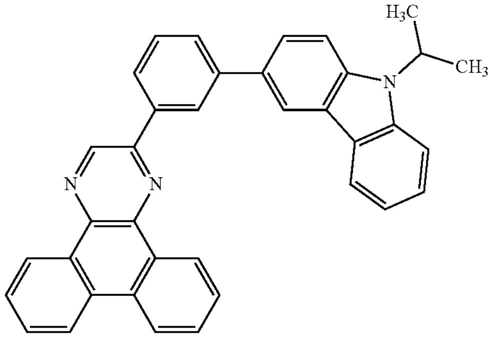
(469)
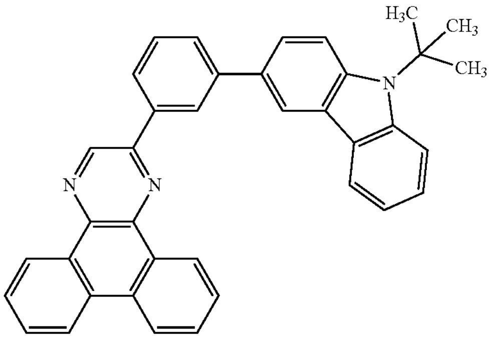
(470)
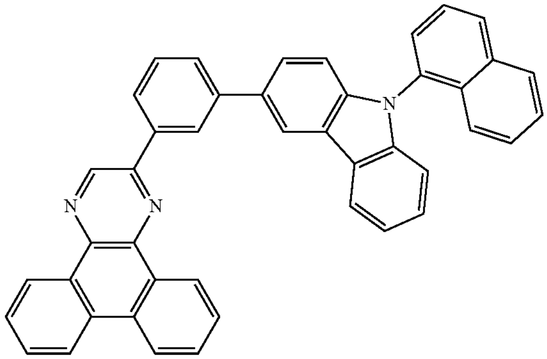
(471)
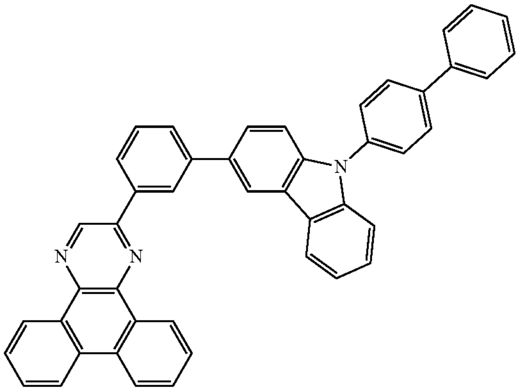
(472)
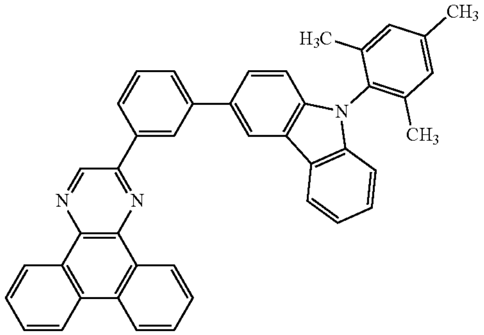
(473)
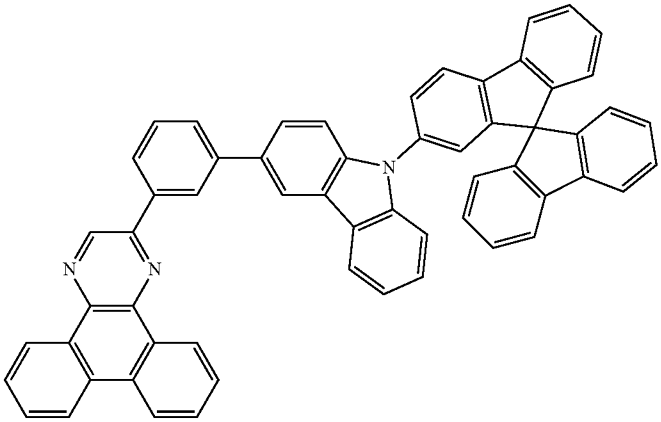

-continued
[Chemical Formula 52]
(474)
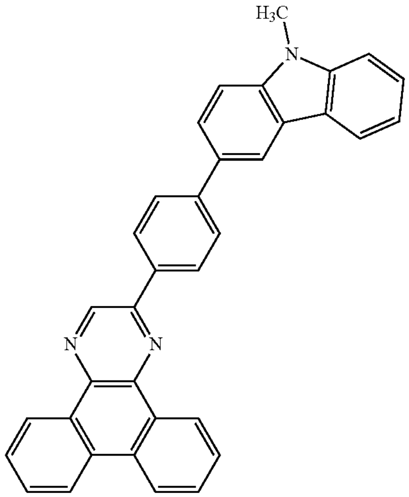
(475)
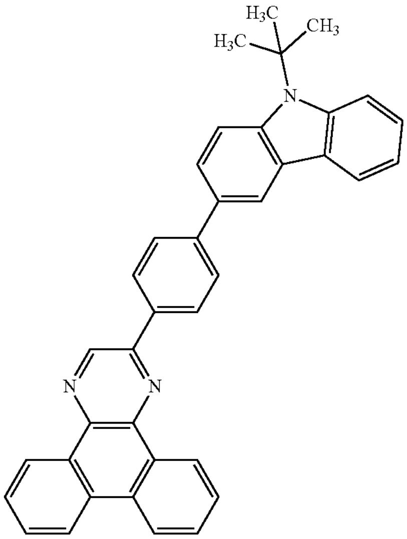
(476)
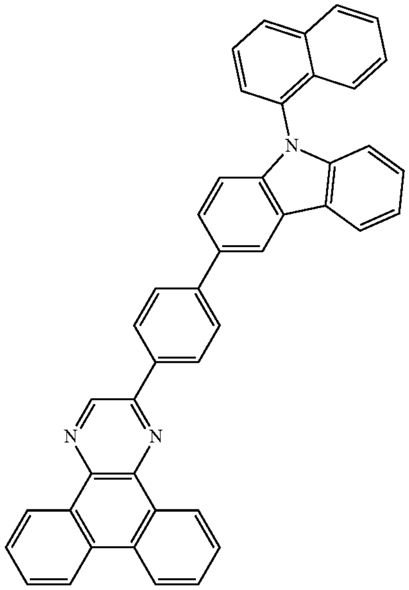
(477)
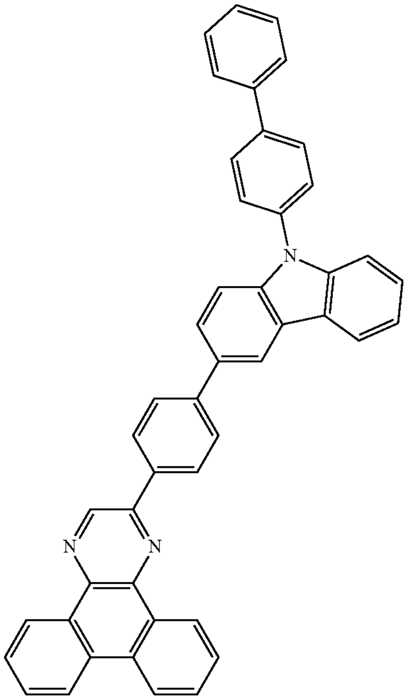

-continued
(478)
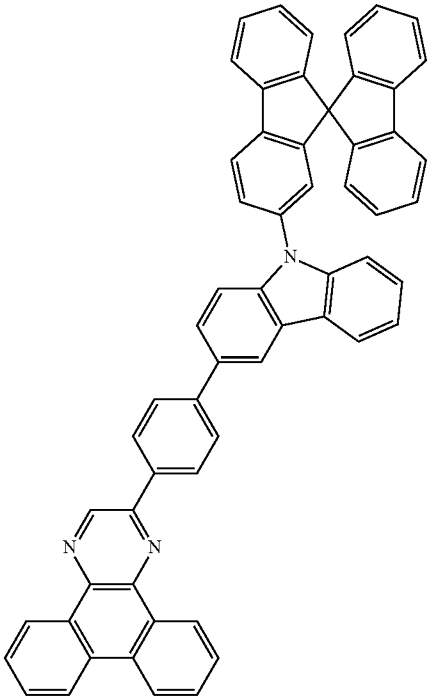
(479)
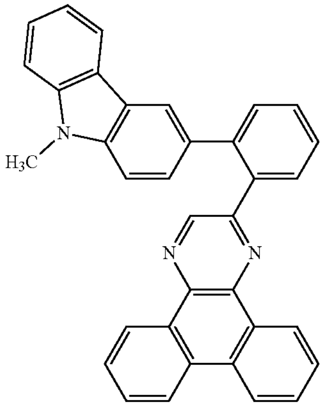
(480)
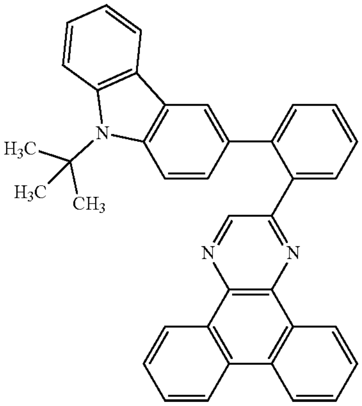
(481)
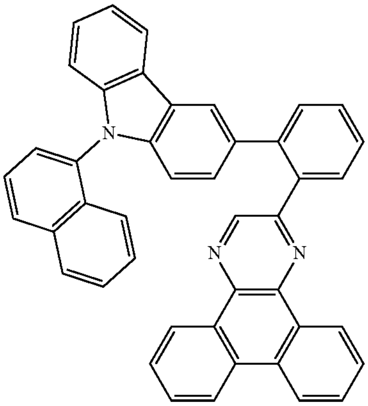
[Chemical Formula 53]
(482)
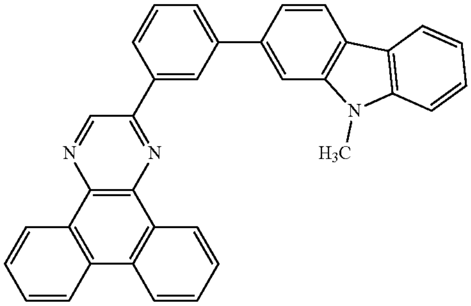
(483)
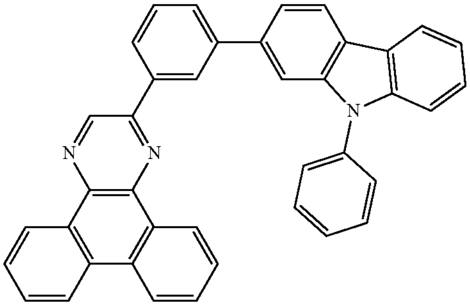

-continued
(484)
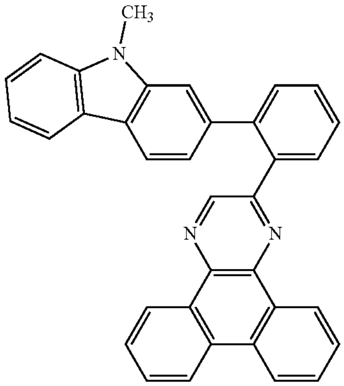
(485)
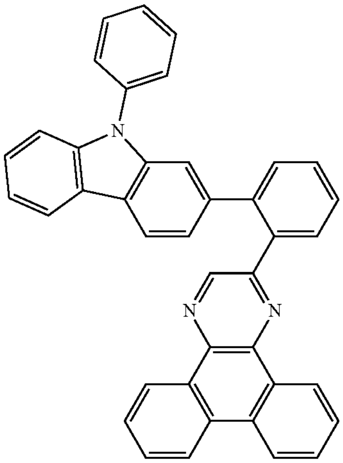
(486)
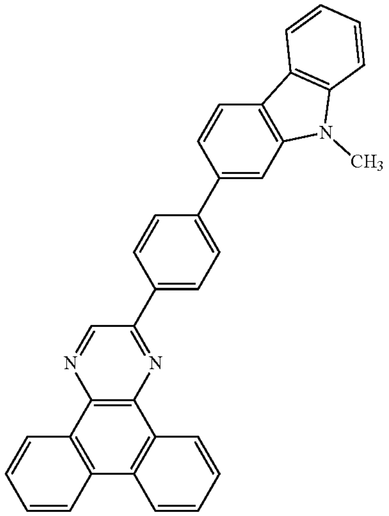
(487)
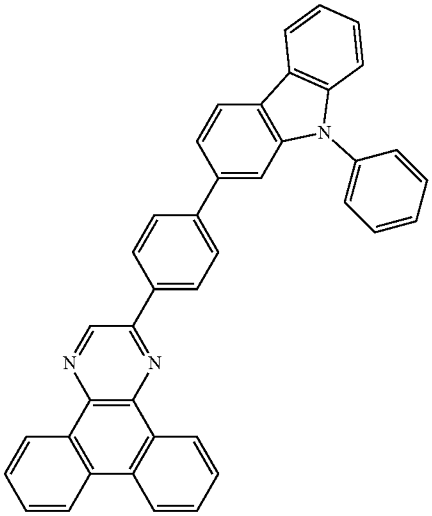
[Chemical Formula 54]
(500)
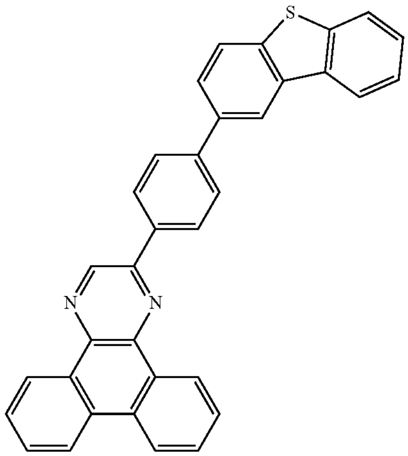
(501)
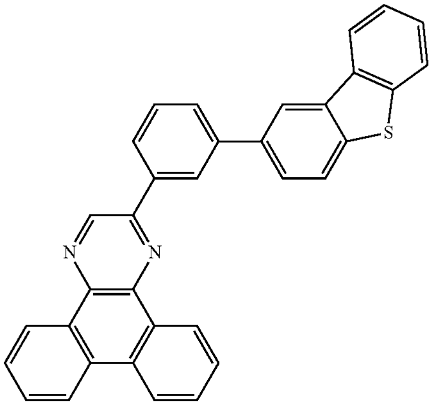

-continued
(502)
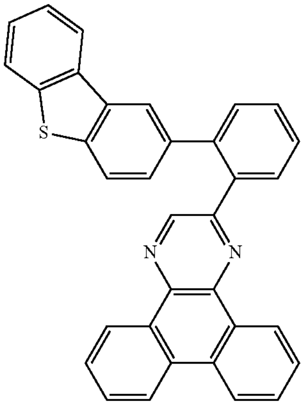
(503)
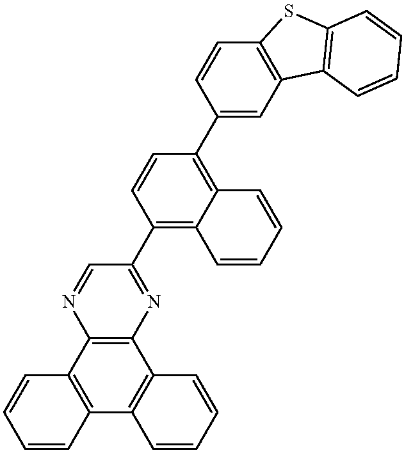
(504)
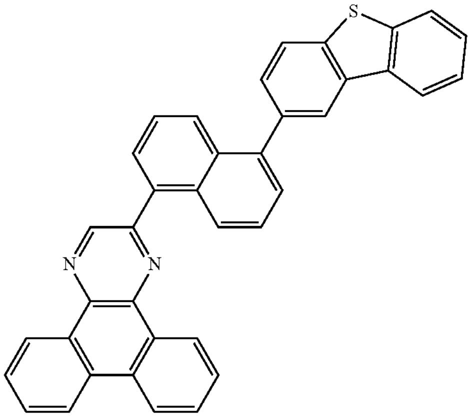
(505)
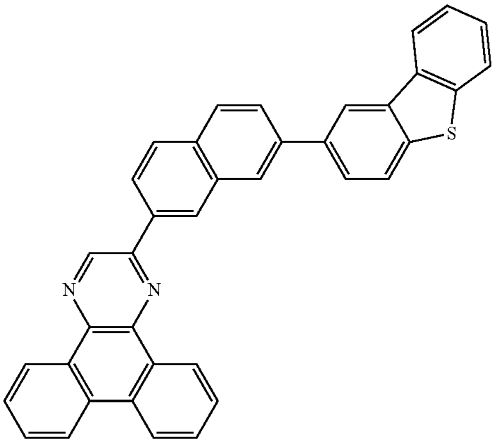
(506)
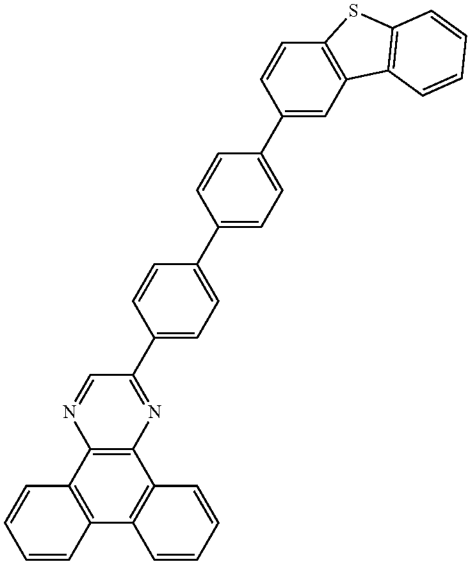
(507)
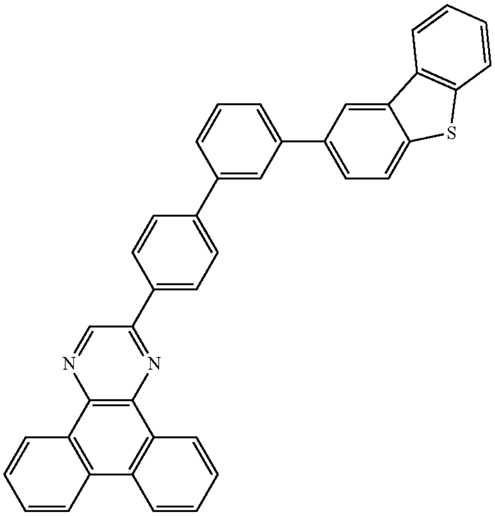

-continued
(508)
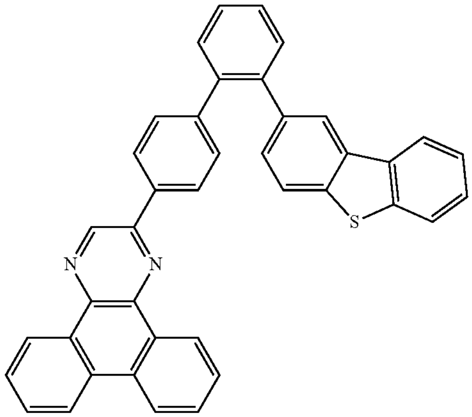
[Chemical Formula 55]
(509)
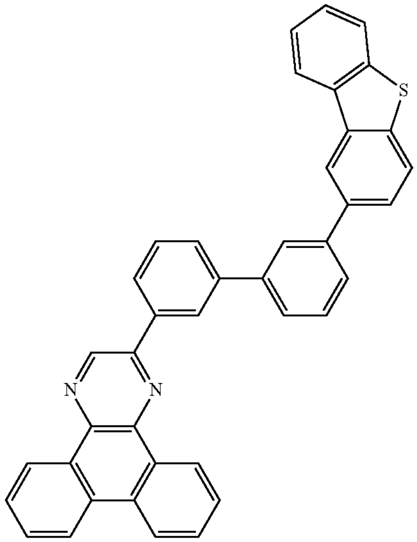
(510)
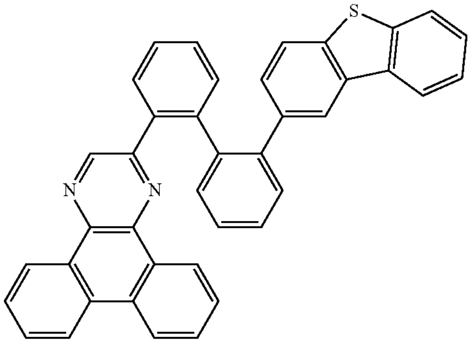
(511)
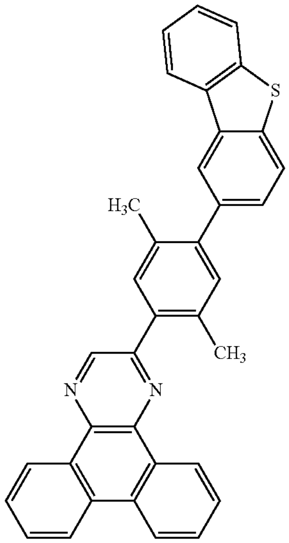
(512)
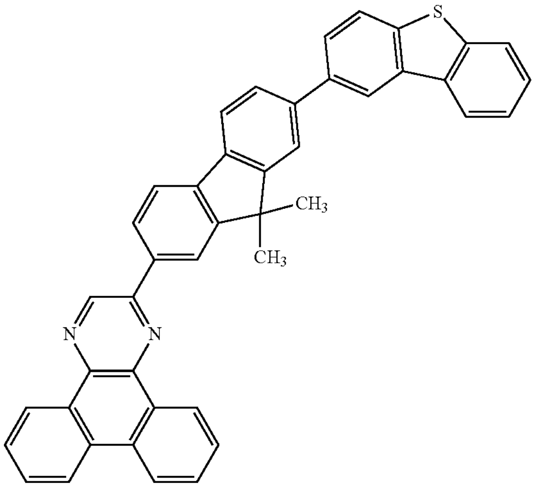

-continued
(513)
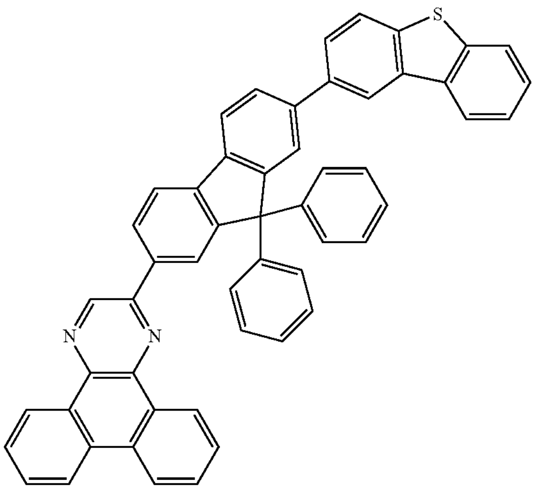
(514)
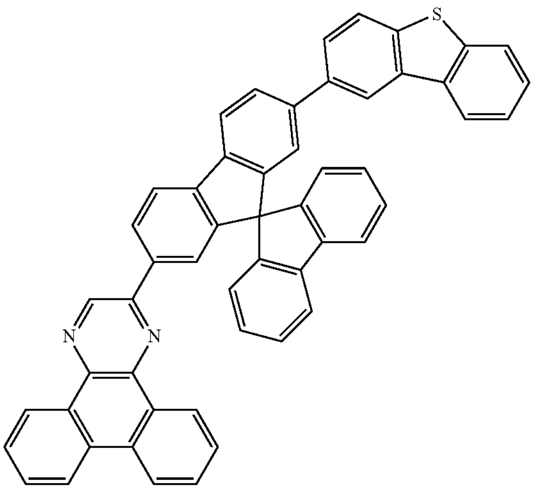
(515)
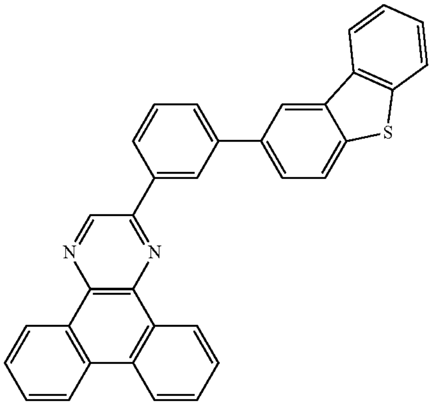
[Chemical Formula 56]
(516)
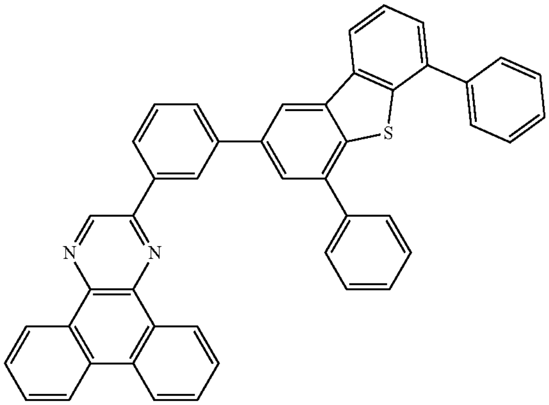
(517)
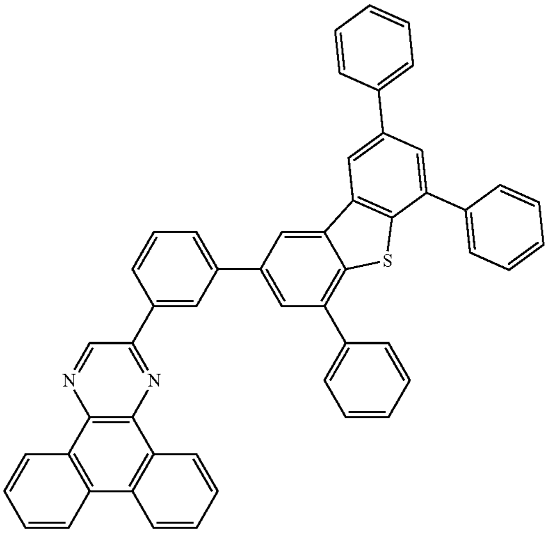

-continued
(518)
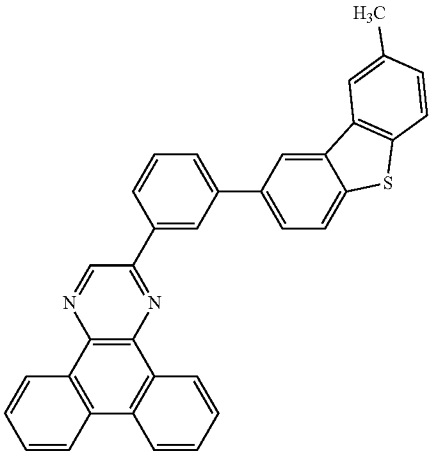
(519)
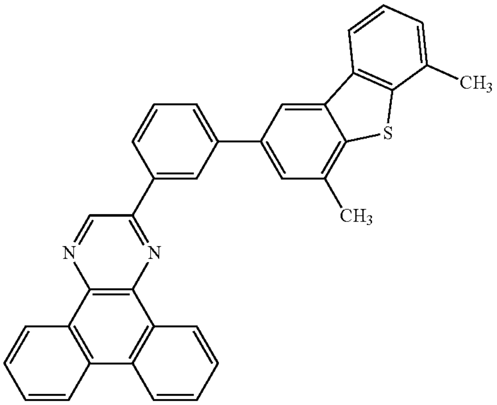
(520)
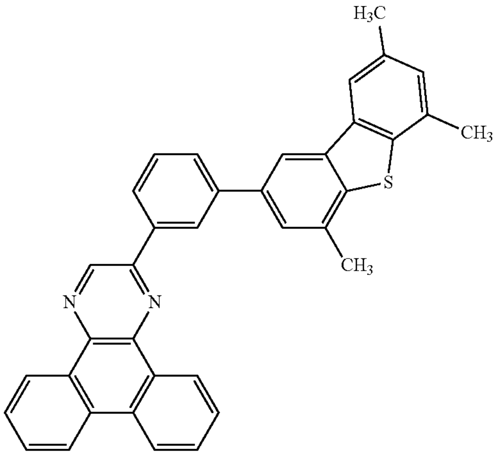
(521)
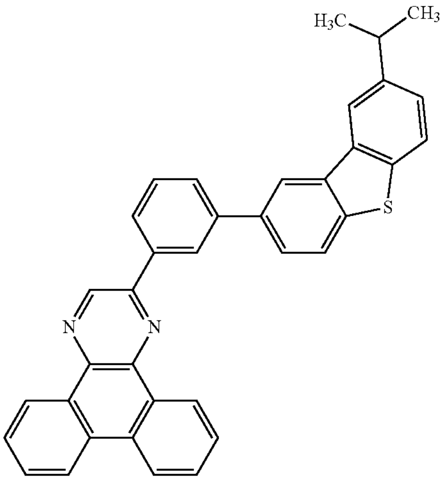
(522)
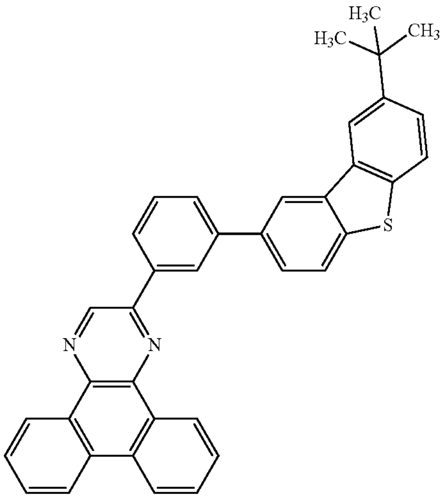
(523)
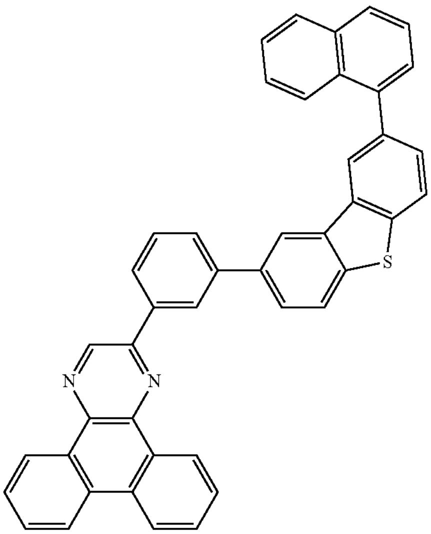

-continued
[Chemical Formula 57]
(524)
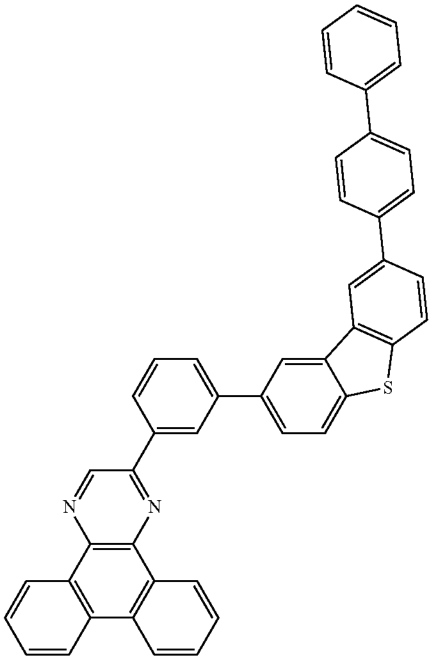
(525)
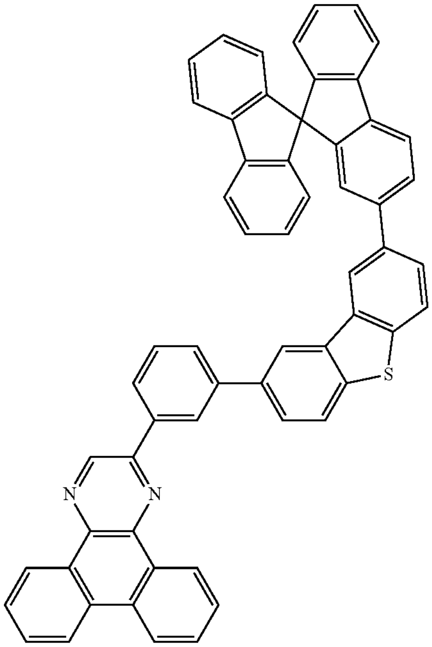
(526)
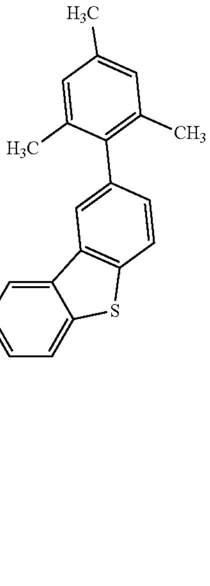
(527)
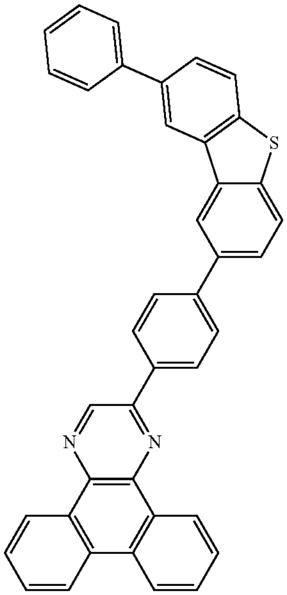

-continued
(528)
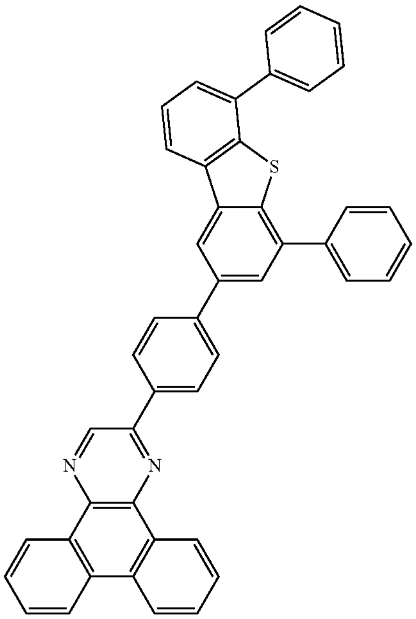
(529)
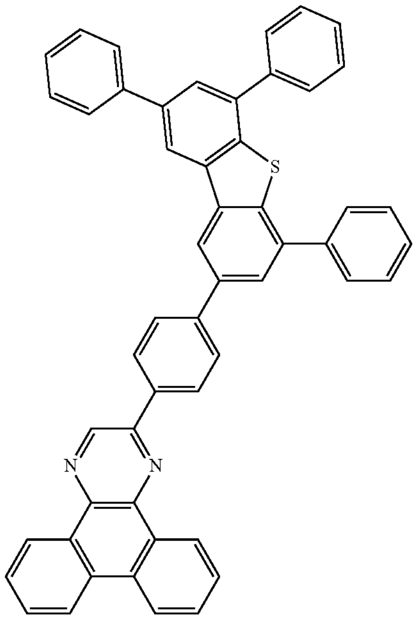
(530)
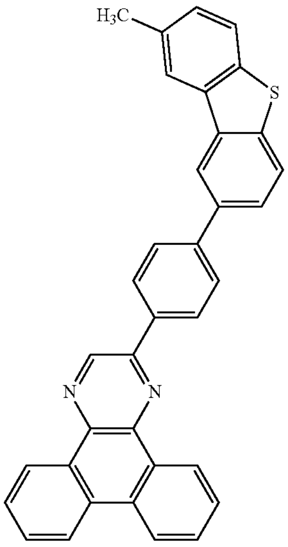
(531)
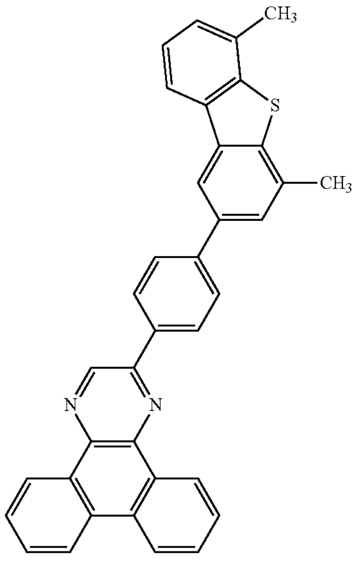

-continued
(532)
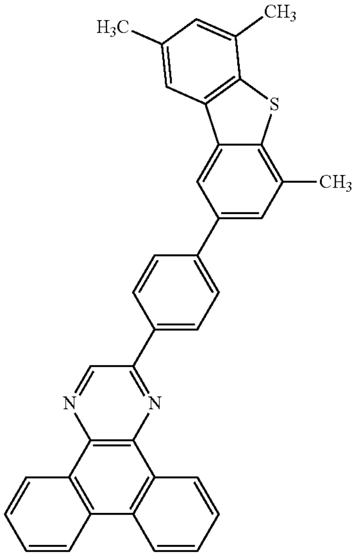
[Chemical Formula 58]
(533)
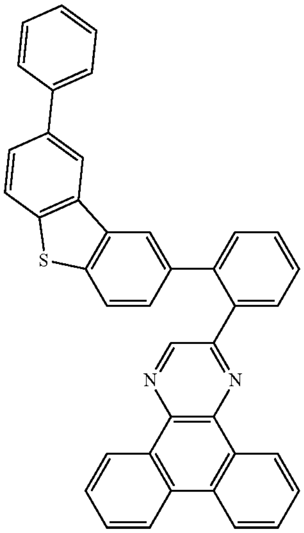
(534)
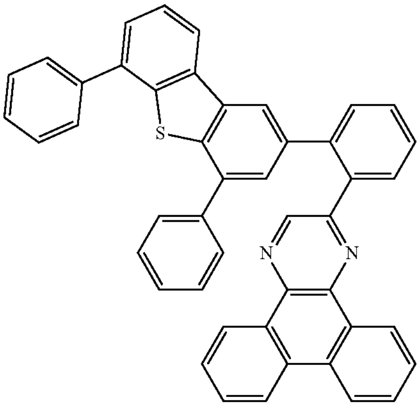
(535)
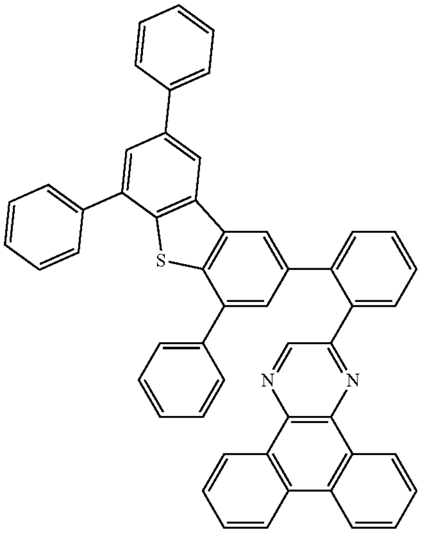
(536)
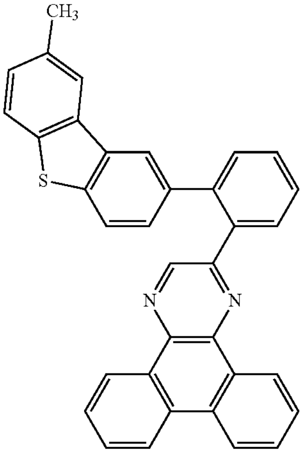

-continued
(537)
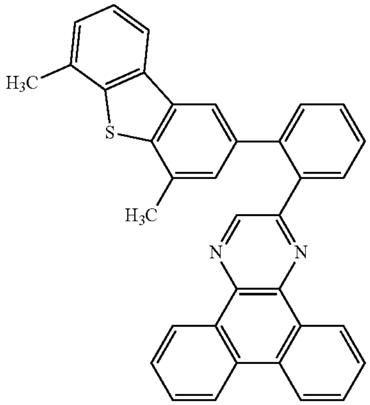
(538)
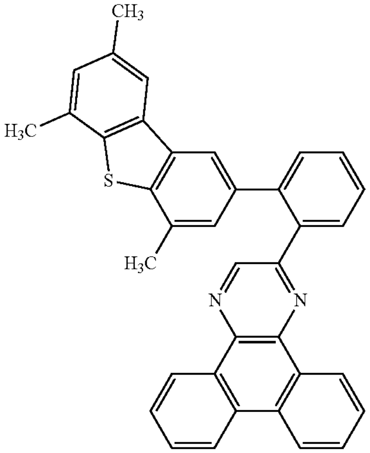
(539)
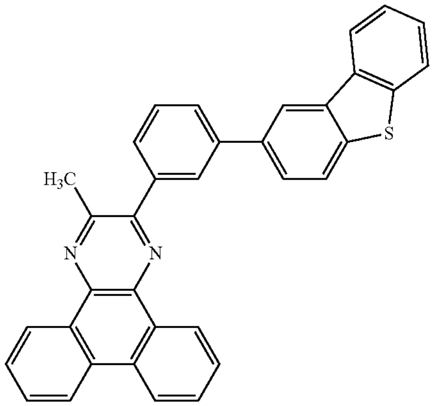
(540)
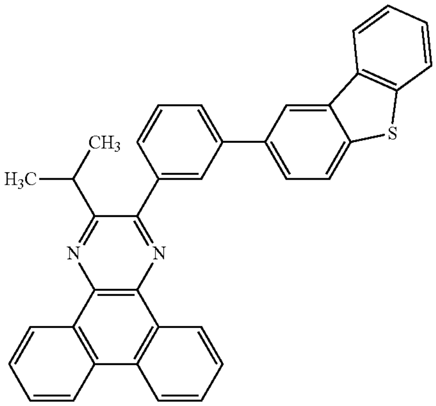
(541)
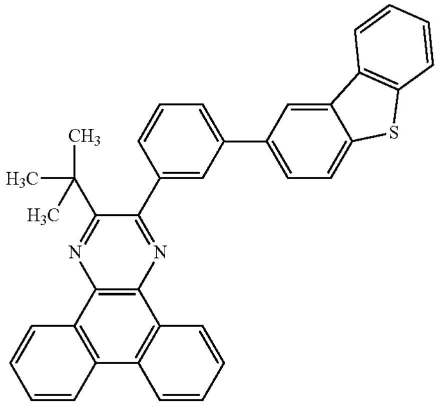
[Chemical Formula 59]
(542)
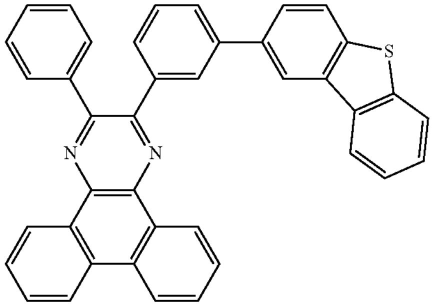
(543)
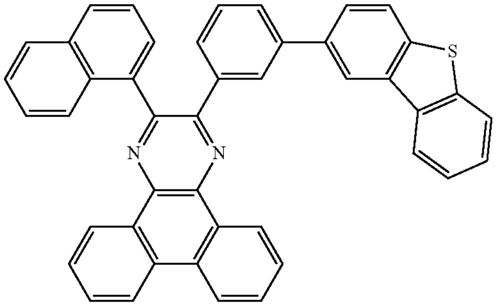

-continued
(544)
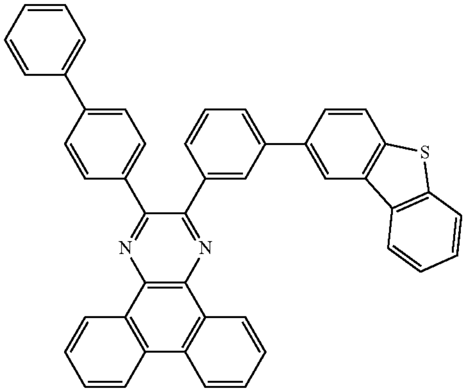
(545)
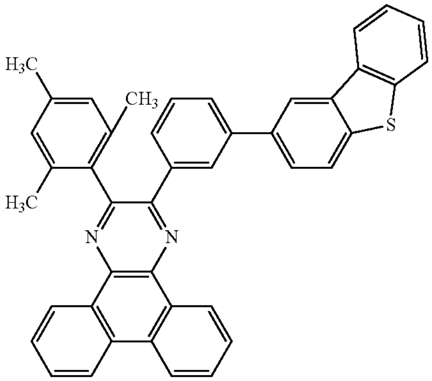
(546)
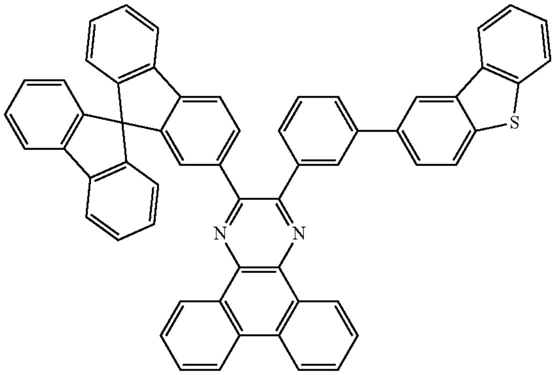
(547)
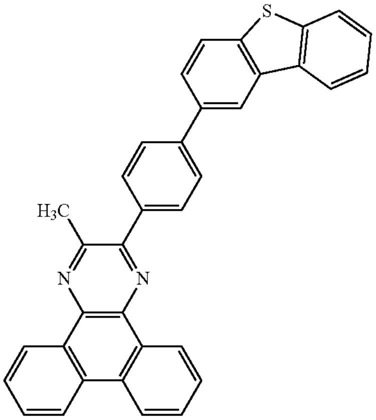
(548)
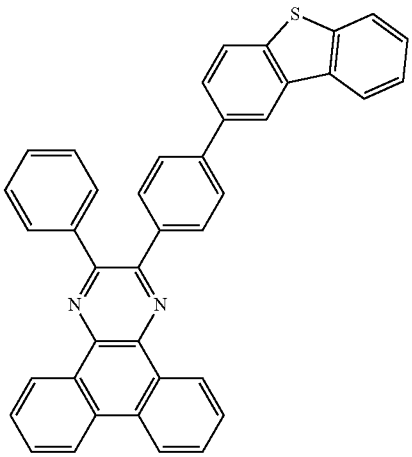
(549)
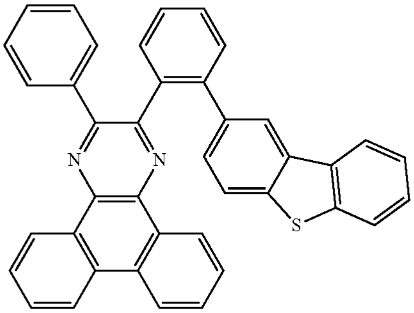
(550)
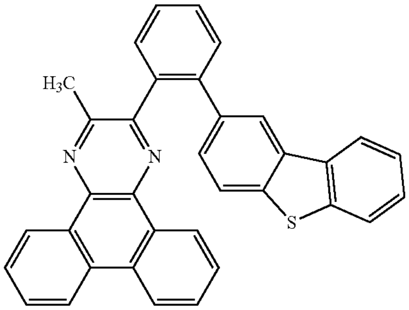

-continued
[Chemical Formula 60]
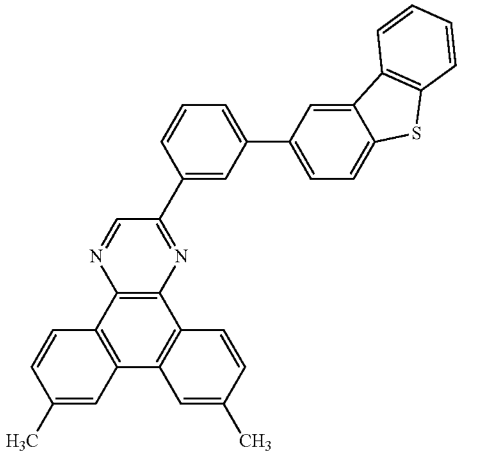
(551)
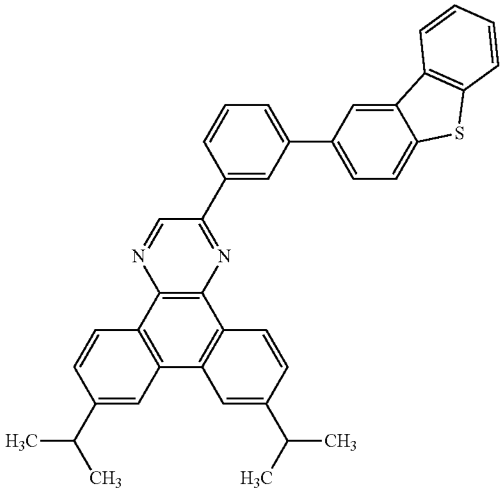
(552)
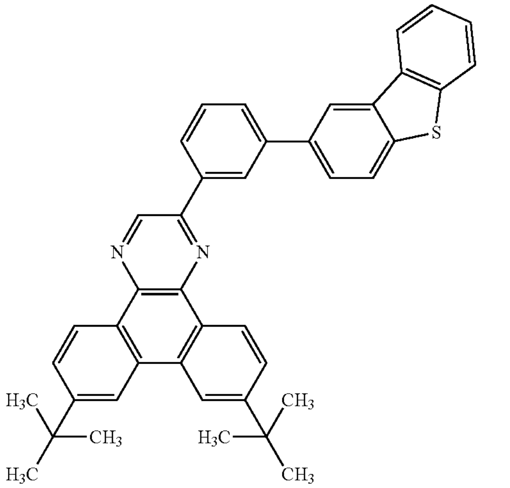
(553)
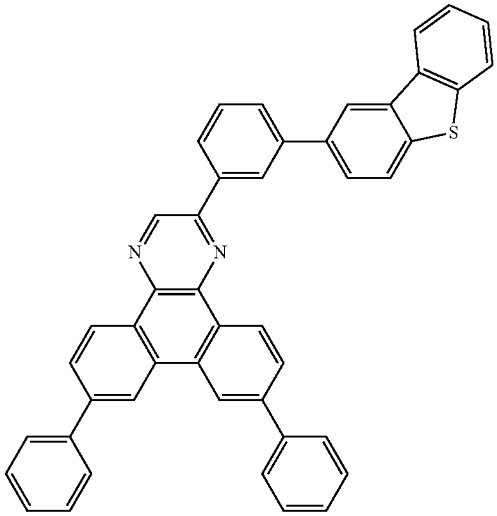
(554)

-continued
(555)
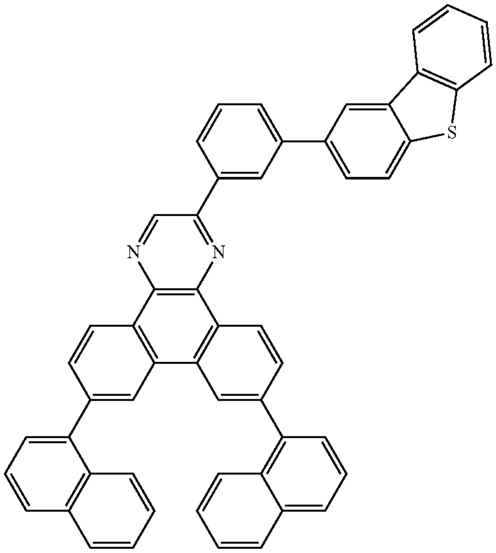
(556)
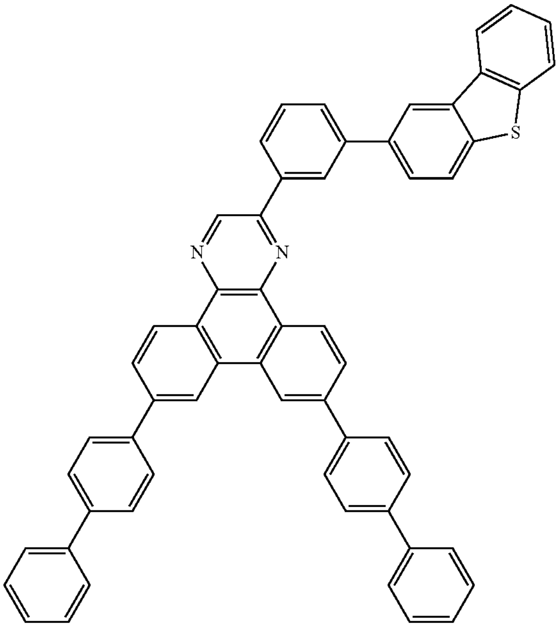
(557)
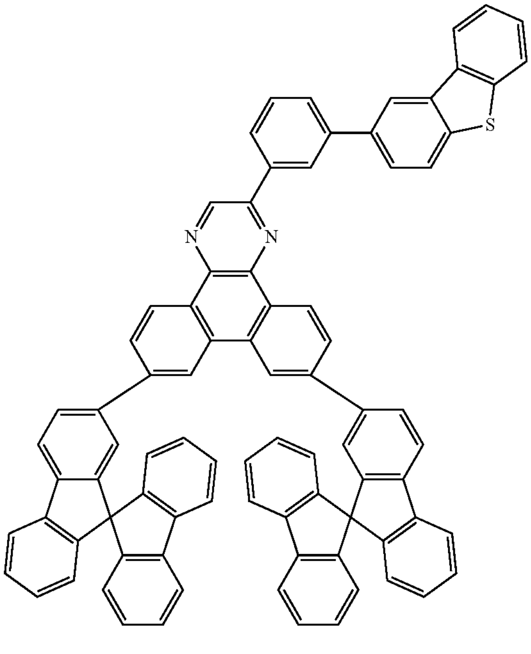
(558)
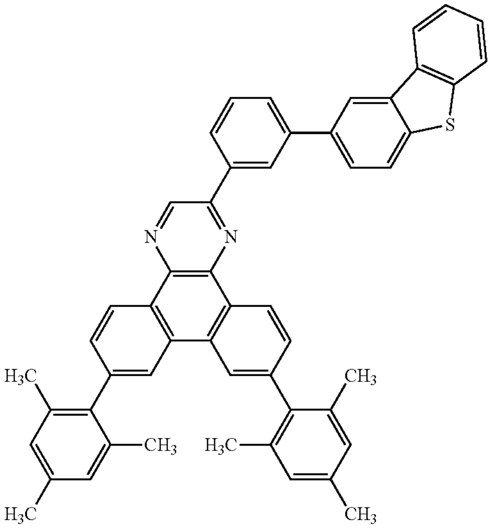

-continued
[Chemical Formula 61]
(559)
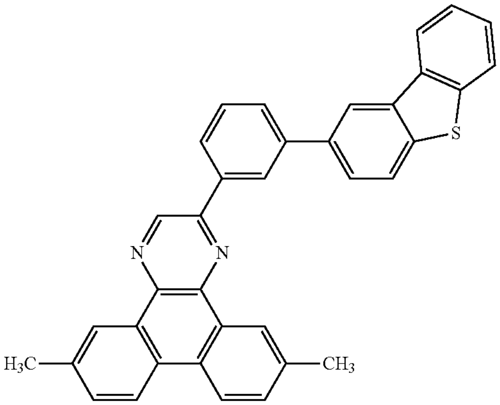
(560)
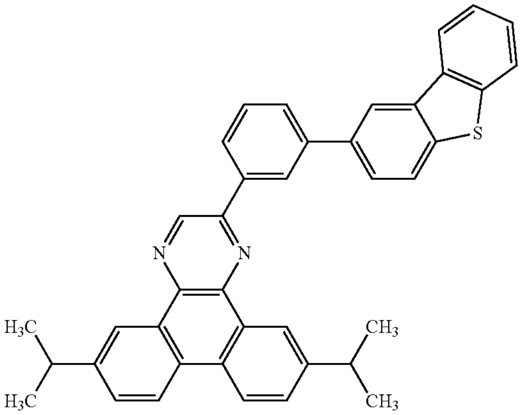
(561)
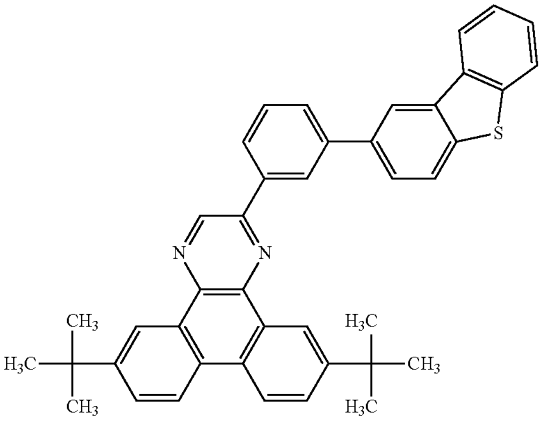
(562)
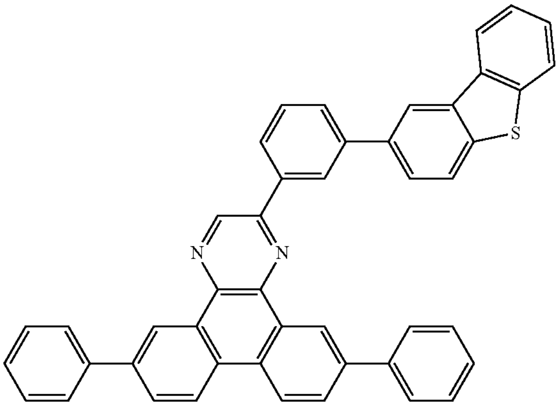
(563)
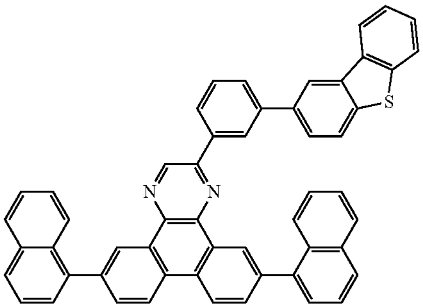
(564)
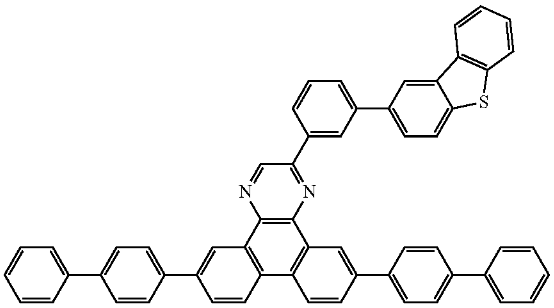
(565)
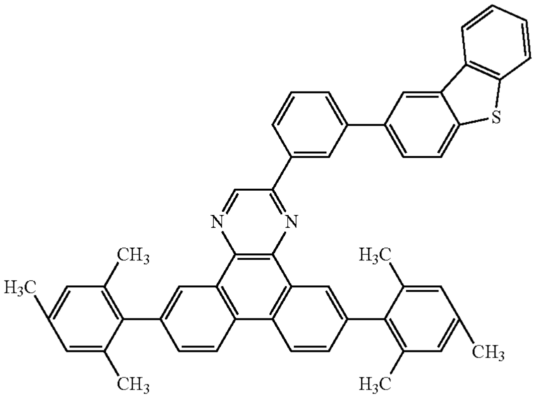

-continued
(566)
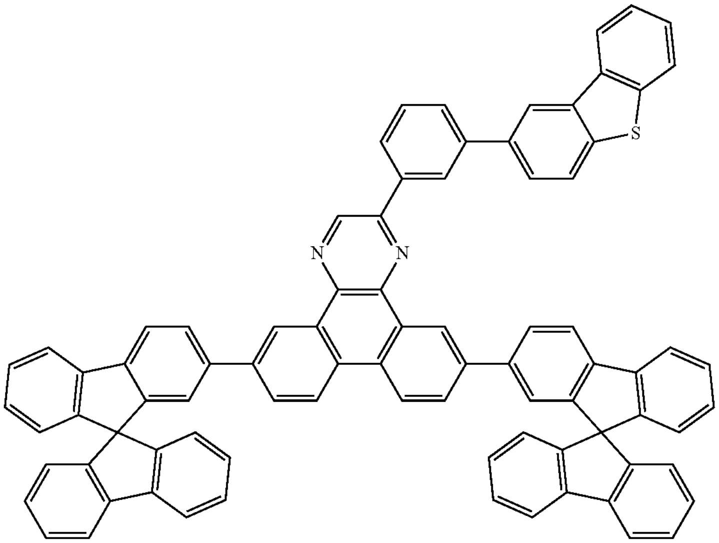
[Chemical Formula 62]
(567)
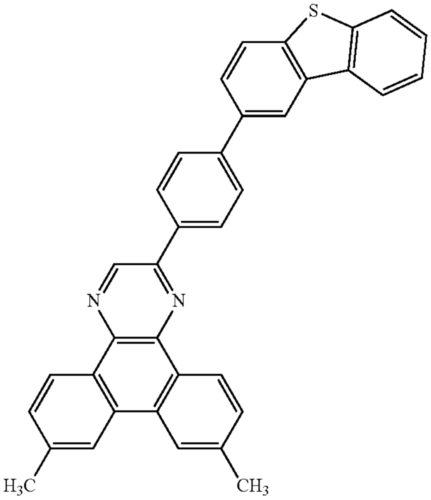
(568)
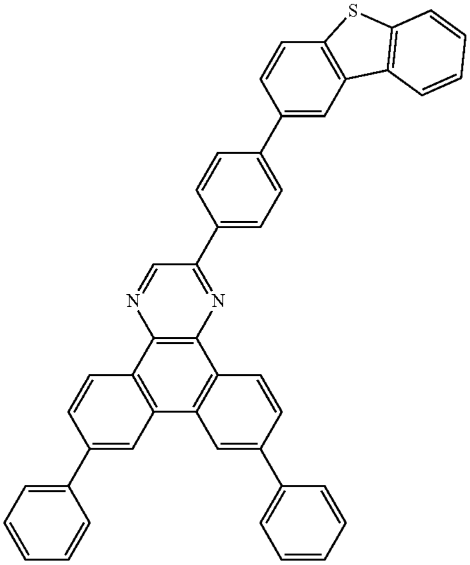

-continued
(569)
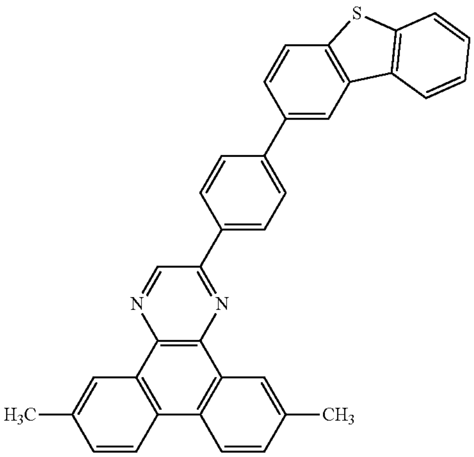
(570)
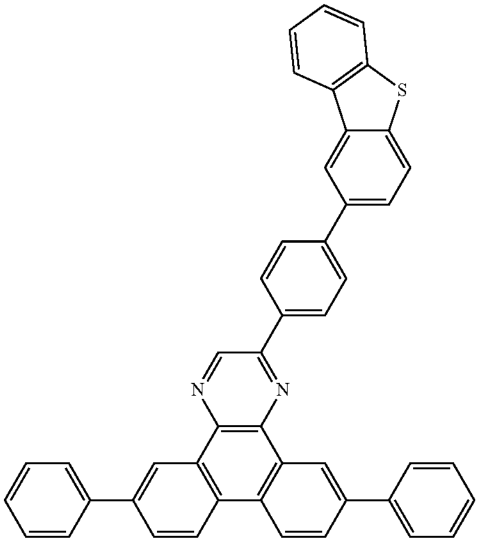
(571)
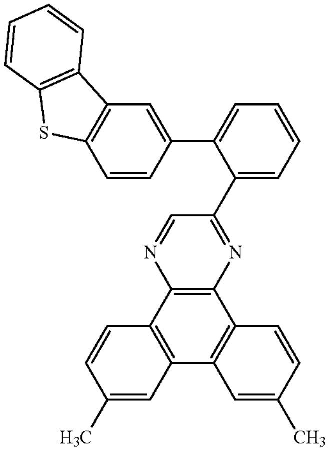
(572)
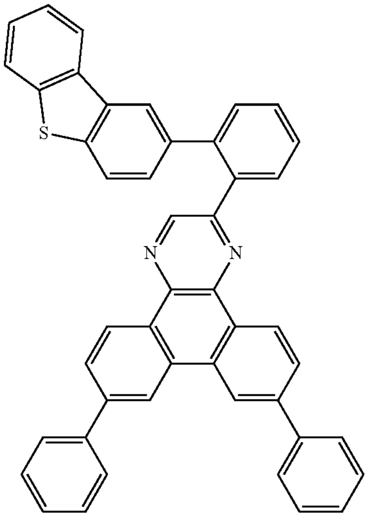
(573)
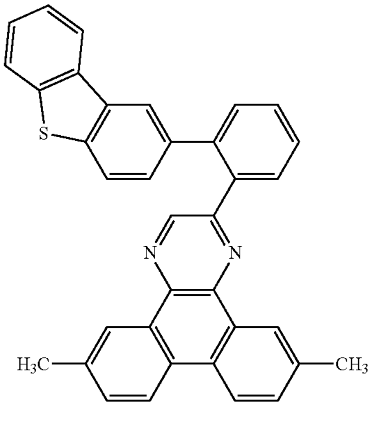
(574)
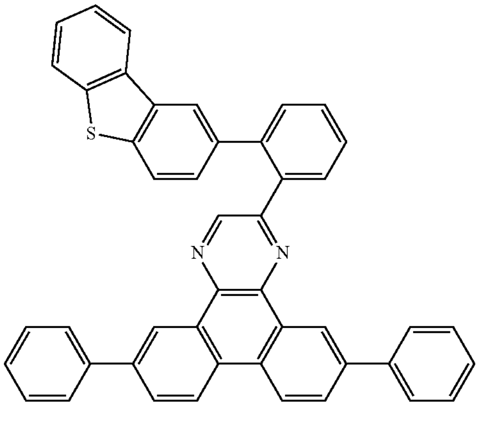

-continued
[Chemical Formula 63]
(600)
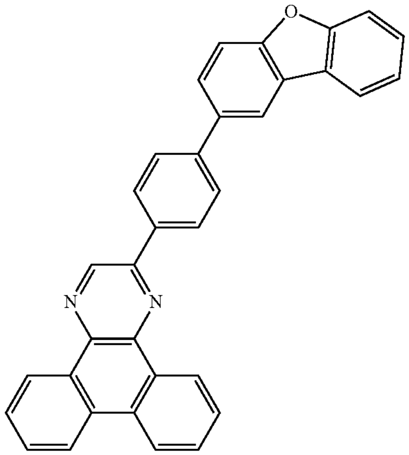
(601)
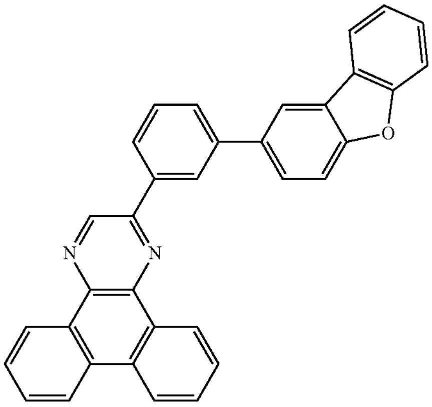
(602)
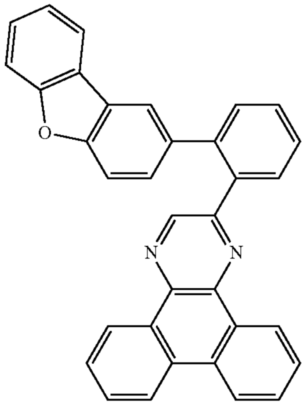
(603)
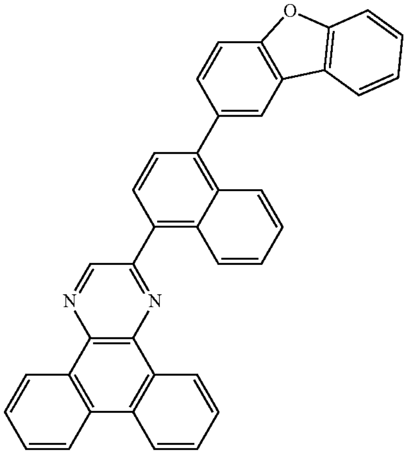
(604)
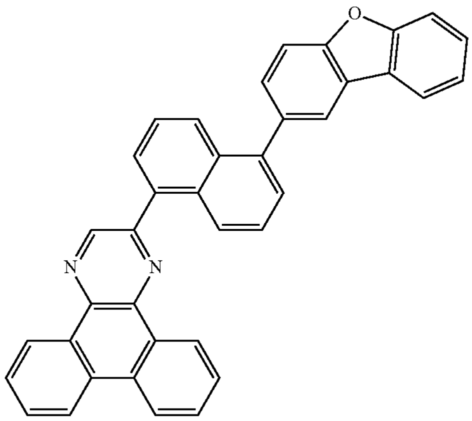
(605)
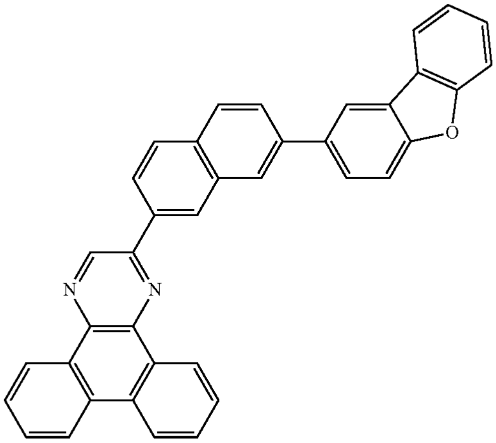

-continued
(606)
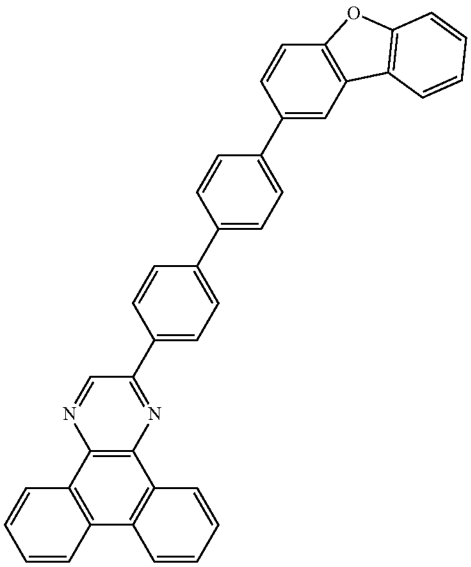
(607)
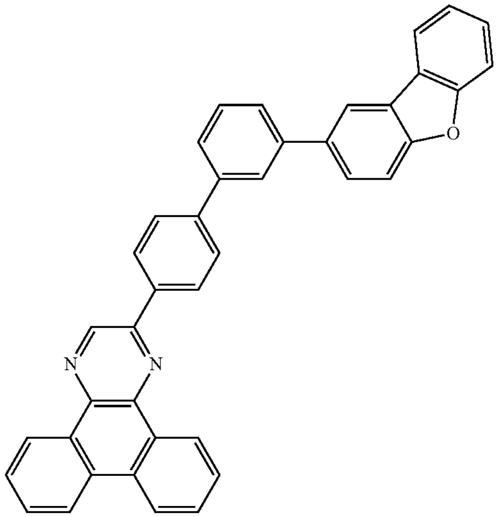
(608)
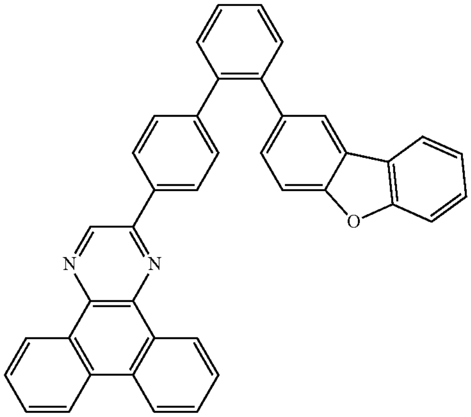
[Chemical Formula 64]
(609)
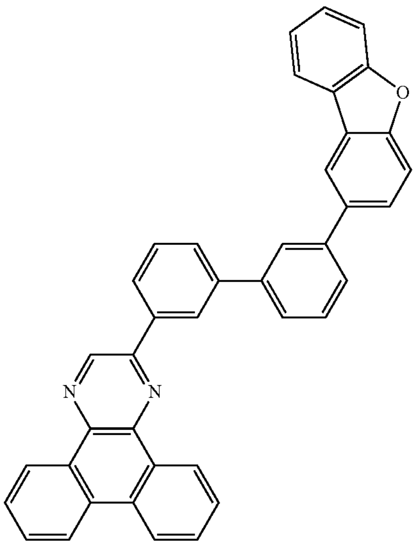
(610)
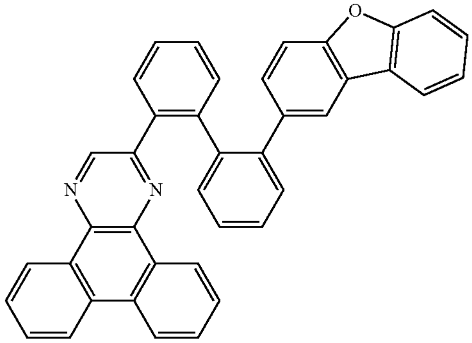

-continued
(611)
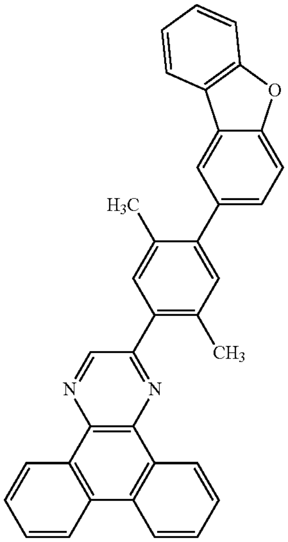
(612)
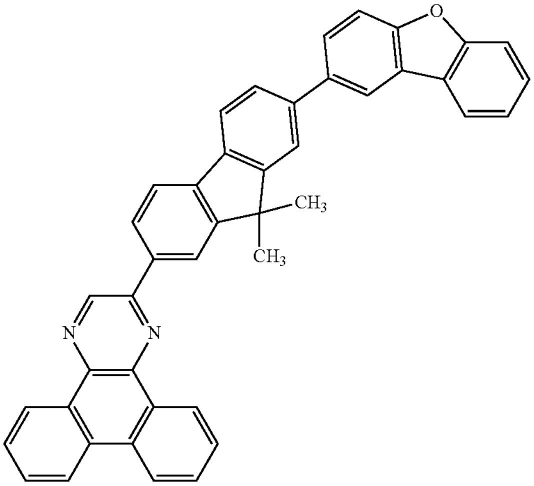
(613)
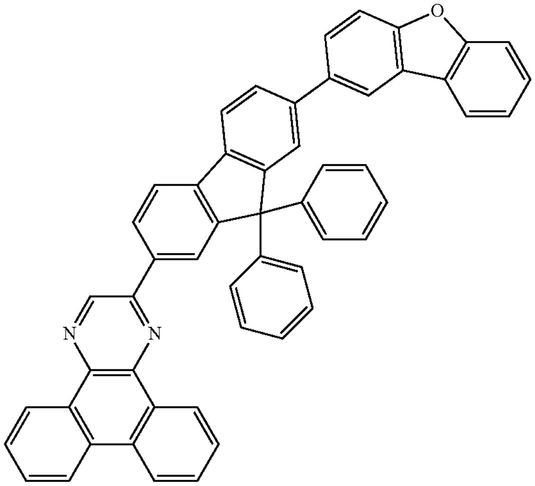
(614)
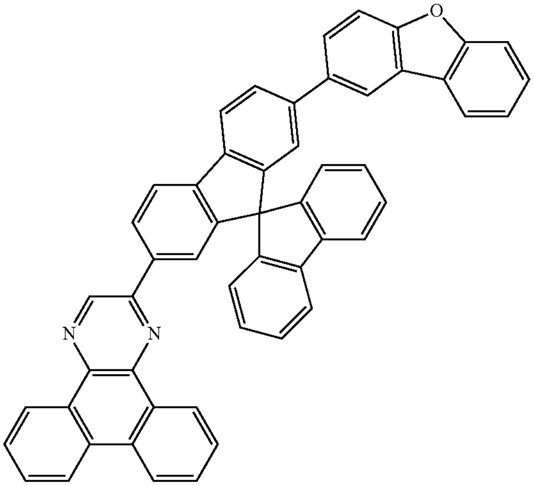
(615)
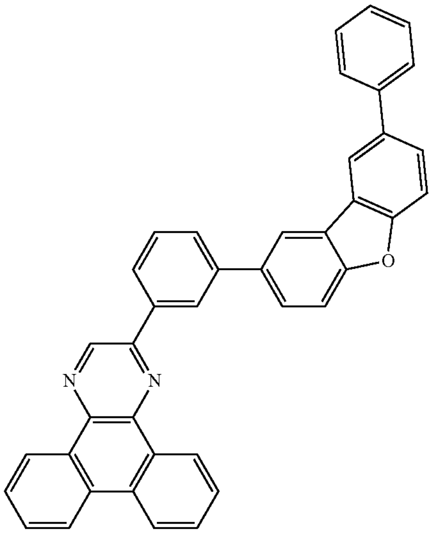

-continued
[Chemical Formula 65]
(616)
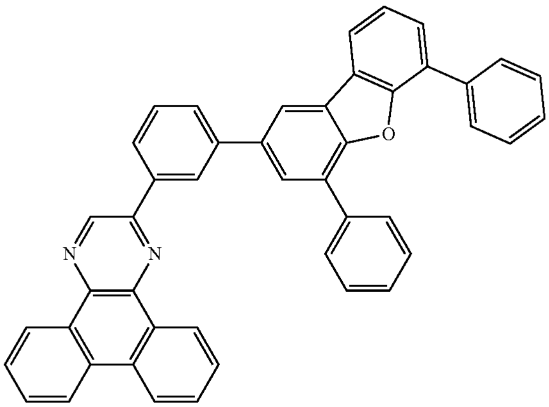
(617)
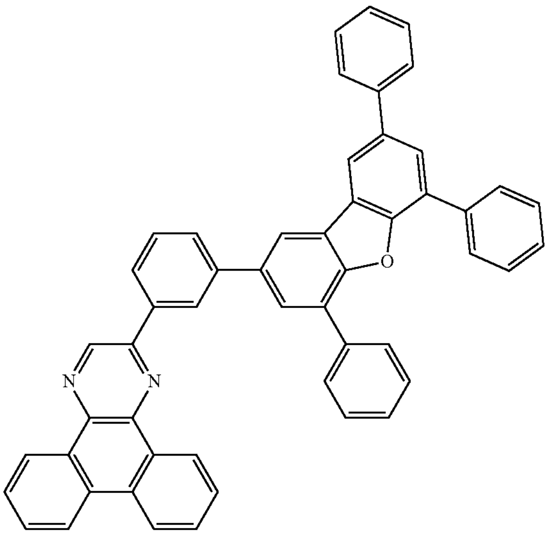
(618)
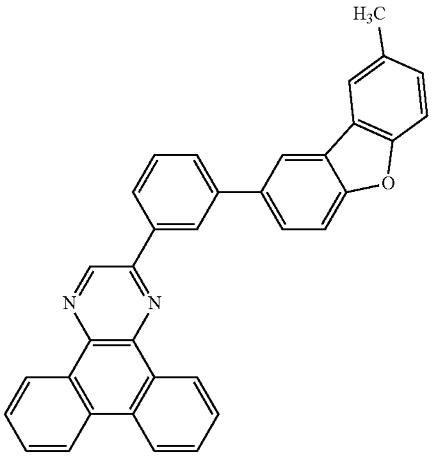
(619)
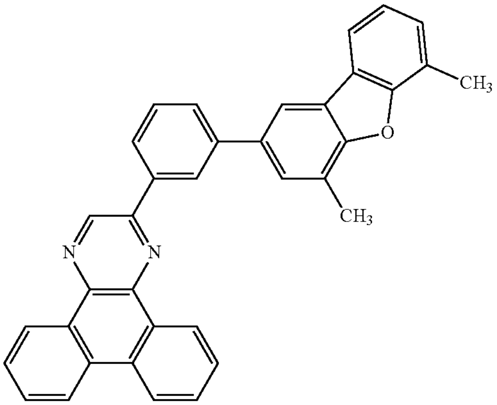
(620)
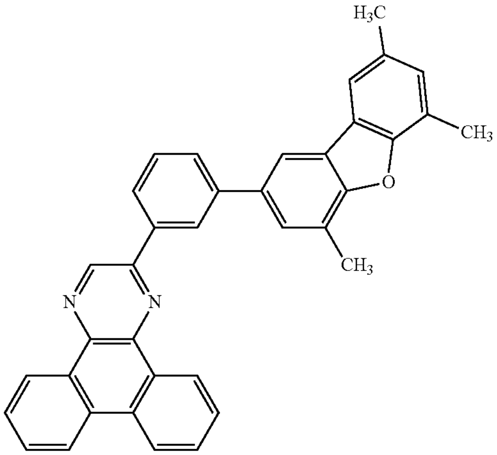
(621)
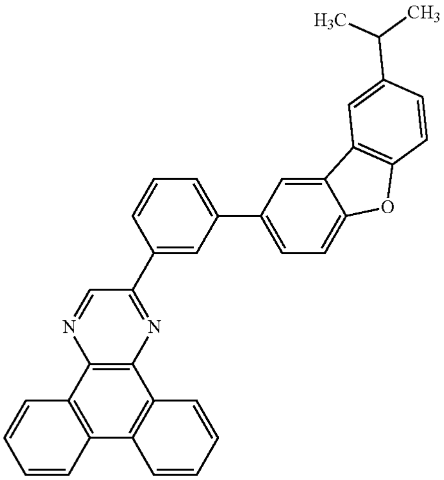

-continued
(622)
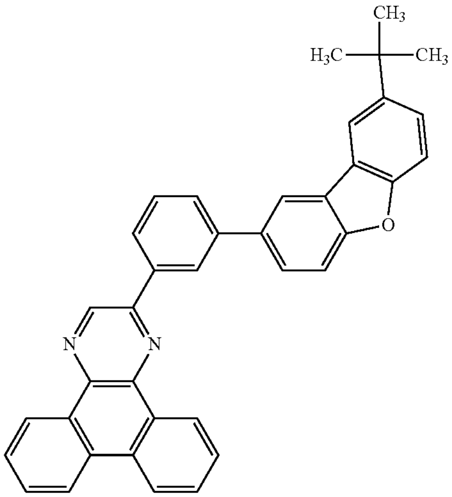
(623)
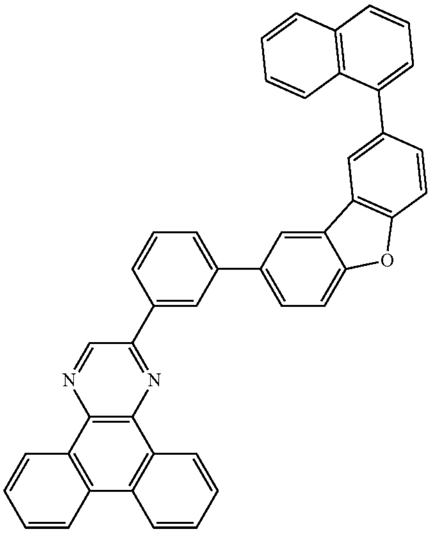
[Chemical Formula 66]
(624)
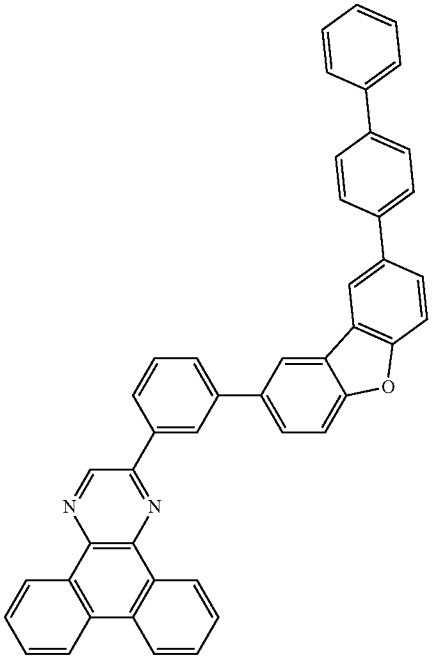
(625)
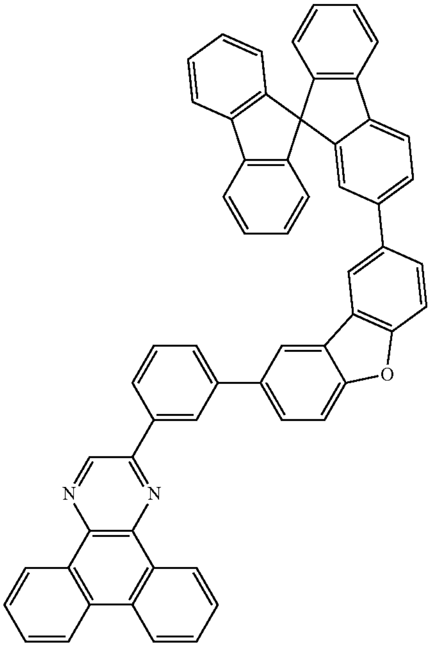

-continued
(626)
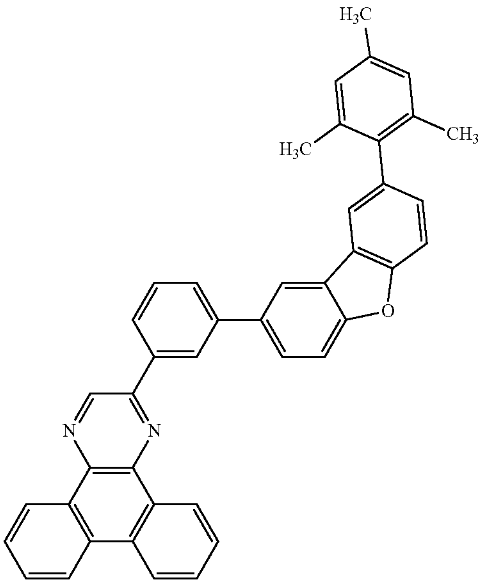
(627)
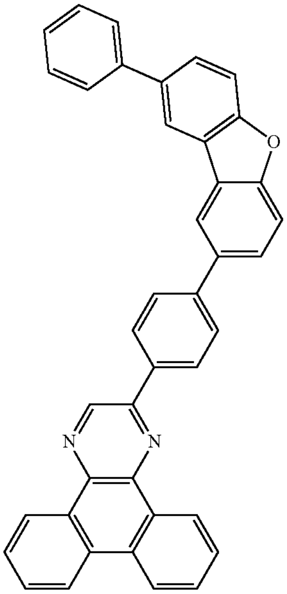
(628)
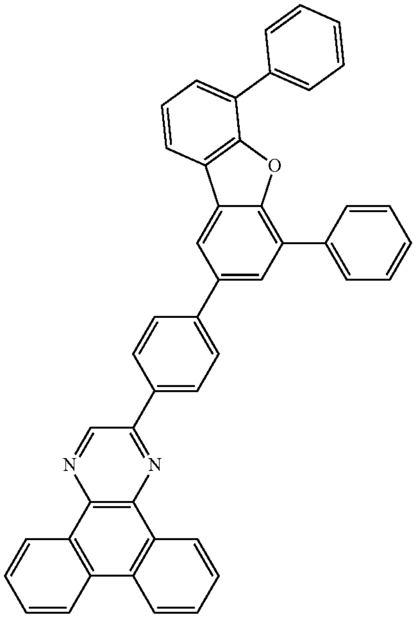
(629)
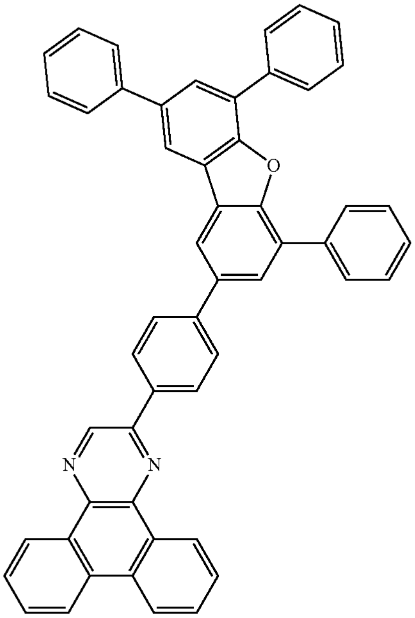

-continued
(630)
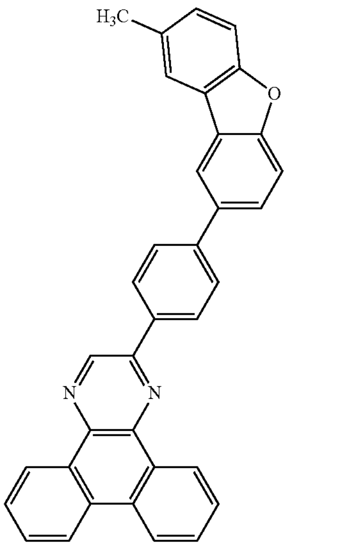
(631)
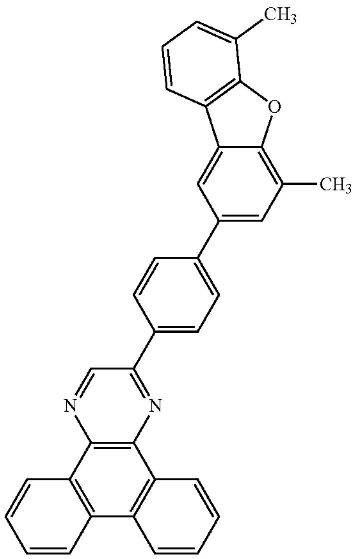
(632)
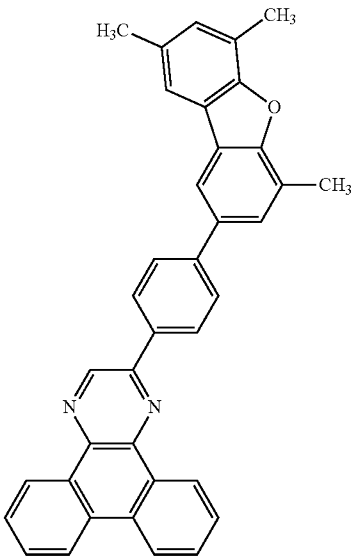

-continued
[Chemical Formula 67]
(633)
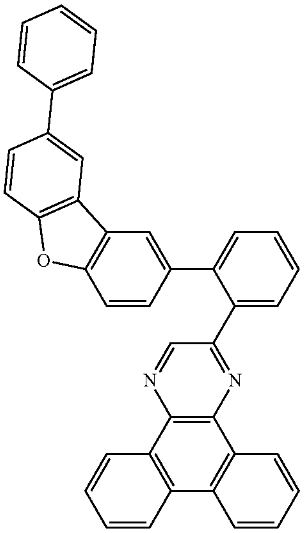
(634)
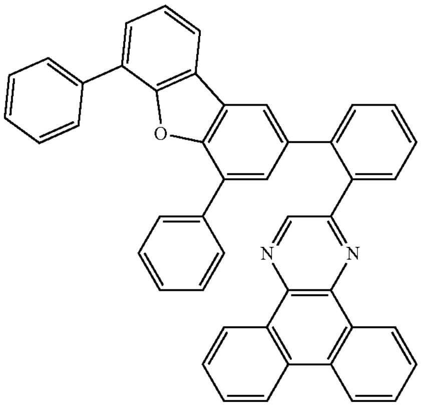
(635)
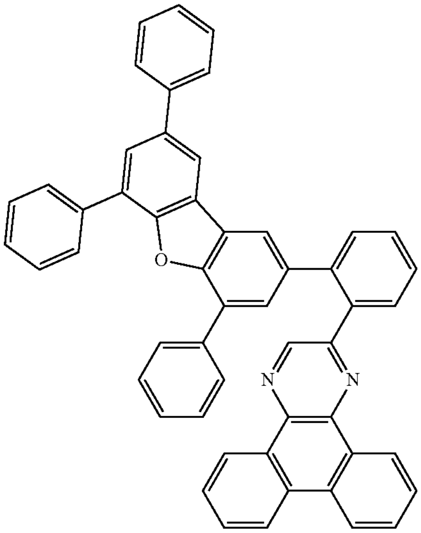
(636)
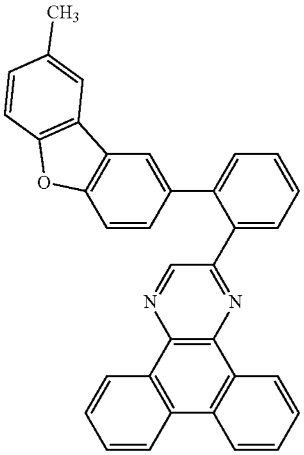
(637)
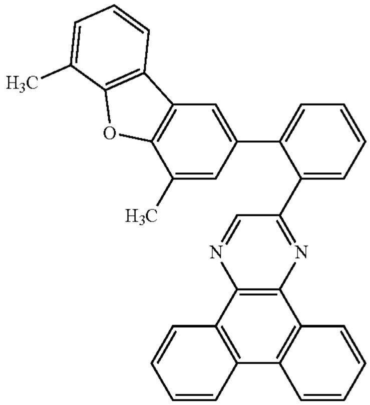
(638)
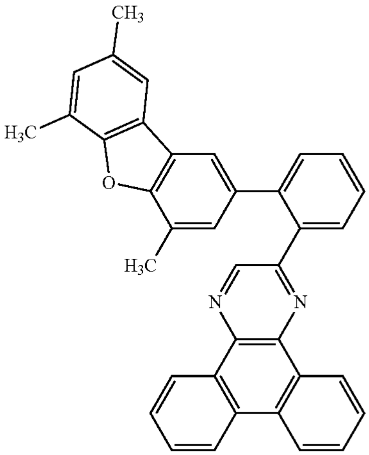

-continued
(639)
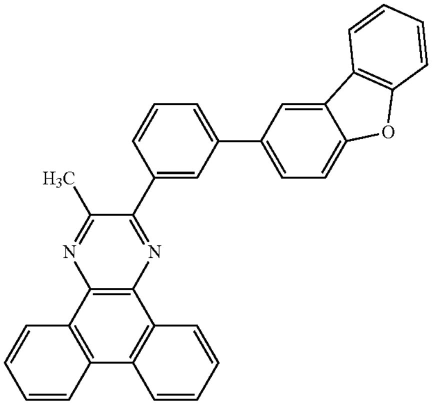
(640)
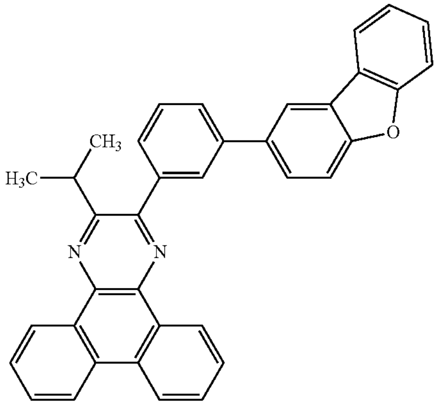
(641)
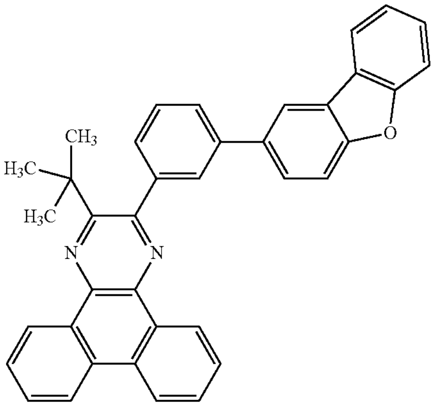
[Chemical Formula 68]
(642)
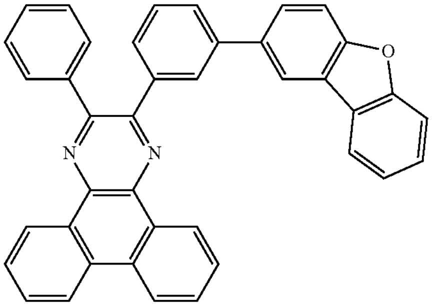
(643)
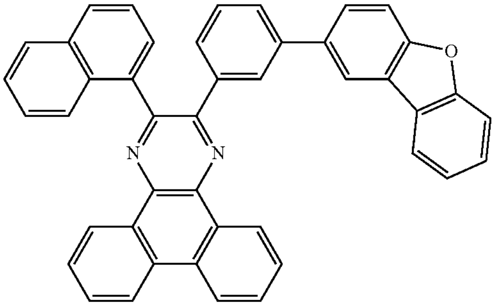
(644)
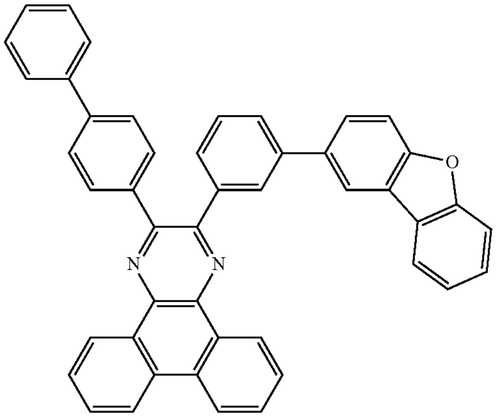
(645)
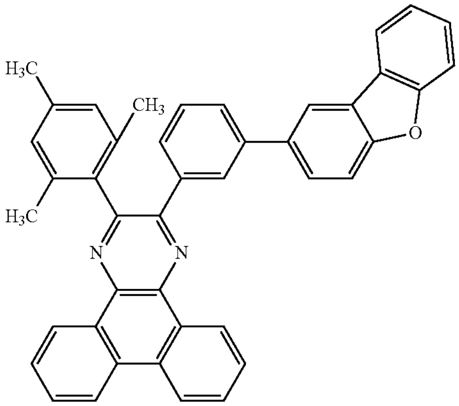

-continued
(646)
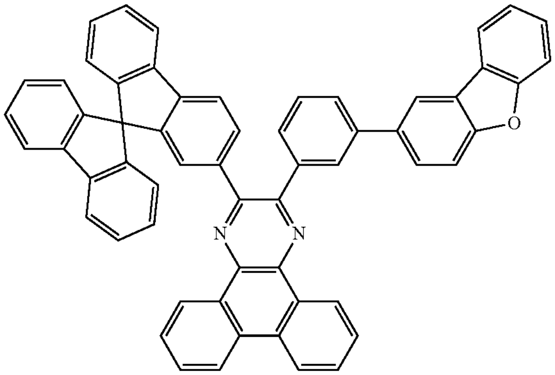
(647)
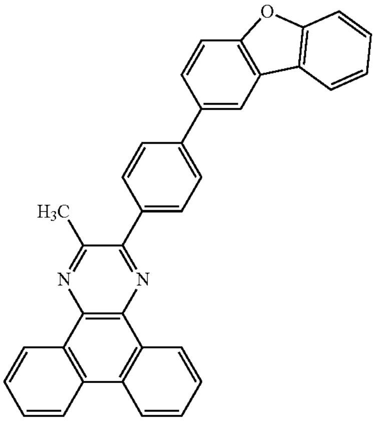
(648)
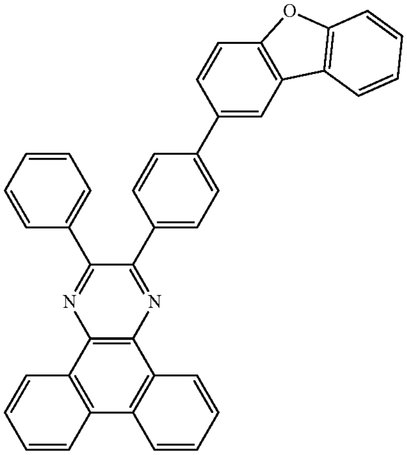
(649)
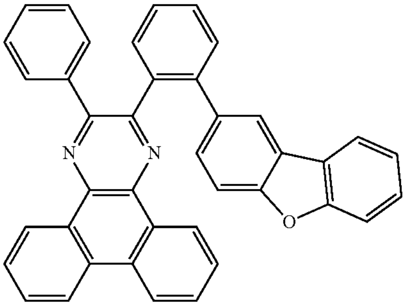
(650)
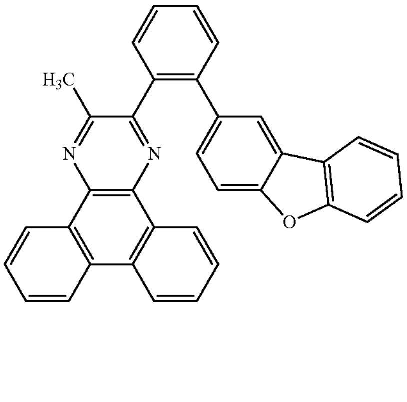

-continued
[Chemical Formula 69]
(651)
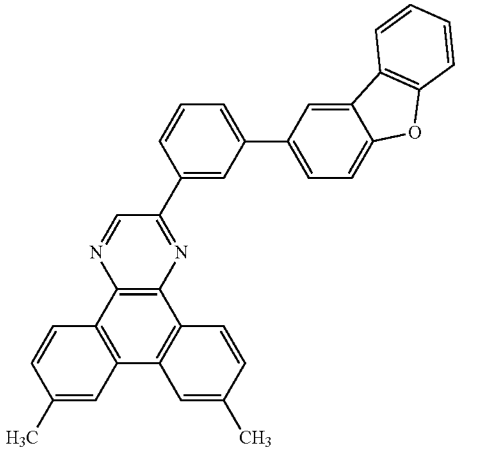
(652)
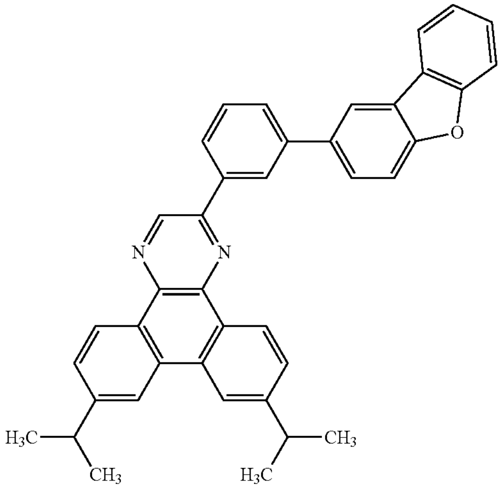
(653)
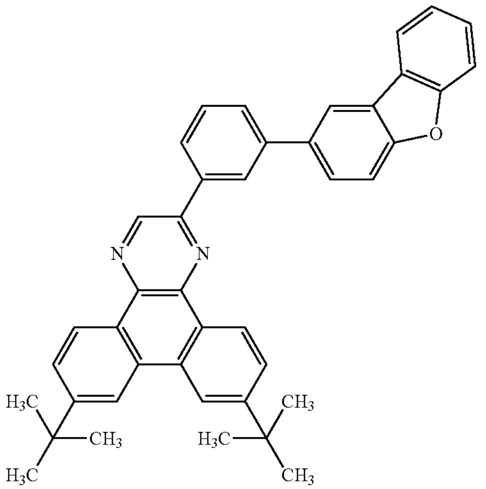
(654)
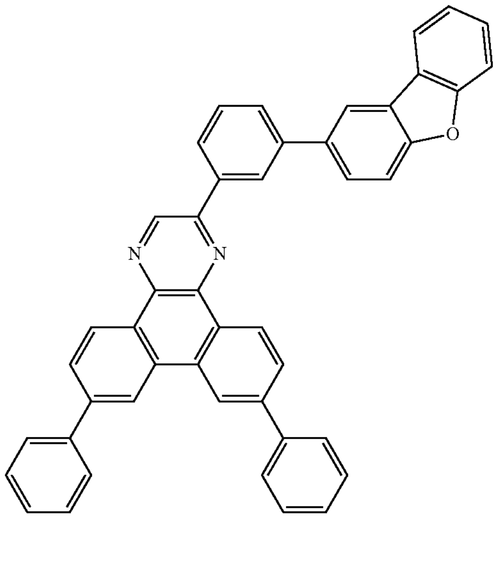

-continued
(655)
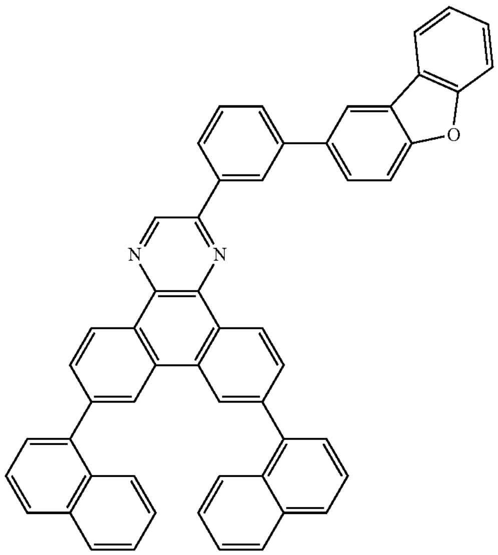
(656)
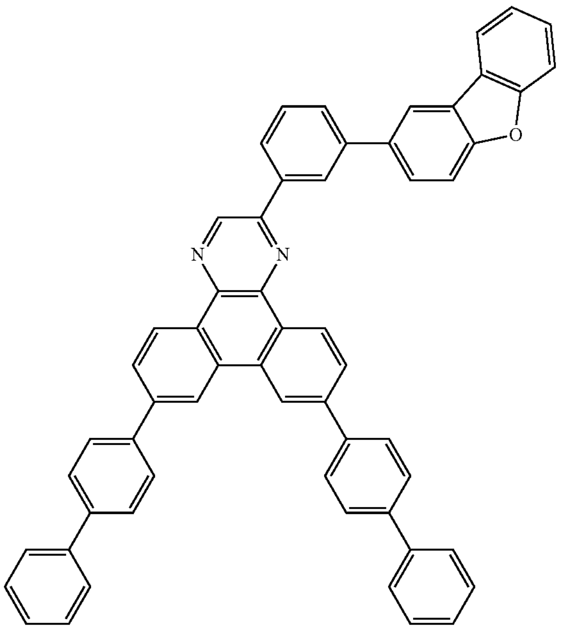
(657)
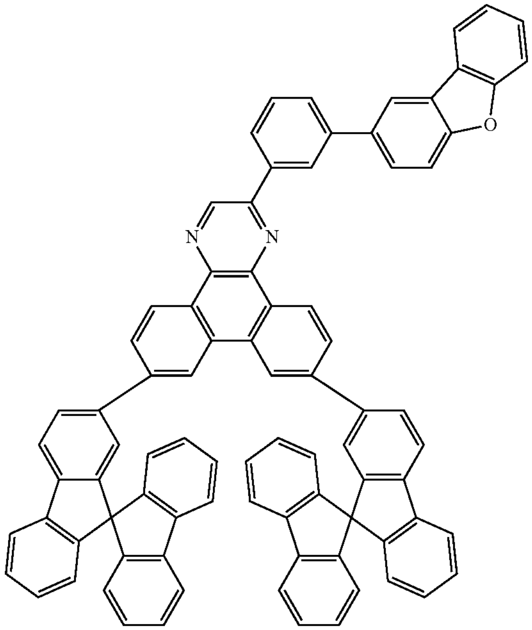
(658)
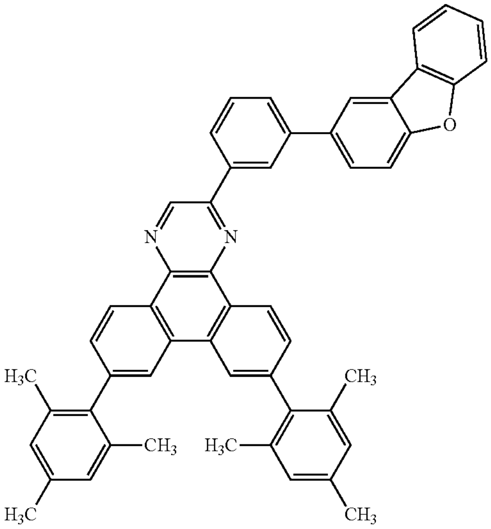

-continued
[Chemical Formula 70
(659)
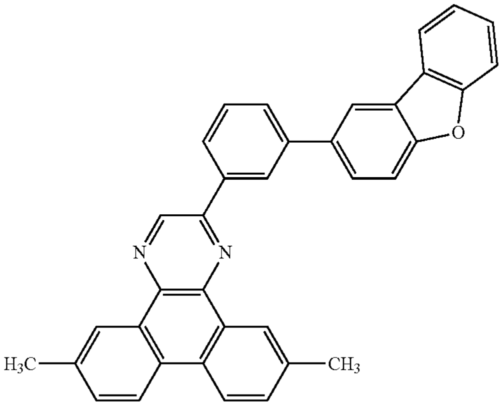
(660)
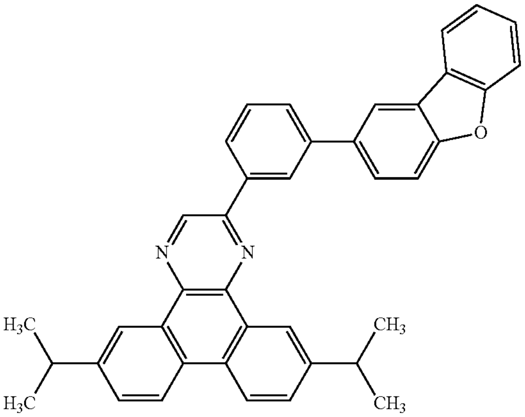
(661)
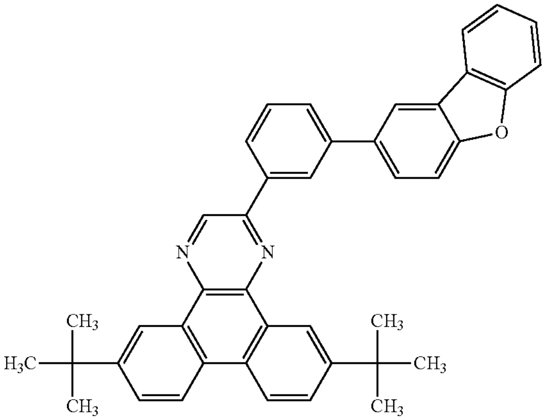
(662)
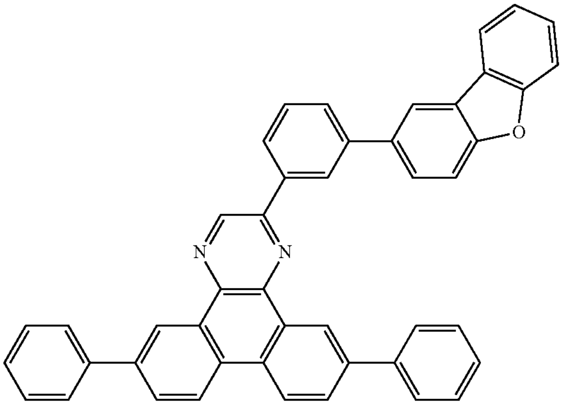
(663)
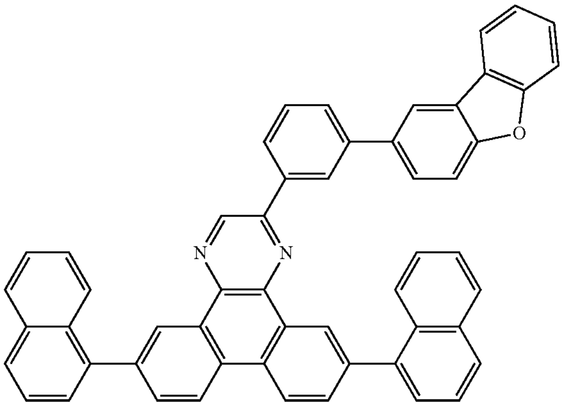

-continued
(664)
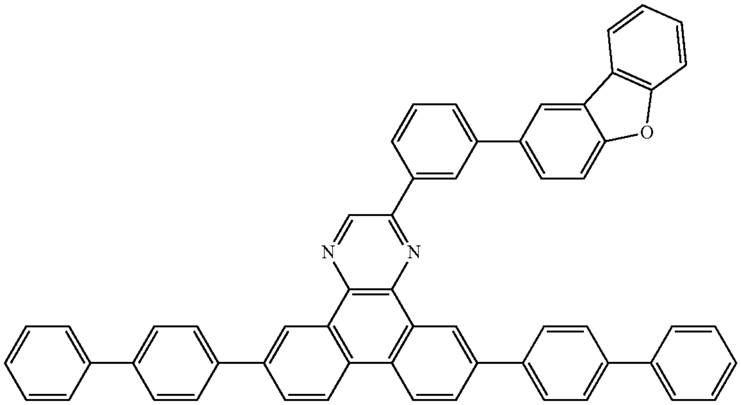
(665)
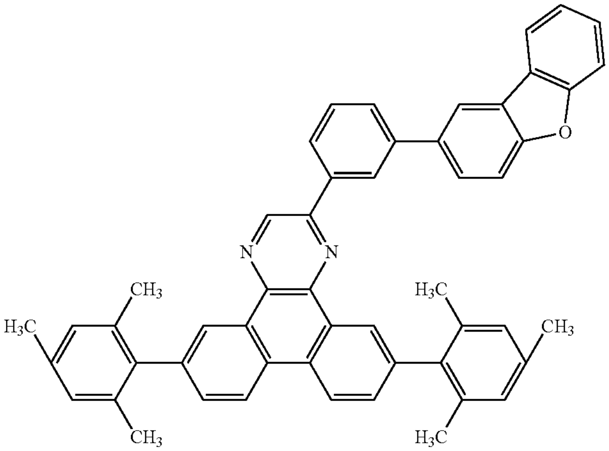
(666)
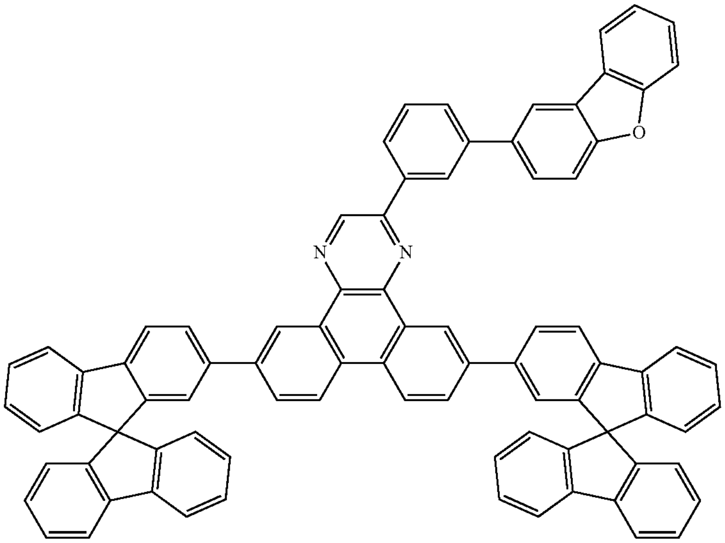

-continued
[Chemical Formula 71]
(667)
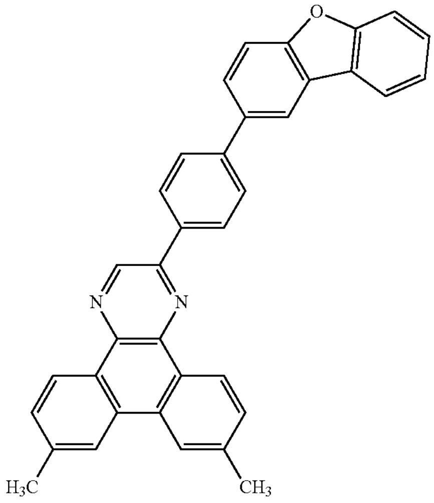
(668)
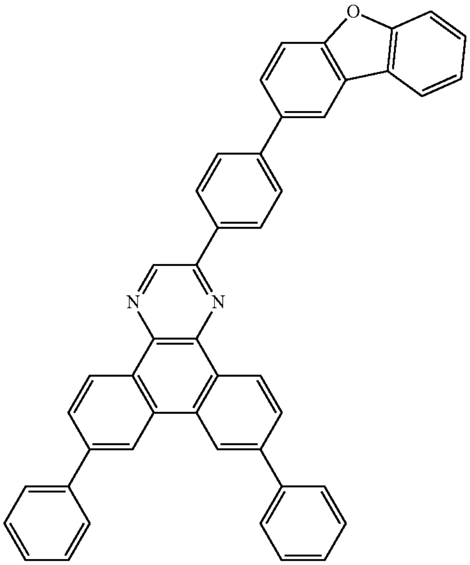
(669)
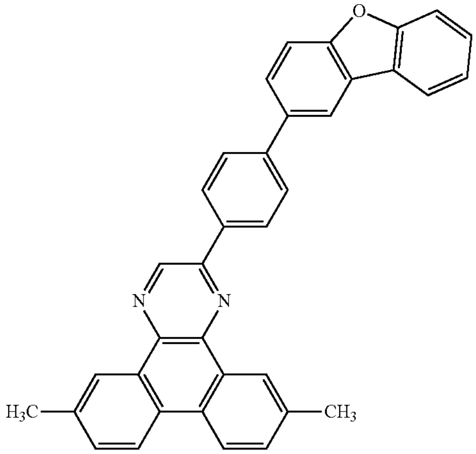
(670)
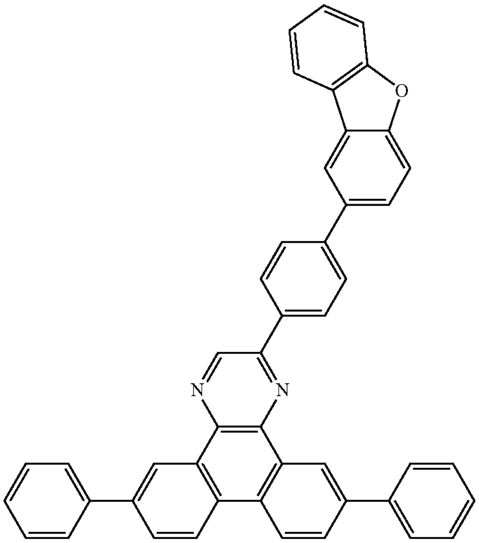
(671)
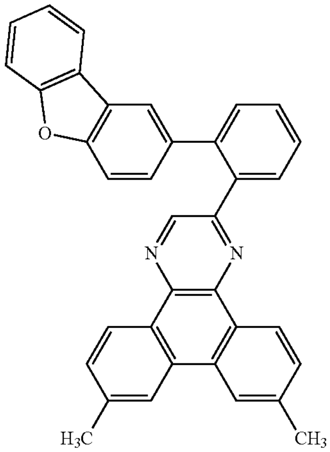
(672)
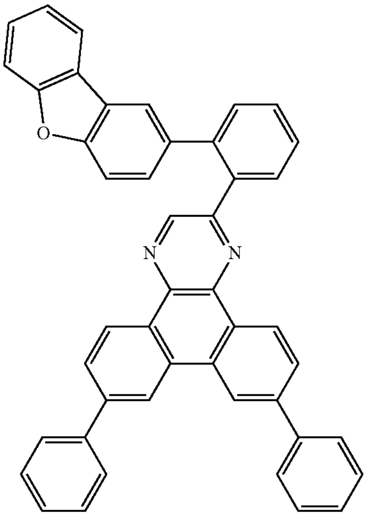

-continued (673)

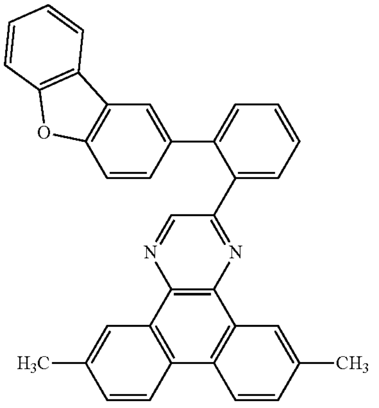

(674)

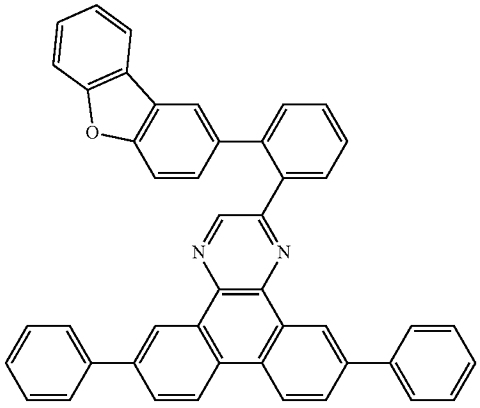

A variety of reactions can be applied to a method of synthesizing a heterocyclic compound of one embodiment of the present invention. For example, synthesis reactions described below enable the synthesis of a heterocyclic compound of one embodiment of the present invention represented by General Formula (G1). Note that the method of synthesizing a heterocyclic compound which is one embodiment of the present invention is not limited to the synthesis methods below.

<Method 1 of Synthesizing Heterocyclic Compound Represented by General Formula (G1)>

First, Synthesis Scheme (A-1) is illustrated below.

[Chemical Formula 72]

(A-1)

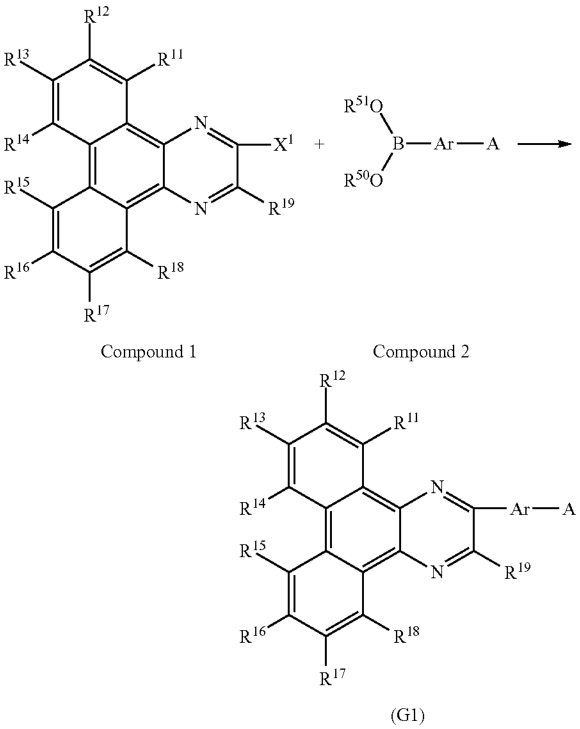

Compound 1

Compound 2

(G1)

The heterocyclic compound (G1) of one embodiment of the present invention can be synthesized as illustrated in Synthesis Scheme (A-1). Specifically, a halide of a dibenzo[f,h]quinoxaline derivative (Compound 1) is coupled with boronic acid or an organoboron compound of a carbazole derivative, a dibenzofuran derivative, or a dibenzothiophene derivative (Compound 2) by a Suzuki-Miyaura reaction, whereby the heterocyclic compound (G1) described in this embodiment can be obtained.

In Synthesis Scheme (A-1), A represents any of a substituted or unsubstituted carbazolyl group, a substituted or unsubstituted dibenzothiophenyl group, and a substituted or unsubstituted dibenzofuranyl group. Ar represents an arylene group having 6 to 13 carbon atoms. The arylene group may have one or more substituents, and the substituents may be bonded to form a ring. $R^{11}$ to $R^{19}$ separately represent any of hydrogen, an alkyl group having 1 to 4 carbon atoms, and a substituted or unsubstituted aryl group having 6 to 13 carbon atoms. $R^{50}$ and $R^{51}$ separately represent hydrogen or an alkyl group having 1 to 6 carbon atoms. In Synthesis Scheme (A-1), $R^{50}$ and $R^{51}$ may be bonded to each other to form a ring. Further, $X^1$ represents a halogen.

Examples of the palladium catalyst that can be used in Synthesis Scheme (A-1) include, but are not limited to, palladium(II) acetate, tetrakis(triphenylphosphine)palladium (0), bis(triphenylphosphine)palladium(II) dichloride, and the like.

Examples of the ligand of the palladium catalyst which can be used in Synthesis Scheme (A-1) include, but are not limited to, tri(ortho-tolyl)phosphine, triphenylphosphine, tricyclohexylphosphine, and the like.

Examples of the base that can be used in Synthesis Scheme (A-1) include, but are not limited to, organic bases such as sodium tert-butoxide, inorganic bases such as potassium carbonate and sodium carbonate, and the like.

Examples of the solvent that can be used in Synthesis Scheme (A-1) include, but are not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. It is more preferable to use a mixed solvent of toluene and water, a mixed solvent of toluene, ethanol, and water, or a mixed solvent of water and an ether such as ethylene glycol dimethyl ether.

As a coupling reaction illustrated in Synthesis Scheme (A-1), the Suzuki-Miyaura reaction using the organoboron compound or the boronic acid represented by Compound 2 may be replaced with a cross coupling reaction using an organoaluminum compound, an organozirconium compound, an organozinc compound, an organotin compound, or the like. However, the present invention is not limited thereto.

Further, in the Suzuki-Miyaura Coupling Reaction illustrated in Synthesis Scheme (A-1), an organoboron compound or boronic acid of a dibenzo[f,h]quinoxaline derivative may be coupled with a halide of a carbazole derivative, a dibenzofuran derivative, or a dibenzothiophene derivative or with a carbazole derivative, a dibenzofuran derivative, or a dibenzothiophene derivative which has a triflate group as a substituent, by the Suzuki-Miyaura reaction.

Thus, a heterocyclic compound of this embodiment can be synthesized.

<Method 2 of Synthesizing Heterocyclic Compound Represented by General Formula (G1)>

Another method of synthesizing the heterocyclic compound represented by General Formula (G1) will be described below. First, Synthesis Scheme (B-1) in which a boron compound of A is used as a material is illustrated below.

[Chemical Formula 73]

(B-1)

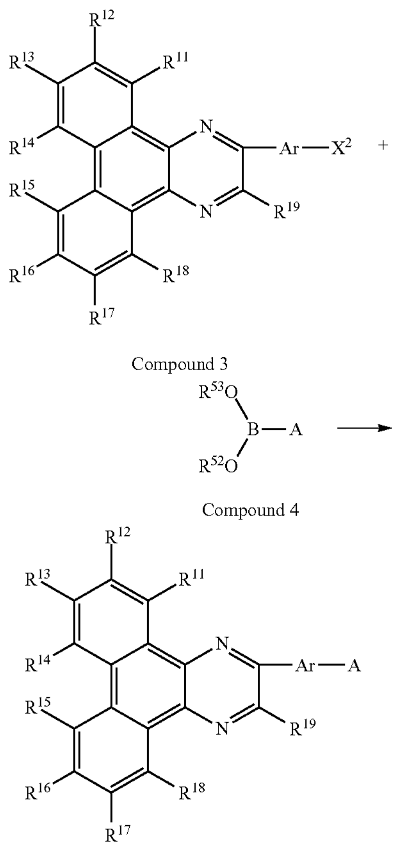

Compound 3

Compound 4

(G1)

As illustrated in Synthesis Scheme (B-1), a halide of a dibenzo[f,h]quinoxaline derivative (Compound 3) is coupled with an organoboron compound or boronic acid of a carbazole derivative, a dibenzofuran derivative, or a dibenzothiophene derivative (Compound 4) by a Suzuki-Miyaura reaction, whereby the heterocyclic compound (G1) described in this embodiment can be obtained.

In Synthesis Scheme (B-1), A represents any of a substituted or unsubstituted carbazolyl group, a substituted or unsubstituted dibenzothiophenyl group, and a substituted or unsubstituted dibenzofuranyl group. Ar represents an arylene group having 6 to 13 carbon atoms. The arylene group may have one or more substituents, and the substituents may be bonded to form a ring. $R^{11}$ to $R^{19}$ separately represent hydrogen, an alkyl group having 1 to 4 carbon atoms, or a substituted or unsubstituted aryl group having 6 to 13 carbon atoms. $R^{52}$ and $R^{53}$ separately represent hydrogen or an alkyl group having 1 to 6 carbon atoms. In Synthesis Scheme (B-1), $R^{52}$ and $R^{53}$ may be bonded to each other to form a ring. Further, $X^2$ represents a halogen or a triflate group, and, as a halogen, preferably iodine or bromine.

Examples of the palladium catalyst that can be used in Synthesis Scheme (B-1) include, but are not limited to, palladium(II) acetate, tetrakis(triphenylphosphine)palladium (0), bis(triphenylphosphine)palladium(II) dichloride, and the like.

Examples of the ligand of the palladium catalyst which can be used in Synthesis Scheme (B-1) include, but are not limited to, tri(ortho-tolyl)phosphine, triphenylphosphine, tricyclohexylphosphine, and the like.

Examples of the base that can be used in Synthesis Scheme (B-1) include, but are not limited to, organic bases such as sodium tert-butoxide, inorganic bases such as potassium carbonate and sodium carbonate, and the like.

Examples of the solvent that can be used in Synthesis Scheme (B-1) include, but are not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. It is more preferable to use a mixed solvent of toluene and water, a mixed solvent of toluene, ethanol, and water, or a mixed solvent of water and an ether such as ethylene glycol dimethyl ether.

As a coupling reaction illustrated in Synthesis Scheme (B-1), the Suzuki-Miyaura reaction using the organoboron compound or the boronic acid represented by Compound 4 may be replaced with a cross coupling reaction using an organoaluminum compound, an organozirconium compound, an organozinc compound, an organotin compound, or the like. However, the present invention is not limited thereto. Further, in this coupling, a triflate group or the like may be used other than a halogen; however, the present invention is not limited thereto.

Further, in the Suzuki-Miyaura Coupling Reaction illustrated in Synthesis Scheme (B-1), an organoboron compound or boronic acid of a dibenzo[f,h]quinoxaline derivative may be coupled with a halide of a carbazole derivative, a dibenzofuran derivative, or a dibenzothiophene derivative or with a carbazole derivative, a dibenzofuran derivative, or a dibenzothiophene derivative which has a triflate group as a substituent, by the Suzuki-Miyaura reaction.

To synthesize the heterocyclic compound represented by General Formula (G1) in which A is a substituted or unsubstituted N-carbazolyl group, the following Synthesis Scheme (B-2) is employed, thereby obtaining the heterocyclic compound represented by General Formula (G2-2).

[Chemical Formula 74]

(B-2)

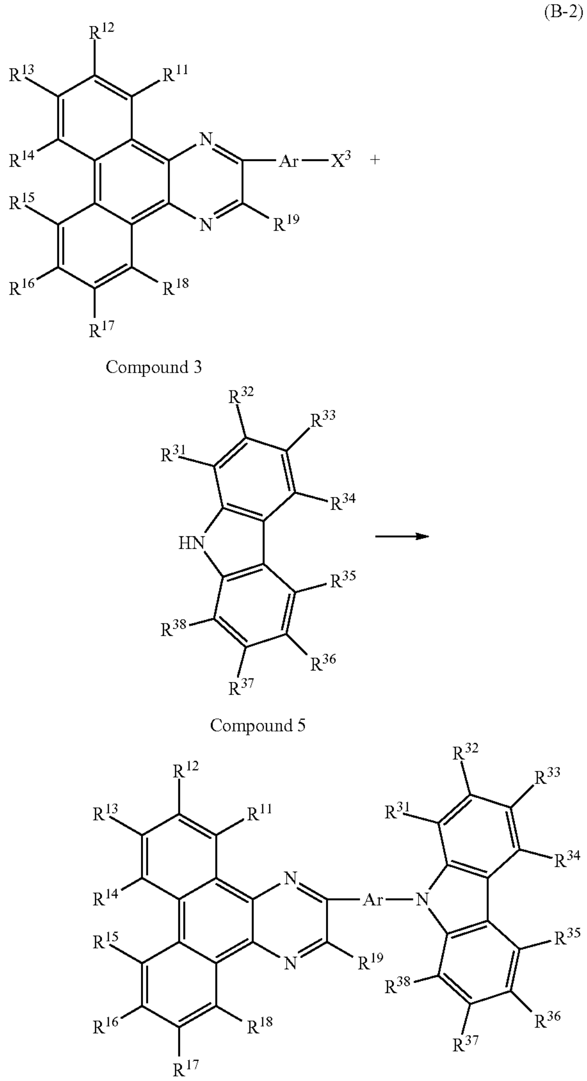

Compound 3

Compound 5

(G2-2)

As illustrated in Synthesis Scheme (B-2), a halide of a dibenzo[f,h]quinoxaline derivative (Compound 3) is coupled with a 9H-carbazole derivative (Compound 5) using a metal catalyst, metal, or a metal compound in the presence of a base, whereby the heterocyclic compound (G2-2) described in this embodiment can be obtained.

In Synthesis Scheme (B-2), $R^{11}$ to $R^{19}$ separately represent hydrogen, an alkyl group having 1 to 4 carbon atoms, or a substituted or unsubstituted aryl group having 6 to 13 carbon atoms. Ar represents an arylene group having 6 to 13 carbon atoms. The arylene group may have one or more substituents, and the substituents may be bonded to form a ring. $R^{31}$ to $R^{38}$ separately represent hydrogen, an alkyl group having 1 to 4 carbon atoms, or a substituted or unsubstituted aryl group having 6 to 13 carbon atoms. Further, $X^3$ represents a halogen or a triflate group, and, as a halogen, preferably iodine or bromine.

In the case where the Hartwig-Buchwald reaction is performed in Synthesis Scheme (B-2), bis(dibenzylideneacetone)palladium(0), palladium(II) acetate, or the like can be given as the palladium catalyst that can be used.

Examples of the ligand of the palladium catalyst which can be used in Synthesis Scheme (B-2) include tri(tert-butyl) phosphine, tri(n-hexyl)phosphine, tricyclohexylphosphine, and the like.

Examples of the base that can be used in Synthesis Scheme (B-2) include organic bases such as sodium tert-butoxide, inorganic bases such as potassium carbonate, and the like.

Examples of the solvent that can be used in Synthesis Scheme (B-2) include toluene, xylene, benzene, tetrahydrofuran, and the like.

Other than the Hartwig-Buchwald reaction, the Ullmann reaction or the like may be used, and the reaction that can be used is not limited to these.

Thus, the heterocyclic compound of this embodiment can be synthesized.

A heterocyclic compound of one embodiment of the present invention has a wide band gap. Accordingly, by use of such a heterocyclic compound for a light-emitting element, as a host material of a light-emitting layer in which a light-emitting substance is dispersed, high current efficiency can be obtained. In particular, a heterocyclic compound of one embodiment of the present invention is suitably used as a host material in which a phosphorescent compound is dispersed. Further, since a heterocyclic compound of this embodiment is a substance having a high electron-transport property, it can be suitably used as a material for an electron-transport layer in a light-emitting element. By the use of a heterocyclic compound of this embodiment, a light-emitting element having low driving voltage can be realized. In addition, a light-emitting element having high current efficiency can be realized. A light-emitting element having a long lifetime can also be realized. Furthermore, by the use of this light-emitting element, a light-emitting device, an electronic device, and a lighting device each having reduced power consumption can be obtained.

Embodiment 2

In Embodiment 2, light-emitting elements of embodiment of the present invention will be described with reference to FIGS. 1A and 1B.

One embodiment of the present invention is a light-emitting element including a compound in which a dibenzo[f,h]quinoxaline ring and a hole-transport skeleton are bonded through an arylene group.

A compound with a quinoxaline skeleton has a high electron-transport property, and use of such a compound for a light-emitting element enables the element to have low driving voltage. However, a quinoxaline skeleton has a planar structure. Since a compound having a planar structure is easily crystallized when formed into a film, use of such a compound for light-emitting elements causes the elements to have a short a lifetime. Furthermore, a quinoxaline skeleton is poor at accepting holes. When a compound that cannot easily accept holes is used as a host material of a light-emitting layer, the region of electron-hole recombination concentrates on an interface of the light-emitting layer, leading to a reduction in the lifetime of the light-emitting element. It is likely that these problems will be solved by the introduction of a hole-transport skeleton into the molecule. However, if a hole-transport skeleton is directly bonded to a quinoxaline skeleton, the conjugated system extends to cause a decrease in band gap and a decrease in triplet excitation energy.

Nevertheless, the present inventors have found that the above problems can be solved by using, for a light-emitting element, a compound in which a dibenzo[f,h]quinoxaline ring and a hole-transport skeleton are bonded through an arylene group.

The above-described compound has a hole-transport skeleton in addition to a dibenzo[f,h]quinoxaline ring, making it easy to accept holes. Accordingly, by use of the compound as a host material of a light-emitting layer, electrons and holes recombine in the light-emitting layer, so that it is possible to suppress the decrease in the lifetime of the light-emitting element. Furthermore, the introduction of a hole-transport skeleton enables the compound to have a three-dimensionally bulky structure, and the compound is difficult to crystallize when formed into a film. By the use of the compound for a light-emitting element, the element can have a long lifetime. Moreover, in this compound, since a dibenzo[f,h]quinoxaline ring and a hole-transport skeleton are bonded through an arylene group, decreases in band gap and triplet excitation energy can be prevented as compared with a compound in which a dibenzo[f,h]quinoxaline ring and a hole-transport skeleton are directly bonded. By the use of the compound for a light-emitting element, the element can have high current efficiency.

Thus, the compound described above can be suitably used as a material for an organic device such as a light-emitting element or an organic transistor.

As the hole-transport skeleton, a π-electron rich heteroaromatic ring is preferable. As the π-electron rich heteroaromatic ring, a carbazole ring, a dibenzofuran ring, or a dibenzothiophene ring is preferable. As the arylene group, any of a substituted or unsubstituted phenylene group and a substituted or unsubstituted biphenyldiyl group is preferable.

One embodiment of the present invention is a light-emitting element including a heterocyclic compound represented by General Formula (G0) below.

[Chemical Formula 75]

E-Ar-A (G0)

In General Formula (G0), A represents any of a substituted or unsubstituted carbazolyl group, a substituted or unsubstituted dibenzothiophenyl group, and a substituted or unsubstituted dibenzofuranyl group, E represents substituted or unsubstituted dibenzo[f,h]quinoxaline, and Ar represents an arylene group having 6 to 13 carbon atoms. The arylene group may have one or more substituents, and the substituents may be bonded to form a ring.

Figure 1B:
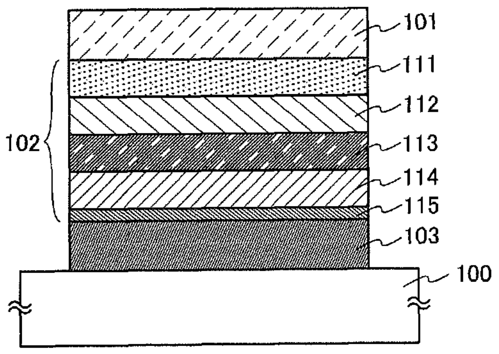

Embodiment 2 gives descriptions of light-emitting elements each including 2-[3-(dibenzothiophen-4-yl)phenyl]dibenzo[f,h]quinoxaline (abbreviation: 2mDBTPDBq-II) represented by Structural Formula (101) in Embodiment 1, which is an example of the above compounds, referring to FIGS. 1A and 1B.

In a light-emitting element of this embodiment, the EL layer having at least a light-emitting layer is interposed between a pair of electrodes. The EL layer may also have a plurality of layers in addition to the light-emitting layer. The plurality of layers is a combination of a layer containing a substance having a high carrier-injection property and a layer containing a substance having a high carrier-transport property which are stacked so that a light-emitting region is formed in a region away from the electrodes, that is, so that carriers recombine in a region away from the electrodes. In this specification, the layer containing a substance having a high carrier-injection or -transport property is also referred to as a functional layer which functions to inject or transport carriers, for example. As a functional layer, a hole-injection layer, a hole-transport layer, an electron-injection layer, an electron-transport layer, or the like can be used.

In the light-emitting element of this embodiment illustrated in FIG. 1A, an EL layer 102 having a light-emitting layer 113 is provided between a pair of electrodes, a first electrode 101 and a second electrode 103. The EL layer 102 includes a hole-injection layer 111, a hole-transport layer 112, the light-emitting layer 113, an electron-transport layer 114, and an electron-injection layer 115. The light-emitting element in FIG. 1A includes the first electrode 101 formed over a substrate 100, the hole-injection layer 111, the hole-transport layer 112, the light-emitting layer 113, the electron-transport layer 114, and the electron-injection layer 115 which are stacked over the first electrode 101 in this order, and the second electrode 103 provided thereover. Note that, in the light-emitting element described in this embodiment, the first electrode 101 functions as an anode and the second electrode 103 functions as a cathode.

The substrate 100 is used as a support of the light-emitting element. For example, glass, quartz, plastic, or the like can be used for the substrate 100. A flexible substrate may also be used. The flexible substrate is a substrate that can be bent, such as a plastic substrate made of polycarbonate, polyaiylate, or polyether sulfone, for example. A film (made of polypropylene, polyester, vinyl, polyvinyl fluoride, vinyl chloride, or the like), an inorganic film formed by evaporation, or the like can also be used. Note that materials other than these can be used as long as they can function as a support of the light-emitting element.

For the first electrode 101, a metal, an alloy, an electrically conductive compound, a mixture thereof, or the like which has a high work function (specifically, a work function of 4.0 eV or more) is preferably used. Specific examples include indium oxide-tin oxide (ITO: indium tin oxide), indium tin oxide containing silicon or silicon oxide, indium oxide-zinc oxide (IZO: indium zinc oxide), indium oxide containing tungsten oxide and zinc oxide (IWZO), and the like. Films of these conductive metal oxides are usually formed by sputtering; however, a sol-gel method or the like may also be used. For example, a film of indium oxide-zinc oxide (IZO) can be formed by a sputtering method using a target obtained by adding 1 wt % to 20 wt % of zinc oxide to indium oxide. A film of indium oxide (IWZO) containing tungsten oxide and zinc oxide can be formed by a sputtering method using a target obtained by adding 0.5 wt % to 5 wt % of tungsten oxide and 0.1 wt % to 1 wt % of zinc oxide to indium oxide. Further, gold, platinum, nickel, tungsten, chromium, molybdenum, iron, cobalt, copper, palladium, nitrides of metal materials (e.g., titanium nitride), and the like can be given.

However, when a layer which is in contact with the first electrode 101 and included in the EL layer 102 is formed using a composite material including an organic compound and an electron acceptor (an acceptor) described later, the first electrode 101 can be formed using any of a variety of metals, alloys, and electrically conductive compounds, a mixture thereof, and the like regardless of work function. For example, aluminum, silver, an alloy containing aluminum (e.g., Al—Si), or the like can also be used.

The EL layer 102 formed over the first electrode 101 includes at least the light-emitting layer 113, and part of the EL layer 102 contains a heterocyclic compound which is one embodiment of the present invention. A known substance can also be used for part of the EL layer 102, and either a low molecular compound or a high molecular compound can be used. Note that substances forming the EL layer 102 may consist of organic compounds or may include an inorganic compound as a part.

As illustrated in FIGS. 1A and 1B, the EL layer 102 is formed by stacking as appropriate the hole-injection layer 111, the hole-transport layer 112, the electron-transport layer 114, the electron-injection layer 115, and the like in combination as well as the light-emitting layer 113.

The hole-injection layer 111 is a layer including a substance having a high hole-injection property. Examples of the substance having a high hole-injection property which can be used include metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide. A phthalocyanine-based compound such as phthalocyanine (abbreviation: $H_2Pc$), or copper(II) phthalocyanine (abbreviation: CuPc) can also be used.

Any of the following aromatic amine compounds which are low molecular organic compounds can also be used: 4,4',4"-tris(N,N-diphenylamino)triphenylamine (abbreviation: TDATA); 4,4',4"-tris[N-(3-methylphenyl)-N-phenylamino]triphenylamine (abbreviation: MTDATA); 4,4'-bis[N-(4-diphenylaminophenyl)-N-phenylamino]biphenyl (abbreviation: DPAB); 4,4'-bis(N-{4-[N'-(3-methylphenyl)-N'-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like.

High molecular compounds (such as oligomers, dendrimers, or polymers) can also be used. The following high molecular compounds can be given as examples: poly(N-vinylcarbazole) (abbreviation: PVK); poly(4-vinyltriphenylamine) (abbreviation: PVTPA); poly[N-(4-{N'-[4-(4-diphenylamino)phenyl]phenyl-N=phenylamino}phenyl)methacryla mide] (abbreviation: PTPDMA); poly[N,N'-bis(4-butylphenyl)-N,N'-bis(phenyl)benzidine] (abbreviation: Poly-TPD); and the like. A high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can also be used.

For the hole-injection layer 111, a composite material including an organic compound and an electron acceptor (an acceptor) may be used. Such a composite material is excellent in a hole-injection property and a hole-transport property because the electron acceptor causes generation of holes. In this case, the organic compound is preferably a material excellent in transporting the generated holes (a substance having a high hole-transport property).

As the organic compound used for the composite material, a variety of compounds can be used, such as aromatic amine compounds, carbazole derivatives, aromatic hydrocarbons, and high molecular compounds (such as oligomers, dendrimers, or polymers). The organic compound used for the composite material is preferably an organic compound having a high hole-transport property. Specifically, a substance having a hole mobility of $10^{-6}$ $cm^2/Vs$ or more is preferably used. Note that other than these substances, any substance that has a property of transporting more holes than electrons may be used. The organic compounds which can be used for the composite material are specifically given below.

Examples of the organic compounds that can be used for the composite material include: aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD) 4-phenyl-4'-(9-phenylfluoren-9-yl)triphenylamine (abbreviation: BPAFLP); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl-2,3,5,6-tetraphenylbenzene.

Any of the following aromatic hydrocarbon compounds can be used: 2-tert-butyl-9,10-di(2-naphthyl)anthracene (abbreviation: t-BuDNA); 2-tert-butyl-9,10-di(1-naphthyl)anthracene, 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 9,10-bis[2-(1-naphthyl)phenyl)-2-tert-butylanthracene; 9,10-bis[2-(1-naphthyl)phenyl]anthracene; and 2,3,6,7-tetramethyl-9,10-di(1-naphthyl)anthracene.

Any of the following aromatic hydrocarbon compounds can be used: 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; pentacene; coronene, 4,4'-bis(2,2-diphenylvinyl)biphenyl (abbreviation: DPVBi); and 9,10-bis[4-(2,2-diphenylvinyl)phenyl]anthracene (abbreviation: DPVPA).

As the electron acceptor, organic compounds such as 7,7,8,8-tetracyano-2,3,5,6-tetrafluoroquinodimethane (abbreviation: $F_4$-TCNQ) and chloranil and transition metal oxides can be given. Oxides of metals belonging to Groups 4 to 8 in the periodic table can be also given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide, which is easy to handle owing to its stability in the air and low hygroscopic property, is especially preferable.

Note that the composite material may be formed using a high molecular compound such as PVK, PVTPA, PTPDMA, or Poly-TPD and an electron acceptor, which are described above, so as to be used for the hole-injection layer 111.

The hole-transport layer 112 is a layer including a substance having a high hole-transport property. As the substance having a high hole-transport property, any of the following aromatic amine compounds can be used, for example: NPB; TPD; BPAFLP; 4,4'-bis[N-(9,9-dimethylfluoren-2-yl)-N-phenylamino]biphenyl (abbreviation: DFLDPBi); and 4,4'-bis[N-(spiro-9,9'-bifluoren-2-yl)-N-phenylamino]biphenyl (abbreviation: BSPB). The substances given here are mainly substances having a hole mobility of $10^{-6}$ $cm^2/Vs$ or more. Note that other than these substances, any substance that has a property of transporting more holes than electrons may be used. The layer including a substance having a high hole-transport property is not limited to a single layer, and may be a stack of two or more layers containing any of the above substances.

For the hole-transport layer 112, a carbazole derivative such as CBP, CzPA, or PCzPA or an anthracene derivative such as t-BuDNA, DNA, or DPAnth may also be used.

For the hole-transport layer 112, a high molecular compound such as PVK, PVTPA, PTPDMA, or Poly-TPD can also be used.

The light-emitting layer 113 is a layer including a light-emitting substance. Note that in Embodiment 2, the case where 2mDBTPDBq-II described in Embodiment 1 is used for the light-emitting layer is described. For the light-emitting layer in which a light-emitting substance (a guest material) is dispersed in another substance (a host material), 2mDBTPDBq-II can be used as the host material. The guest material which is a light-emitting substance is dispersed in 2mDBTPDBq-II, whereby light emission can be obtained from the guest material. Thus, a compound of one embodiment of the present invention, in which a dibenzo[f,h]quinoxaline ring and a hole-transport skeleton are bonded through an arylene group, is effective in its use as a host material in a light-emitting layer.

In addition, more than one kind of substances can be used as the substances (host materials) in which the light-emitting substance (guest material) is dispersed. The light-emitting layer may thus include another material as a host material in addition to 2mDBTPDBq-II.

As the light-emitting substance, for example, a fluorescent compound which emits fluorescence or a phosphorescent compound which emits phosphorescence can be used. The phosphorescent compounds that can be used for the light-emitting layer 113 will be given. Examples of the materials that emits blue light include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA), and the like. In addition, examples of the materials that emits green light include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Further, examples of the materials that emits yellow light include rubrene, 5,12-bis(1,1'-biphenyl-4-yl)-6,11-diphenyltetracene (abbreviation: BPT), and the like. Furthermore, examples of the materials that emits red light include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho [1,2-a]fluoranthene-3,10-d iamine (abbreviation: p-mPhAFD), and the like.

In addition, the phosphorescent compounds that can be used for the light-emitting layer 113 will be given. Examples of the materials that emits green light include tris(2-phenylpyridinato-N,$C^{2'}$)iridium(III) (abbreviation: $[Ir(ppy)_3]$), bis(2-phenylpyridinato-N,$C^{2'}$)iridium(III)acetylacetonate (abbreviation: $[Ir(ppy)_2(acac)]$), bis(1,2-diphenyl-1H-benzimidazolato)iridium(III) acetylacetonate (abbreviation: $[Ir(pbi)_2(acac)]$), bis(benzo[h]quinolinato)iridium(III) acetylacetonate (abbreviation: $[Ir(bzq)_2(acac)]$), tris(benzo[h]quinolinato)iridium(III) (abbreviation: $[Ir(bzq)_3]$), and the like. Examples of the materials that emits yellow light include bis(2,4-diphenyl-1,3-oxazolato-N,$C^{2'}$)iridium(III)acetylacetonate (abbreviation: $[Ir(dpo)_2(acac)]$), bis[2-(4'-(perfluorophenylphenyl)pyridinato]iridium(III)acetylacetonate (abbreviation: $[Ir(p\text{-}PF\text{-}ph)_2(acac)]$), bis(2-phenylbenzothiazolato-N,$C^{2'}$)iridium(III)acetylacetonate (abbreviation: $[Ir(bt)_2(acac)]$), (acetylacetonato)bis[2,3-bis(4-fluorophenyl)-5-methylpyrazinato]iridium(III) (abbreviation: $[Ir(Fdppr\text{-}Me)_2(acac)]$), (acetylacetonato)bis[2-(4-methoxyphenyl)-3,5-dimethylpyrazinato]iridium(III) (abbreviation: $[Ir(dmmoppr)_2(acac)]$), and the like. Examples of the materials that emits orange light include tris(2-phenylquinolinato-N,$C^{2'}$)iridium(III) (abbreviation: $[Ir(pq)_3]$), bis(2-phenylquinolinato-N,$C^{2'}$)iridium(III)acetylacetonate (abbreviation: $[Ir(pq)_2(acac)]$), (acetylacetonato)bis(3,5-dimethyl-2-phenylpyrazinato)iridium(III) (abbreviation: $[Ir(mppr\text{-}Me)_2(acac)]$), (acetylacetonato)bis(5-isopropyl-3-methyl-2-phenylpyrazinato)iridium(III) (abbreviation: $[Ir(mppr\text{-}iPr)_2(acac)]$), and the like. Examples of the materials that emits red light include organometallic complexes such as bis[2-(2'-benzo[4,5-α]thienyl)pyridinato-N,$C^{3'}$)iridium(III) acetylacetonate (abbreviation: $[Ir(btp)_2(acac)]$), bis(1-phenylisoquinolinato-N,$C^{2'}$)iridium(III) acetylacetonate (abbreviation: $[Ir(piq)_2(acac)]$), (acetylacetonato)bis[2,3-bis(4-fluorophenyl)quinoxalinato]iridium(III) (abbreviation: $[Ir(Fdpq)_2(acac)]$), acetylacetonato)bis(2,3,5-triphenylpyrazinato)iridium(III) (abbreviation: $[Ir(tppr)_2(acac)]$), (dipivaloylmethanato)bis(2,3,5-triphenylpyrazinato)iridium(III) (abbreviation: $[Ir(tppr)_2(dpm)]$), and (2,3,7,8,12,13,17,18-octaethyl-21H,23H-porphine)platinum(II) (abbreviation: PtOEP). Any of the following rare-earth metal complexes can be used as a phosphorescent compound: tris(acetylacetonato)(monophenanthroline)terbium(III) (abbreviation: $[Tb(acac)_3(Phen)]$); tris(1,3-diphenyl-1,3-propanedionato)(monophenanthroline)europium(III) (abbreviation: $[Eu(DBM)_3(Phen)]$); and tris[1-(2-thenoyl)-3,3,3-trifluoroacetonato](monophenanthroline)europium(III) (abbreviation: $[Eu(TTA)_3(Phen)]$), because light emission is from a rare-earth metal ion (electron transfer between different multiplicities) in such a rare-earth metal complex.

Note that in a compound which is one embodiment of the present invention, in which a dibenzo[f,h]quinoxaline ring and a hole-transport skeleton are bonded through an arylene group, a dibenzo[f,h]quinoxaline skeleton is considered as the skeleton where the LUMO level is predominantly located. Further, the compound has a deep LUMO level of at least −2.8 eV or less, specifically −2.9 eV or less on the basis of cyclic voltammetry (CV) measurements. For example, the LUMO level of 2mDBTPDBq-II is found to be −2.96 eV by CV measurements. Furthermore, the LUMO level of the above-described phosphorescent compound having a pyrazine skeleton, such as $[Ir(mppr\text{-}Me)_2(acac)]$, $[Ir(mppr\text{-}iPr)_2(acac)]$, $[Ir(tppr)_2(acac)]$, or $[Ir(tppr)_2(dpm)]$, is substantially equally deep. Therefore, when a light-emitting layer includes a compound of one embodiment of the present invention, in which a dibenzo[f,h]quinoxaline ring and a hole-transport skeleton are bonded through an arylene group, as a host material, and a phosphorescent compound having a pyrazine skeleton as a guest material, traps for electrons in the light-emitting layer can be reduced to a minimum, and extremely low-voltage driving can be realized.

As the light-emitting substance, a high molecular compound can be used. Specifically, examples of the materials that emits blue light include poly(9,9-dioctylfluorene-2,7-diyl) (abbreviation: PFO), poly[(9,9-dioctylfluorene-2,7-diyl)-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]}(abbreviation: TAB-PFH), and the like. Further, examples of the materials that emits green light include poly(p-phenylenevinylene) (abbreviation: PPV), poly[(9,9-dihexylfluorene-2,7-diyl)-altco-(benzo[2,1,3]thiadiazole-4,7-diyl)] (abbreviation: PFBT), poly[(9,9-dioctyl-2,7-divinylenefluorenylene)-alt-co-(2-methoxy-5-(2-ethylhexyloxy)-1,4-phenylene)], and the like. Furthermore, examples of the materials that emits orange to red light include poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like.

The electron-transport layer 114 is a layer including a substance having a high electron-transport property. As the substance having a high electron-transport property, the following metal complexes having a quinoline skeleton or a benzoquinoline skeleton can be given: tris(8-quinolinolato)aluminum (abbreviation: Alq); tris(4-methyl-8-quinolinolato)aluminum (abbreviation: $Almq_3$); bis(10-hydroxybenzo[h]-quinolinato)beryllium (abbreviation: $BeBq_2$); and bis(2-methyl-8-quinolinolato)(4-phenylphenolato)aluminum (abbreviation: BAlq). A metal complex having an oxazole-based or thiazole-based ligand, such as bis[2-(2-hydroxyphenyl)benzoxazolato]zinc (abbreviation: $Zn(BOX)_2$) or bis[2-(2-hydroxyphenyl)benzothiazolato]zinc (abbreviation: $Zn(BTZ)_2$), or the like can also be used. Other than metal complexes, 2-(4-biphenylyl)-5-(4-tert-butylphenyl)-1,3,4-oxadiazole (abbreviation: PBD), 1,3-bis[5(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can be used. The substances described here are mainly materials having an electron mobility of $10^{-6}$ $cm^2/Vs$ or more. Further, the electron-transport layer is not limited to a single layer, and may be a stack of two or more layers containing any of the above substances are stacked.

The electron-injection layer 115 is a layer including a substance having a high electron-injection property. For the electron-injection layer 115, an alkali metal, an alkaline-earth metal, or a compound thereof, such as lithium, cesium, calcium, lithium fluoride, cesium fluoride, calcium fluoride, or lithium oxide, can be used. A rare-earth metal compound like erbium fluoride can also be used. The above-mentioned substances for forming the electron-transport layer 114 can also be used.

Alternatively, a composite material including an organic compound and an electron donor (a donor) may be used for the electron-injection layer 115. Such a composite material is excellent in an electron-injection property and an electron-transport property because the electron donor causes generation of electrons. In this case, the organic compound is preferably a material excellent in transporting the generated electrons. Specifically, for example, the substances for forming the electron-transport layer 114 (e.g., a metal complex or a heteroaromatic compound), which are described above, can be used. The electron donor is preferably a substance showing an electron-donating property with respect to the organic compound. Specifically, an alkali metal, an alkaline-earth metal, and a rare-earth metal are preferable, and lithium, cesium, magnesium, calcium, erbium, ytterbium, and the like can be given. Alkali metal oxides or alkaline-earth metal oxides are also preferable and lithium oxide, calcium oxide, barium oxide, and the like can be given. A Lewis base such as magnesium oxide can also be used. An organic compound such as tetrathiafulvalene (abbreviation: HF) can also be used.

The hole-injection layer 111, the hole-transport layer 112, the light-emitting layer 113, the electron-transport layer 114, and the electron-injection layer 115, which are described above, can each be formed by a method such as an evaporation method (including a vacuum evaporation method), an inkjet method, or a coating method.

When the second electrode 103 functions as a cathode, the second electrode 103 is preferably formed using a metal, an alloy, an electrically-conductive compound, a mixture thereof, or the like having a low work function (preferably, a work function of 3.8 eV or less). Specifically, any of the following can be used: elements belonging to Group 1 or Group 2 of the periodic table, that is, alkali metals such as lithium and cesium, alkaline-earth metals such as magnesium, calcium, and strontium, or alloys thereof (e.g., Mg—Ag or Al—Li]); rare-earth metals such as europium or ytterbium or alloys thereof; aluminum; silver; and the like.

However, when a layer which is in contact with the second electrode 103 and included in the EL layer 102 is formed using a composite material including an organic compound and an electron donor (a donor) described above, a variety of conductive materials such as aluminum, silver, ITO, and indium tin oxide containing silicon or silicon oxide can be used regardless of work function.

Note that the second electrode 103 can be formed by a vacuum evaporation method or a sputtering method. In the case where a silver paste or the like is used, a coating method, an inkjet method, or the like can be used.

In the above-described light-emitting element, a current flows due to a potential difference generated between the first electrode 101 and the second electrode 103, and holes and electrons recombine in the EL layer 102, so that light is emitted. Then, this emitted light is extracted out through one or both of the first electrode 101 and the second electrode 103. One or both of the first electrode 101 and the second electrode 103 are thus have a property of transmitting visible light.

Further, the structure of the layers provided between the first electrode 101 and the second electrode 103 is not limited to the above described structure. A structure other than the above may alternatively be employed as long as a light-emitting region in which holes and electrons recombine is provided in a portion away from the first electrode 101 and the second electrode 103 in order to prevent quenching due to proximity of the light-emitting region to metal.

In other words, there is no particular limitation on a stack structure of the layers. A layer including a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like may freely be combined with a light-emitting layer including 2mDBTPDBq-II as a host material.

Since 2mDBTPDBq-II is a substance having a high electron-transport property, 2mDBTPDBq-II can also be used for the electron-transport layer. In other words, a compound of one embodiment of the present invention, in which a dibenzo[f,h]quinoxaline ring and a hole-transport skeleton are bonded through an arylene group, can be used for the electron-transport layer.

Furthermore, if a compound of one embodiment of the present invention, in which a dibenzo[f,h]quinoxaline ring and a hole-transport skeleton are bonded through an arylene group, is applied to both the light-emitting layer (especially as a host material in the light-emitting layer) and the electron-transport layer, extremely low-voltage driving can be realized.

In the light-emitting element illustrated in FIG. 1B, the EL layer 102 is provided between the first electrode 101 and the second electrode 103 over the substrate 100. The EL layer 102 includes the hole-injection layer 111, the hole-transport layer 112, the light-emitting layer 113, the electron-transport layer 114, and the electron-injection layer 115. The light-emitting element in FIG. 1B includes the second electrode 103 serving as a cathode over the substrate 100, the electron-injection layer 115, the electron-transport layer 114, the light-emitting layer 113, the hole-transport layer 112, and the hole-injection layer 111 which are stacked over the second electrode 103 in this order, and the first electrode 101 provided thereover which serves as an anode.

A method of forming the light-emitting element will now be specifically described.

In a light-emitting element of this embodiment, the EL layer is interposed between the pair of electrodes. The EL layer has at least the light-emitting layer, and the light-emitting layer is formed using 2mDBTPDBq-II as a host material. Further, the EL layer may include a functional layer (e.g., the hole-injection layer, the hole-transport layer, the electron-transport layer, or the electron-injection layer) in addition to the light-emitting layer. The electrodes (the first electrode and the second electrode), the light-emitting layer, and the functional layer may be formed by any of the wet processes such as a droplet discharging method (an inkjet method), a spin coating method, and a printing method, or by a dry processes such as a vacuum evaporation method, a CVD method, and a sputtering method. A wet process allows formation at atmospheric pressure with a simple device and by a simple process, thereby having the effects of simplifying the process and improving productivity. In contrast, a dry process does not need dissolution of a material and enables use of a material that has low solubility in a solution, thereby expanding the range of material choices.

All the thin films included in a light-emitting element may be formed by a wet method. In this case, the light-emitting element can be manufactured with only facilities needed for a wet process. Alternatively, the following method may be employed: formation of the stacked layers up to formation of the light-emitting layer is performed by a wet process whereas the functional layer, the first electrode, and the like which are stacked over the light-emitting layer are formed by a dry process. Further alternatively, the following method may be employed: the second electrode and the functional layer are formed by a dry process before the formation of the light-emitting layer whereas the light-emitting layer, the functional layer stacked thereover, and the first electrode are formed by a wet process. Needless to say, this embodiment is not limited to these, and a light-emitting element can be formed by appropriate selection from a wet method and a dry method depending on a material to be used, necessary film thickness, and the interface state.

In this embodiment, a light-emitting element is fabricated over a substrate made of glass, plastic or the like. By forming a plurality of such light-emitting elements over one substrate, a passive matrix light-emitting device can be manufactured. Further, a light-emitting element may be fabricated in such a manner that a thin film transistor (TFT), for example, is be formed over a substrate made of glass, plastic, or the like and the element is formed over an electrode electrically connected to the TFT. Thus, an active matrix light-emitting device in which the TFT controls the driving of the light-emitting element can be manufactured. Note that there is no particular limitation on the structure of the TFT. Either a staggered TFT or an inverted staggered TFT may be employed. In addition, there is no particular limitation on the crystallinity of a semiconductor used for the TFT, and an amorphous semiconductor or a crystalline semiconductor may be used. In addition, a driver circuit formed over a TFT substrate may be formed with both n-channel TFTs and p-channel TFTs or may be formed with either n-channel TFTs or p-channel TFTs.

Thus, a light-emitting element can be fabricated using 2mDBTPDBq-II described in Embodiment 1. By the use of a compound of one embodiment of the present invention, in which a dibenzo[f,h]quinoxaline ring and a hole-transport skeleton are bonded through an arylene group, for a light-emitting element, the light-emitting element can have low driving voltage, high current efficiency, and a long lifetime.

Furthermore, a light-emitting device (such as an image display device) using a light-emitting element of one embodiment of the present invention which is obtained as above can have low power consumption.

Note that, by the use of a light-emitting element described in this embodiment, it is possible to fabricate a passive matrix light-emitting device or an active matrix light-emitting device in which a thin film transistor (TFT) controls the driving of the light-emitting element.

This embodiment can be implemented in appropriate combination with any of the other embodiments.

Embodiment 3

In this embodiment, modes of light-emitting elements having a structure in which a plurality of light-emitting units is stacked (hereinafter, referred to as a stacked-type element) will be described with reference to FIGS. 2A and 2B. These light-emitting element are each a light-emitting element including a plurality of light-emitting units between a first electrode and a second electrode.

Figure 2A:
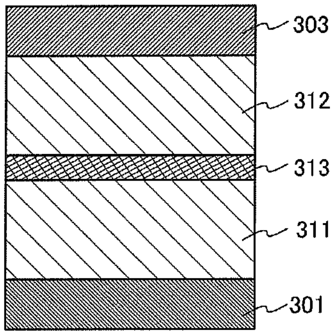
FIGS. 2A and 2B each illustrate a light-emitting element of one embodiment of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. The first electrode 301 and the second electrode 303 can be the same as those in Embodiment 2. Further, the first light-emitting unit 311 and the second light-emitting unit 312 may have the same or different structures. The first light-emitting unit 311 and the second light-emitting unit 312 may be the same as those in Embodiment 2, or either of the units may be the same as that in Embodiment 2.

Further, a charge generation layer 313 is provided between the first light-emitting unit 311 and the second light-emitting unit 312. When a voltage is applied between the first electrode 301 and the second electrode 303, the charge generation layer 313 functions to inject electrons into one light-emitting unit and inject holes into the other light-emitting unit. In this embodiment, when a voltage is applied to the first electrode 301 so that the potential thereof is higher than that of the second electrode 303, the charge generation layer 313 injects electrons into the first light-emitting unit 311 and injects holes into the second light-emitting unit 312.

Note that the charge generation layer 313 preferably has a property of transmitting visible light in terms of light extraction efficiency. Further, the charge generation layer 313 functions even when it has lower conductivity than the first electrode 301 or the second electrode 303.

The charge generation layer 313 may have either a structure including an organic compound having a high hole-transport property and an electron acceptor (an acceptor) or a structure including an organic compound having a high electron-transport property and an electron donor(a donor). Alternatively, both of these structures may be stacked.

In the case of the structure in which an electron acceptor is added to an organic compound having a high hole-transport property, any of the following substances can be used as the organic compound having a high hole-transport property, for example: the heterocyclic compounds of embodiments of the present invention; aromatic amine compounds such as NPB, TPD, TDATA, MTDATA, and 4,4'-bis[N-(spiro-9,9'-bifluoren-2-yl)-N-phenylamino]biphenyl (abbreviation: BSPB); or the like. The substances given here are mainly materials having a hole mobility of $10^{-6}$ $cm^2/Vs$ or more. Note that other than the above substances, any organic compound that has a property of transporting more holes than electrons may be used.

Further, as the electron acceptor, 7,7,8,8-tetracyano-2,3,5,6-tetrafluoroquinodimethane (abbreviation: $F_4$-TCNQ), chloranil, and the like can be given. In addition, transition metal oxides can be given. Moreover, oxides of metals belonging to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable because they have a high electron-accepting property. Among these metal oxides, molybdenum oxide, which is easy to handle, is preferred owing to its stability in air and low hygroscopic property.

In contrast, in the case of the structure in which an electron donor is added to an organic compound having a high electron-transport property, as the organic compound having a high electron-transport property, a metal complex having a quinoline skeleton or a benzoquinoline skeleton, such as Alq, $Almq_3$, $BeBq_2$, or BAlq, or the like can be used, for example. A metal complex having an oxazole-based ligand or a thiazole-based ligand, such as $Zn(BOX)_2$ or $Zn(BTZ)_2$ can also be used. Other than such metal complexes, PBD, OXD-7, TAZ, BPhen, BCP, or the like can be used. The substances given here are mainly materials having an electron mobility of $10^{-6}$ $cm^2/Vs$ or more. Note that other than the above substances, any organic compound that has a property of transporting more electrons than holes may be used.

Further, as the electron donor, any of alkali metals, alkaline-earth metals, rare-earth metals, metals belonging to Group 13 of the periodic table, or oxides or carbonates thereof can be used. Specifically, lithium, cesium, magnesium, calcium, ytterbium, indium, lithium oxide, cesium carbonate, or the like is preferably used. An organic compound such as tetrathianaphthacene may also be used as the electron donor.

Note that by the formation of the charge generation layer 313 using a material described above, it is possible to suppress an increase in driving voltage caused by stacking the EL layers.

Figure 2B:
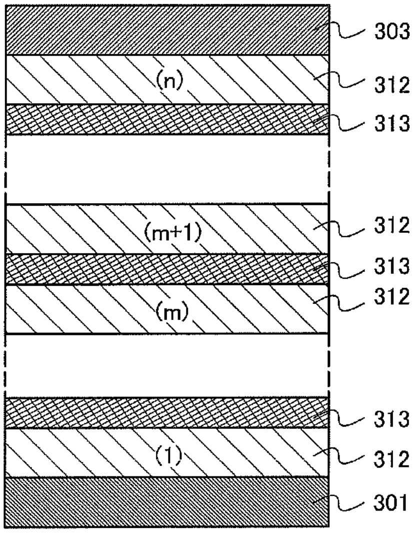

In this embodiment, the light-emitting element having two light-emitting units is described, and a light-emitting element having a stack of three or more light-emitting units can also be employed as illustrated in FIG. 2B. A plurality of light-emitting units which are partitioned by a charge generation layer is arranged between a pair of electrodes, as in the light-emitting element according to this embodiment, whereby it is possible to realize an element having a long lifetime which can emit light with a high luminance while current density is kept low.

With light-emitting units having emission colors different from each other, the light-emitting element as a whole can be made to emit light with a desired color. For example, in a light-emitting element having two light-emitting units, the emission colors of the first light-emitting unit and the second light-emitting unit are made complementary; thus, the light-emitting element which emits white light as a whole can be obtained. Note that the term "complementary" means color relationship in which an achromatic color is obtained when colors are mixed. That is, white light emission can be obtained by mixture of light obtained from substances emitting lights with complementary colors. The same can be applied to a light-emitting element which has three light-emitting units. For example, the light-emitting element as a whole can emit white light when the emission color of the first light-emitting unit is red, the emission color of the second light-emitting unit is green, and the emission color of the third light-emitting unit is blue.

Note that this embodiment can be combined with any other embodiment as appropriate.

Embodiment 4

In Embodiment 4, a light-emitting device having a light-emitting element of one embodiment of the present invention will be described with reference to FIGS. 3A and 3B. Note that FIG. 3A is a top view illustrating the light-emitting device, and FIG. 3B is a cross-sectional view taken along lines A-B and C-D of FIG. 3A.

Figure 3A:
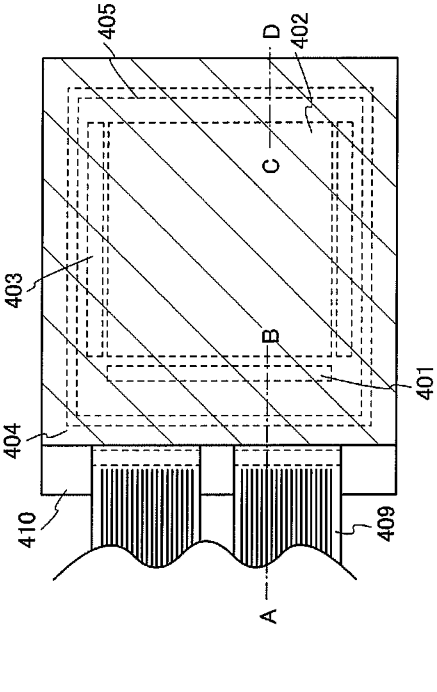
FIGS. 3A and 3B illustrate a light-emitting device of one embodiment of the present invention.
Figure 3B:
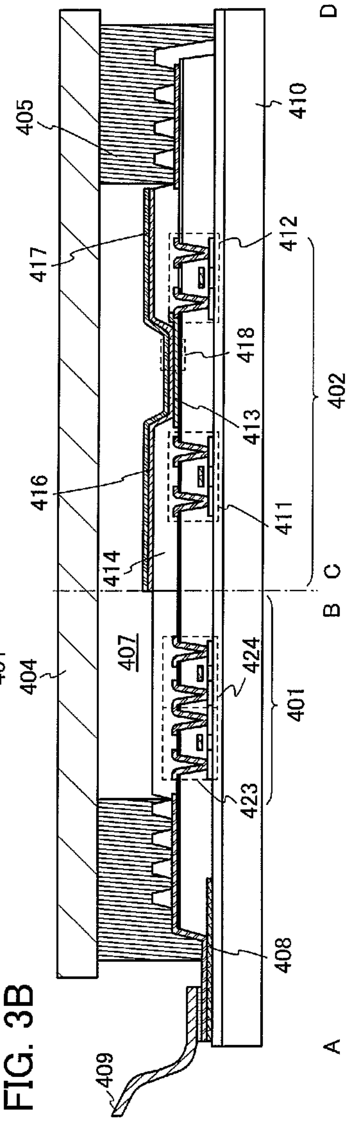

In FIG. 3A, reference numeral 401 denotes a driver circuit portion (a source driver circuit), reference numeral 402 denotes a pixel portion, and reference numeral 403 denotes a driver circuit portion (a gate driver circuit), which are each indicated by dotted lines. Reference numeral 404 denotes a sealing substrate, reference numeral 405 denotes a sealant, and a portion enclosed by the sealant 405 is a space.

Note that a lead wiring 408 is a wiring for transmitting signals that are to be inputted to the source driver circuit 401 and the gate driver circuit 403, and receives a video signal, a clock signal, a start signal, a reset signal, and the like from an FPC (flexible printed circuit) 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure will be described with reference to FIG. 3B. The driver circuit portion and the pixel portion are formed over an element substrate 410. Here, the source driver circuit 401 which is the driver circuit portion and one pixel in the pixel portion 402 are illustrated.

Note that as the source driver circuit 401, a CMOS circuit which includes an n-channel TFT 423 and a p-channel TFT 424 is formed. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413. Here, the insulator 414 is formed by using a positive type photosensitive acrylic resin film.

In order to improve coverage, the insulator 414 is provided such that either an upper end portion or a lower end portion of the insulator 414 has a curved surface with a curvature. For example, when positive photosensitive acrylic is used as a material for the insulator 414, it is preferable that only an upper end portion of the insulator 414 have a curved surface with a radius of curvature (0.2 μm to 3 μm). For the insulator 414, it is also possible to use either a negative type that becomes insoluble in an etchant by light irradiation or a positive type that becomes soluble in an etchant by light irradiation.

A light-emitting layer 416 and a second electrode 417 are formed over the first electrode 413. Here, as a material for forming the first electrode 413 functioning as the anode, a material having a high work function is preferably used. For example, it is possible to use a single layer of an ITO film, an indium tin oxide film that includes silicon, an indium oxide film that includes 2 wt % to 20 wt % of zinc oxide, a titanium nitride film, a chromium film, a tungsten film, a Zn film, a Pt film, or the like, a stacked layer of a titanium nitride film and a film that mainly includes aluminum, a three-layer structure of a titanium nitride film, a film that mainly includes aluminum and a titanium nitride film, or the like. Note that, when a stacked layer structure is employed, resistance of a wiring is low and a favorable ohmic contact is obtained.

In addition, the light-emitting layer 416 is formed by any of various methods such as an evaporation method using an evaporation mask, a droplet discharging method like an inkjet method, a printing method, and a spin coating method. The light-emitting layer 416 includes a heterocyclic compound described in Embodiment 1. Further, another material included in the light-emitting layer 416 may be a low molecular material, an oligomer, a dendrimer, a high molecular material, or the like.

As a material used for the second electrode 417 which is formed over the light-emitting layer 416 and serves as a cathode, it is preferable to use a material having a low work function (e.g., Al, Mg, Li, Ca, or an alloy or a compound thereof such as Mg—Ag, Mg—In, Al—Li, LiF, or $CaF_2$). In order that light generated in the light-emitting layer 416 be transmitted through the second electrode 417, a stack of a metal thin film having a reduced thickness and a transparent conductive film (e.g., ITO, indium oxide containing 2 wt % to 20 wt % of zinc oxide, indium oxide-tin oxide that includes silicon or silicon oxide, or zinc oxide) is preferably used for the second electrode 417.

The sealing substrate 404 is attached to the element substrate 410 with the sealant 405; thus, a light-emitting element 418 is provided in the space 407 enclosed by the element substrate 410, the sealing substrate 404, and the sealant 405. Note that the space 407 may be filled with filler such as an inert gas (e.g., nitrogen or argon) or with the sealant 405.

Note that as the sealant 405, an epoxy-based resin is preferably used. Such a material is desirably a material that transmits as little moisture or oxygen as possible. As a material used for the sealing substrate 404, a glass substrate, a quartz substrate, or a plastic substrate formed of FRP (fiberglass-reinforced plastics), PVF (polyvinyl fluoride), polyester, acrylic, or the like can be used.

As described above, the active matrix light-emitting device having a light-emitting element of one embodiment of the present invention can be obtained.

Figure 4A:
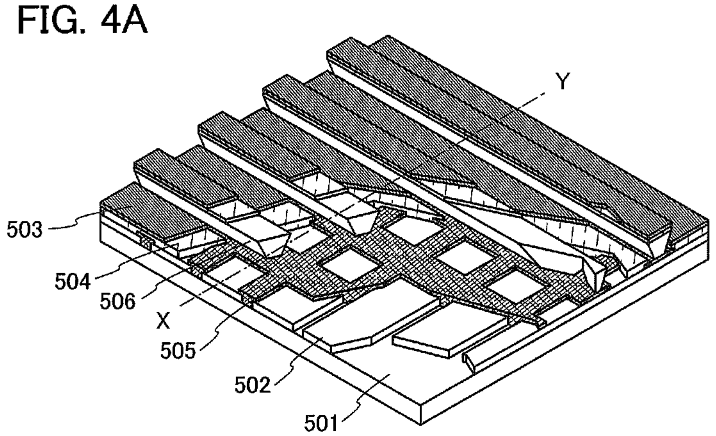
FIGS. 4A and 4B illustrate a light-emitting device of one embodiment of the present invention.
Figure 4B:
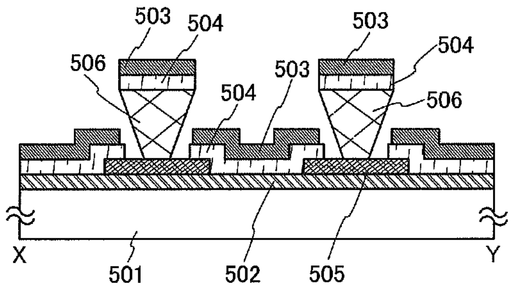

Further, a light-emitting element of the present invention can be used for a passive matrix light-emitting device as well as the above active matrix light-emitting device. FIGS. 4A and 4B illustrate a perspective view and a cross-sectional view of a passive matrix light-emitting device using a light-emitting element of the present invention. Note that FIG. 4A is a perspective view of the light-emitting device, and FIG. 4B is a cross-sectional view taken along line X-Y of FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 are aslope so that a distance between both the sidewalls is gradually narrowed toward the surface of the substrate. In other words, a cross section taken along the direction of the short side of the partition layer 506 is trapezoidal, and the base (side facing in a direction parallel to the plane direction of the insulating layer 505 and being in contact with the insulating layer 505) is shorter than the upper side (side facing in the direction parallel to the plane direction of the insulating layer 505 and not being in contact with the insulating layer 505). By providing of the partition layer 506 in such a manner, a defect of a light-emitting element due to static electricity or the like can be prevented.

Thus, the passive matrix light-emitting device having a light-emitting element of one embodiment of the present invention can be obtained.

The light-emitting devices described in this embodiment (the active matrix light-emitting device and the passive matrix light-emitting device) are both formed using a light-emitting element of one embodiment of the present invention, thereby having low power consumption.

Note that this embodiment can be combined with any other embodiment as appropriate.

Embodiment 5

Embodiment 5 will give descriptions of electronic devices including a light-emitting device of one embodiment of the present invention described in Embodiment 4 as a part. Examples of the electronic devices include cameras such as video cameras and digital cameras, goggle type displays, navigation systems, audio reproducing devices (e.g., car audio systems and audio systems), computers, game machines, portable information terminals (e.g., mobile computers, cellular phones, portable game machines, and electronic books), image reproducing devices in which a recording medium is provided (specifically, devices that are capable of reproducing recording media such as digital versatile discs (DVDs) and provided with a display device that can display an image), and the like. Specific examples of these electronic devices are illustrated in FIGS. 5A to 5D.

Figure 5A:
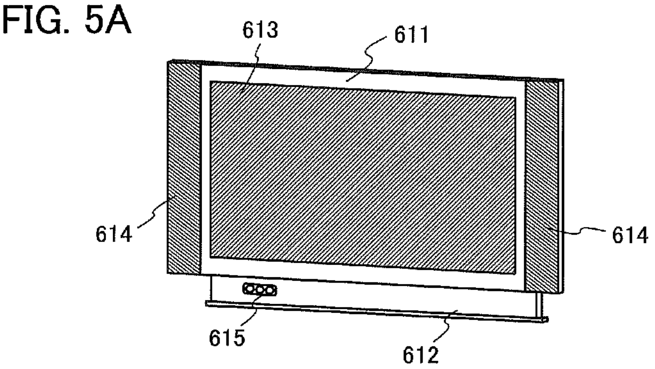
FIGS. 5A to 5D each illustrate an electronic device of one embodiment of the present invention.

FIG. 5A illustrates a television set according to one embodiment of the present invention, which includes a housing 611, a supporting base 612, a display portion 613, speaker portions 614, video input terminals 615, and the like. In this television set, a light-emitting device of one embodiment of the present invention can be applied to the display portion 613. Since a light-emitting device of one embodiment of the present invention has low driving voltage, high current efficiency, and a long lifetime, by the application of the light-emitting device of one embodiment of the present invention, a television set having high reliability and reduced power consumption can be obtained.

Figure 5B:
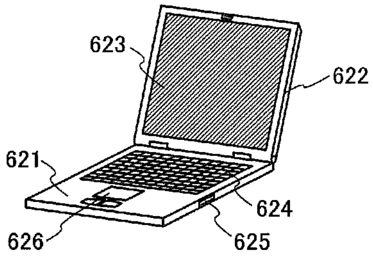

FIG. 5B illustrates a computer according to one embodiment of the present invention, which includes a main body 621, a housing 622, a display portion 623, a keyboard 624, an external connection port 625, a pointing device 626, and the like. In this computer, the light-emitting device of the present invention can be applied to the display portion 623. Since a light-emitting device of one embodiment of the present invention has low driving voltage, high current efficiency, and a long lifetime, by the application of the light-emitting device of one embodiment of the present invention, a computer having high reliability and reduced power consumption can be obtained.

Figure 5C:
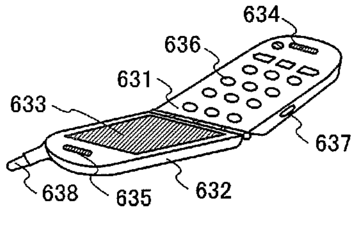

FIG. 5C illustrates a cellular phone of one embodiment of the present invention, which includes a main body 631, a housing 632, a display portion 633, an audio input portion 634, an audio output portion 635, operation keys 636, an external connection port 637, an antenna 638, and the like. In this cellular phone, the light-emitting device of the present invention can be applied to the display portion 633. Since a light-emitting device of one embodiment of the present invention has low driving voltage, high current efficiency, and a long lifetime, by the application of the light-emitting device of one embodiment of the present invention, a cellular phone having high reliability and reduced power consumption can be obtained.

Figure 5D:
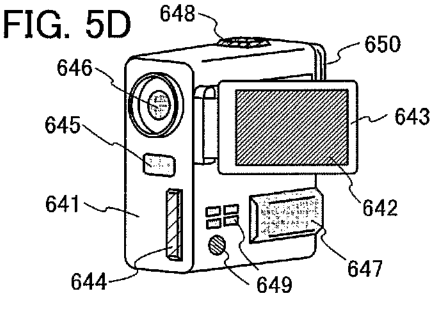

FIG. 5D illustrates a camera of one embodiment of the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this camera, a light-emitting device of one embodiment of the present invention can be applied to the display portion 642. Since a light-emitting device of one embodiment of the present invention has low driving voltage, high current efficiency, and a long lifetime, by the application of the light-emitting device of one embodiment of the present invention, a camera having high reliability and reduced power consumption can be obtained.

As thus described, application range of a light-emitting device of one embodiment of the present invention is quite wide, and this light-emitting device can be applied to electronic devices of a variety of fields. With use of a light-emitting device of one embodiment of the present invention, an electronic device having high reliability and reduced power consumption can be obtained.

Figure 6:
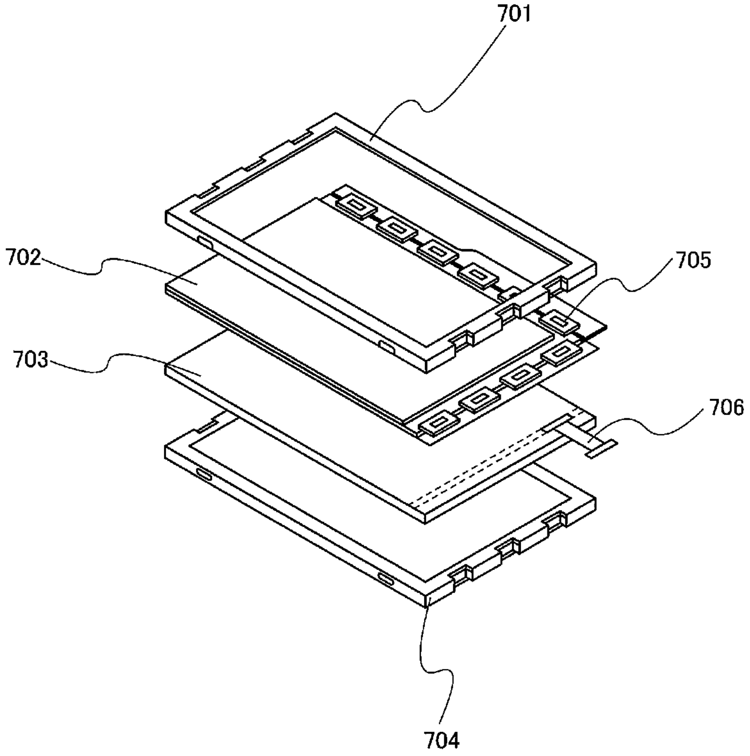
FIG. 6 illustrates a liquid crystal display device of one embodiment of the present invention.

Moreover, a light-emitting device of one embodiment of the present invention can be used as a lighting device. FIG. 6 illustrates an example of a liquid crystal display device using a light-emitting device of one embodiment of the present invention as a backlight. The liquid crystal display device illustrated in FIG. 6 includes a housing 701, a liquid crystal layer 702, a backlight 703, and a housing 704. The liquid crystal layer 702 is electrically connected to a driver IC 705. The light-emitting device of one embodiment of the present invention is used as the backlight 703, and a current is supplied to the backlight 703 through a terminal 706.

By using a light-emitting device of one embodiment of the present invention as a backlight of a liquid crystal display device as described above, a backlight having reduced power consumption can be obtained. Moreover, since a light-emitting device of one embodiment of the present invention is a lighting device for planar light emission and the enlargement of the light-emitting device is possible, the area of the backlight can also be made larger. Thus, a liquid crystal display device having reduced power consumption and a large area can be obtained.

Figure 7:
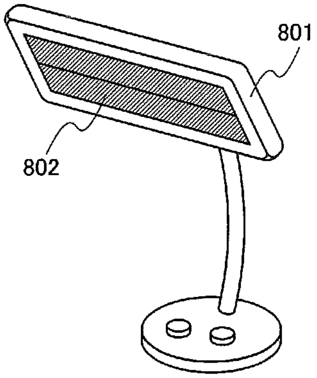
FIG. 7 illustrates a lighting device of one embodiment of the present invention.

FIG. 7 illustrates an example in which a light-emitting device of one embodiment of the present invention is used for a desk lamp which is a lighting device. The desk lamp illustrated in FIG. 7 has a housing 801 and a light source 802, and a light-emitting device of one embodiment of the present invention is used as the light source 802. Since the light-emitting device of one embodiment of the present invention has low driving voltage, high current efficiency, and a long lifetime, by its application, a desk lamp having high reliability and reduced power consumption can be obtained.

Figure 8:
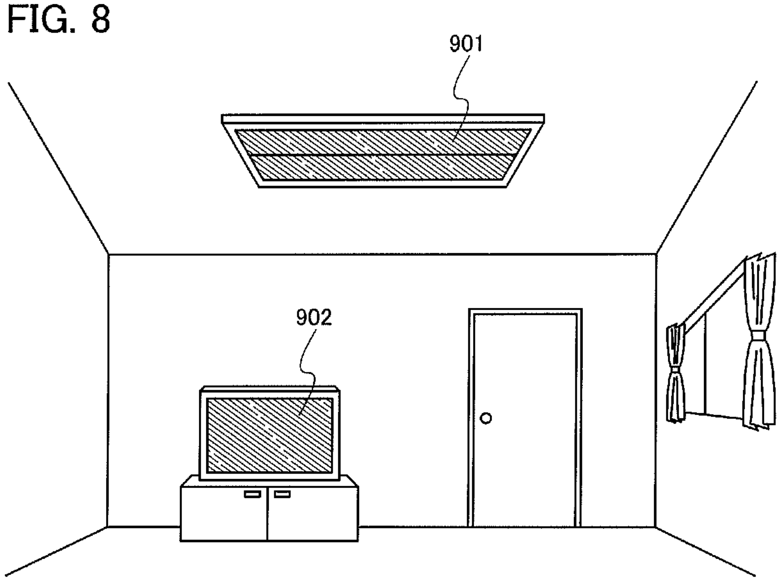
FIG. 8 illustrates a lighting device of one embodiment of the present invention.

FIG. 8 illustrates an example in which a light-emitting device of one embodiment of the present invention is used for an indoor lighting device 901. Since the light-emitting device of one embodiment of the present invention can have a larger area, it can be used as a lighting device having a large area. Further, since the light-emitting device of one embodiment of the present invention has low driving voltage, high current efficiency, and a long lifetime, by the application of the light-emitting device of one embodiment of the present invention, a lighting device having high reliability and reduced power consumption can be obtained. In a room where the light-emitting device of one embodiment of the present invention is used as the indoor lighting device 901 as above, a television set 902 of one embodiment of the present invention as described referring to FIG. 5A can be installed so that pubic broadcasting and movies can be watched.

Note that this embodiment can be combined with any other embodiment as appropriate.

Example 1

Synthesis Example 1

This example gives descriptions of a method of synthesizing 2-[3-(dibenzothiophen-4-yl)phenyl]dibenzo[f,h]quinoxaline (abbreviation: 2mDBTPDBq-II) represented by the following Structural Formula (101).

[Chemical Formula 76]

(101)

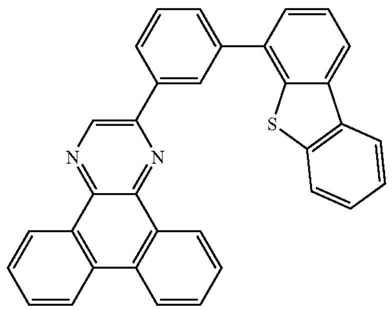

[Synthesis of 2mDBTPDBq-II]

A scheme for the synthesis of 2mDBTPDBq-II is illustrated in (C-1).

[Chemical Formula 77]

(C-1)

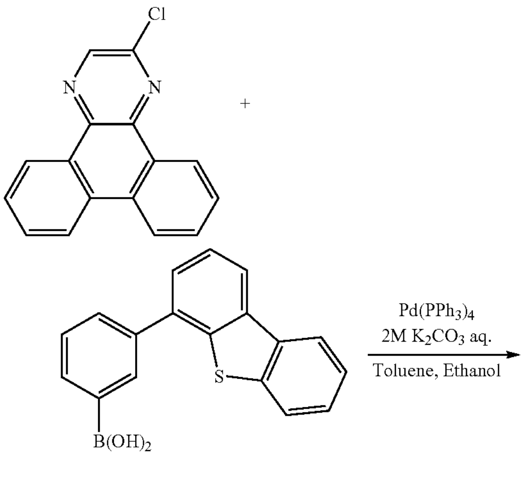

-continued

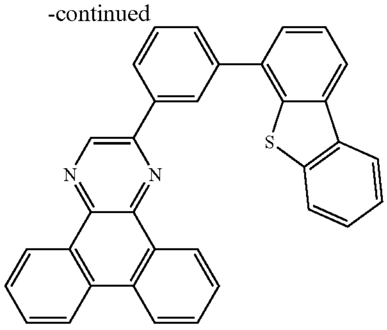

(101)

In a 2-L three-neck flask were put 5.3 g (20 mmol) of 2-chlorodibenzo[f,h]quinoxaline, 6.1 g (20 mmol) of 3-(dibenzothiophen-4-yl)phenylboronic acid, 460 mg (0.4 mmol) of tetrakis(triphenylphosphine)palladium(0), 300 mL of toluene, 20 mL of ethanol, and 20 mL of a 2M aqueous potassium carbonate solution. This mixture was degassed by stirring under reduced pressure, and the air in the flask was replaced with nitrogen. This mixture was stirred under a nitrogen stream at 100° C. for 7.5 hours. After cooled to room temperature, the obtained mixture was filtered to give a white substance. The substance obtained by the filtration was washed well with water and ethanol in this order, and then dried. The obtained solid was dissolved in about 600 mL of hot toluene, followed by suction filtration through Celite (produced by Wako Pure Chemical Industries, Ltd., Catalog No. 531-16855) and Florisil (produced by Wako Pure Chemical Industries, Ltd., Catalog No. 540-00135), whereby a clear colorless filtrate was obtained. The obtained filtrate was concentrated and purified by silica gel column chromatography. The chromatography was carried out using hot toluene as a developing solvent. Acetone and ethanol were added to the solid obtained here, followed by irradiation with ultrasonic waves. Then, the generated suspended solid was filtered and the obtained solid was dried to give 7.85 g of a white powder in 80% yield, which was the substance to be produced.

The above produced substance was relatively soluble in hot toluene, but is a material that is easy to precipitate when cooled. Further, the substance was poorly soluble in other organic solvents such as acetone and ethanol. Hence, the utilization of these different degrees of solubility resulted in a high-yield synthesis by a simple method as above. Specifically, after the reaction finished, the mixture was returned to room temperature and the precipitated solid was collected by filtration, whereby most impurities were able to be easily removed. Further, by the column chromatography with hot toluene as a developing solvent, the produced substance, which is easy to precipitate, was able to be readily purified.

By a train sublimation method, 4.0 g of the obtained white powder was purified. In the purification, the white powder was heated at 300° C. under a pressure of 5.0 Pa with a flow rate of argon gas of 5 mL/min. After the purification, 3.5 g of a white powder was obtained in a yield of 88%, which was the substance to be produced.

A nuclear magnetic resonance (NMR) method identified this compound as 2-[3-(dibenzothiophen-4-yl)phenyl]dibenzo[f,h]quinoxaline (abbreviation: 2mDBTPDBq-II), which was the substance to be produced.

$^1$H NMR data of the obtained substance are as follows: $^1$H NMR ($CDCl_3$, 300 MHz): δ (ppm)=7.45-7.52 (m, 2H), 7.59-7.65 (m, 2H), 7.71-7.91 (m, 7H), 8.20-8.25 (m, 2H), 8.41 (d, J=7.8 Hz, 1H), 8.65 (d, J=7.5 Hz, 2H), 8.77-8.78 (m, 1H), 9.23 (dd, J=7.2 Hz, 1.5 Hz, 1H), 9.42 (dd, J=7.8 Hz, 1.5 Hz, 1H), 9.48 (s, 1H).

Figure 9A:
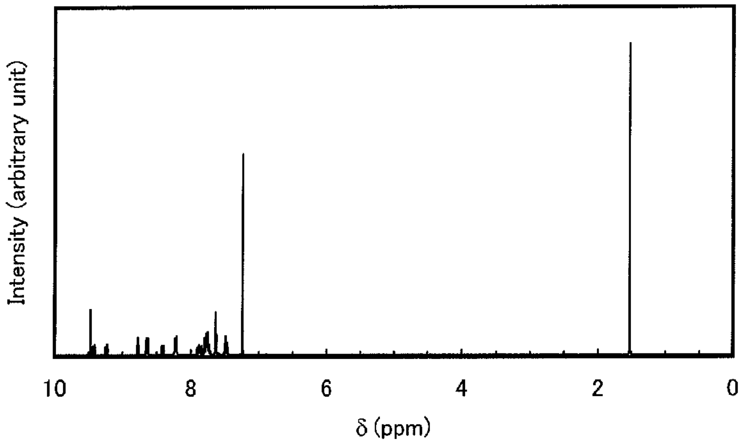
FIGS. 9A and 9B show $^{1}$H NMR charts of 2-[3-(dibenzothiophen-4-yl)phenyl]dibenzo[f,h]quinoxaline (abbreviation: 2mDBTPDBq-II).
Figure 9B:
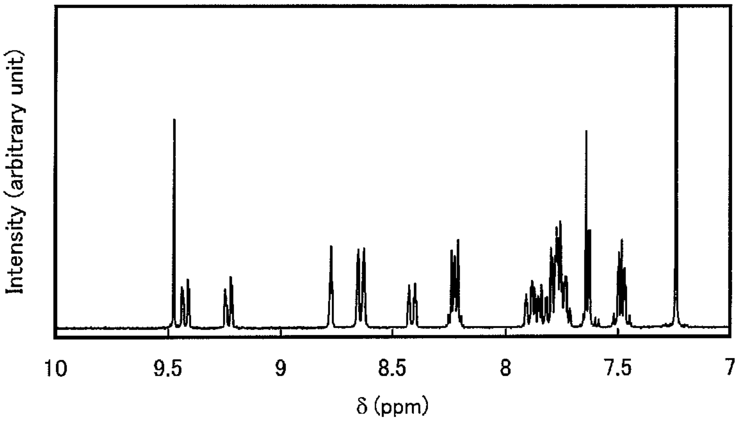

FIGS. 9A and 9B illustrate the $^1$H NMR charts. Note that FIG. 9B is a chart showing an enlarged part of FIG. 9A in the range of 7.0 ppm to 10.0 ppm.

Figure 10A:
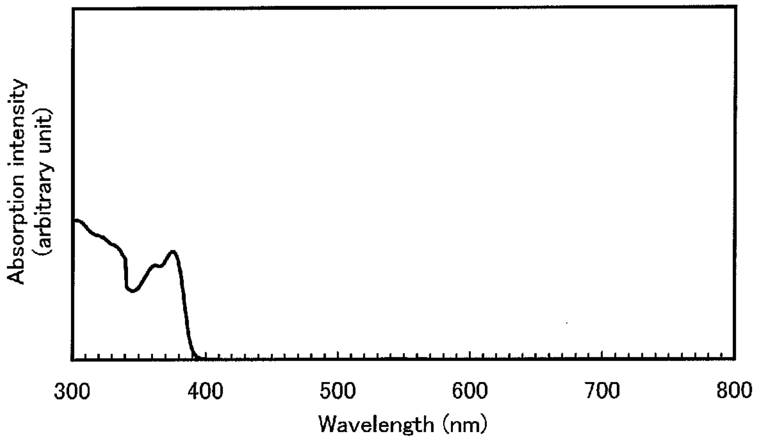
FIGS. 10A and 10B show respectively an absorption spectrum and an emission spectrum of a toluene solution of 2mDBTPDBq-II.
Figure 10B:
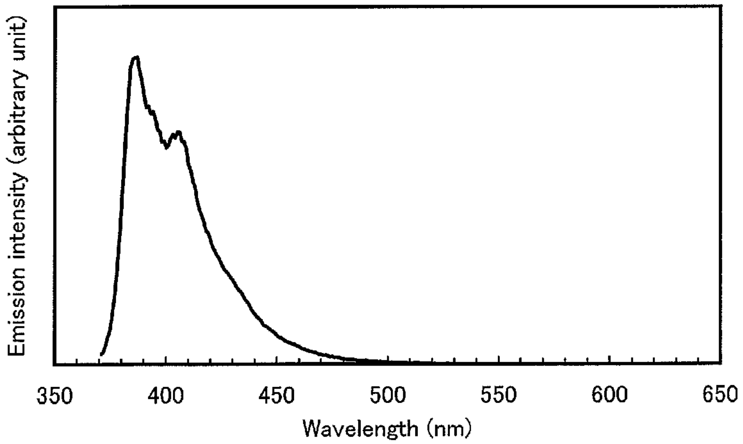
Figure 11A:
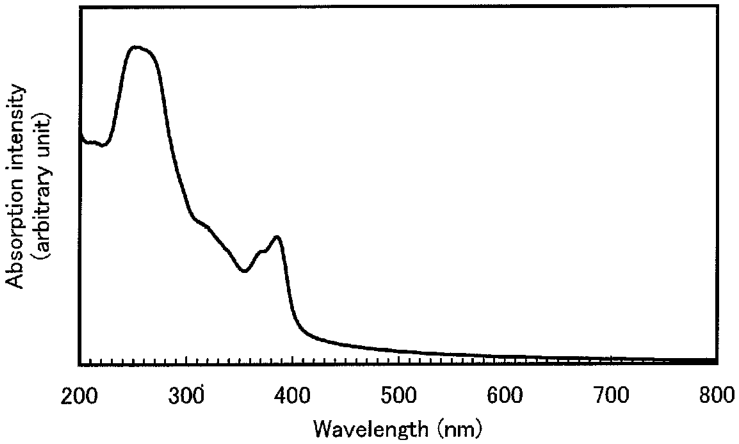
FIGS. 11A and 11B show respectively an absorption spectrum and an emission spectrum of a thin film of 2mDBTPDBq-II.
Figure 11B:
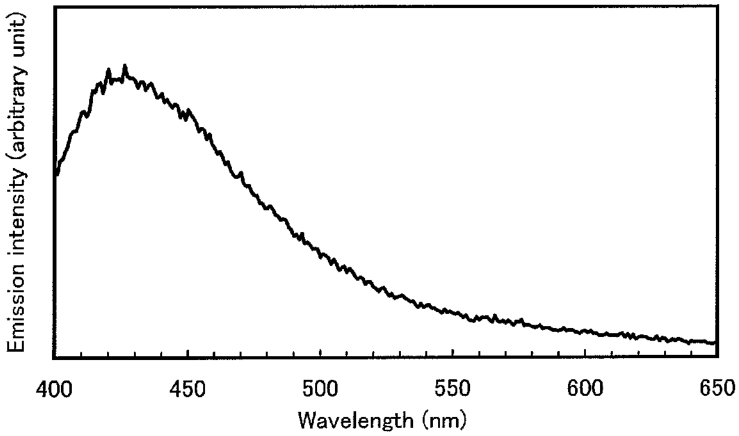

Further, FIG. 10A shows an absorption spectrum of a toluene solution of 2mDBTPDBq-II, and FIG. 10B shows an emission spectrum thereof. FIG. 11A shows an absorption spectrum of a thin film of 2mDBTPDBq-II, and FIG. 11B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 10A and 10B and FIGS. 11A and 11B, the horizontal axis represents wavelength (nm) and the vertical axis represents intensity (arbitrary unit). In the case of the toluene solution, an absorption peak was observed at around 375 nm, and emission wavelength peaks were 386 nm and 405 nm (at an excitation wavelength of 363 nm). In the case of the thin film, absorption peaks were observed at around 250 nm, 312 nm, 369 nm, and 385 nm, and an emission wavelength peak was 426 nm (at an excitation wavelength of 385 nm).

Example 2

Synthesis Example 2

This example gives descriptions of a method of synthesizing 2-[4-(3,6-diphenyl-9H-carbazol-9-yl)phenyl]dibenzo[f,h]quinoxaline (abbreviation: 2CzPDBq-III) represented by the following Structural Formula (338).

[Chemical Formula 78]

(338)

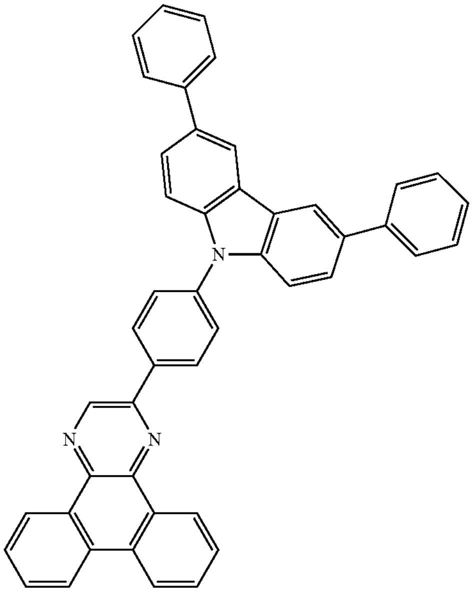

[Synthesis of 2CzPDBq-III]

A scheme for the synthesis of 2CzPDBq-III is illustrated in (C-2).

[Chemical Formula 79]

(C-2)

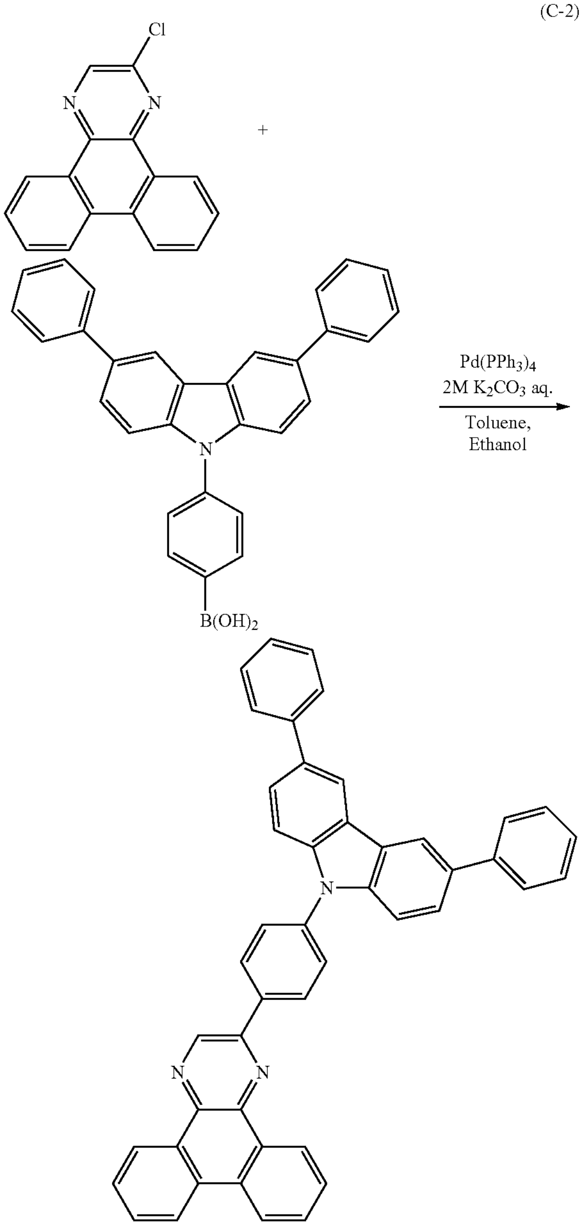

(338)

In a 50-mL three-neck flask were put 0.6 g (2.3 mmol) of 2-chlorodibenzo[f,h]quinoxaline, 1.1 g (2.5 mmol) of 4-(3,6-diphenyl-9H-carbazol-9-yl)phenylboronic acid, 10 mL of toluene, 2 mL of ethanol, and 3 mL of a 2M aqueous potassium carbonate solution. This mixture was degassed by stirring under reduced pressure, and the air in the flask was replaced with nitrogen. To this mixture was added 89 mg (75 μmol) of tetrakis(triphenylphosphine)palladium(0). This mixture was stirred under a nitrogen stream at 80° C. for 5 hours. After a predetermined time had elapsed, water was added to the obtained mixture, and organic substances were extracted from the aqueous layer with chloroform. The obtained solution of the extracted organic substances was combined with the organic layer, the mixture was washed with saturated brine, and the organic layer was dried with magnesium sulfate. The obtained mixture was gravity filtered, and the filtrate was concentrated to give a solid. The obtained solid was dissolved in toluene, and the toluene solution was suction filtered through Celite (produced by Wako Pure Chemical Industries, Ltd., Catalog No. 531-16855), Florisil (produced by Wako Pure Chemical Industries, Ltd., Catalog No. 540-00135), and alumina, and the filtrate was concentrated to give a solid. After methanol was added to this solid and the methanol suspension was irradiated with ultrasonic waves, the solid was suction filtered to give a solid. This obtained solid was washed with toluene. The obtained solid was recrystallized from toluene, giving 1.0 g of a yellow powder in a yield of 65%, which was the substance to be produced.

By a train sublimation method, 0.97 g of the obtained yellow powder was purified. In the purification, the yellow powder was heated at 350° C. under a pressure of 2.4 Pa with a flow rate of argon gas of 5 mL/min. After the purification, 0.92 g of a yellow powder was obtained in a yield of 95%, which was the substance to be produced.

A nuclear magnetic resonance (NMR) method identified this compound as 2-[4-(3,6-diphenyl-9H-carbazol-9-yl)phenyl]dibenzo[f,h]quinoxaline (abbreviation: 2CzPDBq-III), which was the substance to be produced.

$^1$H NMR data of the obtained substance are as follows: $^1$H NMR ($CDCl_3$, 300 MHz): δ (ppm)=7.35 (t, J=7.2 Hz, 2H), 7.49 (t, J=7.2 Hz, 4H), 7.63 (d, J=8.1 Hz, 2H), 7.73-7.90 (m, 12H), 8.42 (d, J=1.5 Hz, 2H), 8.62-8.69 (m, 4H), 9.25-9.28 (m, 1H), 9.45-9.48 (m, 1H), 9.50 (s, 1H).

Figure 12A:
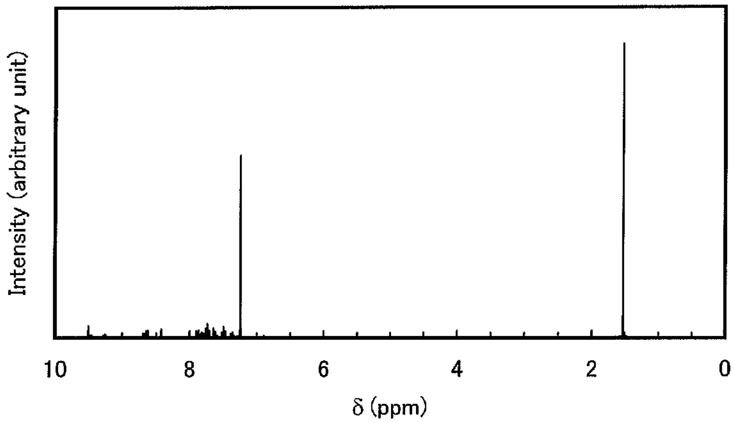
FIGS. 12A and 12B show $^{1}$H NMR charts of 2-[4-(3,6-diphenyl-9H-carbazol-9-yl)phenyl]dibenzo[f,h]quinoxaline (abbreviation: 2CzPDBq-III).
Figure 12B:
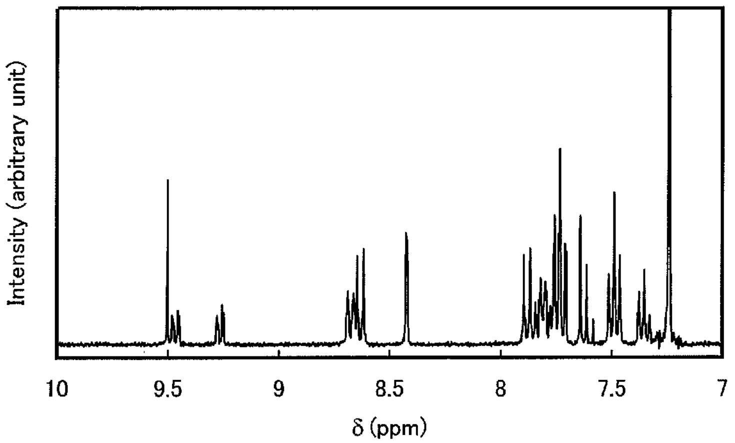

FIGS. 12A and 12B illustrate the $^1$H NMR charts. Note that FIG. 12B is a chart showing an enlarged part of FIG. 12A in the range of 7.0 ppm to 10.0 ppm.

Figure 13A:
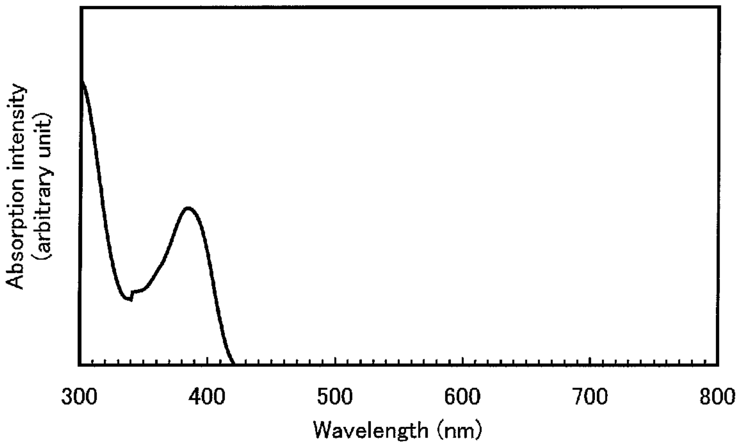
FIGS. 13A and 13B show respectively an absorption spectrum and an emission spectrum of a toluene solution of 2CzPDBq-III.
Figure 13B:
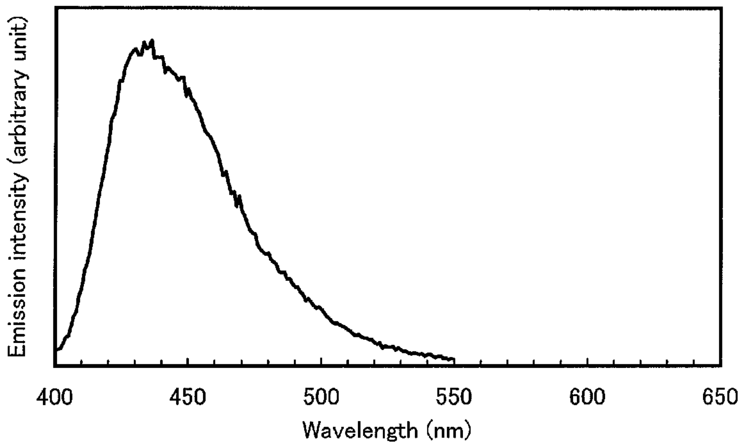
Figure 14A:
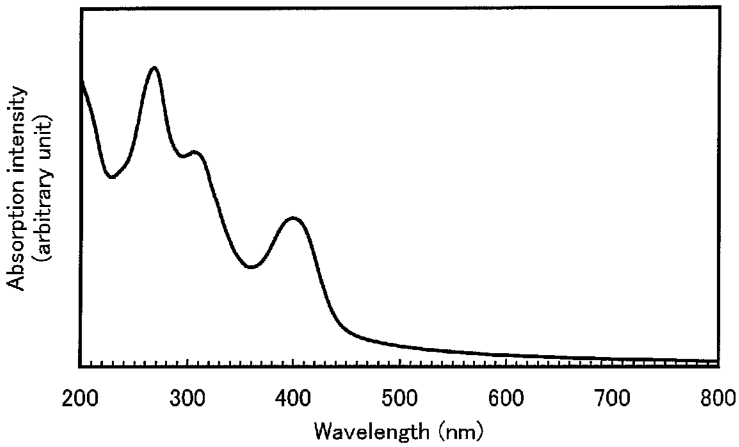
FIGS. 14A and 14B show respectively an absorption spectrum and an emission spectrum of a thin film of 2CzPDBq-III.
Figure 14B:
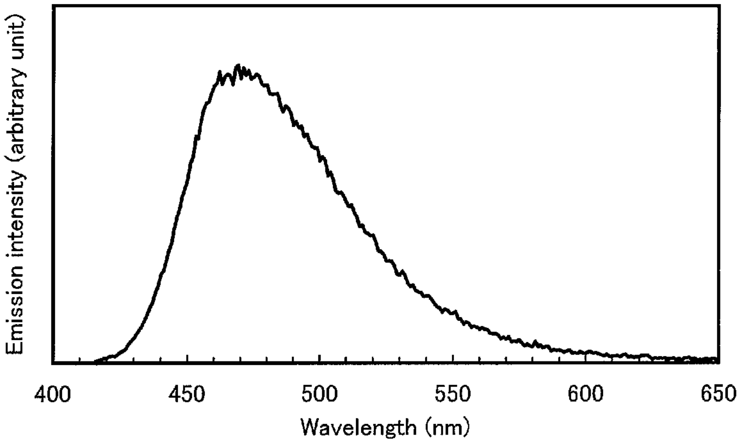

Further, FIG. 13A shows an absorption spectrum of a toluene solution of 2CzPDBq-III, and FIG. 13B shows an emission spectrum thereof. FIG. 14A shows an absorption spectrum of a thin film of 2CzPDBq-III, and FIG. 14B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 13A and 13B and FIGS. 14A and 14B, the horizontal axis represents wavelength (nm) and the vertical axis represents intensity (arbitrary unit). In the case of the toluene solution, an absorption peak was observed at around 385 nm, and an emission wavelength peak was 436 nm (at an excitation wavelength of 385 nm). In the case of the thin film, absorption peaks were observed at around 267 nm, 307 nm, and 399 nm, and an emission wavelength peak was 469 nm (at an excitation wavelength of 396 nm).

Example 3

Figure 18:
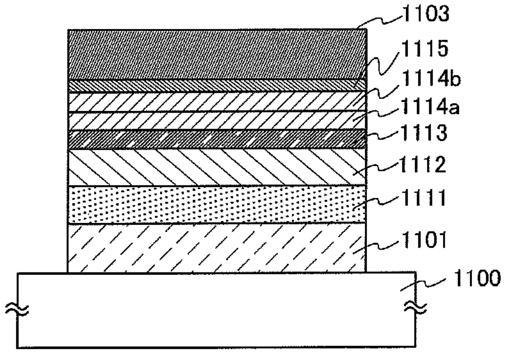
FIG. 18 illustrates a light-emitting element of Examples.

In this example, a light-emitting element of one embodiment of the present invention will be described referring to FIG. 18. Chemical formulae of materials used in this example are illustrated below.

[Chemical Formula 80]
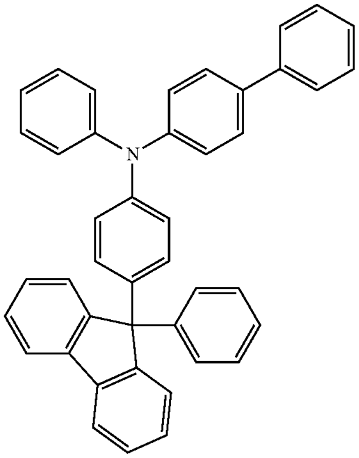
BPAFLP
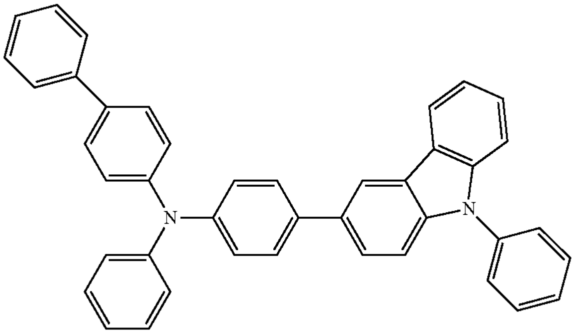
PCBA1BP
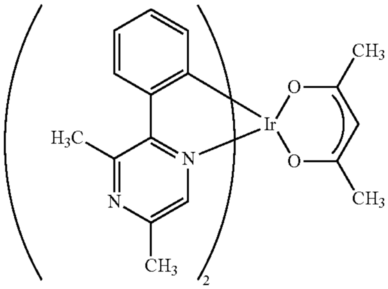
Ir(mppr-Me)$_2$acac
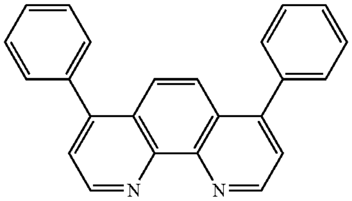
BPhen
-continued
[Chemical Formula 81]
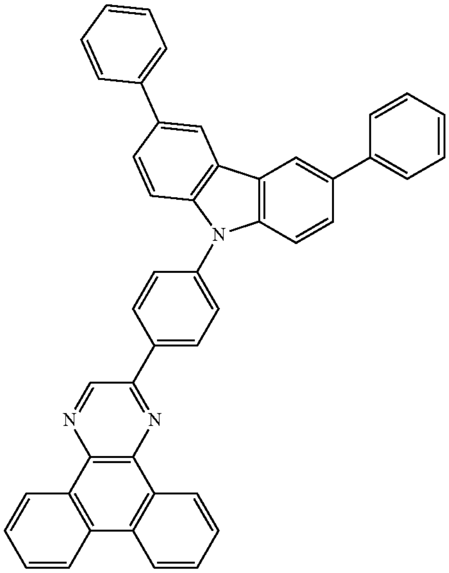
2CzPDBq-III
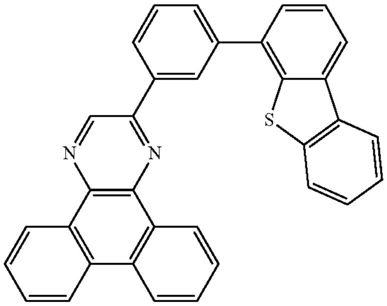
2mDBTPDBq-II
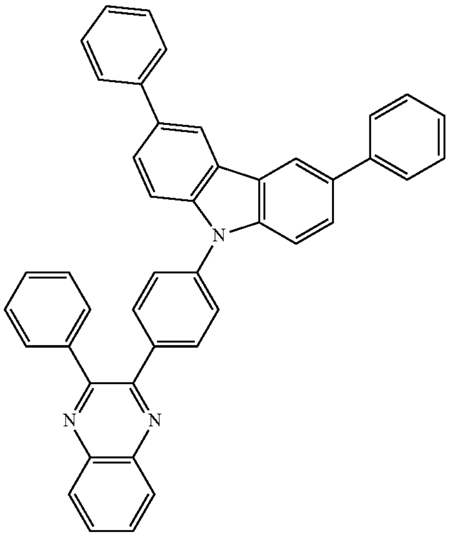
Cz1PQ-III -continued

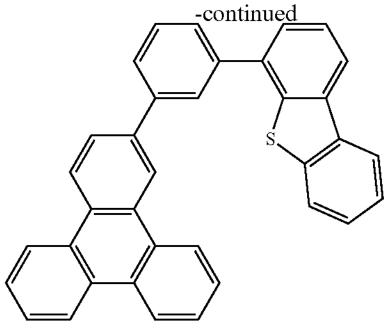

mDBTPTp-II

Methods of fabricating Light-emitting Element 1, Light-emitting Element 2, Reference Light-emitting Element 3, and Reference Light-emitting Element 4 of this example will be described below.

(Light-Emitting Element 1)

First, indium tin oxide containing silicon oxide (ITSO) was deposited over a glass substrate 1100 by a sputtering method, whereby a first electrode 1101 was formed. Note that its thickness was set to 110 nm and the electrode area was set to 2 mm×2 mm. Here, the first electrode 1101 is an electrode that functions as an anode of the light-emitting element.

Next, as pretreatment for forming the light-emitting element over the substrate 1100, after washing of a surface of the substrate with water and baking that was performed at 200° C. for one hour, UV ozone treatment was performed for 370 seconds.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. Then, by an evaporation method using resistance heating, 4-phenyl-4'-(9-phenylfluoren-9-yl)triphenylamine (abbreviation: BPAFLP) and molybdenum(VI) oxide were co-evaporated to form a hole-injection layer 1111 over the first electrode 1101. The thickness of the hole-injection layer 1111 was set to 40 nm, and the weight ratio of BPAFLP to molybdenum(VI) oxide was adjusted to 4:2 (=BPAFLP:molybdenum(VI) oxide). Note that the co-evaporation method refers to an evaporation method in which evaporation is carried out from a plurality of evaporation sources at the same time in one treatment chamber.

Next, a BPAFLP film was formed to a thickness of 20 nm over the hole-injection layer 1111, whereby a hole-transport layer 1112 was formed.

Further, 2-[4-(3,6-diphenyl-9H-carbazol-9-yl)phenyl]dibenzo[f,h]quinoxaline (abbreviation: 2CzPDBg-III) synthesized in Example 2, 4-phenyl-4'-(9-phenyl-9H-carbazol-3-yl)triphenylamine (abbreviation: PCBA1BP), and (acetylacetonato)bis(3,5-dimethyl-2-phenylpyrazinato)iridium(III) (abbreviation: [Ir(mppr-Me)$_2$(acac)]) were co-evaporated to form a light-emitting layer 1113 over the hole-transport layer 1112. The weight ratio of 2CzPDBq-III to PCBA1BP and [Ir(mppr-Me)$_2$(acac)] was adjusted to 1:0.15:0.06 (=2CzPDBq-III:PCBA1BP:[Ir(mppr-Me)$_2$(acac)]). The thickness of the light-emitting layer 1113 was set to 40 nm.

Further, a 2CzPDBq-III film was formed to a thickness of 10 nm over the light-emitting layer 1113, whereby a first electron-transport layer **1114*a*** was formed.

Then, a bathophenanthroline (abbreviation: BPhen) film was formed to a thickness of 20 nm over the first electron-transport layer **1114*a*, whereby a second electron-transport layer 1114*b*** was formed.

Further, a lithium fluoride (LiF) film was formed to a thickness of 1 nm over the second electron-transport layer **1114*b* by evaporation, whereby an electron-injection layer 1115** was formed.

Lastly, an aluminum film was formed to a thickness of 200 nm by evaporation as a second electrode 1103 functioning as a cathode. Thus, Light-emitting Element 1 of this example was fabricated.

Note that, in the above evaporation process, evaporation was all performed by a resistance heating method.

(Light-Emitting Element 2)

The light-emitting layer 1113 of Light-emitting Element 2 was formed by co-evaporation of 2-[3-(dibenzothiophen-4-yl)phenyl]dibenzo[f,h]quinoxaline (abbreviation: 2mDBTPDBq-II) synthesized in Example 1, PCBA1BP, and [Ir(mppr-Me)$_2$(acac)]. The weight ratio of 2mDBTPDBq-II to PCBA1BP and [Ir(mppr-Me)$_2$(acac)] was adjusted to 1:0.25:0.06 (=2mDBTPDBq-II:PCBA1BP:[Ir(mppr-Me)$_2$(acac)]). The thickness of the light-emitting layer 1113 was set to 40 nm.

The first electron-transport layer **1114*a* of Light-emitting Element 2 was formed with a 10-nm-thick 2mDBTPDBq-II film. The components other than the light-emitting layer 1113 and the first electron-transport layer 1114*a*** were formed in the same manner as those of Light-emitting Element 1.

(Reference Light-Emitting Element 3)

The light-emitting layer 1113 of Reference Light-emitting Element 3 was formed by co-evaporation of 2-[4-(3,6-diphenyl-9H-carbazol-9-yl)phenyl]-3-phenylquinoxaline (abbreviation: Cz1PQ-III), PCBA1BP, and [Ir(mppr-Me)$_2$(acac)]. The weight ratio of Cz1PQ-III to PCBA1BP and [Ir(mppr-Me)$_2$(acac)] was adjusted to 1:0.3:0.06 (=Cz1PQ-III:PCBA1BP:[Ir(mppr-Me)$_2$(acac)]). The thickness of the light-emitting layer 1113 was set to 40 nm.

The first electron-transport layer **1114*a* of Reference Light-emitting Element 3 was formed with a 10-nm-thick Cz1PQ-III film. The components other than the light-emitting layer 1113 and the first electron-transport layer 1114*a*** were formed in the same manner as those of Light-emitting Element 1.

(Reference Light-Emitting Element 4)

The light-emitting layer 1113 of Reference Light-emitting Element 4 was formed by co-evaporation of 4-[3-(triphenylen-2-yl)phenyl]dibenzothiophene (abbreviation: mDBTPTp-II), PCBA1BP, and [Ir(mppr-Me)$_2$(acac)]. The weight ratio of mDBTPTp-II to PCBA1BP and [Ir(mppr-Me)$_2$(acac)] was adjusted to 1:0.15:0.06 (=mDBTPTp-II:PCBA1BP:[Ir(mppr-Me)$_2$(acac)]). The thickness of the light-emitting layer 1113 was set to 40 nm.

The first electron-transport layer **1114*a* of Reference Light-emitting Element 4 was formed with a 10-nm-thick mDBTPTp-II film. The components other than the light-emitting layer 1113 and the first electron-transport layer 1114*a*** were formed in the same manner as those of Light-emitting Element 1.

Table 1 shows element structures of Light-emitting Elements 1 and 2 and Reference Light-emitting Elements 3 and 4 obtained as described above.

TABLE 1

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 1 | ITSO 110 nm | BPAFLP: $MoO_x$ (=4:2) 40 nm | BPAFLP 20 nm | 2CzPDBq-III: PCBA1BP: $[Ir(mppr\text{-}Me)_2(acac)]$ (=1:0.15:0.06) 40 nm | 2CzPDBq-III 10 nm | BPhen 20 nm | LiF 1 nm | Al 200 nm |
| Light-emitting element 2 | ITSO 110 nm | BPAFLP: $MoO_x$ (=4:2) 40 nm | BPAFLP 20 nm | 2mDBTPDBq-II: PCBA1BP: $[Ir(mppr\text{-}Me)_2(acac)]$ (=1:0.25:0.06) 40 nm | 2mDBTPDBq-II 10 nm | BPhen 20 nm | LiF 1 nm | Al 200 nm |
| Reference light-emitting element 3 | ITSO 110 nm | BPAFLP: $MoO_x$ (=4:2) 40 nm | BPAFLP 20 nm | Cz1PQ-III: PCBA1BP: $[Ir(mppr\text{-}Me)_2(acac)]$ (=1:0.3:0.06) 40 nm | Cz1PQ-III 10 nm | BPhen 20 nm | LiF 1 nm | Al 200 nm |
| Reference light-emitting element 4 | ITSO 110 nm | BPAFLP: $MoO_x$ (=4:2) 40 nm | BPAFLP 20 nm | mDBTPTp-II: PCBA1BP: $[Ir(mppr\text{-}Me)_2(acac)]$ (=1:0.15:0.06) 40 nm | mDBTPTp-II 10 nm | BPhen 20 nm | LiF 1 nm | Al 200 nm |

In a glove box containing a nitrogen atmosphere, Light-emitting Elements 1 and 2 and Reference Light-emitting Elements 3 and 4 were sealed with a glass substrate so as not to be exposed to air. Then, operation characteristics of these elements were measured. Note that the measurements were carried out at room temperature (in the atmosphere kept at 25° C.).

Figure 15:
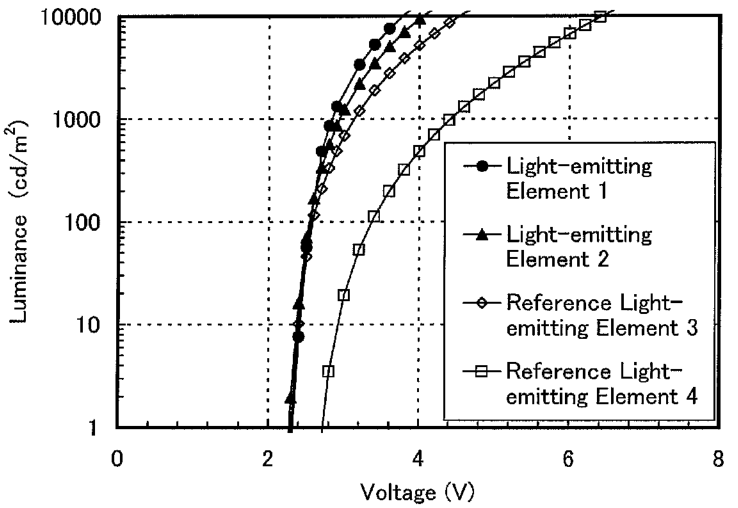
FIG. 15 shows voltage vs. luminance characteristics of light-emitting elements of Example 3.
Figure 16:
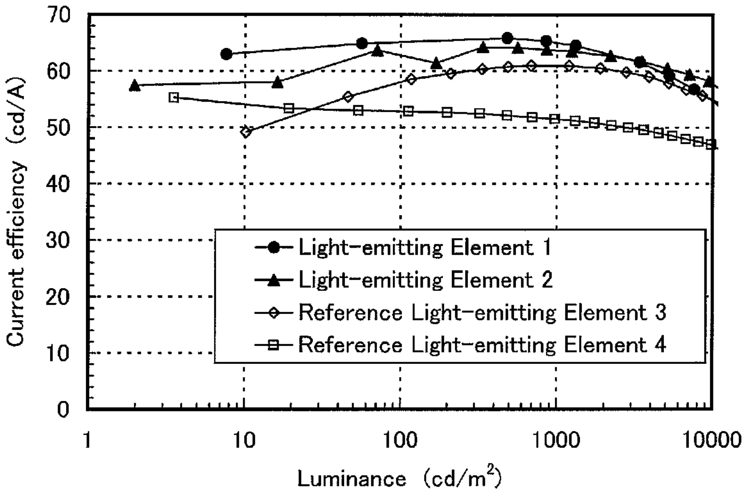
FIG. 16 shows luminance vs. current efficiency characteristics of the light-emitting elements of Example 3.

FIG. 15 shows the voltage vs. luminance characteristics of Light-emitting Elements 1 and 2 and Reference Light-emitting Elements 3 and 4. In FIG. 15, the horizontal axis represents voltage (V) and the vertical axis represents luminance ($cd/m^2$). In addition, FIG. 16 shows the luminance vs. current efficiency characteristics of the elements. In FIG. 16, the horizontal axis represents luminance ($cd/m^2$) and the vertical axis represents current efficiency (cd/A). Further, Table 2 shows the voltage (V), current density ($mA/cm^2$), CIE chromaticity coordinates (x, y), current efficiency (cd/A), and external quantum efficiency (%) of each light-emitting element at a luminance of around 1000 $cd/m^2$.

TABLE 2

| | Voltage (V) | Current density ($mA/cm^2$) | Chromaticity x | Chromaticity y | Luminance ($cd/m^2$) | Current efficiency (cd/A) | External quantum efficiency (%) |
|---|---|---|---|---|---|---|---|
| Light-emitting element 1 | 2.8 | 1.3 | 0.54 | 0.46 | 850 | 65 | 24 |
| Light-emitting element 2 | 2.9 | 1.4 | 0.54 | 0.46 | 860 | 64 | 23 |
| Reference Light-emitting element 3 | 3.2 | 2.0 | 0.53 | 0.46 | 1200 | 61 | 22 |
| Reference Light-emitting element 4 | 4.4 | 1.9 | 0.55 | 0.45 | 970 | 52 | 18 |

As shown in Table 2, the CIE chromaticity coordinates (x, y) of Light-emitting Element 1 were (0.54, 0.46) at a luminance of 850 $cd/m^2$. The CIE chromaticity coordinates (x, y) of Light-emitting Element 2 were (0.54, 0.46) at a luminance of 860 $cd/m^2$. The CIE chromaticity coordinates (x, y) of Reference Light-emitting Element 3 were (0.53, 0.46) at a luminance of 1200 $cd/m^2$. The CIE chromaticity coordinates (x, y) of Reference Light-emitting Element 4 were (0.55, 0.45) at a luminance of 970 $cd/m^2$. It is found that all these light-emitting elements exhibited light emission from $[Ir(mppr\text{-}Me)_2(acac)]$.

FIG. 15 reveals that Light-emitting Elements 1 and 2 each have low driving voltage and high current efficiency. A structural difference in the compounds each used as a host material of a light-emitting layer between Light-emitting Element 2 and Reference Light-emitting Element 4 is that a dibenzo[f,h]quinoxaline skeleton is included in Light-emitting Element 2 while a triphenylene skeleton is included in Reference Light-emitting Element 4. Which of a dibenzo[f,h]quinoxaline skeleton or a triphenylene skeleton was included made a differences in voltage vs. luminance characteristics and luminance vs. current efficiency characteristics between Light-emitting Element 2 and Reference Light-emitting Element 4. It is thus confirmed that, like a heterocyclic compound of one embodiment of the present invention, a compound having a dibenzo[f,h]quinoxaline skeleton is effective in realizing high voltage vs. luminance characteristics and high luminance vs. current efficiency characteristics.

Figure 17:
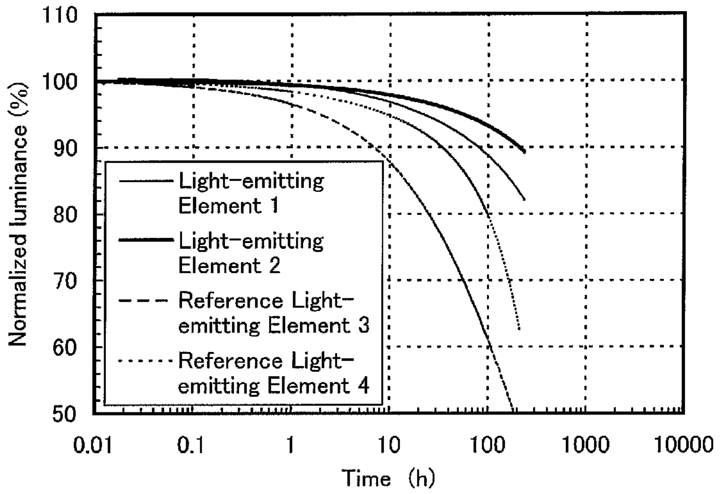
FIG. 17 shows results of reliability tests of the light-emitting elements of Example 3.

Next, Light-emitting Elements 1 and 2 and Reference Light-emitting Elements 3 and 4 were subjected to reliability tests. Results of the reliability tests are shown in FIG. 17. In FIG. 17, the vertical axis represents normalized luminance (%) with an initial luminance of 100%, and the horizontal axis represents driving time (h) of the elements. In the reliability tests, the light-emitting elements of this example were driven under the conditions where the current density was constant and the initial luminance was 5000 cd/$m^2$. FIG. 17 shows that Light-emitting Element 1 kept 82% of the initial luminance after driving for 230 hours and Light-emitting Element 2 kept 89% of the initial luminance after driving for 230 hours. The luminance of Reference Light-emitting Element 3 decreases to 62% of the initial luminance after 210 hours, and the luminance of Reference Light-emitting Element 4 decreases to 69% of the initial luminance after 210 hours. These results of the reliability tests revealed that Light-emitting Elements 1 and 2 each had a long lifetime. Note that, from these results, when the initial luminance is 5000 cd/$m^2$, the luminance half life of Light-emitting Element 2, whose lifetime was the longest, is estimated at about 6000 hours. When the initial luminance is changed to 1000 cd/$m^2$, which is of practical use, this luminance half life corresponds to 150000 hours, indicating that the lifetime is extremely long.

A dibenzo[f,h]quinoxaline skeleton is included in Light-emitting Element 1 while a quinoxaline skeleton is included in Reference Light-emitting Element 3. Whether a dibenzo[f,h]quinoxaline skeleton is included or not made a difference in the results of the reliability tests between Light-emitting Element 1 and Reference Light-emitting Element 3. It is thus confirmed that, like a heterocyclic compound of one embodiment of the present invention, having a dibenzo[f,h]quinoxaline skeleton is effective in realizing a light-emitting element with much higher reliability.

As described above, by the use of 2mDBTPDBq-II produced in Example 1 and 2CzPDBq-III produced in Example 2, each as a host material of a light-emitting layer, the light-emitting elements having a long lifetime were able to be fabricated.

Example 4

Synthesis Example 3

This example gives descriptions of a method of synthesizing 2-[4-(dibenzothiophen-4-yl)phenyl]dibenzo[f,h]quinoxaline (abbreviation: 2 DBTPDBq-II) represented by the following Structural Formula (100).

[Chemical Formula 82]

(100)

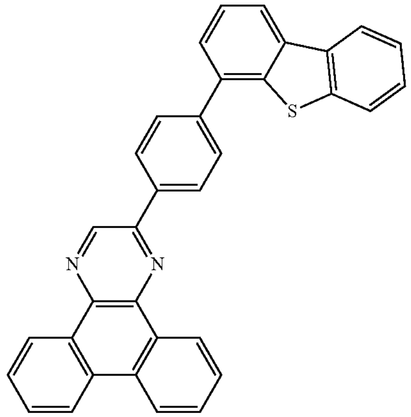

[Synthesis of 2 DBTPDBq-II]

A scheme for the synthesis of 2 DBTPDBq-II is illustrated in (C-3).

[Chemical Formula 83]

(C-3)

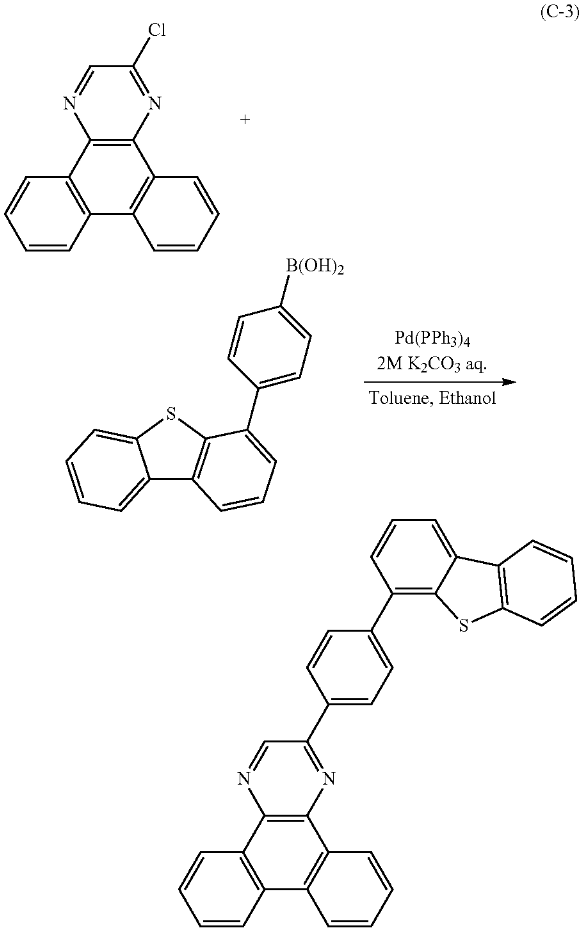

(101)

In a 100-mL three-neck flask were put 2.7 g (10 mmol) of 2-chlorodibenzo[f,h]quinoxaline, 3.4 g (11 mmol) of 4-(dibenzothiophen-4-yl)phenylboronic acid, 80 mL of toluene, 8.0 mL of ethanol, and 15 mL of a 2M aqueous potassium carbonate solution. The mixture was degassed by stirring under reduced pressure, and the air in the flask was replaced with nitrogen. To this mixture was added 0.24 mg (0.20 mmol) of tetrakis(triphenylphosphine)palladium(0). This mixture was stirred under a nitrogen stream at 80° C. for 24 hours. After a predetermined time had elapsed, the precipitated solid was suction filtered to give a solid. Ethanol was added to this solid, followed by irradiation with ultrasonic waves. The solid was suction filtered to give a solid. The obtained solid was dissolved in toluene, and the toluene solution was suction filtered through Celite (produced by Wako Pure Chemical Industries, Ltd., Catalog No. 531-16855) and alumina, and the filtrate was concentrated to give a solid. This solid was recrystallized from toluene to give 3.2 g of a yellow powder in 65% yield.

By a train sublimation method, 1.3 g of the obtained yellow powder was purified. In the purification, the yellow powder was heated at 310° C. under a pressure of 3.0 Pa with a flow rate of argon gas of 5 mL/min. After the purification, 1.1 g of a yellow powder was obtained in a yield of 85%, which was the substance to be produced.

A nuclear magnetic resonance (NMR) method identified this compound as 2-[4-(dibenzothiophen-4-yl)phenyl]dibenzo[f,h]quinoxaline (abbreviation: 2 DBTPDBq-II), which was the substance to be produced.

$^1$H NMR data of the obtained substance are as follows: $^1$H NMR ($CDCl_3$, 300 MHz): δ=7.50-7.53 (m, 2H), 7.62-7.65 (m, 2H), 7.80-7.91 (m, 5H), 8.03 (d, J=8.4 Hz, 2H), 8.23-8.26 (m, 2H), 8.56 (d, J=8.1 Hz, 2H), 8.70 (d, J=7.8 Hz, 2H), 9.30 (dd, J=7.8 Hz, 1.8 Hz, 1H), 9.49-9.51 (m, 21-1).

Figure 19A:
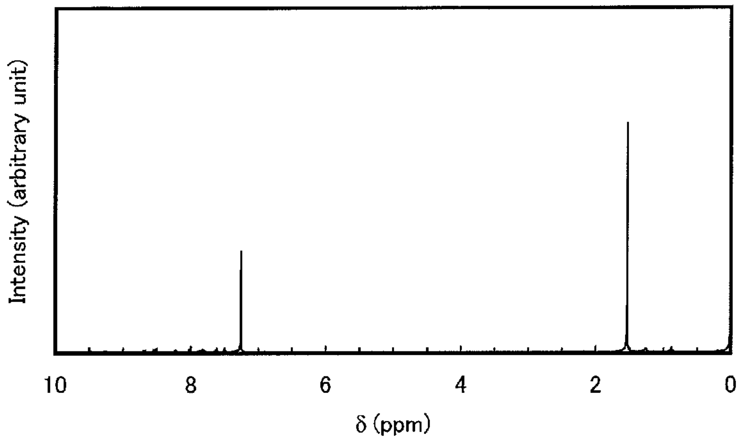
FIGS. 19A and 19B show $^{1}$H NMR charts of 2-[4-(dibenzothiophen-4-yl)phenyl]dibenzo[f,h]quinoxaline (abbreviation: 2 DBTPDBq-II).
Figure 19B:
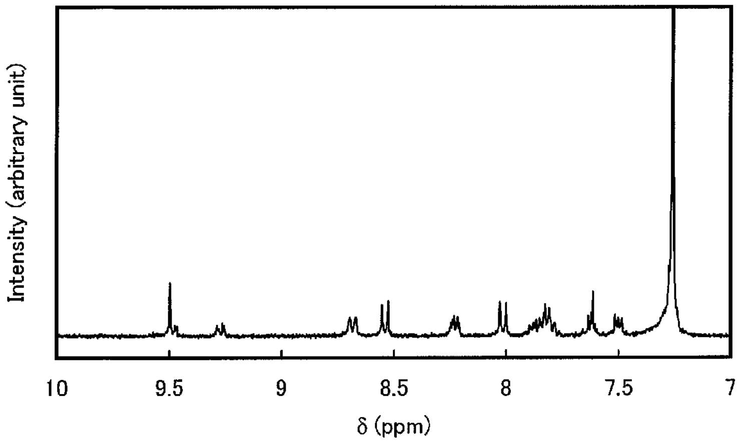

FIGS. 19A and 19B illustrate the NMR charts. Note that FIG. 19B is a chart showing an enlarged part of FIG. 19A in the range of 7.0 ppm to 10.0 ppm.

Figure 20A:
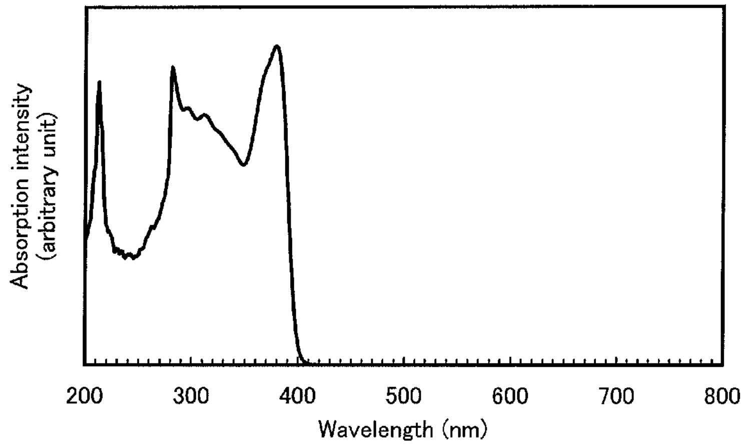
FIGS. 20A and 20B show respectively an absorption spectrum and an emission spectrum of a toluene solution of 2 DBTPDBq-II.
Figure 20B:
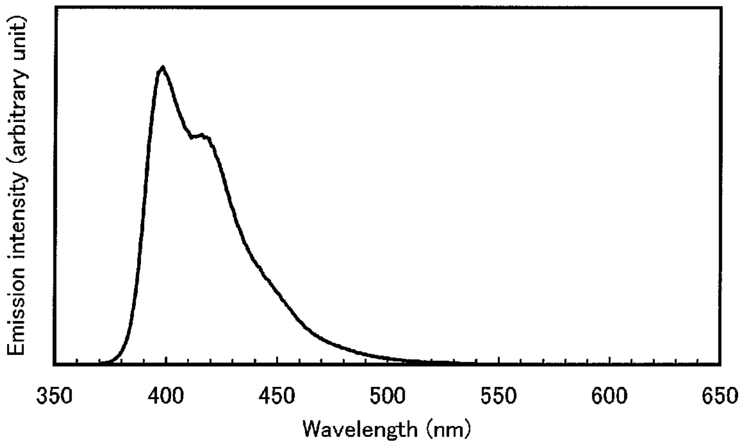
Figure 21A:
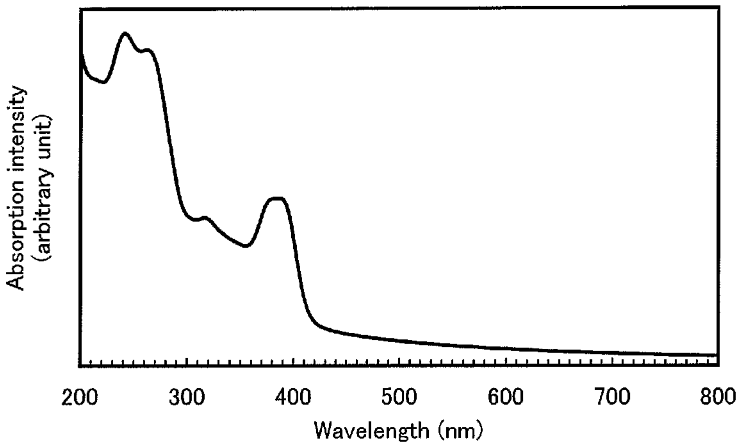
FIGS. 21A and 21B show respectively an absorption spectrum and an emission spectrum of a thin film of 2 DBTPDBq-II.
Figure 21B:
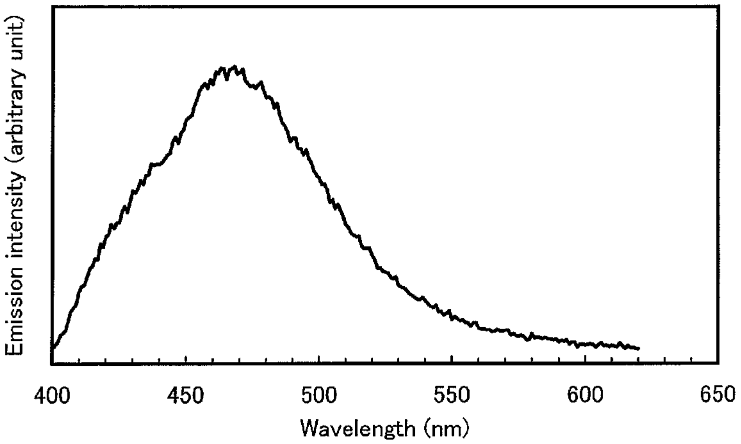

Further, FIG. 20A shows an absorption spectrum of a toluene solution of 2 DBTPDBq-II, and FIG. 20B shows an emission spectrum thereof. FIG. 21A shows an absorption spectrum of a thin film of 2 DBTPDBq-II, and FIG. 21B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 20A and 20B and FIGS. 21A and 21B, the horizontal axis represents wavelength (nm) and the vertical axis represents intensity (arbitrary unit). In the case of the toluene solution, absorption peaks were observed at around 294 nm, 309 nm, and 375 nm, and emission wavelength peaks were 398 nm and 416 nm (at an excitation wavelength of 350 nm). In the case of the thin film, absorption peaks were observed at around 241 nm, 262 nm, 316 nm, and 386 nm, and an emission wavelength peak was 468 nm (at an excitation wavelength of 386 nm).

Example 5

Synthesis Example 4

This example gives descriptions of a method of synthesizing 2-[3'-(dibenzothiophen-4-yl)biphenyl-3-yl]dibenzo[f,h]quinoxaline (abbreviation: 2mDBTBPDBq-II) represented by the following Structural Formula (109).

[Chemical Formula 84]

(109)

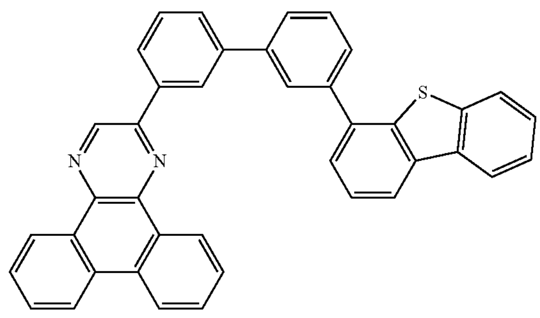

[Synthesis of 2mDBTBPDBq-II]

A scheme for the synthesis of 2mDBTBPDBq-II is illustrated in (C-4).

[Chemical Formula 85]

(C-4)

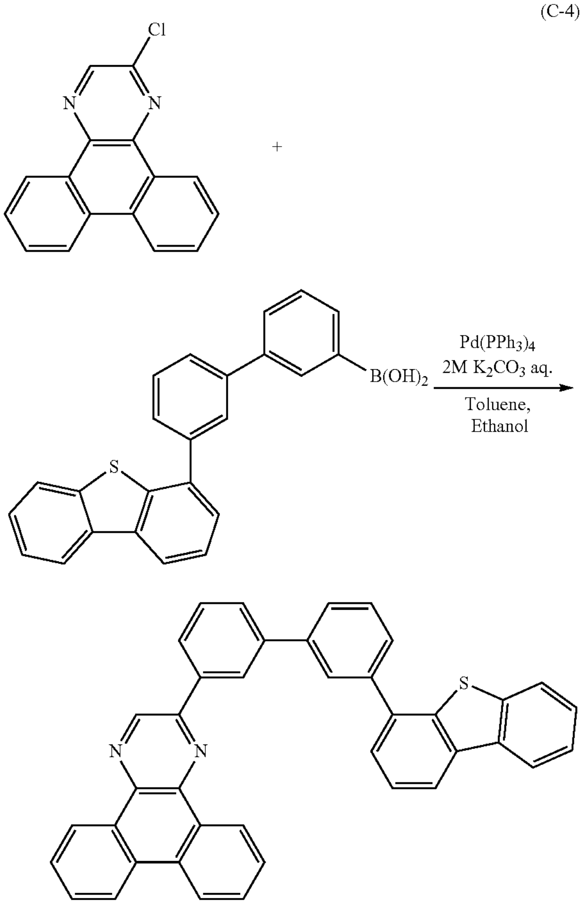

(109)

In a 200-mL three-neck flask were put 0.83 g (3.2 mmol) of 2-chlorodibenzo[f,h]quinoxaline, 1.3 g (3.5 mmol) of 3'-(dibenzothiophen-4-yl)-3-biphenylboronic acid, 40 mL of toluene, 4 mL of ethanol, and 5 mL of a 2M aqueous potassium carbonate solution. This mixture was degassed by stirring under reduced pressure, and the air in the flask was replaced with nitrogen. To this mixture was added 80 mg (70

μmol) of tetrakis(triphenylphosphine)palladium(0). This mixture was stirred under a nitrogen stream at 80° C. for 16 hours. After a predetermined time had elapsed, the precipitated solid was separated by filtration to give a yellow solid. Ethanol was added to this solid, followed by irradiation with ultrasonic waves. The solid was suction filtered to give a solid. The obtained solid was dissolved in toluene, and the toluene solution was suction filtered through alumina and Celite (produced by Wako Pure Chemical Industries, Ltd., Catalog No. 531-16855), and the filtrate was concentrated to give a yellow solid. Further, this solid was recrystallized from toluene to give 1.1 g of a yellow powder in 57% yield.

By a train sublimation method, 1.1 g of the obtained yellow powder was purified. In the purification, the yellow powder was heated at 300° C. under a pressure of 6.2 Pa with a flow rate of argon gas of 15 mL/min. After the purification, 0.80 g of a yellow powder was obtained in a yield of 73%, which was the substance to be produced.

A nuclear magnetic resonance (NMR) method identified this compound as 243'-(dibenzothiophen-4-yl)biphenyl-3-yl] dibenzo[f,h]quinoxaline (abbreviation: 2mDBTBPDBq-II), which was the substance to be produced.

$^1$H NMR data of the obtained substance are as follows: $^1$H NMR ($CDCl_3$, 300 MHz): δ=7.46-7.50 (m, 2H), 7.61 (d, J=4.5 Hz, 2H), 7.67-7.89 (m, 10H), 8.17-8.24 (m, 3H), 8.35 (d, J=8.1 Hz, 1H), 8.65-8.70 (m, 3H), 9.24-9.27 (m, 1H), 9.44-9.48 (m, 2H).

Figure 22A:
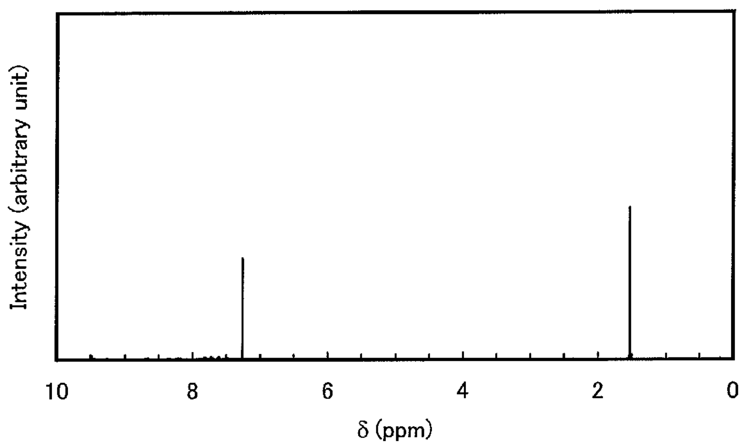
FIGS. 22A and 22B show $^{1}$H NMR charts of 2-[3'-(dibenzothiophen-4-yl)biphenyl-3-yl]dibenzo[f,h]quinoxaline (abbreviation: 2mDBTBPDBq-II).
Figure 22B:
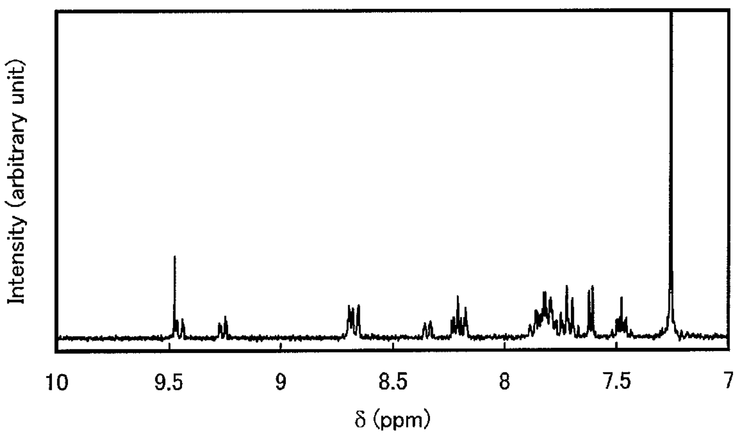

FIGS. 22A and 22B illustrate the $^1$H NMR charts. Note that FIG. 22B is a chart showing an enlarged part of FIG. 22A in the range of 7.0 ppm to 10.0 ppm.

Figure 23A:
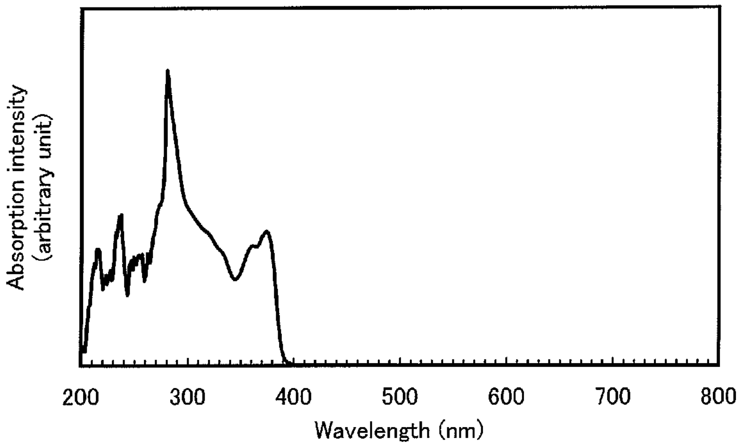
FIGS. 23A and 23B show respectively an absorption spectrum and an emission spectrum of a toluene solution of 2mDBTBPDBq-II.
Figure 23B:
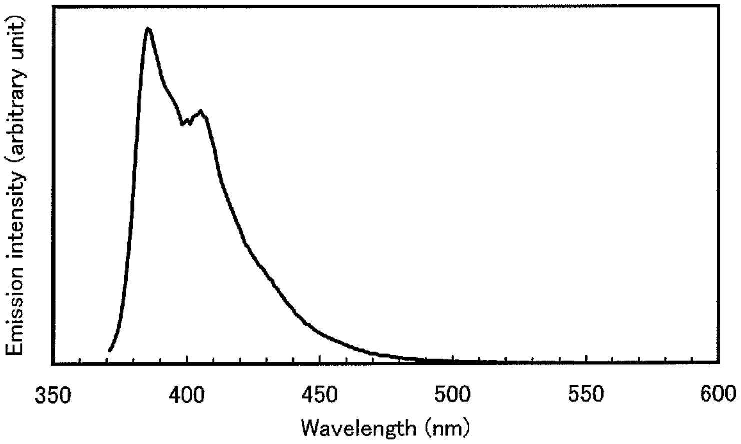
Figure 24A:
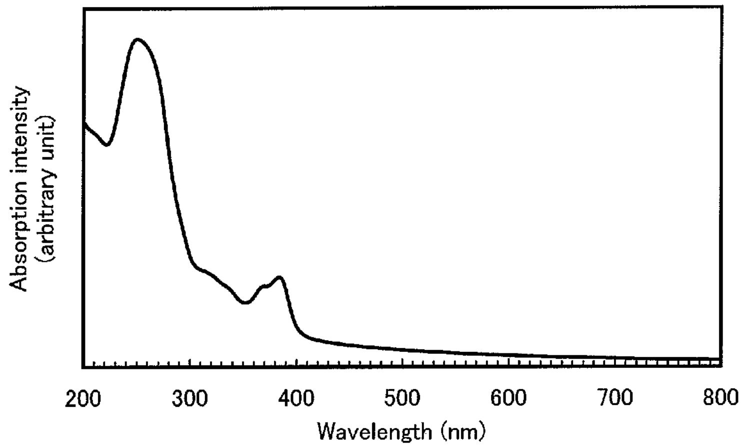
FIGS. 24A and 24B show respectively an absorption spectrum and an emission spectrum of a thin film of 2mDBTBPDBq-II.
Figure 24B:
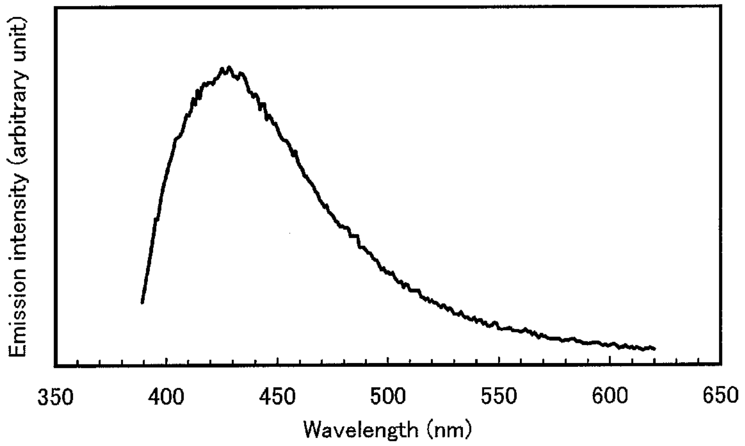

Further, FIG. 23A shows an absorption spectrum of a toluene solution of 2mDBTBPDBq-II, and FIG. 23B shows an emission spectrum thereof. FIG. 24A shows an absorption spectrum of a thin film of 2mDBTBPDBq-II, and FIG. 24B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 23A and 23B and FIGS. 24A and 24B, the horizontal axis represents wavelength (nm) and the vertical axis represents intensity (arbitrary unit). In the case of the toluene solution, absorption peaks were observed at around 361 nm and 374 nm, and emission wavelength peaks were 385 nm and 405 nm (at an excitation wavelength of 363 nm). In the case of the thin film, absorption peaks were observed at around 207 nm, 250 nm, 313 nm, 332 nm, 368 nm, and 384 nm, and an emission wavelength peak was 428 nm (at an excitation wavelength of 383 nm).

Example 6

Synthesis Example 5

This example gives descriptions of a method of synthesizing 2-[3-(2,8-diphenyldibenzothiophen-4-yl)phenyl]dibenzo [f,h]quinoxaline (abbreviation: 2mDBTPDBq-III) represented by the following Structural Formula (116).

[Chemical Formula 86]

(116)

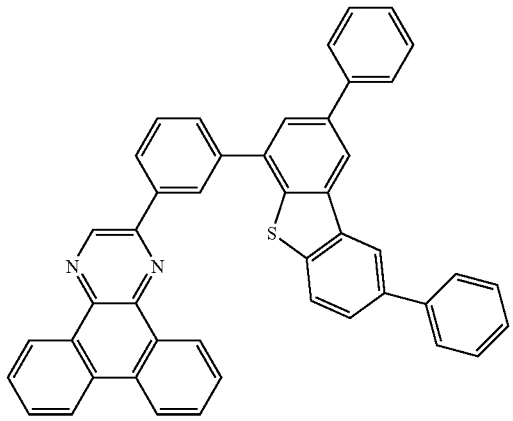

[Synthesis of 2mDBTPDBq-III]

A scheme for the synthesis of 2mDBTPDBq-III is illustrated in (C-5).

[Chemical Formula 87]

(C-5)

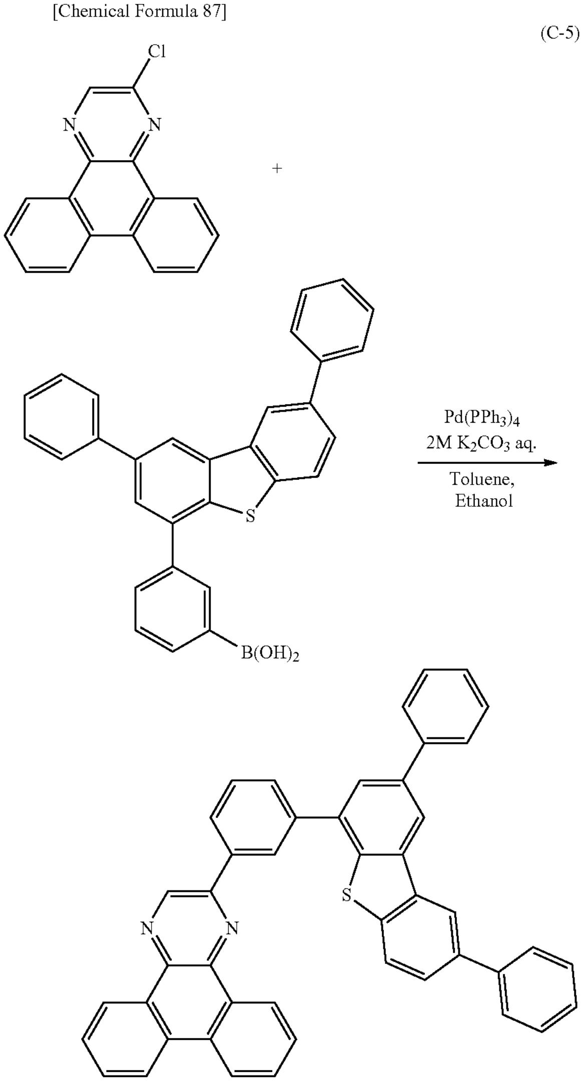

(116)

In a 100-mL three-neck flask were put 0.40 g (1.5 mmol) of 2-chlorodibenzo[f,h]quinoxaline, 0.68 g (1.5 mmol) of 3-(2,8-diphenyldibenzothiophen-4-yl)phenylboronic acid, 15 mL of toluene, 2.0 mL of ethanol, and 1.5 mL of a 2M aqueous potassium carbonate solution. This mixture was degassed by stirring under reduced pressure, and the air in the flask was replaced with nitrogen. To this mixture was added 51 mg (43 μmol) of tetrakis(triphenylphosphine)palladium(0). This mixture was stirred under a nitrogen stream at 80° C. for 4 hours. After a predetermined time had elapsed, water was added to the obtained mixture, and organic substances were extracted from the aqueous layer with toluene. The obtained solution of the extracted organic substances was combined with the organic layer, the mixture was washed with saturated brine, and the organic layer was dried with magnesium sulfate. The obtained mixture was gravity filtered, and the filtrate was concentrated to give a solid. The obtained solid was dissolved in toluene, and the toluene solution was suction filtered through alumina, Florisil (produced by Wako Pure Chemical Industries, Ltd., Catalog No. 540-00135), and Celite (produced by Wako Pure Chemical Industries, Ltd., Catalog No. 531-16855), and the obtained filtrate was concentrated to give a solid. The obtained solid was washed with toluene, and added to methanol, and the methanol suspension was irradiated with ultrasonic waves. A solid was collected by suction filtration to give 0.60 g of a white powder in 61% yield, which was the substance to be produced.

By a train sublimation method, 0.59 g of the obtained white powder was purified. In the purification, the white powder was heated at 330° C. under a pressure of 2.7 Pa with a flow rate of argon gas of 5 mL/min. After the purification, 0.54 g of a white powder was obtained in a yield of 90%, which was the substance to be produced.

A nuclear magnetic resonance (NMR) method identified this compound as 2-[3-(2,8-diphenyldibenzothiophen-4-yl)phenyl]dibenzo[f,h]quinoxaline (abbreviation: 2mDBTPDBq-III), which was the substance to be produced.

$^1H$ NMR data of the obtained substance are as follows: NMR ($CDCl_3$, 300 MHz): δ=7.37-7.55 (m, 6H), 7.73-7.84 (m, 10H), 7.90-7.98 (m, 3H), 8.44-8.48 (m, 3H), 8.65 (dd, J=7.8 Hz, 1.5 Hz, 2H), 8.84-8.85 (m, 1H), 9.27 (dd, J=7.2 Hz, 2.7 Hz, 1H), 9.46 (dd, J=7.8 Hz, 2.1 Hz, 1H), 9.51 (s, 1H).

Figure 25A:
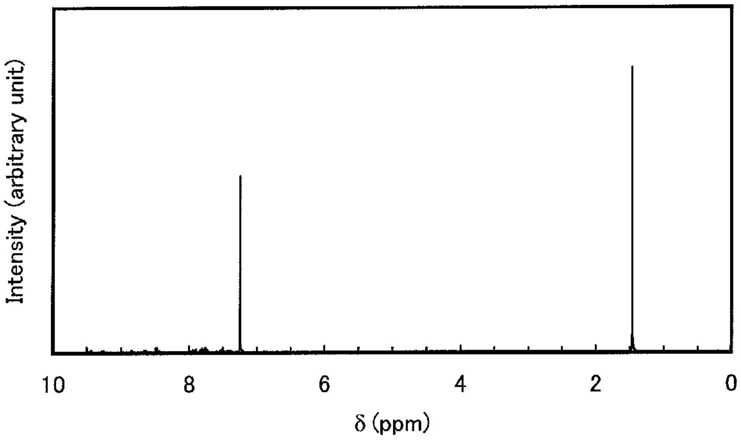
FIGS. 25A and 25B show $^{1}$H NMR charts of 2-[3-(2,8-diphenyldibenzothiophen-4-yl)phenyl]dibenzo[f,h]quinoxaline (abbreviation: 2mDBTPDBq-III).
Figure 25B:
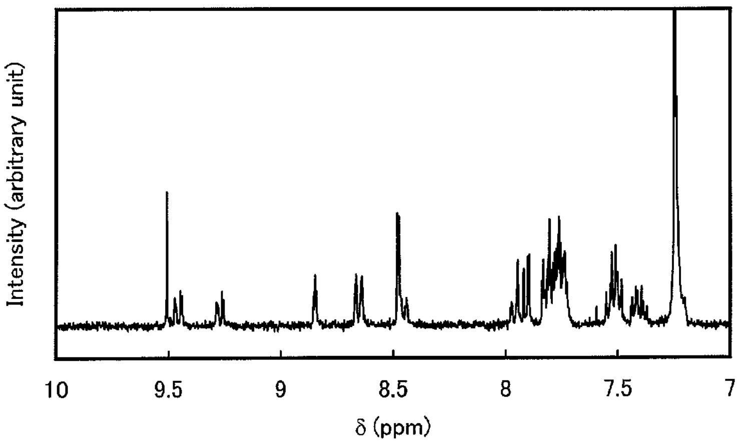

FIGS. 25A and 25B illustrate the $^1H$ NMR charts. Note that FIG. 25B is a chart showing an enlarged part of FIG. 25A in the range of 7.0 ppm to 10.0 ppm.

Figure 26A:
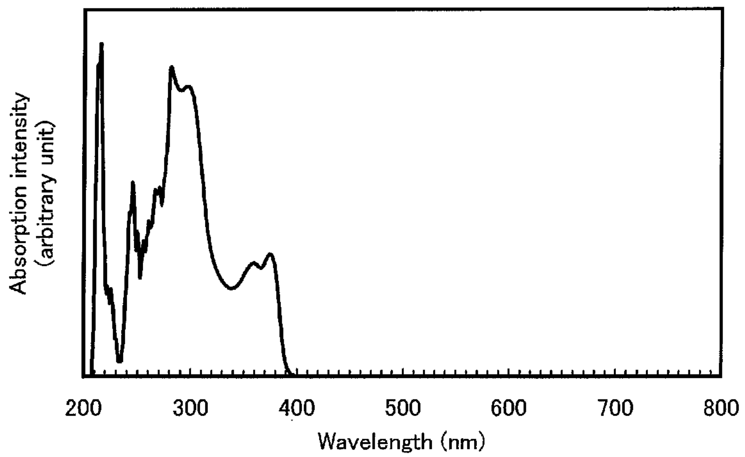
FIGS. 26A and 26B show respectively an absorption spectrum and an emission spectrum of a toluene solution of 2mDBTPDBq-III.
Figure 26B:
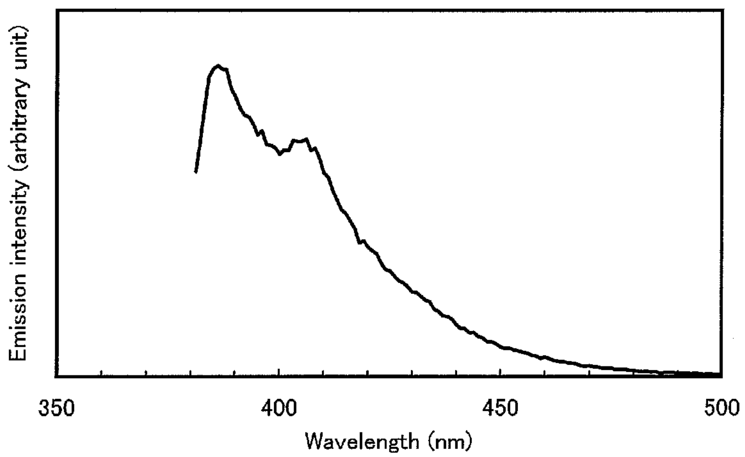
Figure 27A:
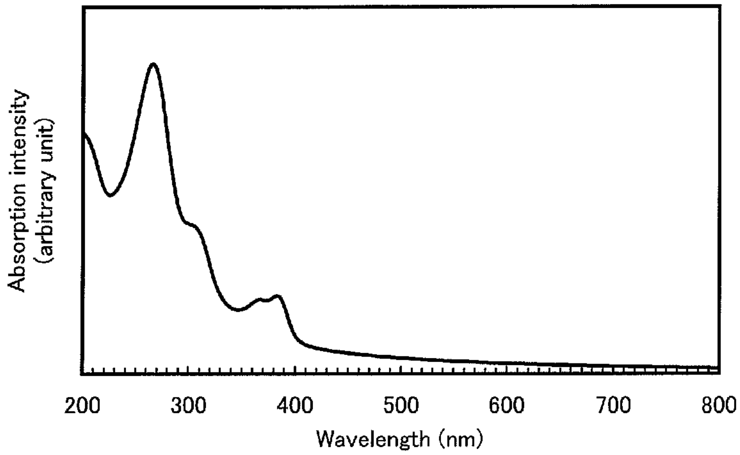
FIGS. 27A and 27B show respectively an absorption spectrum and an emission spectrum of a thin film of 2mDBTPDBq-III.
Figure 27B:
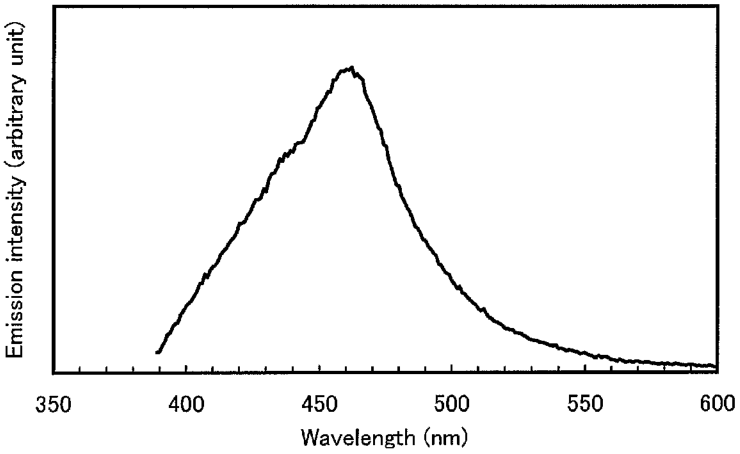

Further, FIG. 26A shows an absorption spectrum of a toluene solution of 2mDBTPDBq-III, and FIG. 26B shows an emission spectrum thereof. FIG. 27A shows an absorption spectrum of a thin film of 2mDBTPDBq-III, and FIG. 27B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 26A and 26B and FIGS. 27A and 27B, the horizontal axis represents wavelength (nm) and the vertical axis represents intensity (arbitrary unit). In the case of the toluene solution, absorption peaks were observed at around 281 nm, 297 nm, 359 nm, and 374 nm, and emission wavelength peaks were 386 nm and 405 nm (at an excitation wavelength of 375 nm). In the case of the thin film, absorption peaks were observed at around 266 nm, 302 nm, 366 nm, and 383 nm, and an emission wavelength peak was 462 nm (at an excitation wavelength of 383 nm).

Example 7

Synthesis Example 6

This example gives descriptions of a method of synthesizing 2-[3-(dibenzothiophen-4-yl)phenyl]-3-phenyldibenzo[f,h]quinoxaline (abbreviation: 3Ph-2mDBTPDBq-II) represented by the following Structural Formula (142).

[Chemical Formula 88]

(142)

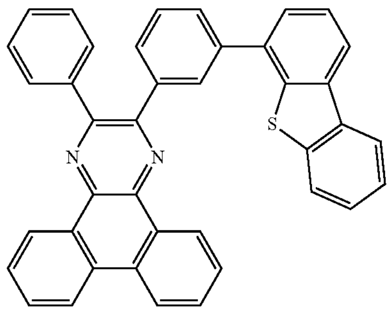

[Synthesis of 3Ph-2mDBTPDBq-II]

A scheme for the synthesis of 3Ph-2mDBTPDBq-II is illustrated in (C-6).

[Chemical Formula 89]

(C-6)

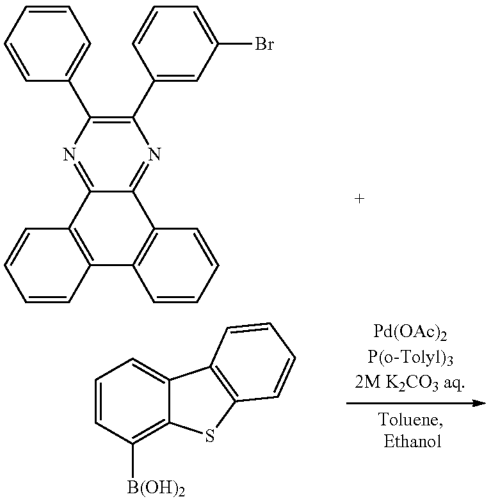

-continued

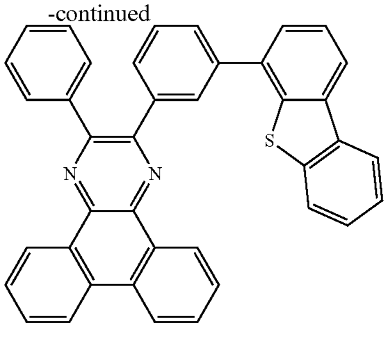

(142)

In a 100-mL three-neck flask were put 1.2 g (2.5 mmol) of 2-(3-bromophenyl)-3-phenyldibenzo[f,h]quinoxaline, 0.63 g (2.8 mmol) of dibenzothiophene-4-boronic acid, 0.12 g (0.39 mmol) of tri(ortho-tolyl)phosphine, 25 mL of toluene, 5.0 mL of ethanol, and 3.0 mL of a 2M aqueous potassium carbonate solution. This mixture was degassed by stirring under reduced pressure, and the air in the flask was replaced with nitrogen. To this mixture was added 40 mg (0.18 mmol) of palladium(II) acetate. This mixture was stirred under a nitrogen stream at 80° C. for 7 hours. After a predetermined time had elapsed, water was added to the obtained mixture, and organic substances were extracted from the aqueous layer with toluene. The obtained solution of the extracted organic substances was combined with the organic layer, the mixture was washed with a saturated aqueous solution of sodium hydrogen carbonate and saturated brine, and the organic layer was dried with magnesium sulfate. The obtained mixture was gravity filtered, and the filtrate was concentrated to give a solid. The obtained solid was purified twice by silica gel column chromatography (with a developing solvent of toluene and hexane in a ratio of 1:1). Further, recrystallization from toluene and methanol gave 0.65 g of a white powder in 46% yield, which was the substance to be produced.

By a train sublimation method, 0.62 g of the obtained white powder was purified. In the purification, the white powder was heated at 285° C. under a pressure of 2.5 Pa with a flow rate of argon gas of 5 mL/min. After the purification, 0.54 g of a white powder was obtained in a yield of 87%, which was the substance to be produced.

A nuclear magnetic resonance (NMR) method identified this compound as 2-[3-(dibenzothiophen-4-yl)phenyl]-3-phenyldibenzo[f,h]quinoxaline (abbreviation: 3Ph-2mDBTPDBq-II), which was the substance to be produced. $^1$H NMR data of the obtained substance are as follows: $^1$H NMR ($CDCl_3$, 300 MHz): δ=7.33 (d, J=7.8 Hz, 1H), 7.44-7.60 (m, 7H), 7.72-7.85 (m, 9H), 8.10-8.20 (m, 3H), 8.65 (d, J=7.8 Hz, 2H), 9.36 (td, J=7.8 Hz, 1.5 Hz, 2H).

Figure 28A:
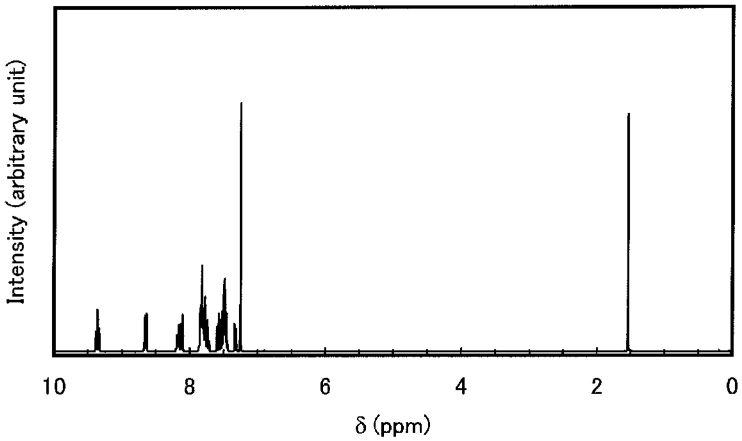
FIGS. 28A and 28B show $^{1}$H NMR charts of 2-[3-(dibenzothiophen-4-yl)phenyl]-3-phenyldibenzo[f,h]quinoxaline (abbreviation: 3Ph-2mDBTPDBq-II).
Figure 28B:
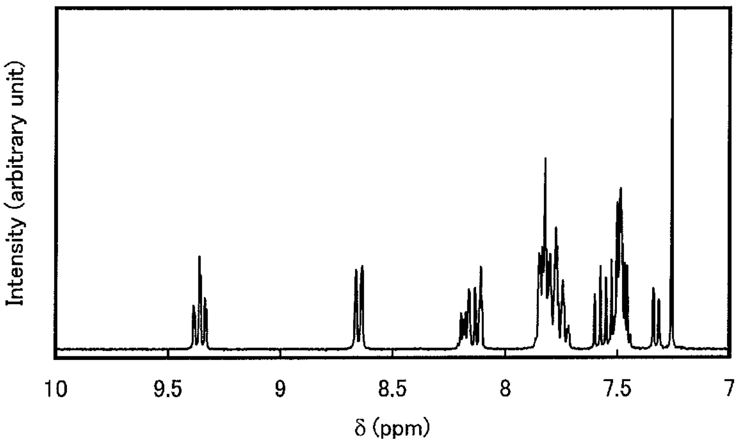

FIGS. 28A and 28B illustrate the $^1$H NMR charts. Note that FIG. 28B is a chart showing an enlarged part of FIG. 28A in the range of 7.0 ppm to 10.0 ppm.

Figure 29A:
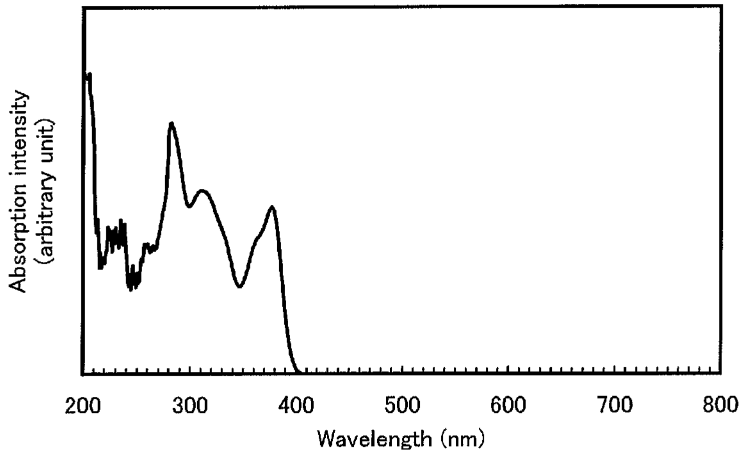
FIGS. 29A and 29B show respectively an absorption spectrum and an emission spectrum of a toluene solution of 3Ph-2mDBTPDBq-II.
Figure 29B:
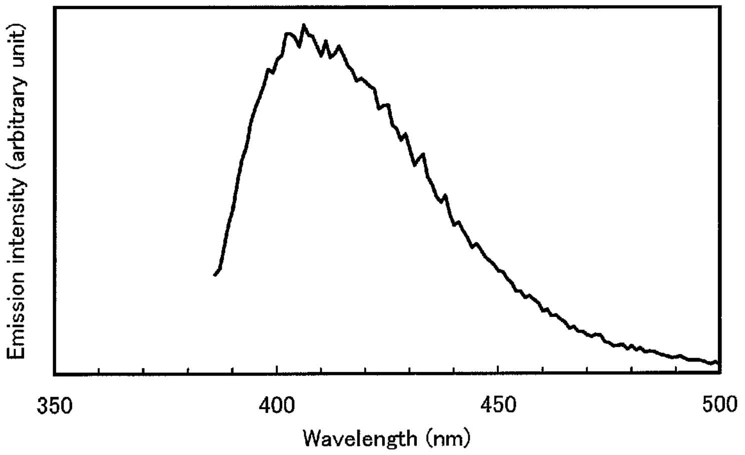
Figure 30A:
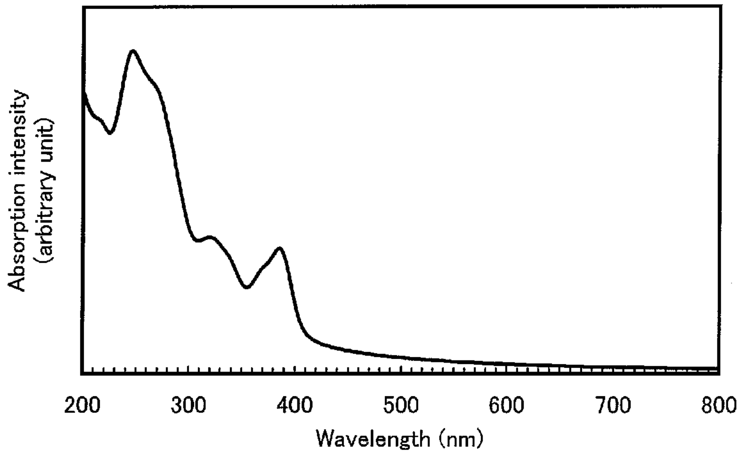
FIGS. 30A and 30B show respectively an absorption spectrum and an emission spectrum of a thin film of 3Ph-2mDBTPDBq-II.
Figure 30B:
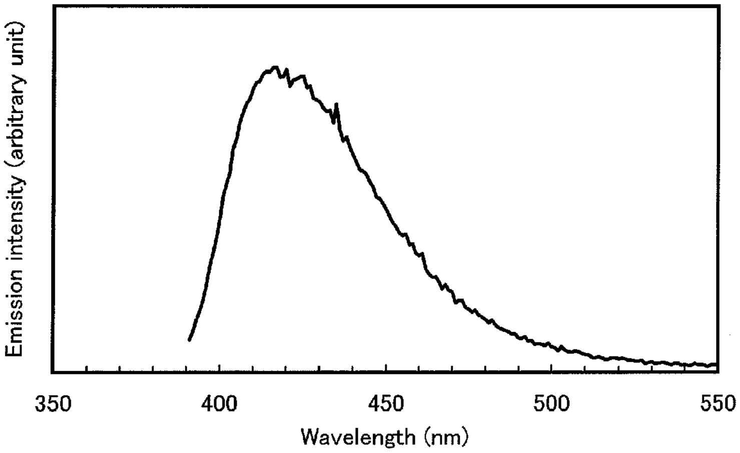

Further, FIG. 29A shows an absorption spectrum of a toluene solution of 3Ph-2mDBTPDBq-II, and FIG. 29B shows an emission spectrum thereof. FIG. 30A shows an absorption spectrum of a thin film of 3Ph-2mDBTPDBq-II, and FIG. 30B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 29A and 29B and FIGS. 30A and 30B, the horizontal axis represents wavelength (nm) and the vertical axis represents intensity (arbitrary unit). In the case of the toluene solution, absorption peaks were observed at around 303 nm and 377 nm, and an emission wavelength peak was 406 nm (at an excitation wavelength of 378 nm). In the case of the thin film, absorption peaks were observed at around 212 nm, 246 nm, 265 nm, 322 nm, 370 nm, and 385 nm, and an emission wavelength peak was 416 nm (at an excitation wavelength of 385 nm).

Example 8

Synthesis Example 7

This example gives descriptions of a method of synthesizing 2-[3-(dibenzofuran-4-yl)phenyl]dibenzo[f,h]quinoxaline (abbreviation: 2mDBFPDBq-II) represented by the following Structural Formula (201).

[Chemical Formula 90]

(201)

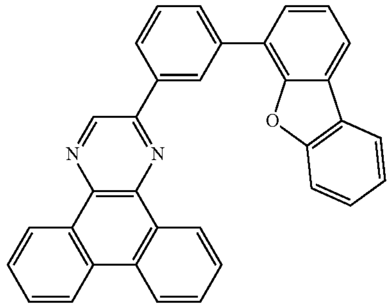

[Synthesis of 2mDBFPDBq-II]

A scheme for the synthesis of 2mDBFPDBq-II is illustrated in (C-7).

[Chemical Formula 91]

(C-7)

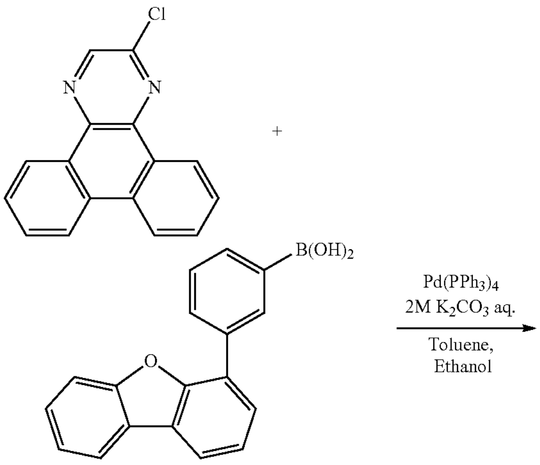

-continued

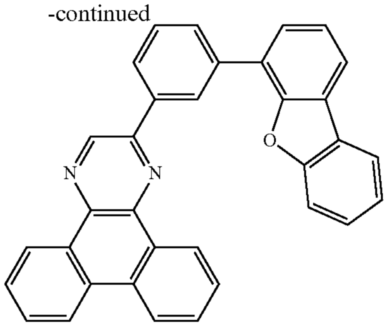

(201)

In a 200-mL three-neck flask were put 1.0 g (3.8 mmol) of 2-chlorodibenzo[f,h]quinoxaline, 1.2 g (4.2 mmol) of 3-(dibenzofuran-4-yl)phenylboronic acid, 50 mL of toluene, 5.0 mL of ethanol, and 5.0 mL of a 2M aqueous potassium carbonate solution. This mixture was degassed by stirring under reduced pressure, and the air in the flask was replaced with nitrogen. To this mixture was added 0.10 mg (0.10 mmol) of tetrakis(triphenylphosphine)palladium(0). This mixture was stirred at 80° C. for 8 hours under a nitrogen stream. After a predetermined time had elapsed, the precipitated solid was separated by filtration to give a white solid. Further, water and toluene were added to the filtrate, and organic substances were extracted from the aqueous layer of the obtained filtrate with toluene. The solution of the extracted organic substances was combined with the organic layer, the mixture was washed with a saturated aqueous solution of sodium hydrogen carbonate and saturated brine, followed by drying with magnesium sulfate. The obtained mixture was gravity filtered, and then the filtrate was concentrated to give a brown solid. The obtained solids were combined, the obtained solids were dissolved in toluene, and the toluene solution was suction filtered through alumina and Celite (produced by Wako Pure Chemical Industries, Ltd., Catalog No. 531-16855). The obtained filtrate was concentrated to give a white solid. This solid was purified by silica gel column chromatography (with a developing solvent of toluene and hexane in a ratio of 1:10). The obtained fractions were concentrated to give a yellow powder. Further, this solid was recrystallized from toluene to give 0.68 g of a yellow powder in 33% yield, which was the substance to be produced.

By a train sublimation method, 0.68 g of the obtained yellow powder was purified. In the purification, the yellow powder was heated at 280° C. under a pressure of 2.2 Pa with a flow rate of argon gas of 10 mL/min. After the purification, 0.43 g of a yellow powder was obtained in a yield of 67%, which was the substance to be produced.

A nuclear magnetic resonance (NMR) method identified this compound as 2-[3-(dibenzofuran-4-yl)phenyl]dibenzo[f,h]quinoxaline (abbreviation: 2mDBFPDBq-II), which was the substance to be produced.

$^1$H NMR data of the obtained substance are as follows: $^1$H NMR ($CDCl_3$, 300 MHz): δ=7.41 (t, J=7.8 Hz, 1H), 7.49-7.61 (m, 2H), 7.68 (d, J=8.4 Hz, 1H), 7.76-7.84 (m, 6H), 8.02-8.10 (m, 3H), 8.41 (d, J=7.8 Hz, 1H), 8.67 (d, J=7.8 Hz, 2H), 8.96-8.97 (m, 1H), 9.25-9.28 (m, 1H), 9.47-9.51 (m, 2H).

Figure 31A:
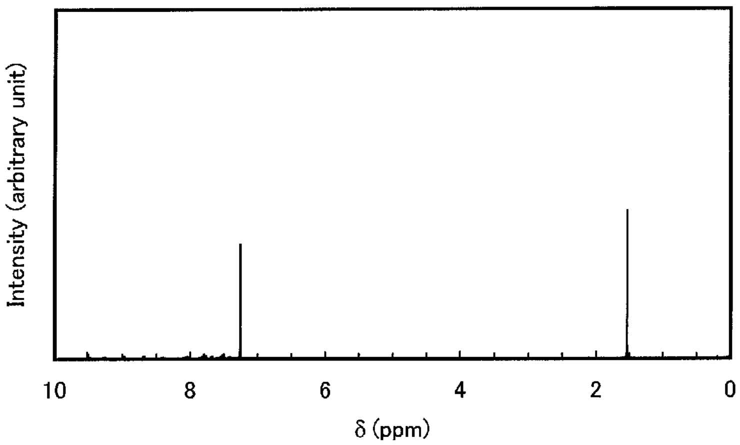
FIGS. 31A and 31B show $^{1}$H NMR charts of 2-[3-(dibenzofuran-4-yl)phenyl]dibenzo[f,h]quinoxaline (abbreviation: 2mDBFPDBq-II).
Figure 31B:
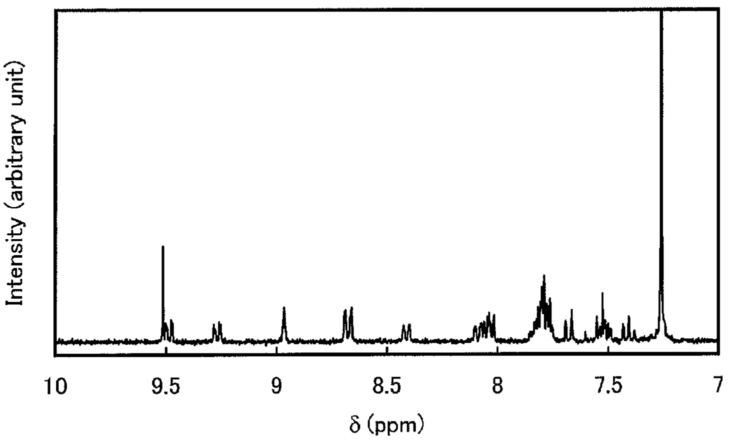

FIGS. 31A and 31B illustrate the $^1$H NMR charts. Note that FIG. 31B is a chart showing an enlarged part of FIG. 31A in the range of 7.0 ppm to 10.0 ppm.

Figure 32A:
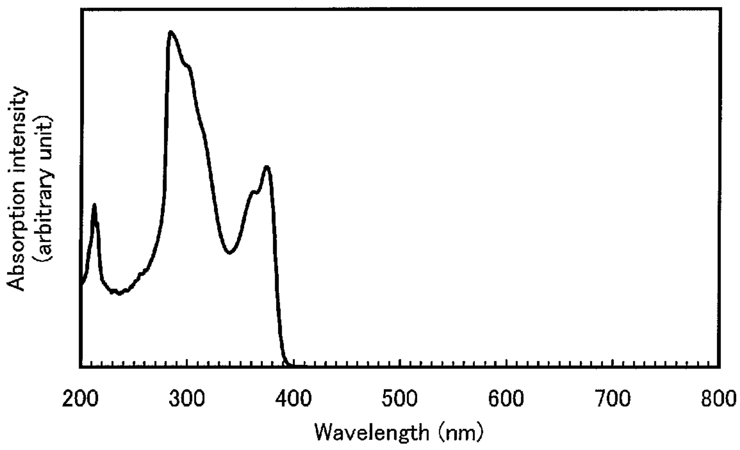
FIGS. 32A and 32B show respectively an absorption spectrum and an emission spectrum of a toluene solution of 2mDBFPDBq-II.
Figure 32B:
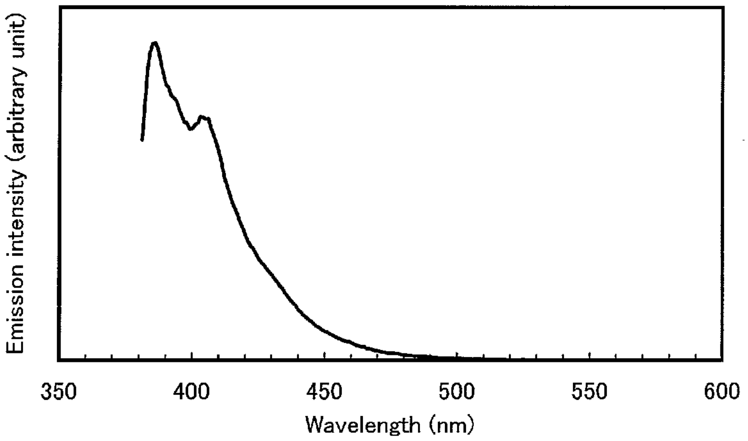
Figure 33A:
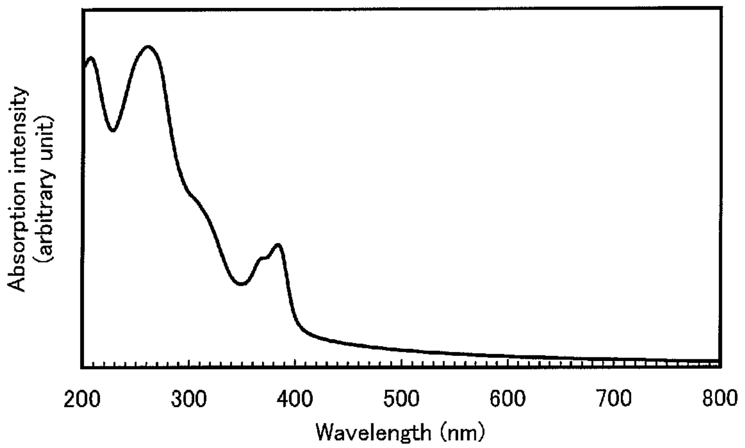
FIGS. 33A and 33B show respectively an absorption spectrum and an emission spectrum of a thin film of 2mDBFPDBq-II.
Figure 33B:
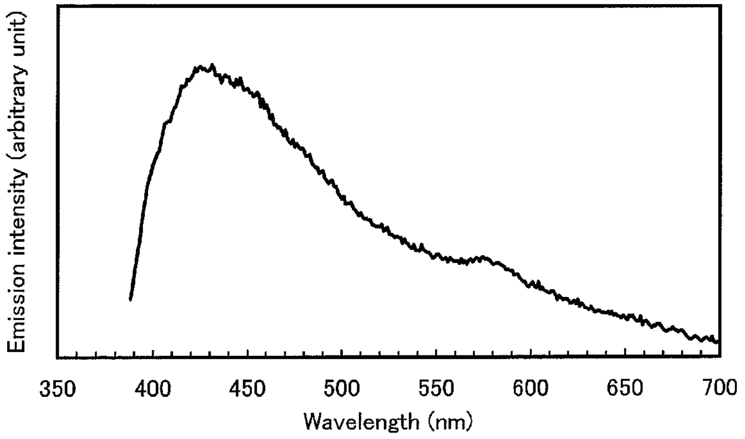

Further, FIG. 32A shows an absorption spectrum of a toluene solution of 2mDBFPDBq-II, and FIG. 32B shows an emission spectrum thereof. FIG. 33A shows an absorption spectrum of a thin film of 2mDBFPDBq-II, and FIG. 33B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 32A and 32B and FIGS. 33A and 33B, the horizontal axis represents wavelength (nm) and the vertical axis represents intensity (arbitrary unit). In the case of the toluene solution, absorption peaks were observed at around 361 nm and 374 nm, and emission wavelength peaks were 386 nm and 403 nm (at an excitation wavelength of 374 nm). In the case of the thin film, absorption peaks were observed at around 207 nm, 260 nm, 304 nm, 369 nm, and 384 nm, and emission wavelength peaks were 425 nm and 575 nm (at an excitation wavelength of 382 nm).

Example 9

Synthesis Example 8

This example gives descriptions of a method of synthesizing 2-[3'-(9H-carbazol-9-yl)biphenyl-3-yl]-dibenzo[f,h]quinoxaline (abbreviation: 2mCzBPDBq) represented by the following Structural Formula (309).

[Chemical Formula 92]

(309)

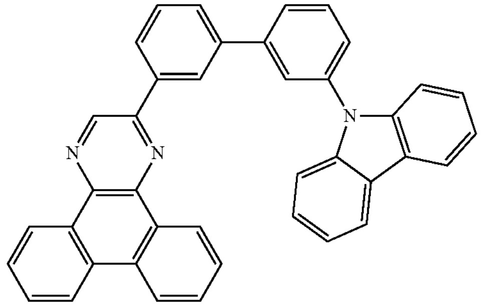

[Synthesis of 2mCzBPDBq]

A scheme for the synthesis of 2mCzBPDBq is illustrated in (C-8).

[Chemical Formula 93]

(C-8)

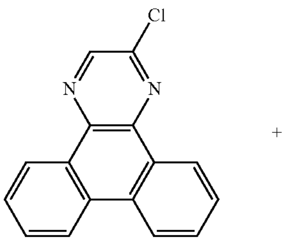

-continued

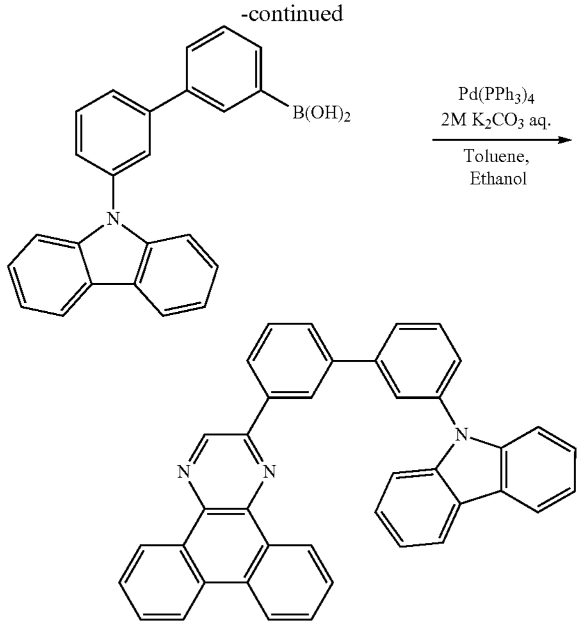

(309)

In a 200-mL three-neck flask were put 1.0 g (4.0 mmol) of 2-chlorodibenzo[f,h]quinoxaline, 1.6 g (4.4 mmol) of 3'-(9H-carbazol-9-yl)-3-biphenylboronic acid, 50 mL of toluene, 5 mL of ethanol, and 6.0 mL of a 2M aqueous potassium carbonate solution. This mixture was degassed by stirring under reduced pressure, and the air in the flask was replaced with nitrogen. To this mixture was added 0.10 g (90 μmol) of tetrakis(triphenylphosphine)palladium(0). This mixture was stirred under a nitrogen stream at 80° C. for 16 hours. After a predetermined time had elapsed, water was added to this mixture, and organic substances were extracted from the aqueous layer of the obtained filtrate with toluene. The solution of the extracted organic substances was combined with the organic layer, the mixture was washed with a saturated aqueous solution of sodium hydrogen carbonate and saturated brine, followed by drying with magnesium sulfate. The obtained mixture was gravity filtered, and then the filtrate was concentrated to give a solid. This solid was purified by silica gel column chromatography (with a developing solvent of toluene and hexane in a ratio of 1:3). The obtained fractions were concentrated to give a solid. Further, recrystallization from toluene gave 0.32 g of a white powder in 15% yield.

By a train sublimation method, 0.32 g of the obtained white powder was purified. In the purification, the white powder was heated at 300° C. under a pressure of 5.1 Pa with a flow rate of argon gas of 15 mL/min. After the purification, 0.12 g of a white powder was obtained in a yield of 38%, which was the substance to be produced.

A nuclear magnetic resonance (NMR) method identified this compound as 2-[3'-(9H-carbazol-9-yl)biphenyl-3-yl]dibenzo[f,h]quinoxaline (abbreviation: 2mCzBPDBq), which was the substance to be produced.

$^1H$ NMR data of the obtained substance are as follows: $^1H$ NMR ($CDCl_3$, 300 MHz): δ=7.26-7.35 (m, 2H), 7.43-7.49 (m, 2H), 7.56 (d, J=8.4 Hz, 2H), 7.61-7.88 (m, 9H), 7.97-7.99 (m, 1H), 8.19 (d, J=7.8 Hz, 2H), 8.33-8.36 (m, 1H), 8.65-8.67 (m, 3H), 9.25 (dd, J=7.8 Hz, 1.8 Hz, 1H), 9.41 (dd, J=7.8 Hz, 1.5 Hz, 1H), 9.45 (s, 1H).

Figure 34A:
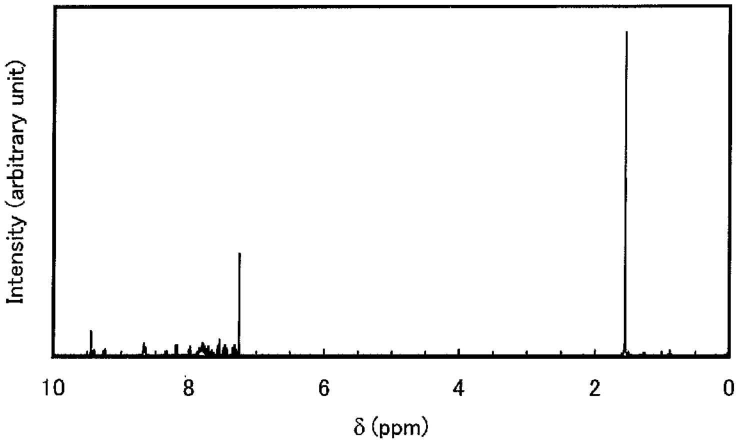
FIGS. 34A and 34B show $^{1}$H NMR charts of 2-[3'-(9H-carbazol-9-yl)biphenyl-3-yl]dibenzo[f,h]quinoxaline (abbreviation: 2mCzBPDBq).
Figure 34B:
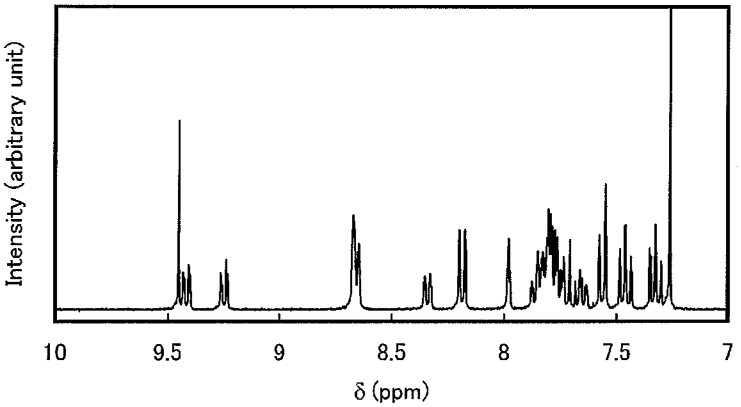

FIGS. 34A and 34B illustrate the $^1H$ NMR charts. Note that FIG. 34B is a chart showing an enlarged part of FIG. 34A in the range of 7.0 ppm to 10.0 ppm.

Figure 35A:
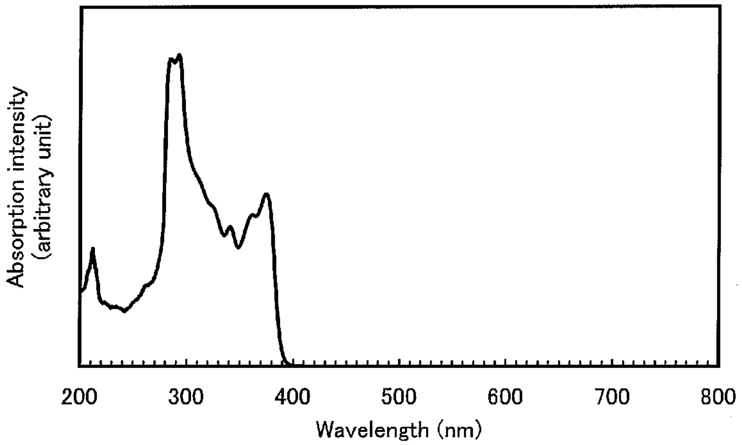
FIGS. 35A and 35B show respectively an absorption spectrum and an emission spectrum of a toluene solution of 2mCzBPDBq.
Figure 35B:
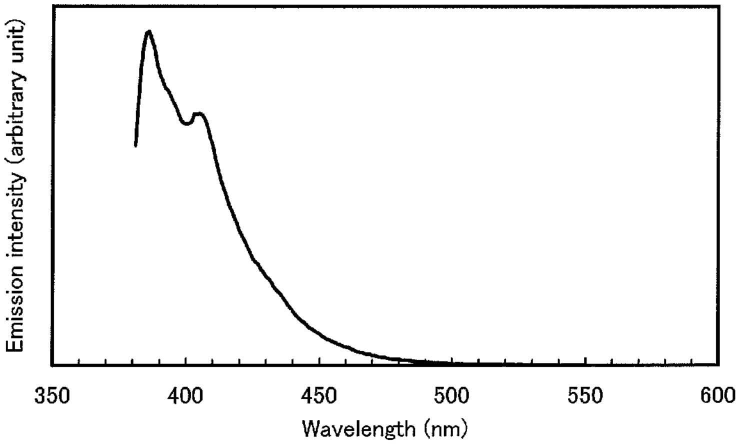
Figure 36A:
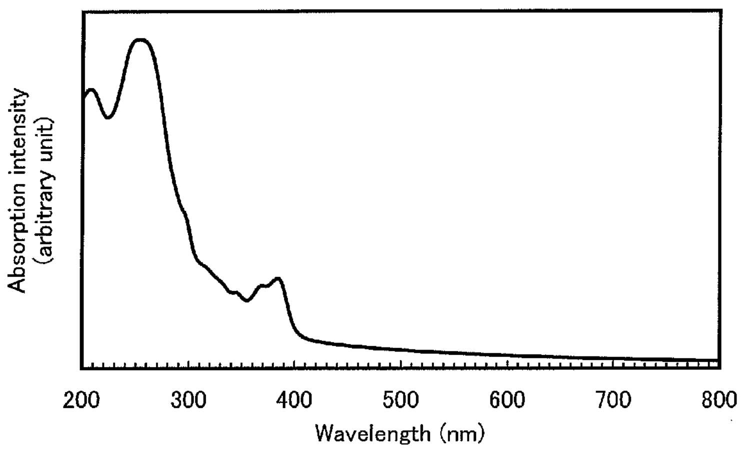
FIGS. 36A and 36B show respectively an absorption spectrum and an emission spectrum of a thin film of 2mCzBPDBq.
Figure 36B:
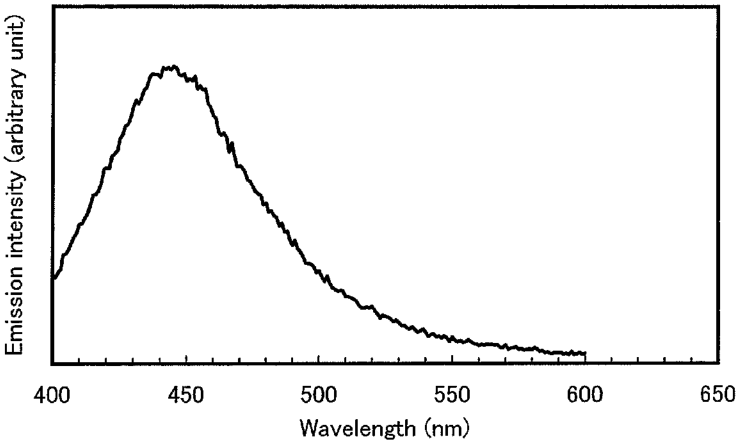

Further, FIG. 35A shows an absorption spectrum of a toluene solution of 2mCzBPDBq, and FIG. 35B shows an emission spectrum thereof. FIG. 36A shows an absorption spectrum of a thin film of 2mCzBPDBq, and FIG. 36B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 35A and 35B and FIGS. 36A and 36B, the horizontal axis represents wavelength (nm) and the vertical axis represents intensity (arbitrary unit). In the case of the toluene solution, absorption peaks were observed at around 341 nm, 362 nm, and 374 nm, and emission wavelength peaks were 386 nm and 403 nm (at an excitation wavelength of 374 nm). In the case of the thin film, absorption peaks were observed at around 208 nm, 253 nm, 294 nm, 313 nm, 328 nm, 345 nm, 369 nm, and 384 nm, and an emission wavelength peak was 444 nm (at an excitation wavelength of 382 nm).

Example 10

Synthesis Example 9

This example gives descriptions of a method of synthesizing 2-[3-(3,6-diphenyl-9H-carbazol-9-yl)phenyl]dibenzo[f,h]quinoxaline (abbreviation: 2mCzPDBq-III) represented by the following Structural Formula (326).

[Chemical Formula 94]

(326)

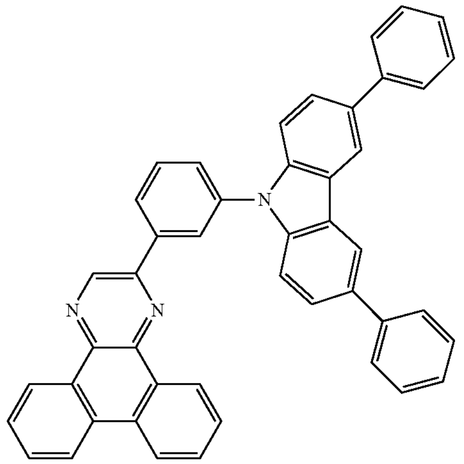

[Synthesis of 2mCzPDBq-III]

A scheme for the synthesis of 2mCzPDBq-III is illustrated in (C-9).

[Chemical Formula 95]

(C-9)

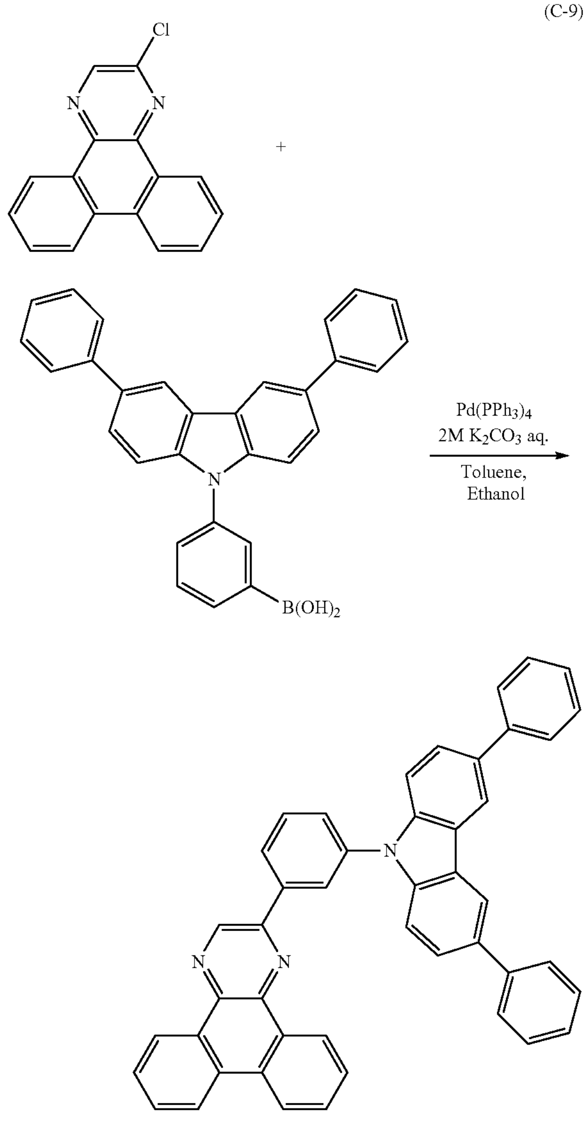

(326)

In a 100-mL three-neck flask were put 0.54 g (2.0 mmol) of 2-chlorodibenzo[f,h]quinoxaline, 0.94 g (2.1 mmol) of 3-(3,6-diphenyl-9H-carbazol-9-yl)phenylboronic acid, 20 mL of toluene, 2.0 mL of ethanol, and 2.0 mL of a 2M aqueous potassium carbonate solution. This mixture was degassed by stirring under reduced pressure, and the air in the flask was replaced with nitrogen. To this mixture was added 46 mg (39 μmol) of tetrakis(triphenylphosphine)palladium(0). This mixture was stirred under a nitrogen stream at 80° C. for 11 hours. After a predetermined time had elapsed, water was added to the obtained mixture, and organic substances were extracted from the aqueous layer with toluene. The obtained solution of the extracted organic substances was combined with the organic layer, the mixture was washed with saturated brine, and the organic layer was dried with magnesium sulfate. The obtained mixture was gravity filtered, and the filtrate was concentrated to give a solid. The obtained solid was dissolved in toluene, and the toluene solution was suction filtered through alumina, Florisil (produced by Wako Pure Chemical Industries, Ltd., Catalog No. 540-00135), and Celite (produced by Wako Pure Chemical Industries, Ltd., Catalog No. 531-16855), and the obtained filtrate was concentrated to give a solid. The obtained solid was purified by silica gel column chromatography (with a developing solvent of toluene and hexane in a ratio of 2:1). Further, recrystallization from toluene gave 0.90 g of a yellow powder in 70% yield, which was the substance to be produced.

By a train sublimation method, 0.89 g of the obtained yellow powder was purified. In the purification, the yellow powder was heated at 310° C. under a pressure of 3.0 Pa with a flow rate of argon gas of 5 mL/min. After the purification, 0.80 g of a yellow powder was obtained in a yield of 89%, which was the substance to be produced.

A nuclear magnetic resonance (NMR) method identified this compound as 2-[3-(3,6-diphenyl-9H-carbazol-9-yl)phenyl]dibenzo[f,h]quinoxaline (abbreviation: 2mCzPDBq-III), which was the substance to be produced.

$^1$H NMR data of the obtained substance are as follows: $^1$H NMR ($CDCl_3$, 300 MHz): δ=7.37 (t, J=7.2 Hz, 2H), 7.50 (t, J=7.2 Hz, 4H), 7.63 (d, J=8.4 Hz, 2H), 7.71-7.84 (m, 11H), 7.88 (t, J=7.8 Hz, 1H), 8.43-8.46 (m, 3H), 8.64-8.68 (m, 3H), 9.25 (dd, J=7.8 Hz, 1.8 Hz, 1H), 9.36 (dd, J=7.8 Hz, 1.5 Hz, 1H), 9.47 (s, 1H).

Figure 37A:
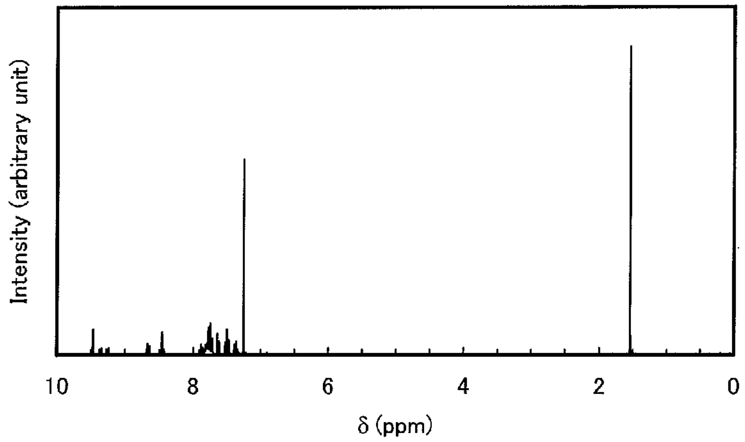
FIGS. 37A and 37B show $^{1}$H NMR charts of 2-[3-(3,6-diphenyl-9H-carbazol-9-yl)phenyl]-dibenzo[f,h]quinoxaline (abbreviation: 2mCzPDBq-III).
Figure 37B:
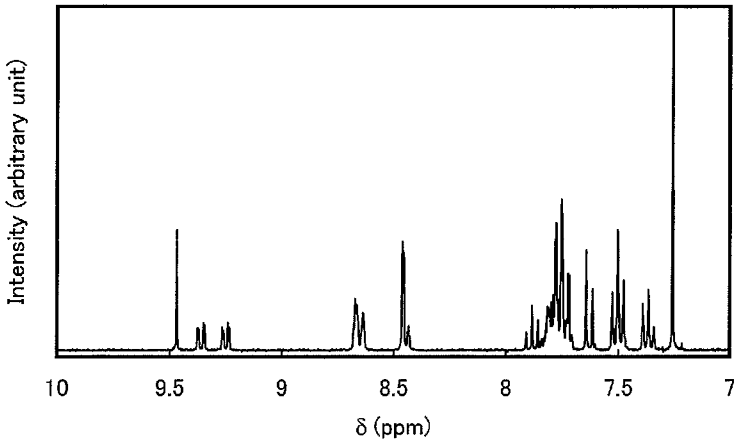

FIGS. 37A and 37B illustrate the $^1$H NMR charts. Note that FIG. 37B is a chart showing an enlarged part of FIG. 37A in the range of 7.0 ppm to 10.0 ppm.

Figure 38A:
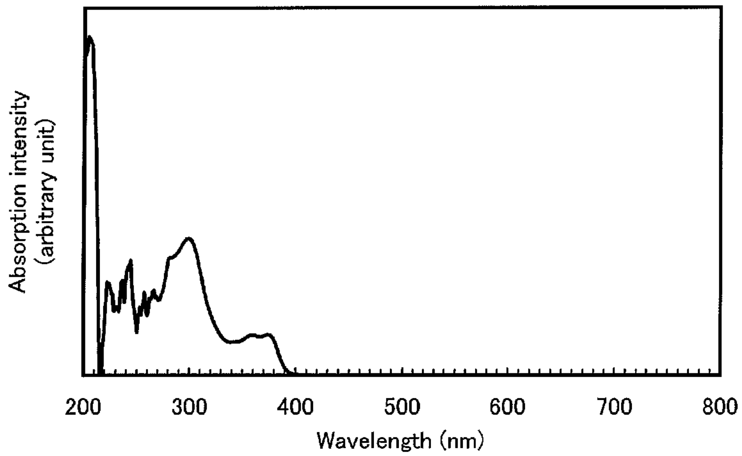
FIGS. 38A and 38B show respectively an absorption spectrum and an emission spectrum of a toluene solution of 2mCzPDBq-III.
Figure 38B:
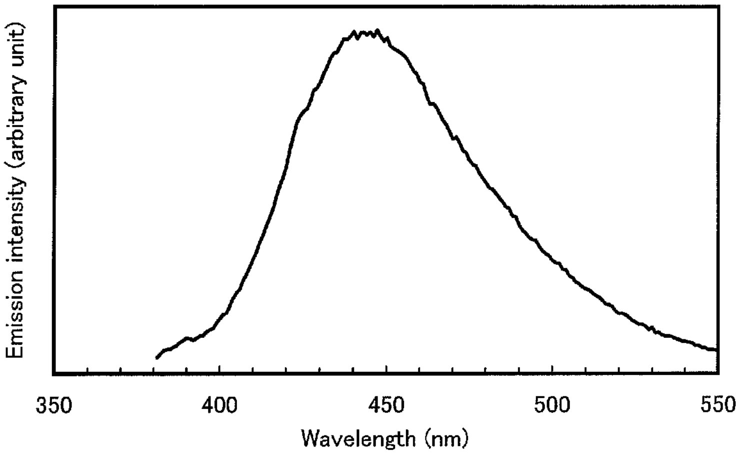
Figure 39A:
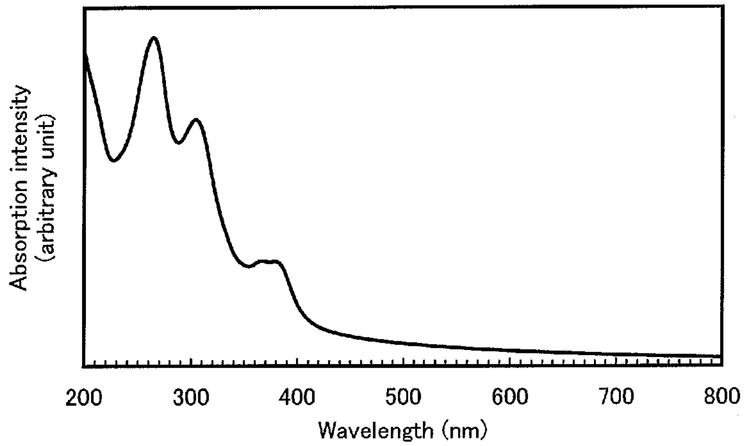
FIGS. 39A and 39B show respectively an absorption spectrum and an emission spectrum of a thin film of 2mCzPDBq-III.
Figure 39B:
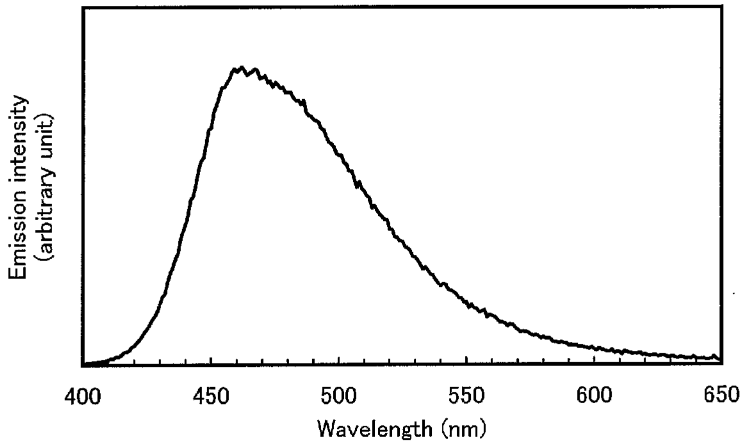

Further, FIG. 38A shows an absorption spectrum of a toluene solution of 2mCzPDBq-III, and FIG. 38B shows an emission spectrum thereof. FIG. 39A shows an absorption spectrum of a thin film of 2mCzPDBq-III, and FIG. 39B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 38A and 38B and FIGS. 39A and 39B, the horizontal axis represents wavelength (nm) and the vertical axis represents intensity (arbitrary unit). In the case of the toluene solution, absorption peaks were observed at around 299 nm, 360 nm, and 374 nm, and an emission wavelength peak was 443 nm (at an excitation wavelength of 375 nm). In the case of the thin film, absorption peaks were observed at around 264 nm, 304 nm, 367 nm, and 380 nm, and an emission wavelength peak was 462 nm (at an excitation wavelength of 381 nm).

Example 11

Synthesis Example 10

This example gives descriptions of a method of synthesizing 2-[4-(9-phenyl-9H-carbazol-3-yl)phenyl]dibenzo[f,h]quinoxaline (abbreviation: PCPDBq) represented by the following Structural Formula (400).

[Chemical Formula 96]

(400)

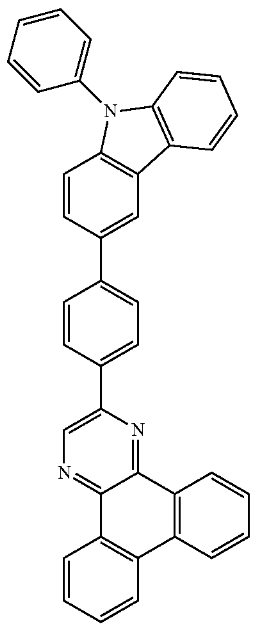

[Synthesis of PCPDBq]

A scheme for the synthesis of PCPDBq is illustrated in (C-10).

[Chemical Formula 97]

(C-10)

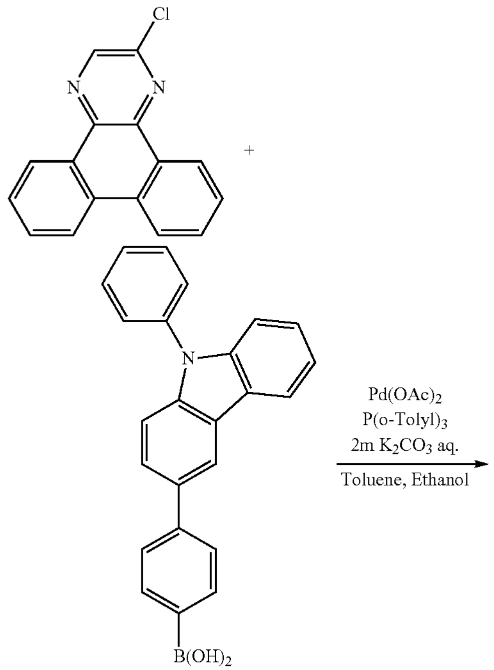

-continued

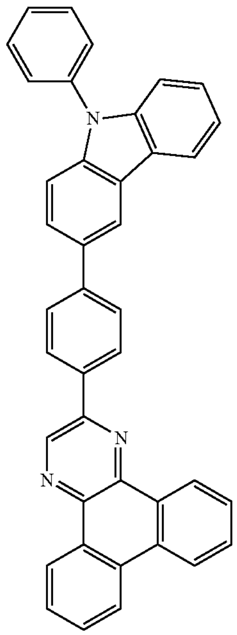

(400)

In a 200-mL three-neck flask were put 1.2 g (4.0 mmol) of 2-chlorodibenzo[f,h]quinoxaline, 1.6 g (4.4 mmol) of 4-(9-phenyl-9H-carbazol-3-yl)phenylboronic acid, 11 mg (0.05 mmol) of palladium(II) acetate, 30 mg (0.1 mmol) of tris(2-methylphenyl)phosphine, 30 mL of toluene, 3 mL of ethanol, and 3 mL of a 2M aqueous potassium carbonate solution. The mixture was degassed by stirring under reduced pressure. Then, the mixture was heated and stirred under a nitrogen atmosphere at 85° C. for 40 hours.

After a predetermined time had elapsed, this mixed liquid was filtered and washed with water and toluene in this order. The substance obtained by the filtration was purified by silica gel column chromatography. At this time, toluene was used as a developing solvent for the chromatography. The obtained fractions were concentrated, and methanol was added thereto, followed by irradiation with ultrasonic waves. The precipitated solid was collected by suction filtration to give 1.2 g of a yellow powder in 55% yield, which was the substance to be produced.

The Rf values of the produced substance and 2-chlorodibenzo[f,h]quinoxaline were respectively 0.28 and 0.38, which were found by silica gel thin layer chromatography (TLC) (with a developing solvent of ethyl acetate and hexane in a ratio of 1:10).

A nuclear magnetic resonance (NMR) method identified this compound as 2-[4-(9-phenyl-9H-carbazol-3-yl)phenyl]dibenzo[f,h]quinoxaline (abbreviation: PCPDBq), which was the substance to be produced.

$^1$H NMR data of the obtained substance are as follows: $^1$H NMR ($CDCl_3$, 300 MHz): δ=7.32-7.37 (m, 1H), 7.43-7.53 (m, 4H), 7.59-7.68 (m, 4H), 7.74-7.86 (m, 5H), 7.97 (d, J=8.1 Hz, 2H), 8.25 (d, J=7.2 Hz, 1H), 8.47-8.50 (m, 3H), 8.66 (d, J=7.8 Hz, 2H), 9.23-9.27 (m, 1H), 9.45-9.49 (m, 2H).

Figure 40A:
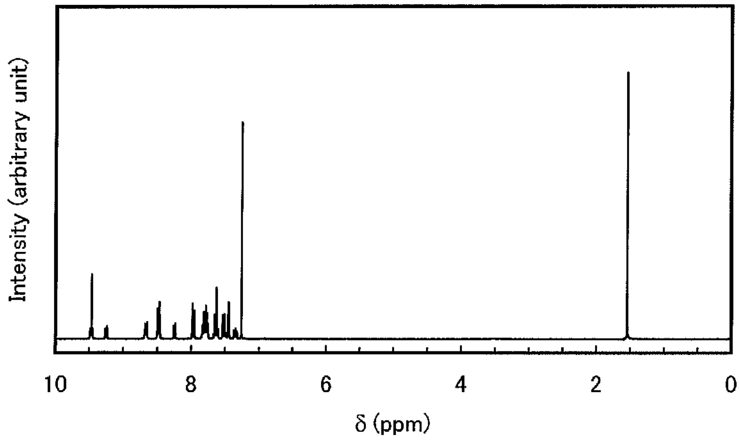
FIGS. 40A and 40B show $^{1}$H NMR charts of 2-[4-(9-phenyl-9H-carbazol-3-yl)phenyl]dibenzo[f,h]quinoxaline (abbreviation: PCPDBq).
Figure 40B:
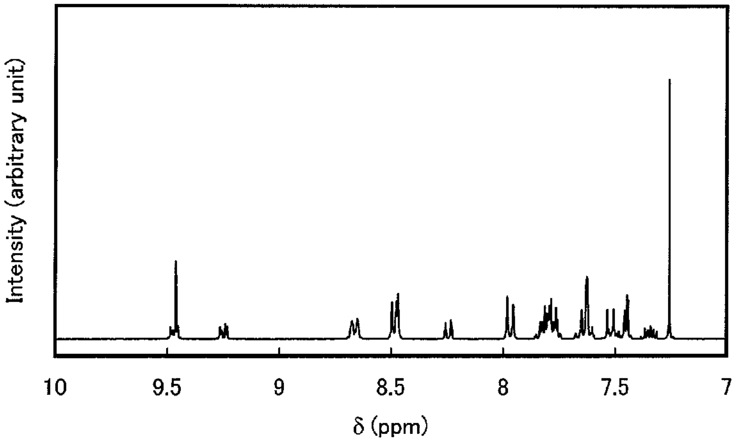

FIGS. 40A and 40B illustrate the $^1$H NMR charts. Note that FIG. 40B is a chart showing an enlarged part of FIG. 40A in the range of 7.0 ppm to 10.0 ppm.

Figure 41A:
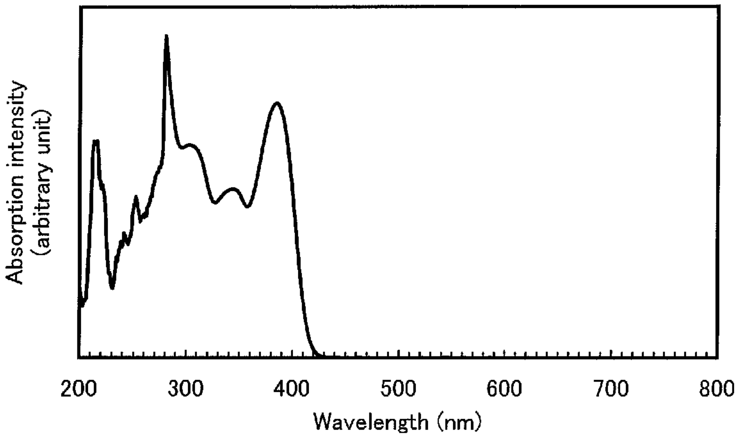
FIGS. 41A and 41B show respectively an absorption spectrum and an emission spectrum of a toluene solution of PCPDBq.
Figure 41B:
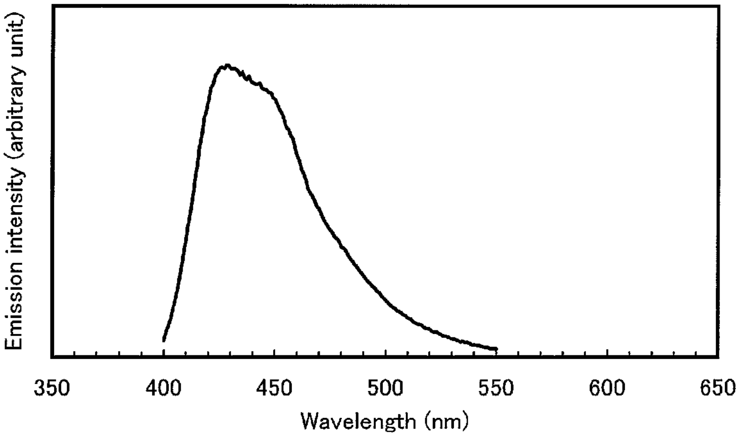
Figure 42A:
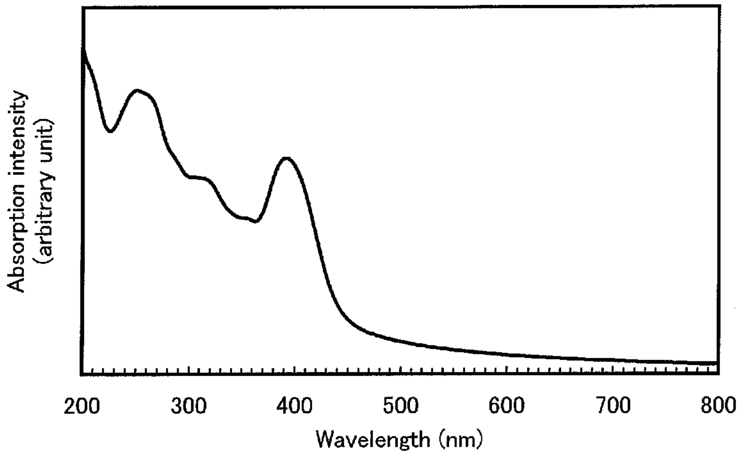
FIGS. 42A and 42B show respectively an absorption spectrum and an emission spectrum of a thin film of PCPDBq.
Figure 42B:
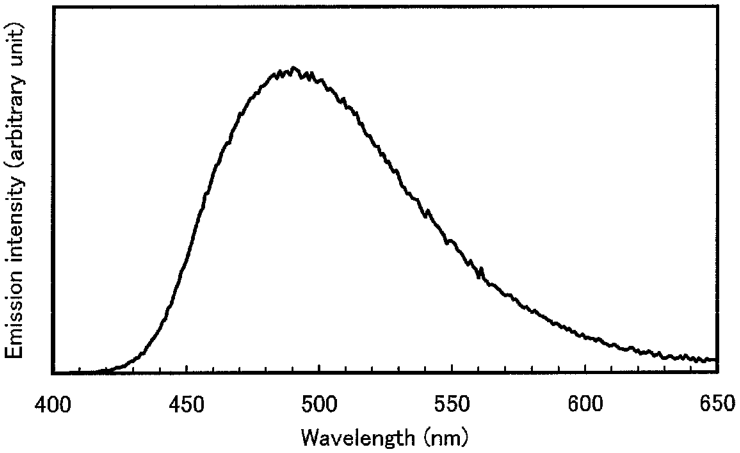

Further, FIG. 41A shows an absorption spectrum of a toluene solution of PCPDBq, and FIG. 41B shows an emission spectrum thereof. FIG. 42A shows an absorption spectrum of a thin film of PCPDBq, and FIG. 42B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 41A and 41B and FIGS. 42A and 42B, the horizontal axis represents wavelength (nm) and the vertical axis represents intensity (arbitrary unit). In the case of the toluene solution, absorption peaks were observed at around 306 nm, 343 nm, and 385 nm, and an emission wavelength peak was 428 nm (at an excitation wavelength of 385 nm). In the case of the thin film, absorption peaks were observed at around 251 nm, 262 nm, 285 nm, 315 nm, 353 nm, and 392 nm, and an emission wavelength peak was 490 nm (at an excitation wavelength of 397 nm).

Example 12

Synthesis Example 11

This example gives descriptions of a method of synthesizing 2-[3-(dibenzothiophen-2-yl)phenyl]dibenzo[f,h]quinoxaline (abbreviation: 2mDBTPDBq) represented by the following Structural Formula (515).

[Chemical Formula 98]

(515)

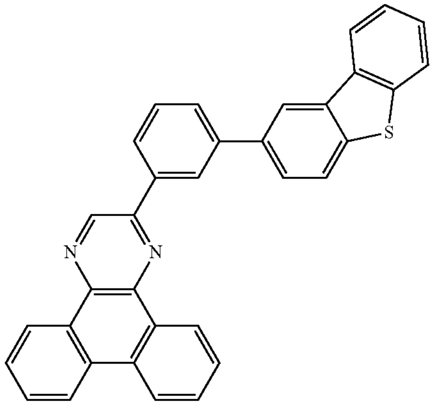

[Synthesis of 2mDBTPDBq]

A scheme for the synthesis of 2mDBTPDBq is illustrated in (C-11).

[Chemical Formula 99]

(C-11)

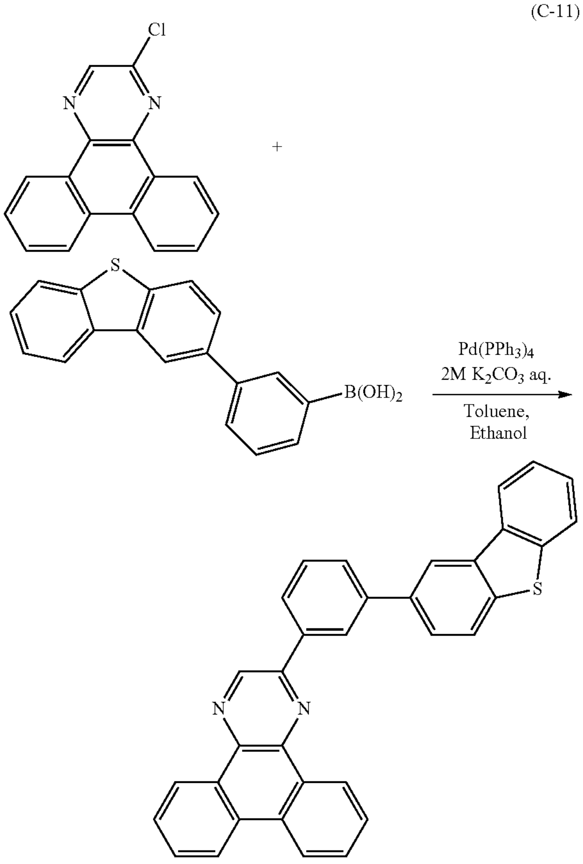

(515)

In a 100-mL three-neck flask were put 0.32 g (1.0 mmol) of 2-chlorodibenzo[f,h]quinoxaline, 0.32 g (1.1 mmol) of 3-(dibenzothiophen-2-yl)phenylboronic acid, 10 mL of toluene, 1 mL of ethanol, and 2.0 mL of a 2M aqueous potassium carbonate solution. This mixture was degassed by stirring under reduced pressure, and the air in the flask was replaced with nitrogen. To this mixture was added 30 mg (20 mol) of tetrakis(triphenylphosphine)palladium(0). This mixture was stirred under a nitrogen stream at 80° C. for 8 hours. After a predetermined time had elapsed, water and toluene were added to this mixture, and organic substances were extracted from the aqueous layer with toluene. The solution of the extracted organic substances was combined with the organic layer, the mixture was washed with a saturated aqueous solution of sodium hydrogen carbonate and saturated brine, followed by drying with magnesium sulfate. The obtained mixture was gravity filtered, and then the filtrate was concentrated to give a solid. The obtained solid was dissolved in toluene, and the toluene solution was suction filtered through alumina and Celite, and the obtained filtrate was concentrated to give a solid. The obtained solid was recrystallized from toluene to give 0.13 g of a white powder in a yield of 26%, which was the substance to be produced.

A nuclear magnetic resonance (NMR) method identified this compound as 2-[3-(dibenzothiophen-2-yl)phenyl]dibenzo[f,h]quinoxaline (abbreviation: 2mDBTPDBq), which was the substance to be produced.

$^1$H NMR data of the obtained substance are as follows: $^1$H NMR ($CDCl_3$, 300 MHz): δ=7.50-7.53 (m, 2H), 7.72-7.93 (m, 8H), 8.02 (d, J=8.4 Hz, 1H), 8.28-8.31 (m, 1H), 8.36 (d, J=7.5 Hz, 1H), 8.50 (d, J=1.5 Hz, 1H), 8.67-8.70 (m, 3H), 9.27 (dd, J=7.8 Hz, 1.8 Hz, 1H), 9.46 (dd, J=7.8 Hz, 1.8 Hz, 1H), 9.51 (s, 1H).

Figure 43A:
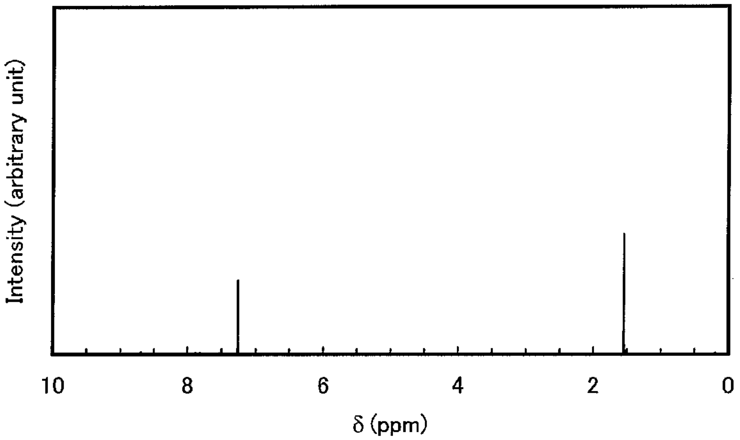
FIGS. 43A and 43B show $^{1}$H NMR charts of 2-[3-(dibenzothiophen-2-yl)phenyl]dibenzo[f,h]quinoxaline (abbreviation: 2mDBTPDBq).
Figure 43B:
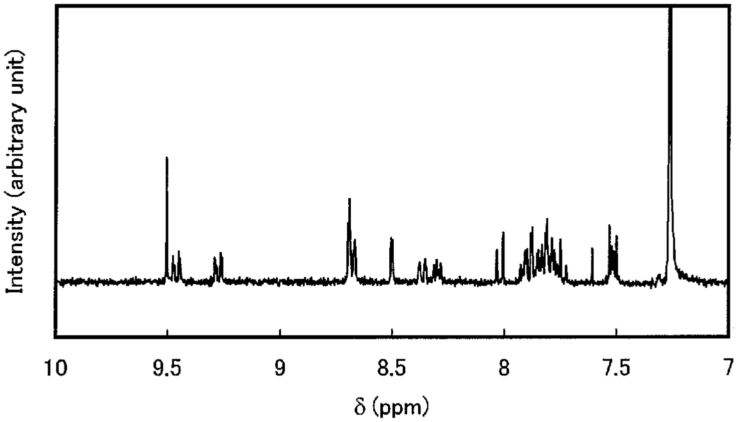

FIGS. 43A and 43B illustrate the $^1$H NMR charts. Note that FIG. 43B is a chart showing an enlarged part of FIG. 43A in the range of 7.0 ppm to 10.0 ppm.

Figure 44A:
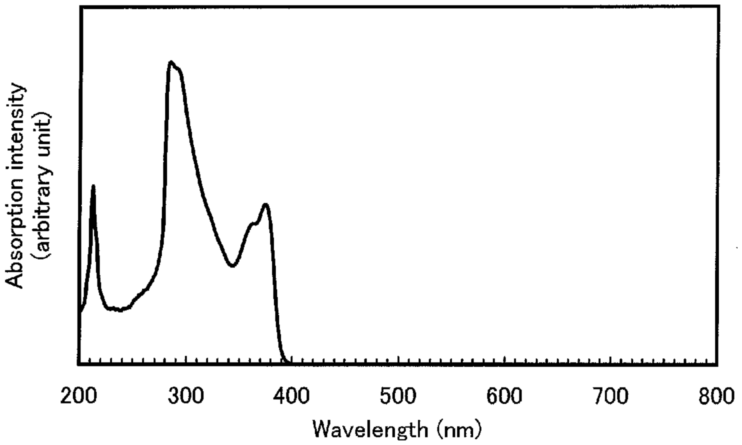
FIGS. 44A and 44B show respectively an absorption spectrum and an emission spectrum of a toluene solution of 2mDBTPDBq.
Figure 44B:
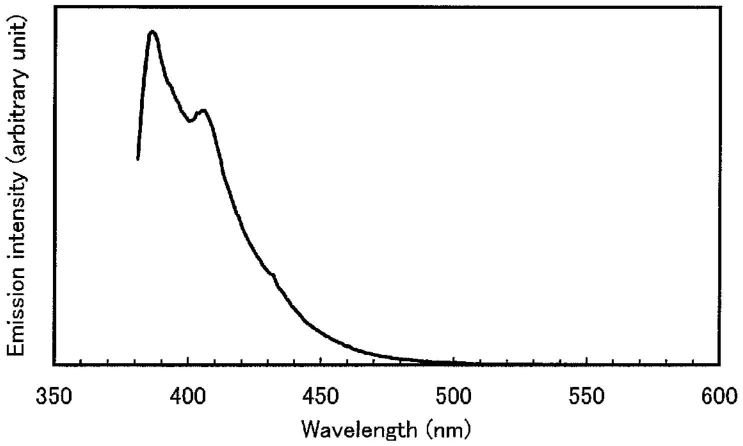
Figure 45A:
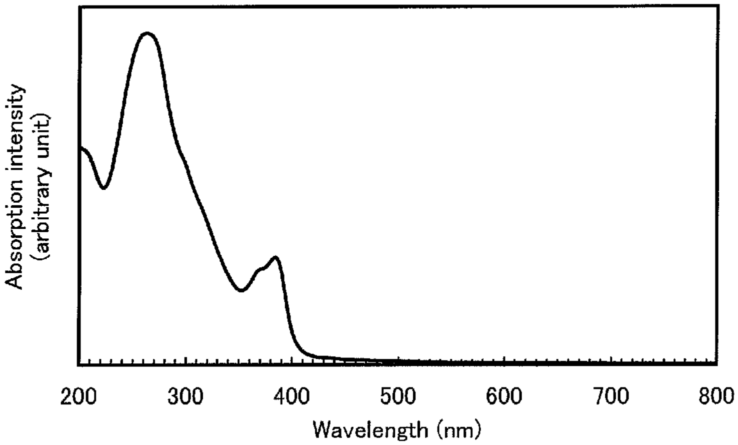
FIGS. 45A and 45B show respectively an absorption spectrum and an emission spectrum of a thin film of 2mDBTPDBq.
Figure 45B:
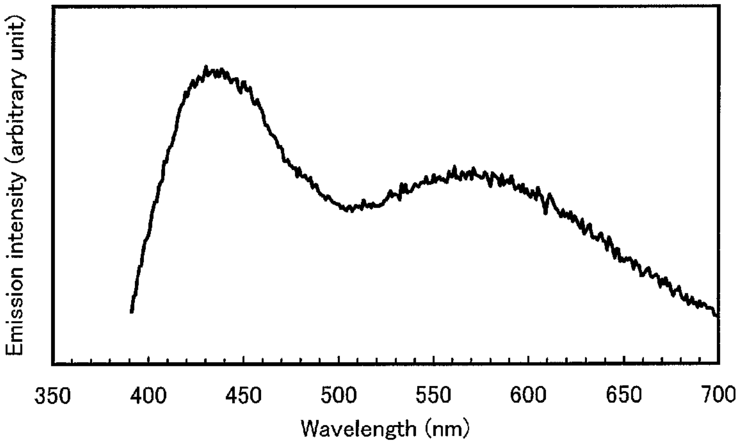

Further, FIG. 44A shows an absorption spectrum of a toluene solution of 2mDBTPDBq, and FIG. 44B shows an emission spectrum thereof. FIG. 45A shows an absorption spectrum of a thin film of 2mDBTPDBq, and FIG. 45B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 44A and 44B and FIGS. 45A and 45B, the horizontal axis represents wavelength (nm) and the vertical axis represents intensity (arbitrary unit). In the case of the toluene solution, absorption peaks were observed at around 362 nm and 374 nm, and emission wavelength peaks were 386 nm and 406 nm (at an excitation wavelength of 374 nm). In the case of the thin film, absorption peaks were observed at around 204 nm, 262 nm, 295 nm, 313 nm, 370 nm, and 384 nm, and emission wavelength peaks were 443 nm and 571 nm (at an excitation wavelength of 384 nm).

Example 13

In this example, a light-emitting element of one embodiment of the present invention will be described referring to FIG. 18. Chemical formulae of materials used in this example are illustrated below. Note that the chemical formulae of the materials which are illustrated above are omitted.

[Chemical Formula 100]

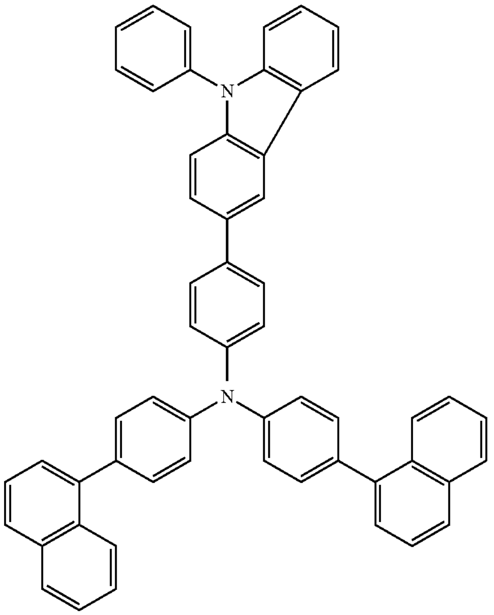

PCBNBB

-continued

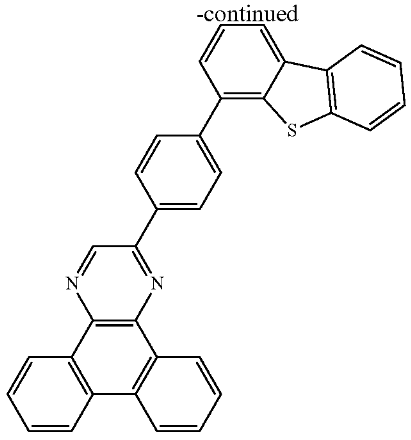

2DBTPDBq-II

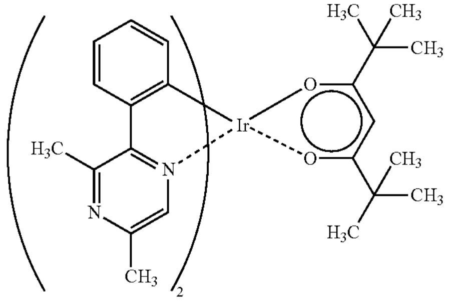

[Ir(mppr-Me)$_2$(dpm)]

A method of fabricating Light-emitting Element 5 of this example will be described below.

(Light-Emitting Element 5)

First, ITSO was deposited over the glass substrate 1100 by a sputtering method, whereby the first electrode 1101 was formed. Note that its thickness was set to 110 nm and the electrode area was set to 2 mm×2 mm. Here, the first electrode 1101 is an electrode that functions as an anode of the light-emitting element.

Next, as pretreatment for forming the light-emitting element over the substrate 1100, after washing of a surface of the substrate with water and baking that was performed at 200° C. for one hour, UV ozone treatment was performed for 370 seconds.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. Then, by an evaporation method using resistance heating, BPAFLP and molybdenum(VI) oxide were co-evaporated to form the hole-injection layer 1111 over the first electrode 1101. The thickness of the hole-injection layer 1111 was set to 40 nm, and the weight ratio of BPAFLP to molybdenum(VI) oxide was adjusted to 4:2 (=BPAFLP:molybdenum(VI) oxide). Note that the co-evaporation method refers to an evaporation method in which evaporation is carried out from a plurality of evaporation sources at the same time in one treatment chamber.

Next, a BPAFLP film was formed to a thickness of 20 nm over the hole-injection layer 1111, whereby the hole-transport layer 1112 was formed.

Further, 2-[4-(dibenzothiophen-4-yl)phenyl]dibenzo[f,h]quinoxaline (abbreviation: 2 DBTPDBq-II) synthesized in Example 4, 4,4'-di(1-naphthyl)-4"-(9-phenyl-9H-carbazol-3-yl)triphenylamine (abbreviation: PCBNBB), and (dipivaloylmethanato)bis(3,5-dimethyl-2-phenylpyrazinato)iridium(III) (abbreviation: [Ir(mppr-Me)$_2$(dpm)]) were co-evaporated to form the light-emitting layer 1113 over the hole-transport layer 1112. The weight ratio of 2 DBTPDBq-II to PCBNBB and [Ir(mppr-Me)$_2$(dpm)] was adjusted to 0.8:0.2:0.05 (=2 DBTPDBq-II:PCBNBB:[Ir(mppr-Me)$_2$(dpm)]). The thickness of the light-emitting layer 1113 was set to 40 nm.

Further, a 2 DBTPDBq-II film was formed to a thickness of 10 nm over the light-emitting layer 1113, whereby the first electron-transport layer 1114*a* was formed.

Then, a BPhen film was formed to a thickness of 20 nm over the first electron-transport layer 1114*a*, whereby the second electron-transport layer 1114*b* was formed.

Further, a LiF film was formed to a thickness of 1 nm over the second electron-transport layer 1114*b* by evaporation, whereby the electron-injection layer 1115 was formed.

Lastly, an aluminum film was formed to a thickness of 200 nm by evaporation as the second electrode 1103 functioning as a cathode. Thus, Light-emitting Element 5 of this example was fabricated.

Note that, in the above evaporation process, evaporation was all performed by a resistance heating method.

Table 3 shows an element structure of Light-emitting Element 5 obtained as described above.

TABLE 3

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 5 | ITSO 110 nm | BPAFLP: MoO*x* (=4:2) 40 nm | BPAFLP 20 nm | 2DBTPDBq-II: PCBNBB: [Ir(mppr-Me)$_2$(dpm)] (=0.8:0.2:0.05) 40 nm | 2DBTPDBq-II 10 nm | BPhen 20 nm | LiF 1 nm | Al 200 nm |

In a glove box containing a nitrogen atmosphere, Light-emitting Element 5 was sealed with a glass substrate so as not to be exposed to air. Then, operation characteristics of the element were measured. Note that the measurements were carried out at room temperature (in the atmosphere kept at 25° C.).

Figure 46:
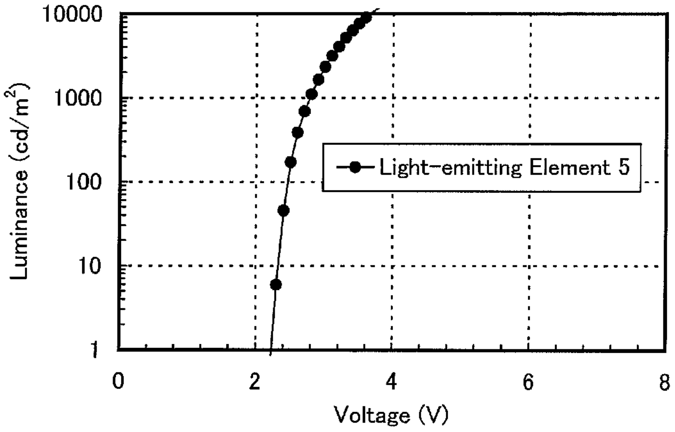
FIG. 46 shows voltage vs. luminance characteristics of a light-emitting element of Example 13.
Figure 47:
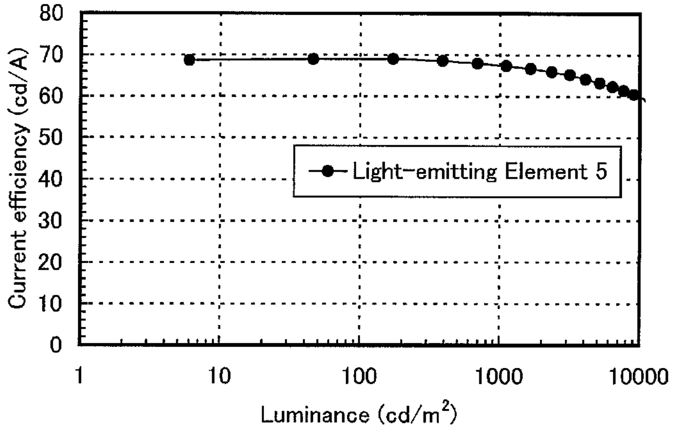
FIG. 47 shows luminance vs. current efficiency characteristics of the light-emitting element of Example 13.

FIG. 46 shows the voltage vs. luminance characteristics of Light-emitting Element 5. In FIG. 46, the horizontal axis represents voltage (V) and the vertical axis represents luminance (cd/m$^2$). In addition, FIG. 47 shows the luminance vs. current efficiency characteristics of the element. In FIG. 47, the horizontal axis represents luminance (cd/m$^2$) and the vertical axis represents current efficiency (cd/A). Further, Table 4 shows the voltage (V), current density (mA/cm$^2$), CIE chromaticity coordinates (x, y), current efficiency (cd/A), and external quantum efficiency (%) of the light-emitting element at a luminance of 1100 cd/m$^2$.

TABLE 4

| | Voltage (V) | Current density (mA/cm$^2$) | Chromaticity x | Chromaticity y | Luminance (cd/m$^2$) | Current efficiency (cd/A) | External quantum efficiency (%) |
|---|---|---|---|---|---|---|---|
| Light-emitting element 5 | 2.8 | 1.6 | 0.55 | 0.45 | 1100 | 67 | 25 |

As shown in Table 4, the CIE chromaticity coordinates (x, y) of Light-emitting Element 5 were (0.55, 0.45) at a luminance of 1100 cd/m$^2$. It is found that Light-emitting Element 5 exhibited light emission from [Ir(mppr-Me)$_2$(dpm)].

FIG. 46 and FIG. 47 reveal that Light-emitting Element 5 has low driving voltage and high current efficiency. It is thus confirmed that a compound to which one embodiment of the present invention is applied is effective in realizing high voltage vs. luminance characteristics and high luminance vs. current efficiency characteristics.

As described above, by using 2 DBTPDBq-II produced in Example 4 as a host material of a light-emitting layer, a light-emitting element having low driving voltage and high current efficiency was able to be fabricated.

Figure 48:
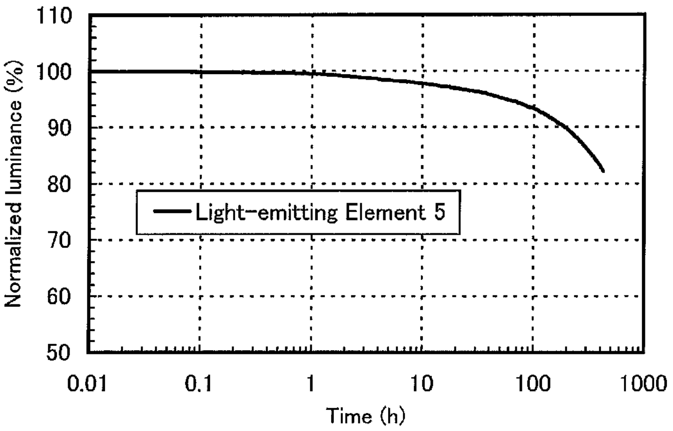
FIG. 48 shows results of reliability tests of the light-emitting element of Example 13.

Next, Light-emitting Element 5 was subjected to reliability tests. Results of the reliability tests are shown in FIG. 48. In FIG. 48, the vertical axis represents normalized luminance (%) with an initial luminance of 100%, and the horizontal axis represents driving time (h) of the element. In the reliability tests, the light-emitting element of this example was driven under the conditions where the current density was constant and the initial luminance was 5000 cd/m$^2$. FIG. 48 shows that Light-emitting Element 5 kept 82% of the initial luminance after driving for 430 hours. These results of the reliability tests revealed that Light-emitting Element 5 had a long lifetime.

As described above, by the use of 2 DBTPDBq-II produced in Example 4 as a host material of a light-emitting layer, a light-emitting element having a long lifetime was able to be fabricated.

Example 14

In this example, a light-emitting element of one embodiment of the present invention will be described referring to FIG. 18. Chemical formulae of materials used in this example are illustrated below. Note that the chemical formulae of the materials which are illustrated above are omitted.

[Chemical Formula 101]

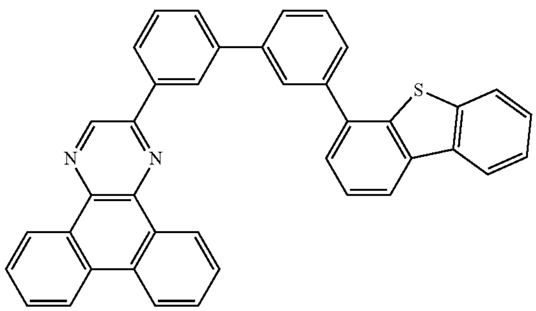

2mDBTBPDBq-II

A method of fabricating Light-emitting Element 6 of this example will be described below.

(Light-Emitting Element 6)

First, the first electrode 1101, the hole-injection layer 1111, and the hole-transport layer 1112 were formed over the glass substrate 1100 in the same manner as those of Light-emitting Element 5 described in Example 13.

Next, 2-[3'-(dibenzothiophen-4-yl)biphenyl-3-yl]dibenzo[f,h]quinoxaline (abbreviation: 2mDBTBPDBq-II) synthesized in Example 5, PCBNBB, and [Ir(mppr-Me)$_2$(dpm)]) were co-evaporated to form the light-emitting layer 1113 over the hole-transport layer 1112. The weight ratio of 2mDBTBPDBq-II to PCBNBB and [Ir(mppr-Me)$_2$(dpm)] was adjusted to 0.8:0.2:0.05 (=2mDBTBPDBq-II:PCBNBB:[Ir(mppr-Me)$_2$(dpm)]). The thickness of the light-emitting layer 1113 was set to 40 nm.

Further, a 2mDBTBPDBq-II film was formed to a thickness of 10 nm over the light-emitting layer 1113, whereby the first electron-transport layer 1114*a* was formed.

Then, a BPhen film was formed to a thickness of 20 nm over the first electron-transport layer 1114*a*, whereby the second electron-transport layer 1114*b* was formed.

Further, a LiF film was formed to a thickness of 1 nm over the second electron-transport layer 1114*b* by evaporation, whereby the electron-injection layer 1115 was formed.

Lastly, an aluminum film was formed to a thickness of 200 nm by evaporation as the second electrode 1103 functioning as a cathode. Thus, Light-emitting Element 6 of this example was fabricated.

Note that, in the above evaporation process, evaporation was all performed by a resistance heating method.

Table 5 shows an element structure of Light-emitting Element 6 obtained as described above.

TABLE 5

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 6 | ITSO 110 nm | BPAFLP: MoO*x* (=4:2) 40 nm | BPAFLP 20 nm | 2mDBTBPDBq-II: PCBNBB: [Ir(mppr-Me)$_2$(dpm)] (=0.8:0.2:0.05) 40 nm | 2mDBTBPDBq-II 10 nm | BPhen 20 nm | LiF 1 nm | Al 200 nm |

In a glove box containing a nitrogen atmosphere, Light-emitting Element 6 was sealed with a glass substrate so as not to be exposed to air. Then, operation characteristics of the element were measured. Note that the measurements were carried out at room temperature (in the atmosphere kept at 25° C.).

Figure 49:
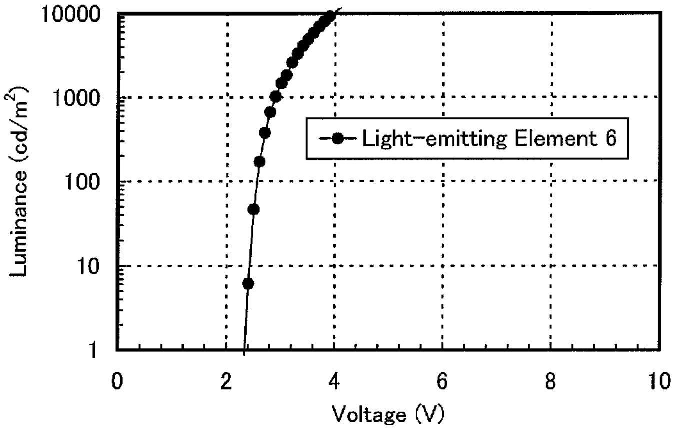
FIG. 49 shows voltage vs. luminance characteristics of a light-emitting element of Example 14.
Figure 50:
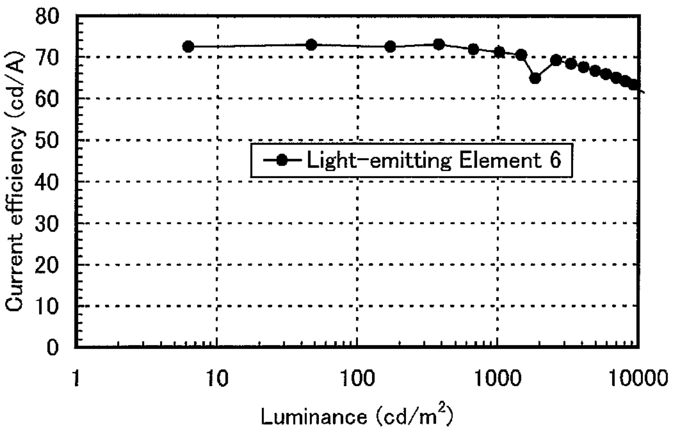
FIG. 50 shows luminance vs. current efficiency characteristics of the light-emitting element of Example 14.

FIG. 49 shows the voltage vs. luminance characteristics of Light-emitting Element 6. In FIG. 49, the horizontal axis represents voltage (V) and the vertical axis represents luminance (cd/m$^2$). In addition, FIG. 50 shows the luminance vs. current efficiency characteristics of the element. In FIG. 50, the horizontal axis represents luminance (cd/m$^2$) and the vertical axis represents current efficiency (cd/A). Further, Table 6 shows the voltage (V), current density (mA/cm$^2$), CIE chromaticity coordinates (x, y), current efficiency (cd/A), and external quantum efficiency (%) of the light-emitting element at a luminance of 1000 cd/m$^2$.

TABLE 6

| | Voltage (V) | Current density (mA/cm$^2$) | Chromaticity x | Chromaticity y | Luminance (cd/m$^2$) | Current efficiency (cd/A) | External quantum efficiency (%) |
|---|---|---|---|---|---|---|---|
| Light-emitting element 6 | 2.9 | 1.4 | 0.53 | 0.47 | 1000 | 71 | 25 |

As shown in Table 6, the CIE chromaticity coordinates (x, y) of Light-emitting Element 6 were (0.53, 0.47) at a luminance of 1000 cd/$m^2$. It is found that Light-emitting Element 6 exhibited light emission from [Ir(mppr-Me)$_2$(dpm)].

FIG. 49 and FIG. 50 reveal that Light-emitting Element 6 has low driving voltage and high current efficiency. It is thus confirmed that a compound to which one embodiment of the present invention is applied is effective in realizing high voltage vs. luminance characteristics and high luminance vs. current efficiency characteristics.

As described above, by using 2mDBTBPDBq-II produced in Example 5 as a host material of a light-emitting layer, a light-emitting element having low driving voltage and high current efficiency was able to be fabricated.

Figure 51:
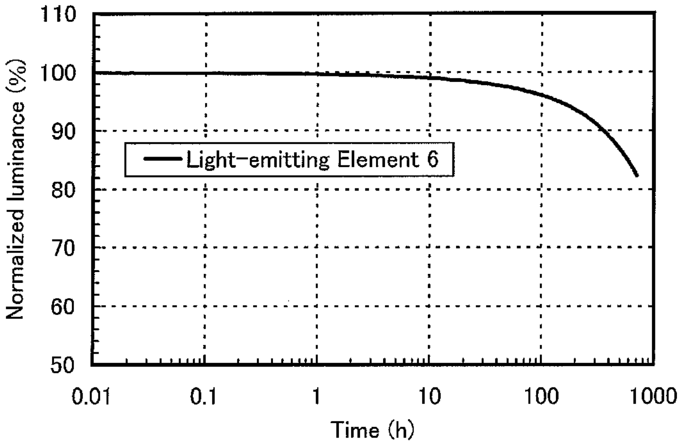
FIG. 51 shows results of reliability tests of the light-emitting element of Example 14.

Next, Light-emitting Element 6 was subjected to reliability tests. Results of the reliability tests are shown in FIG. 51. In FIG. 51, the vertical axis represents normalized luminance (%) with an initial luminance of 100%, and the horizontal axis represents driving time (h) of the element. In the reliability tests, the light-emitting element of this example was driven under the conditions where the current density was constant and the initial luminance was 5000 cd/$m^2$. FIG. 51 shows that Light-emitting Element 6 kept 82% of the initial luminance after driving for 710 hours. These results of the reliability tests revealed that Light-emitting Element 6 had a long lifetime.

As described above, by using 2mDBTBPDBq-II produced in Example 5 as a host material of a light-emitting layer, a light-emitting element having a long lifetime was able to be fabricated. Further, particularly when an arylene group in a compound included in a light-emitting element, through which a dibenzo[f,h]quinoxaline ring and a hole-transport skeleton are bonded, is a biphenyldiyl group, it is found possible to extend the lifetime of the light-emitting element.

Example 15

In this example, a light-emitting element of one embodiment of the present invention will be described referring to FIG. 18. Chemical formulae of materials used in this example are illustrated below. Note that the chemical formulae of the materials which are illustrated above are omitted.

[Chemical Formula 102]

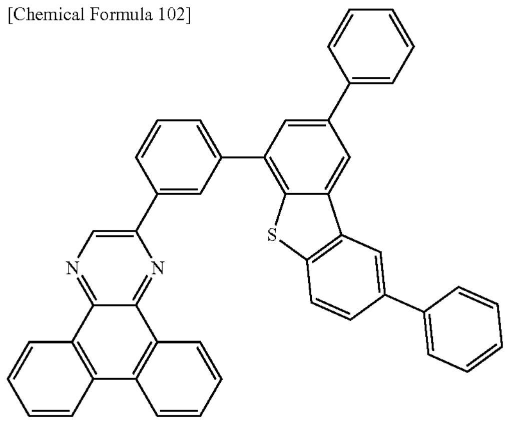

2mDBTPDBq-III

A method of fabricating Light-emitting Element 7 of this example will be described below.

(Light-Emitting Element 7)

First, the first electrode 1101, the hole-injection layer 1111, and the hole-transport layer 1112 were formed over the glass substrate 1100 in the same manner as those of Light-emitting Element 5 described in Example 13.

Next, 2-[3-(2,8-diphenyldibenzothiophen-4-yl)phenyl]dibenzo[f,h]quinoxaline (abbreviation: 2mDBTPDBq-III) synthesized in Example 6, PCBNBB, and [Ir(mppr-Me)$_2$(dpm)]) were co-evaporated to form the light-emitting layer 1113 over the hole-transport layer 1112. The weight ratio of 2mDBTPDBq-III to PCBNBB and [Ir(mppr-Me)$_2$(dpm)] was adjusted to 0.8:0.2:0.05 (=2mDBTPDBq-III:PCBNBB:[Ir(mppr-Me)$_2$(dpm)]). The thickness of the light-emitting layer 1113 was set to 40 nm.

Further, a 2mDBTPDBq-III film was formed to a thickness of 10 nm over the light-emitting layer 1113, whereby the first electron-transport layer 1114*a* was formed.

Then, a BPhen film was formed to a thickness of 20 nm over the first electron-transport layer 1114*a*, whereby the second electron-transport layer 1114*b* was formed.

Further, a LiF film was formed to a thickness of 1 nm over the second electron-transport layer 1114*b* by evaporation, whereby the electron-injection layer 1115 was formed.

Lastly, an aluminum film was formed to a thickness of 200 nm by evaporation as the second electrode 1103 functioning as a cathode. Thus, Light-emitting Element 7 of this example was fabricated.

Note that, in the above evaporation process, evaporation was all performed by a resistance heating method.

Table 7 shows an element structure of Light-emitting Element 7 obtained as described above.

TABLE 7

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 7 | ITSO 110 nm | BPAFLP: MoOx (=4:2) 40 nm | BPAFLP 20 nm | 2mDBTPDBq-III: PCBNBB : [Ir(mppr-Me)$_2$(dpm)] (=0.8:0.2:0.05) 40 nm | 2mDBTPDBq-III 10 nm | BPhen 20 nm | LiF 1 nm | Al 200 nm |

In a glove box containing a nitrogen atmosphere, Light-emitting Element 7 was sealed with a glass substrate so as not to be exposed to air. Then, operation characteristics of the element were measured. Note that the measurements were carried out at room temperature (in the atmosphere kept at 25° C.).

Figure 52:
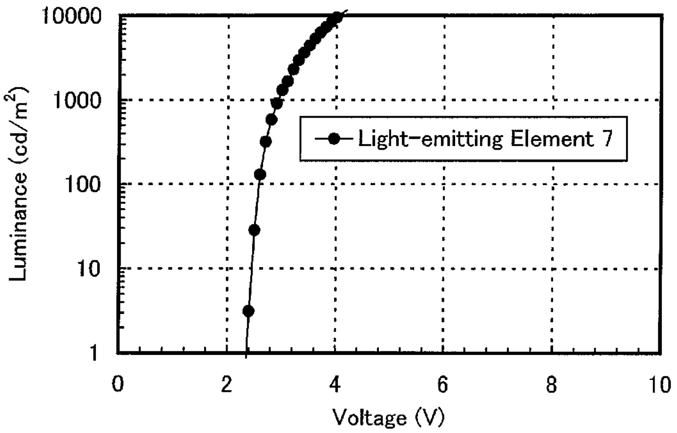
FIG. 52 shows voltage vs. luminance characteristics of a light-emitting element of Example 15.
Figure 53:
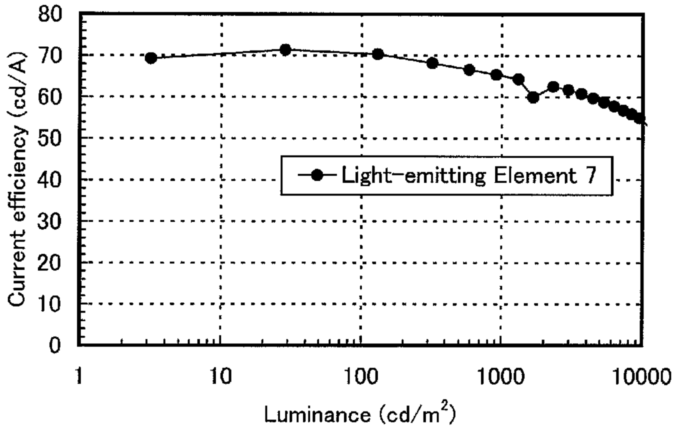
FIG. 53 shows luminance vs. current efficiency characteristics of the light-emitting element of Example 15.

FIG. 52 shows the voltage vs. luminance characteristics of Light-emitting Element 7. In FIG. 52, the horizontal axis represents voltage (V) and the vertical axis represents luminance ($cd/m^2$). In addition, FIG. 53 shows the luminance vs. current efficiency characteristics of the element. In FIG. 53, the horizontal axis represents luminance ($cd/m^2$) and the vertical axis represents current efficiency (cd/A). Further, Table 8 shows the voltage (V), current density ($mA/cm^2$), CIE chromaticity coordinates (x, y), current efficiency (cd/A), and external quantum efficiency (%) of the light-emitting element at a luminance of 910 $cd/m^2$.

[Chemical Formula 103]

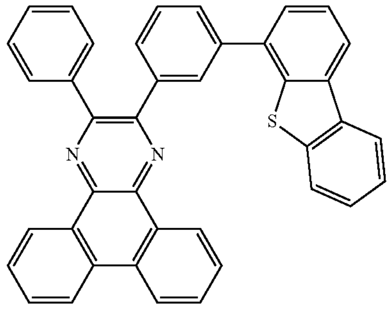

3Ph-2mDBTPDBq-II

TABLE 8

| | Voltage (V) | Current density ($mA/cm^2$) | Chromaticity x | Chromaticity y | Luminance ($cd/m^2$) | Current efficiency (cd/A) | External quantum efficiency (%) |
|---|---|---|---|---|---|---|---|
| Light-emitting element 7 | 2.9 | 1.4 | 0.55 | 0.45 | 910 | 65 | 24 |

As shown in Table 8, the CIE chromaticity coordinates (x, y) of Light-emitting Element 7 were (0.55, 0.45) at a luminance of 910 $cd/m^2$. It is found that Light-emitting Element 7 exhibited light emission from [Ir(mppr-Me)$_2$(dpm)].

FIG. 52 and FIG. 53 reveal that Light-emitting Element 7 has low driving voltage and high current efficiency. It is thus confirmed that a compound to which one embodiment of the present invention is applied is effective in realizing high voltage vs. luminance characteristics and high luminance vs. current efficiency characteristics.

As described above, by using 2mDBTPDBq-III produced in Example 6 as a host material of a light-emitting layer, a light-emitting element having low driving voltage and high current efficiency was able to be fabricated.

Example 16

In this example, a light-emitting element of one embodiment of the present invention will be described referring to FIG. 18. Chemical formulae of materials used in this example are illustrated below. Note that the chemical formulae of the materials which are illustrated above are omitted.

A method of fabricating Light-emitting Element 8 of this example will be described below.

(Light-Emitting Element 8)

First, the first electrode 1101, the hole-injection layer 1111, and the hole-transport layer 1112 were formed over the glass substrate 1100 in the same manner as those of Light-emitting Element 5 described in Example 13.

Next, 2-[3-(dibenzothiophen-4-yl)phenyl]-3-phenyldibenzo[f,h]quinoxaline (abbreviation: 3Ph-2mDBTPDBq-II) synthesized in Example 7, PCBA1BP, and [Ir(mppr-Me)$_2$(acac)]) were co-evaporated to form the light-emitting layer 1113 over the hole-transport layer 1112. The weight ratio of 3Ph-2mDBTPDBq-II to PCBA1BP and [Ir(mppr-Me)$_2$(acac)] was adjusted to 1:0.15:0.06 (=3Ph-2mDBTPDBq-II:PCBA1BP:[Ir(mppr-Me)$_2$(acac)]). The thickness of the light-emitting layer 1113 was set to 40 nm.

Further, a 3Ph-2mDBTPDBq-II film was formed to a thickness of 10 nm over the light-emitting layer 1113, whereby the first electron-transport layer **1114*a*** was formed.

Then, a BPhen film was formed to a thickness of 20 nm over the first electron-transport layer **1114*a*, whereby the second electron-transport layer 1114*b*** was formed.

Further, a LiF film was formed to a thickness of 1 nm over the second electron-transport layer **1114*b* by evaporation, whereby the electron-injection layer 1115** was formed.

Lastly, an aluminum film was formed to a thickness of 200 nm by evaporation as the second electrode 1103 functioning as a cathode. Thus, Light-emitting Element 8 of this example was fabricated.

Note that, in the above evaporation process, evaporation was all performed by a resistance heating method.

Table 9 shows an element structure of Light-emitting Element 8 obtained as described above.

TABLE 9

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 8 | ITSO 110 nm | BPAFLP: MoOx (=4:2) 40 nm | BPAFLP 20 nm | 3Ph-2mDBTPDBq-II: PCBA1BP: [Ir(mppr-Me)$_2$(acac)] (=1:0.15:0.06) 40 nm | 3Ph-2mDBTPDBq-II 10 nm | BPhen 20 nm | LiF 1 nm | Al 200 nm |

In a glove box containing a nitrogen atmosphere, Light-emitting Element 8 was sealed with a glass substrate so as not to be exposed to air. Then, operation characteristics of the element were measured. Note that the measurements were carried out at room temperature (in the atmosphere kept at 25° C.).

Figure 54:
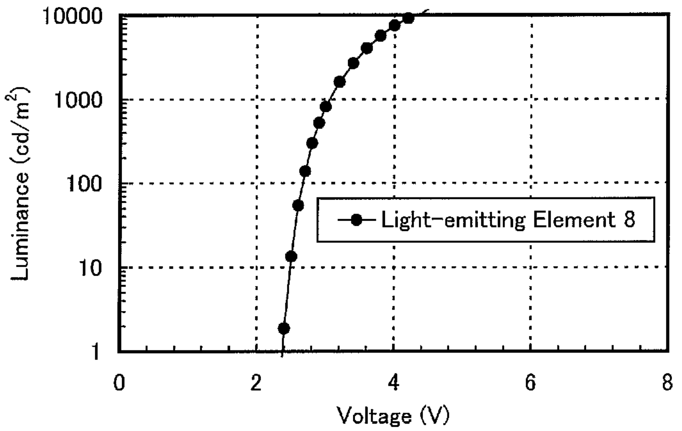
FIG. 54 shows voltage vs. luminance characteristics of a light-emitting element of Example 16.
Figure 55:
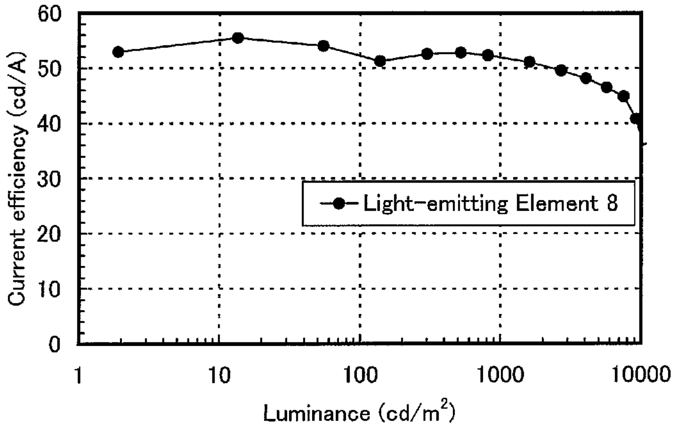
FIG. 55 shows luminance vs. current efficiency characteristics of the light-emitting element of Example 16.

FIG. 54 shows the voltage vs. luminance characteristics of Light-emitting Element 8. In FIG. 54, the horizontal axis represents voltage (V) and the vertical axis represents luminance (cd/m$^2$). In addition, FIG. 55 shows the luminance vs. current efficiency characteristics of the element. In FIG. 55, the horizontal axis represents luminance (cd/m$^2$) and the vertical axis represents current efficiency (cd/A). Further, Table 10 shows the voltage (V), current density (mA/cm$^2$), CIE chromaticity coordinates (x, y), current efficiency (cd/A), and external quantum efficiency (%) of the light-emitting element at a luminance of 810 cd/m$^2$.

TABLE 10

| | Voltage (V) | Current density (mA/cm$^2$) | Chroma-ticity x | Chroma-ticity y | Luminance (cd/m$^2$) | Current efficiency (cd/A) | External quantum efficiency (%) |
|---|---|---|---|---|---|---|---|
| Light-emitting element 8 | 3.0 | 1.6 | 0.55 | 0.45 | 810 | 52 | 20 |

As shown in Table 10, the CIE chromaticity coordinates (x, y) of Light-emitting Element 8 were (0.55, 0.45) at a luminance of 810 cd/m$^2$. It is found that Light-emitting Element 8 exhibited light emission from [Ir(mppr-Me)$_2$(acac)].

FIG. 54 and FIG. 55 reveal that Light-emitting Element 8 has low driving voltage and high current efficiency. It is thus confirmed that a compound to which one embodiment of the present invention is applied is effective in realizing high voltage vs. luminance characteristics and high luminance vs. current efficiency characteristics.

As described above, by using 3Ph-2mDBTPDBq-II produced in Example 7 as a host material of a light-emitting layer, a light-emitting element having low driving voltage and high current efficiency was able to be fabricated.

Example 17

In this example, a light-emitting element of one embodiment of the present invention will be described referring to FIG. 18. Chemical formulae of materials used in this example are illustrated below. Note that the chemical formulae of the materials which are illustrated above are omitted.

[Chemical Formula 104]

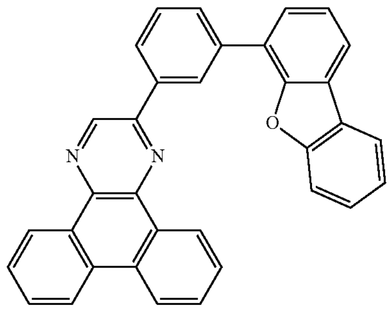

2mDBFPDBq-II

A method of fabricating Light-emitting Element 9 of this example will be described below.

(Light-Emitting Element 9)

First, the first electrode 1101, the hole-injection layer 1111, and the hole-transport layer 1112 were formed over the glass substrate 1100 in the same manner as those of Light-emitting Element 5 described in Example 13.

Next, 2-[3-(dibenzofuran-4-yl)phenyl]dibenzo[1 h]quinoxaline (abbreviation: 2mDBFPDBq-II) synthesized in Example 8, PCBNBB, and [Ir(mppr-Me)$_2$(dpm)]) were co-evaporated to form the light-emitting layer 1113 over the hole-transport layer 1112. The weight ratio of 2mDBFPDBq-II to PCBNBB and [Ir(mppr-Me)$_2$(dpm)] was adjusted to 0.8:0.2:0.05 (=2mDBFPDBq-II:PCBNBB:[Ir(mppr-Me)$_2$(dpm)]). The thickness of the light-emitting layer 1113 was set to 40 nm.

Further, a 2mDBFPDBq-II film was formed to a thickness of 10 nm over the light-emitting layer 1113, whereby the first electron-transport layer 1114*a* was formed.

Then, a bathophenanthroline (abbreviation: BPhen) film was formed to a thickness of 20 nm over the first electron-transport layer 1114*a*, whereby the second electron-transport layer 1114*b* was formed.

Further, a lithium fluoride (LiF) film was formed to a thickness of 1 nm over the second electron-transport layer 1114*b* by evaporation, whereby the electron-injection layer 1115 was formed.

Lastly, an aluminum film was formed to a thickness of 200 nm by evaporation as the second electrode 1103 functioning as a cathode. Thus, Light-emitting Element 9 of this example was fabricated.

Note that, in the above evaporation process, evaporation was all performed by a resistance heating method.

Table 11 shows an element structure of Light-emitting Element 9 obtained as described above.

TABLE 11

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 9 | ITSO 110 nm | BPAFLP: $MoO_x$ (=4:2) 40 nm | BPAFLP 20 nm | 2mDBFPDBq-II: PCBNBB: [Ir(mppr-Me)$_2$(dpm)] (=0.8:0.2:0.05) 40 nm | 2mDBFPDBq-II 10 nm | BPhen 20 nm | LiF 1 nm | Al 200 nm |

In a glove box containing a nitrogen atmosphere, Light-emitting Element 9 was sealed with a glass substrate so as not to be exposed to air. Then, operation characteristics of the element were measured. Note that the measurements were carried out at room temperature (in the atmosphere kept at 25° C.).

Figure 56:
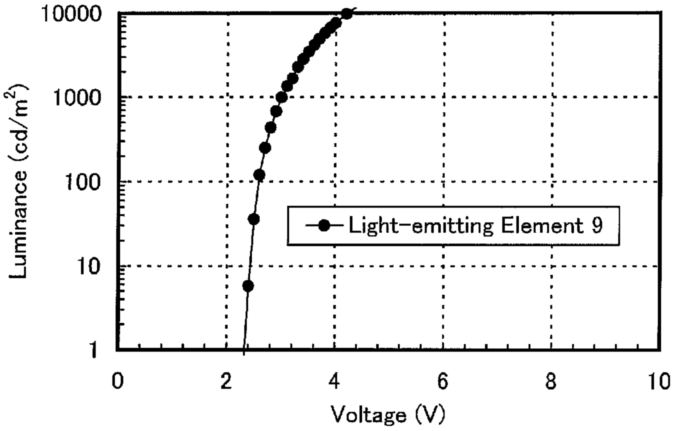
FIG. 56 shows voltage vs. luminance characteristics of a light-emitting element of Example 17.
Figure 57:
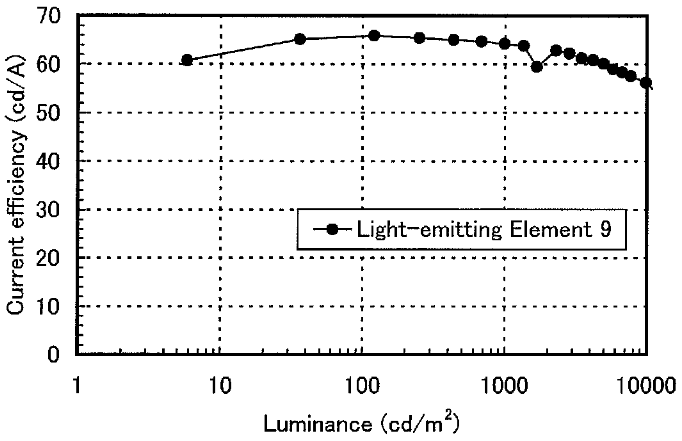
FIG. 57 shows luminance vs. current efficiency characteristics of the light-emitting element of Example 17.

FIG. 56 shows the voltage vs. luminance characteristics of Light-emitting Element 9. In FIG. 56, the horizontal axis represents voltage (V) and the vertical axis represents luminance (cd/m$^2$). In addition, FIG. 57 shows the luminance vs. current efficiency characteristics of the element. In FIG. 57, the horizontal axis represents luminance (cd/m$^2$) and the vertical axis represents current efficiency (cd/A). Further, Table 12 shows the voltage (V), current density (mA/cm$^2$), CIE chromaticity coordinates (x, y), current efficiency (cd/A), and external quantum efficiency (%) of the light-emitting element at a luminance of 990 cd/m$^2$.

TABLE 12

| | Voltage (V) | Current density (mA/cm$^2$) | Chroma-ticity x | Chroma-ticity y | Luminance (cd/m$^2$) | Current efficiency (cd/A) | External quantum efficiency (%) |
|---|---|---|---|---|---|---|---|
| Light-emitting element 9 | 3.0 | 1.5 | 0.55 | 0.45 | 990 | 64 | 24 |

As shown in Table 12, the CIE chromaticity coordinates (x, y) of Light-emitting Element 9 were (0.55, 0.45) at a luminance of 990 cd/m$^2$. It is found that Light-emitting Element 9 exhibited light emission from [Ir(mppr-Me)$_2$(dpm)].

FIG. 56 and FIG. 57 reveal that Light-emitting Element 9 has low driving voltage and high current efficiency. It is thus confirmed that a compound to which one embodiment of the present invention is applied is effective in realizing high voltage vs. luminance characteristics and high luminance vs. current efficiency characteristics.

As described above, by using 2mDBFPDBq-II produced in Example 8 as a host material of a light-emitting layer, a light-emitting element having low driving voltage and high current efficiency was able to be fabricated.

Example 18

In this example, a light-emitting element of one embodiment of the present invention will be described referring to FIG. 18. Chemical formulae of materials used in this example are illustrated below. Note that the chemical formulae of the materials which are illustrated above are omitted.

[Chemical Formula 105]

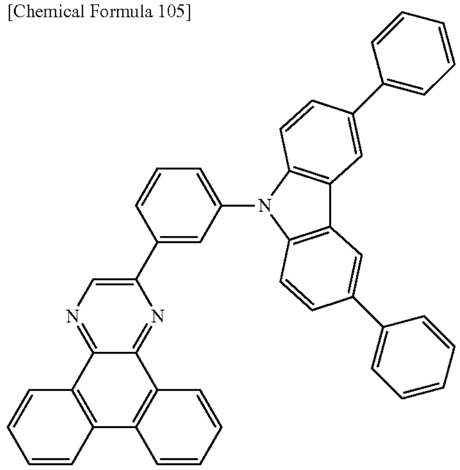

2mCzPDBq-III

A method of fabricating Light-emitting Element 10 of this example will be described below.

(Light-Emitting Element 10)

First, the first electrode 1101, the hole-injection layer 1111, and the hole-transport layer 1112 were formed over the glass substrate 1100 in the same manner as those of Light-emitting Element 5 described in Example 13.

Next, 2-[3-(3,6-diphenyl-9H-carbazol-9-yl)phenyl]dibenzo[f,h]quinoxaline (abbreviation: 2mCzPDBq-III) synthesized in Example 10, PCBNBB, and [Ir(mppr-Me)$_2$(dpm)]) were co-evaporated to form the light-emitting layer 1113 over the hole-transport layer 1112. The weight ratio of 2mCzPDBq-III to PCBNBB and [Ir(mppr-Me)$_2$(dpm)] was adjusted to 0.8:0.2:0.05 (=2mCzPDBq-III:PCBNBB:[Ir(mppr-Me)$_2$(dpm)]). The thickness of the light-emitting layer 1113 was set to 40 nm.

Further, a 2mCzPDBq-III film was formed to a thickness of 10 nm over the light-emitting layer 1113, whereby the first electron-transport layer 1114a was formed.

Then, a BPhen film was formed to a thickness of 20 nm over the first electron-transport layer 1114a, whereby the second electron-transport layer 1114b was formed.

Further, a LiF film was formed to a thickness of 1 nm over the second electron-transport layer 1114b by evaporation, whereby the electron-injection layer 1115 was formed.

Lastly, an aluminum film was formed to a thickness of 200 nm by evaporation as the second electrode 1103 functioning as a cathode. Thus, Light-emitting Element of this example was fabricated.

Note that, in the above evaporation process, evaporation was all performed by a resistance heating method.

Table 13 shows an element structure of Light-emitting Element 10 obtained as described above.

TABLE 13

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 10 | ITSO 110 nm | BPAFLP:MoOx (=4:2) 40 nm | BPAFLP 20 nm | 2mCzPDBq-III:PCBNBB:[Ir(mppr-Me)$_2$(dpm)] (=0.8:0.2:0.05) 40 nm | 2mCzPDBq-III 10 nm | BPhen 20 nm | LiF 1 nm | Al 200 nm |

In a glove box containing a nitrogen atmosphere, Light-emitting Element 10 was sealed with a glass substrate so as not to be exposed to air. Then, operation characteristics of the element were measured. Note that the measurements were carried out at room temperature (in the atmosphere kept at 25° C.).

Figure 58:
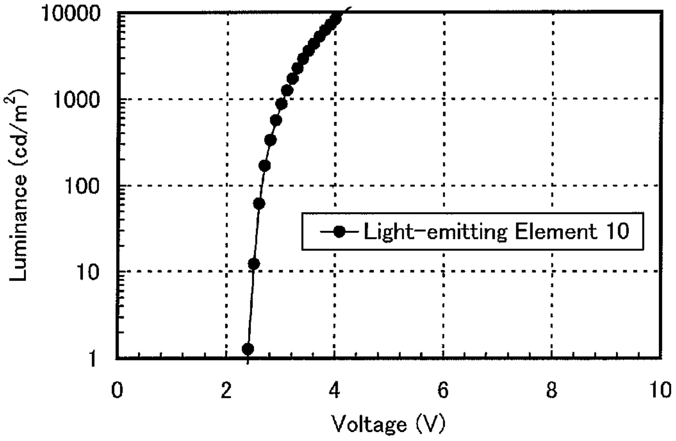
FIG. 58 shows voltage vs. luminance characteristics of a light-emitting element of Example 18.
Figure 59:
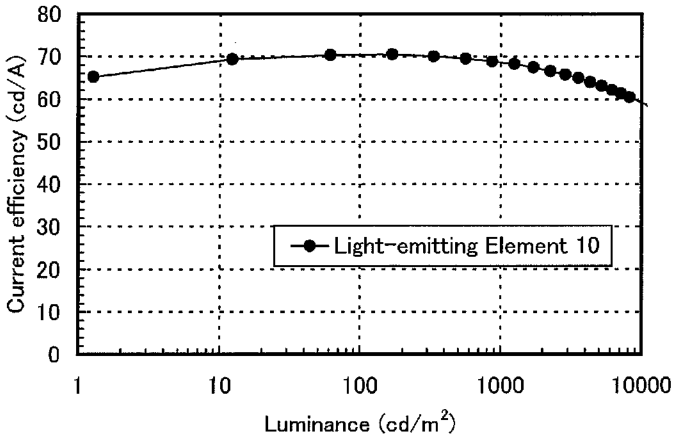
FIG. 59 shows luminance vs. current efficiency characteristics of the light-emitting element of Example 18.

FIG. 58 shows the voltage vs. luminance characteristics of Light-emitting Element 10. In FIG. 58, the horizontal axis represents voltage (V) and the vertical axis represents luminance (cd/m$^2$). In addition, FIG. 59 shows the luminance vs. current efficiency characteristics of the element. In FIG. 59, the horizontal axis represents luminance (cd/m$^2$) and the vertical axis represents current efficiency (cd/A). Further, Table 14 shows the voltage (V), current density (mA/cm$^2$), CIE chromaticity coordinates (x, y), current efficiency (cd/A), and external quantum efficiency (%) of the light-emitting element at a luminance of 870 cd/m$^2$.

As shown in Table 14, the CIE chromaticity coordinates (x, y) of Light-emitting Element 10 were (0.55, 0.45) at a luminance of 870 cd/m$^2$. It is found that Light-emitting Element 10 exhibited light emission from [Ir(mppr-Me)$_2$(dpm)].

FIG. 58 and FIG. 59 reveal that Light-emitting Element 10 has low driving voltage and high current efficiency. It is thus confirmed that a compound to which one embodiment of the present invention is applied is effective in realizing high voltage vs. luminance characteristics and high luminance vs. current efficiency characteristics.

As described above, by using 2mCzPDBq-III produced in Example 10 as a host material of a light-emitting layer, a light-emitting element having low driving voltage and high current efficiency was able to be fabricated.

Example 19

In this example, a light-emitting element of one embodiment of the present invention will be described referring to FIG. 18. Chemical formulae of materials used in this example are illustrated below. Note that the chemical formulae of the materials which are illustrated above are omitted.

TABLE 14

| | Voltage (V) | Current density (mA/cm$^2$) | Chromaticity x | Chromaticity y | Luminance (cd/m$^2$) | Current efficiency (cd/A) | External quantum efficiency (%) |
|---|---|---|---|---|---|---|---|
| Light-emitting element 10 | 3.0 | 1.3 | 0.55 | 0.45 | 870 | 69 | 26 |

[Chemical Formula 106]

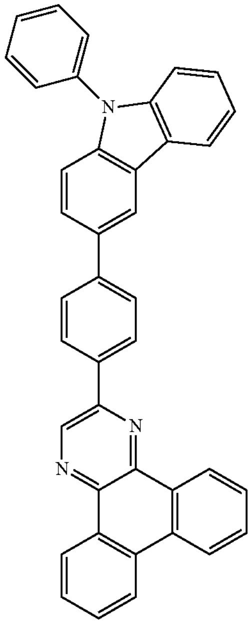

PCPDBq

A method of fabricating Light-emitting Element 11 of this example will be described below.

(Light-Emitting Element 11)

First, the first electrode 1101, the hole-injection layer 1111, and the hole-transport layer 1112 were formed over the glass substrate 1100 in the same manner as those of Light-emitting Element 5 described in Example 13.

Next, 2-[4-(9-phenyl-9H-carbazol-3-yl)phenyl]dibenzo[f, h]quinoxaline (abbreviation: PCPDBq) synthesized in Example 11, PCBNBB, and [Ir(mppr-Me)$_2$(dpm)]) were co-evaporated to form the light-emitting layer 1113 over the hole-transport layer 1112. The weight ratio of PCPDBq to PCBNBB and [Ir(mppr-Me)$_2$(dpm)] was adjusted to 0.8:0.2:0.05 (=PCPDBq:PCBNBB:[Ir(mppr-Me)$_2$(dpm)]). The thickness of the light-emitting layer 1113 was set to 40 nm.

Further, a PCPDBq film was formed to a thickness of 10 inn over the light-emitting layer 1113, whereby the first electron-transport layer 1114*a* was formed.

Then, a bathophenanthroline (abbreviation: BPhen) film was formed to a thickness of 20 nm over the first electron-transport layer 1114*a*, whereby the second electron-transport layer 1114*b* was formed.

Further, a lithium fluoride (LiF) film was formed to a thickness of 1 nm over the second electron-transport layer 1114*b* by evaporation, whereby the electron-injection layer 1115 was formed.

Lastly, an aluminum film was formed to a thickness of 200 nm by evaporation as the second electrode 1103 functioning as a cathode. Thus, Light-emitting Element 11 of this example was fabricated.

Note that, in the above evaporation process, evaporation was all performed by a resistance heating method.

Table 15 shows an element structure of Light-emitting Element 11 obtained as described above.

TABLE 15

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 11 | ITSO 110 nm | BPAFLP: MoO*x* (=4:2) 40 nm | BPAFLP 20 nm | PCPDBq: PCBNBB: [Ir(mppr-Me)$_2$(dpm)] (=0.8:0.2:0.05) 40 nm | PCPDBq 10 nm | BPhen 20 nm | LiF 1 nm | Al 200 nm |

In a glove box containing a nitrogen atmosphere, Light-emitting Element 11 was sealed with a glass substrate so as not to be exposed to air. Then, operation characteristics of the element were measured. Note that the measurements were carried out at room temperature (in the atmosphere kept at 25° C.).

Figure 60:
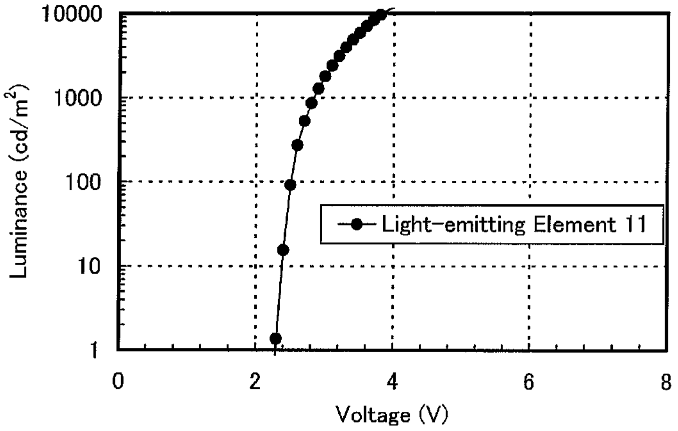
FIG. 60 shows voltage vs. luminance characteristics of a light-emitting element of Example 19.
Figure 61:
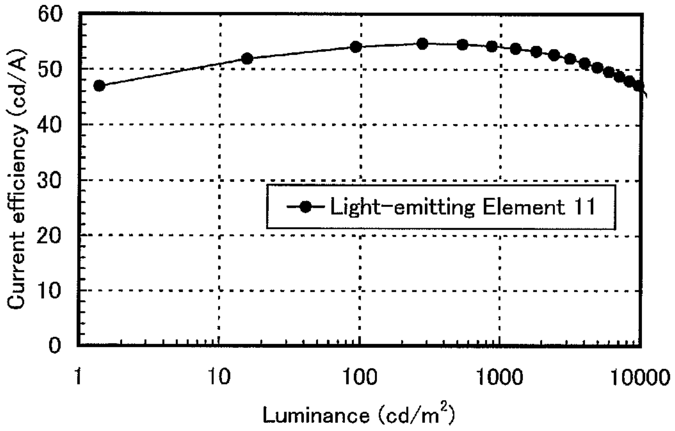
FIG. 61 shows luminance vs. current efficiency characteristics of the light-emitting element of Example 19.

FIG. 60 shows the voltage vs. luminance characteristics of Light-emitting Element 11. In FIG. 60, the horizontal axis represents voltage (V) and the vertical axis represents luminance (cd/m$^2$). In addition, FIG. 61 shows the luminance vs. current efficiency characteristics of the element. In FIG. 61, the horizontal axis represents luminance (cd/m$^2$) and the vertical axis represents current efficiency (cd/A). Further, Table 16 shows the voltage (V), current density (mA/cm$^2$), CIE chromaticity coordinates (x, y), current efficiency (cd/A), and external quantum efficiency (%) of the light-emitting element at a luminance of 860 cd/m$^2$.

TABLE 16

| | Voltage (V) | Current density ($mA/cm^2$) | Chroma-ticity x | Chroma-ticity y | Luminance ($cd/m^2$) | Current efficiency (cd/A) | External quantum efficiency (%) |
|---|---|---|---|---|---|---|---|
| Light-emitting element 11 | 2.8 | 1.6 | 0.55 | 0.44 | 860 | 54 | 21 |

As shown in Table 16, the CIE chromaticity coordinates (x, y) of Light-emitting Element 11 were (0.55, 0.44) at a luminance of 860 $cd/m^2$. It is found that Light-emitting Element 11 exhibited light emission from [Ir(mppr-Me)$_2$(dpm)].

FIG. 60 and FIG. 61 reveal that Light-emitting Element 11 has low driving voltage and high current efficiency. It is thus confirmed that a compound to which one embodiment of the present invention is applied is effective in realizing high voltage vs. luminance characteristics and high luminance vs. current efficiency characteristics.

As described above, by using PCPDBq produced in Example 11 as a host material of a light-emitting layer, a light-emitting element having low driving voltage and high current efficiency was able to be fabricated.

Example 20

In this example, a light-emitting element of one embodiment of the present invention will be described referring to FIG. 18. Chemical formulae of materials used in this example are illustrated below. Note that the chemical formulae of the materials which are illustrated above are omitted.

[Chemical Formula 107]

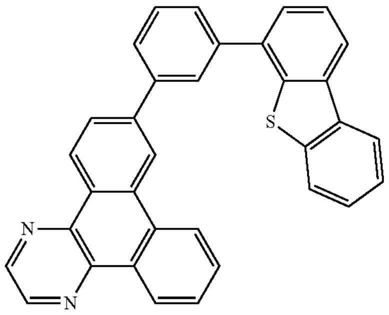

7mDBTPDBq-II (Light-Emitting Element 12)

First, the first electrode 1101, the hole-injection layer 1111, and the hole-transport layer 1112 were formed over the glass substrate 1100 in the same manner as those of Light-emitting Element 5 described in Example 13.

Next, 7-[3-(dibenzothiophen-4-yl)phenyl]dibenzo[f,h]quinoxaline (abbreviation: 7mDBTPDBq-II) (whose synthesis method is described in Reference Example 3), PCBA1BP, and [Ir(mppr-Me)$_2$(acac)]) were co-evaporated to form the light-emitting layer 1113 over the hole-transport layer 1112. The weight ratio of 7mDBTPDBq-II to PCBA1BP and [Ir(mppr-Me)$_2$(acac)] was adjusted to 1:0.15:0.06 (=7mDBTPDBq-II:PCBA1BP:[Ir(mppr-Me)$_2$(acac)]). The thickness of the light-emitting layer 1113 was set to 40 nm.

Further, a 7mDBTPDBq-II film was formed to a thickness of 10 nm over the light-emitting layer 1113, whereby the first electron-transport layer 1114*a* was formed.

Then, a BPhen film was formed to a thickness of 20 nm over the first electron-transport layer 1114*a*, whereby the second electron-transport layer 1114*b* was formed.

Further, a LiF film was formed to a thickness of 1 nm over the second electron-transport layer 1114*b* by evaporation, whereby the electron-injection layer 1115 was formed.

Lastly, an aluminum film was formed to a thickness of 200 nm by evaporation as the second electrode 1103 functioning as a cathode. Thus, Light-emitting Element 12 of this example was fabricated.

Note that, in the above evaporation process, evaporation was all performed by a resistance heating method.

Table 17 shows an element structure of Light-emitting Element 12 obtained as described above.

TABLE 17

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 12 | ITSO 110 nm | BPAFLP:MoO*x* (=4:2) 40 nm | BPAFLP 20 nm | 7mDBTPDBq-II:PCBA1BP:[Ir(mppr-Me)$_2$(acac)] (=1:0.15:0.06) 40 nm | 7mDBTPDBq-II 10 nm | BPhen 20 nm | LiF 1 nm | Al 200 nm |

A method of fabricating Light-emitting Element 12 of this example will be described below.

In a glove box containing a nitrogen atmosphere, Light-emitting Element 12 was sealed with a glass substrate so as not to be exposed to air. Then, operation characteristics of the element were measured. Note that the measurements were carried out at room temperature (in the atmosphere kept at 25° C.).

Figure 62:
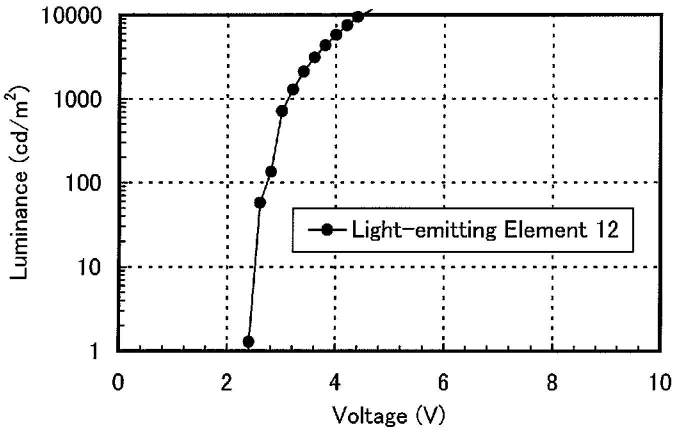
FIG. 62 shows voltage vs. luminance characteristics of a light-emitting element of Example 20.
Figure 63:
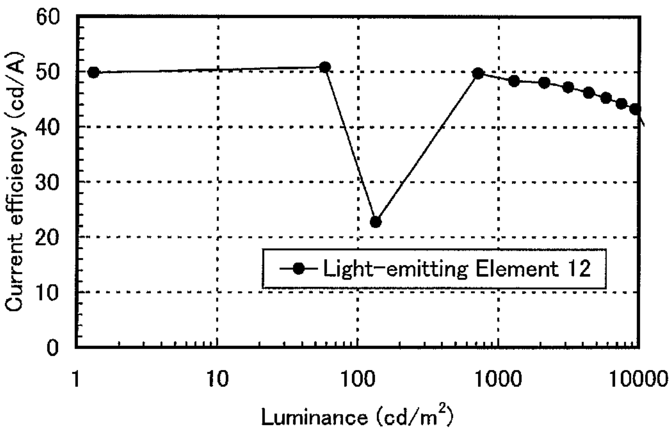
FIG. 63 shows luminance vs. current efficiency characteristics of the light-emitting element of Example 20.

FIG. 62 shows the voltage vs. luminance characteristics of Light-emitting Element 12. In FIG. 62, the horizontal axis represents voltage (V) and the vertical axis represents luminance (cd/$m^2$). In addition, FIG. 63 shows the luminance vs. current efficiency characteristics of the element. In FIG. 63, the horizontal axis represents luminance (cd/$m^2$) and the vertical axis represents current efficiency (cd/A). Further, Table 18 shows the voltage (V), current density (mA/$cm^2$), CIE chromaticity coordinates (x, y), current efficiency (cd/A), and external quantum efficiency (%) of the light-emitting element at a luminance of 720 cd/$m^2$.

TABLE 18

| | Voltage (V) | Current density (mA/$cm^2$) | Chromaticity x | Chromaticity y | Luminance (cd/$m^2$) | Current efficiency (cd/A) | External quantum efficiency (%) |
|---|---|---|---|---|---|---|---|
| Light-emitting element 12 | 3.0 | 1.4 | 0.54 | 0.46 | 720 | 50 | 19 |

As shown in Table 18, the CIE chromaticity coordinates (x, y) of Light-emitting Element 12 were (0.54, 0.46) at a luminance of 720 cd/$m^2$. It is found that Light-emitting Element 12 exhibited light emission from [Ir(mppr-Me)$_2$(acac)].

FIG. 62 and FIG. 63 reveal that Light-emitting Element 12 has low driving voltage and high current efficiency. It is thus confirmed that a compound to which one embodiment of the present invention is applied is effective in realizing high voltage vs. luminance characteristics and high luminance vs. current efficiency characteristics.

As described above, by using 7mDBTPDBq-II as a host material of a light-emitting layer, a light-emitting element having low driving voltage and high current efficiency was able to be fabricated.

Example 21

In this example, a light-emitting element of one embodiment of the present invention will be described referring to FIG. 18. Chemical formulae of materials used in this example are illustrated below. Note that the chemical formulae of the materials which are illustrated above are omitted.

[Chemical Formula 108]

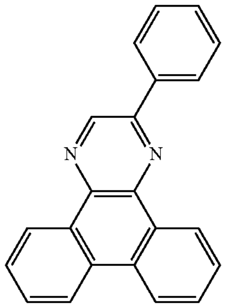

2PDBq

Methods of fabricating Light-emitting Element 13 and Reference Light-emitting Element 14 of this example will be described below.

(Light-Emitting Element 13)

First, the first electrode 1101, the hole-injection layer 1111, and the hole-transport layer 1112 were formed over the glass substrate 1100 in the same manner as those of Light-emitting Element 5 described in Example 13.

Next, 2mDBTPDBq-II, PCBA1BP, and [Ir(mppr-Me)$_2$(acac)]) were co-evaporated to form the light-emitting layer 1113 over the hole-transport layer 1112. The weight ratio of 2mDBTPDBq-II to PCBA1BP and [Ir(mppr-Me)$_2$(acac)] was adjusted to 1:0.25:0.06 (=2mDBTPDBq-II:PCBA1BP:[Ir(mppr-Me)$_2$(acac)]). The thickness of the light-emitting layer 1113 was set to 40 nm.

Further, a 2mDBTPDBq-II film was formed to a thickness of 10 nm over the light-emitting layer 1113, whereby the first electron-transport layer 1114*a* was formed.

Then, a BPhen film was formed to a thickness of 20 nm over the first electron-transport layer 1114*a*, whereby the second electron-transport layer 1114*b* was formed.

Further, a LiF film was formed to a thickness of 1 nm over the second electron-transport layer 1114*b* by evaporation, whereby the electron-injection layer 1115 was formed.

Lastly, an aluminum film was formed to a thickness of 200 nm by evaporation as the second electrode 1103 functioning as a cathode. Thus, Light-emitting Element 13 of this example was fabricated.

Note that, in the above evaporation process, evaporation was all performed by a resistance heating method.

(Reference Light-Emitting Element 14)

The light-emitting layer 1113 of Reference Light-emitting Element 14 was formed by co-evaporation of 2-phenyldibenzo[f,h]quinoxaline (abbreviation: 2PDBq), PCBA1BP, and [Ir(mppr-Me)$_2$(acac)]. The weight ratio of 2PDBq to PCBA1BP and [Ir(mppr-Me)$_2$(acac)] was adjusted to 1:0.25:0.06 (=2PDBq:PCBA1BP:[Ir(mppr-Me)$_2$(acac)]). The thickness of the light-emitting layer 1113 was set to 40 nm.

The first electron-transport layer 1114*a* of Reference Light-emitting Element 14 was formed with a 10-nm-thick 2PDBq film. The components other than the light-emitting layer 1113 and the first electron-transport layer 1114*a* were formed in the same manner as those of Light-emitting Element 13.

Table 19 shows element structures of Light-emitting Element 13 and Reference Light-emitting Element 14 obtained as described above.

TABLE 19

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 13 | ITSO 110 nm | BPAFLP: MoOx (=4:2) 40 nm | BPAFLP 20 nm | 2mDBTPDBq-II: PCBA1BP: $[Ir(mppr-Me)_2(acac)]$ (=1:0.25:0.06) 40 nm | 2mDBTPDBq-II 10 nm | BPhen 20 nm | LiF 1 nm | Al 200 nm |
| Reference light-emitting element 14 | ITSO 110 nm | BPAFLP: MoOx (=4:2) 40 nm | BPAFLP 20 nm | 2PDBq: PCBA1BP: $[Ir(mppr-Me)_2(acac)]$ (=1:0.25:0.06) 40 nm | 2PDBq 10 nm | BPhen 20 nm | LiF 1 nm | Al 200 nm |

In a glove box containing a nitrogen atmosphere, Light-emitting Element 13 and Reference Light-emitting Element 14 were sealed with a glass substrate so as not to be exposed to air. Then, operation characteristics of these elements were measured. Note that the measurements were carried out at room temperature (in the atmosphere kept at 25° C.).

Figure 64:
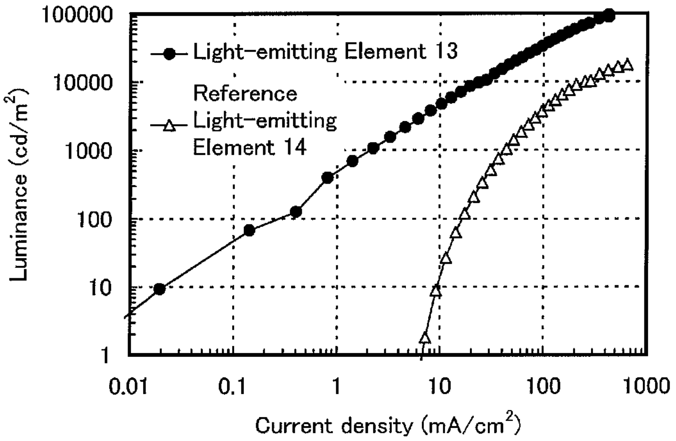
FIG. 64 shows current density vs. luminance characteristics of light-emitting elements of Example 21.
Figure 65:
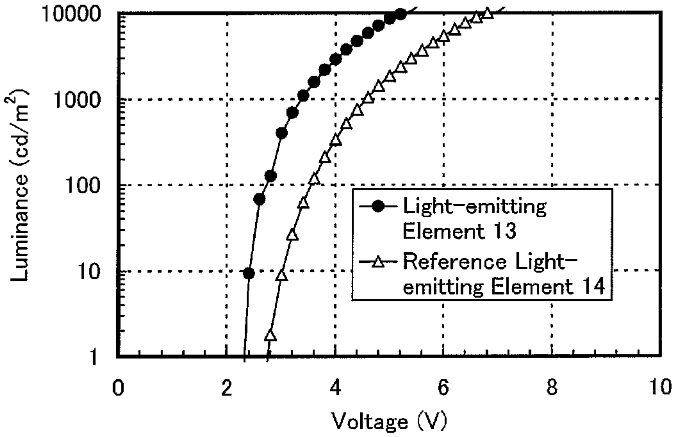
FIG. 65 shows voltage vs. luminance characteristics of the light-emitting elements of Example 21.
Figure 66:
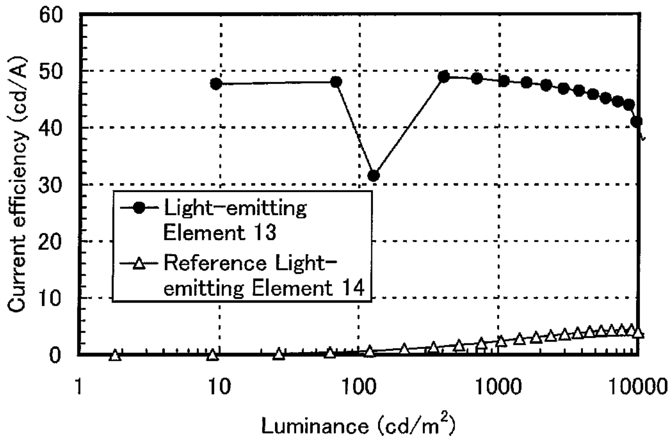
FIG. 66 shows luminance vs. current efficiency characteristics of the light-emitting elements of Example 21.
Figure 67:
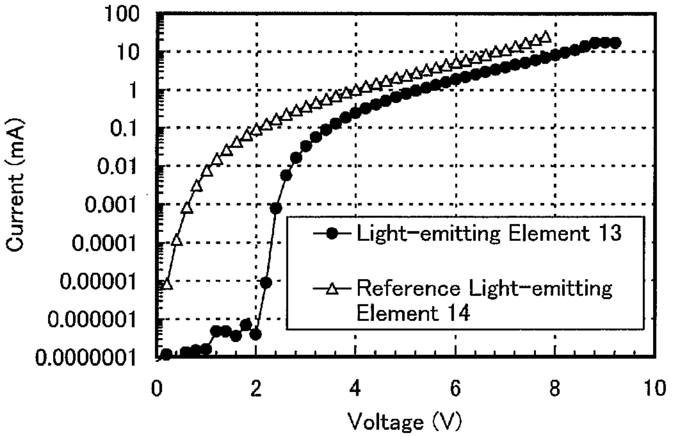
FIG. 67 shows voltage vs. current characteristics of the light-emitting elements of Example 21.

FIG. 64 shows the current density vs. luminance characteristics of Light-emitting Element 13 and Reference Light-emitting Element 14. In FIG. 64, the horizontal axis represents current density ($mA/cm^2$) and the vertical axis represents luminance ($cd/m^2$). In addition, FIG. 65 shows the voltage vs. luminance characteristics. In FIG. 65, the horizontal axis represents voltage (V) and the vertical axis represents luminance ($cd/m^2$). FIG. 66 shows the luminance vs. current efficiency characteristics. In FIG. 66, the horizontal axis represents luminance ($cd/m^2$) and the vertical axis represents current efficiency (cd/A). FIG. 67 shows the voltage vs. current characteristics. In FIG. 67, the horizontal axis represents voltage (V) and the vertical axis represents current (mA). Further, Table 20 shows the voltage (V), current density ($mA/cm^2$), CIE chromaticity coordinates (x, y), current efficiency (cd/A), and external quantum efficiency (%) of the light-emitting element at a luminance of 1100 $cd/m^2$.

TABLE 20

| | Voltage (V) | Current density ($mA/cm^2$) | Chromaticity x | Chromaticity y | Luminance ($cd/m^2$) | Current efficiency (cd/A) | External quantum efficiency (%) |
|---|---|---|---|---|---|---|---|
| Light-emitting element 13 | 3.4 | 2.2 | 0.54 | 0.45 | 1100 | 48 | 19 |
| Reference light-emitting element 14 | 4.6 | 44 | 0.53 | 0.47 | 1100 | 2.4 | 0.9 |

As shown in Table 20, the CIE chromaticity coordinates (x, y) of Light-emitting Element 13 and Reference Light-emitting Element 14 were respectively (0.54, 0.45) and (0.53, 0.47) at a luminance of 1100 $cd/m^2$. It is found that Light-emitting Element 13 and Reference Light-emitting Element 14 each exhibited light emission from $[Ir(mppr-Me)_2(acac)]$.

FIG. 67 reveals that, in a region at voltage lower than the voltage (of about 2V) at which light emission starts, a larger current flows in Reference Light-emitting Element 14 fabricated in this example than in Light-emitting Element 13. In addition, Table 20 indicates that the current efficiency of Reference Light-emitting Element 14 is significantly low. This is considered to be because 2PDBq used for the light-emitting layer 1113 of Reference Light-emitting Element 14 is crystallized and current leakage occurs.

In contrast, FIG. 64, FIG. 65, FIG. 66, and FIG. 67 demonstrate that Light-emitting Element 13 has low driving voltage and high current efficiency. It is thus confirmed that a compound to which one embodiment of the present invention is applied is effective in realizing high voltage vs. luminance characteristics and high luminance vs. current efficiency characteristics.

As described above, by using 2mDBTPDBq-II as a host material of a light-emitting layer, a light-emitting element having low driving voltage and high current efficiency was able to be fabricated.

(Reference Example 1)

A method of synthesizing 4-phenyl-4'-(9-phenylfluoren-9-yl)triphenylamine (abbreviation: BPAFLP) used in Example 3 and the like above will be specifically described. The structure of BPAFLP is illustrated below.

[Chemical Formula 109]

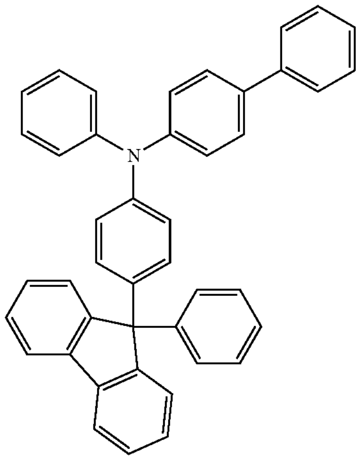

BPAFLP

Step 1: Synthesis Method of 9-(4-Bromophenyl)-9-phenylfluorene

In a 100-mL three-neck flask, 1.2 g (50 mmol) of magnesium was heated and stirred under reduced pressure for 30 minutes, whereby the magnesium was activated. After the flask was cooled to room temperature and was made to have a nitrogen atmosphere, several drops of dibromoethane were added, so that foam formation and heat generation were confirmed. After 12 g (50 mmol) of 2-bromobiphenyl dissolved in 10 mL of diethyl ether was slowly dripped into this mixture, the mixture was stirred and heated under reflux for 2.5 hours, whereby a Grignard reagent was prepared.

In a 500-mL three-neck flask were put 10 g (40 mmol) of 4-bromobenzophenone and 100 mL of diethyl ether. After the Grignard reagent prepared as above was slowly dripped into this mixture, the mixture was heated and stirred under reflux for 9 hours.

After reaction, this mixed liquid was filtered to give a substance. The substance obtained by the filtration was dissolved in 150 mL of ethyl acetate, and 1N-hydrochloric acid was added to the mixture, which was then stirred for 2 hours until it was made acid. The organic layer of this liquid was washed with water. Then, magnesium sulfate was added thereto so that moisture is removed. This suspension was filtered, and the resulting filtrate was concentrated to give a highly viscous liquid.

In a 500-mL recovery flask were put this highly viscous liquid, 50 mL of glacial acetic acid, and 1.0 mL of hydrochloric acid. The mixture was heated and stirred under a nitrogen atmosphere at 130° C. for 1.5 hours to be reacted.

After reaction, this reaction mixed liquid was filtered to give a substance. The substance obtained by the filtration was washed with water, an aqueous sodium hydroxide solution, water, and methanol in this order. Then, the mixture was dried to give 11 g of a white powder in 69% yield, which was the substance to be produced. The reaction scheme of the synthesis method is illustrated in the following (D-1).

[Chemical Formula 110]

(D-1)

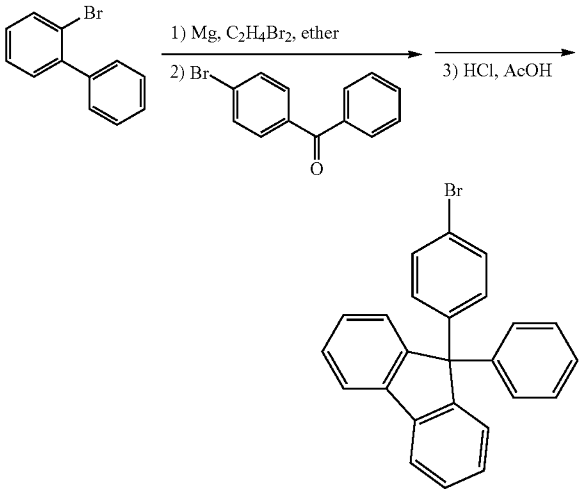

Step 2: Synthesis Method of 4-Phenyl-4'-(9-phenylfluoren-9-yl)triphenylamine (abbreviation: BPAFLP)

In a 100-mL three-neck flask were put 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0). The air in the flask was replaced with nitrogen. Then, 20 mL of dehydrated xylene was added to this mixture. After the mixture was degassed by stirring under reduced pressure, 0.2 mL (0.1 mmol) of tri(tert-butyl)phosphine (a 10 wt % hexane solution) was added to the mixture. This mixture was heated and stirred under a nitrogen atmosphere at 110° C. for 2 hours to be reacted.

After reaction, 200 mL of toluene was added to the reaction mixed liquid, and this suspension was filtered through Florisil (produced by Wako Pure Chemical Industries, Ltd., Catalog No. 540-00135) and Celite (produced by Wako Pure Chemical Industries, Ltd., Catalog No. 531-16855). The filtrate was concentrated, and the resulting substance was purified by silica gel column chromatography (with a developing solvent of toluene and hexane in a ratio of 1:4). The obtained fractions were concentrated, and acetone and methanol were added to the mixture. The mixture was irradiated with ultrasonic waves and then recrystallized to give 4.1 g of a white powder in 92% yield, which was the substance to be produced. The reaction scheme of the synthesis method is illustrated in the following (D-2).

[Chemical Formula 111]

(D-2)

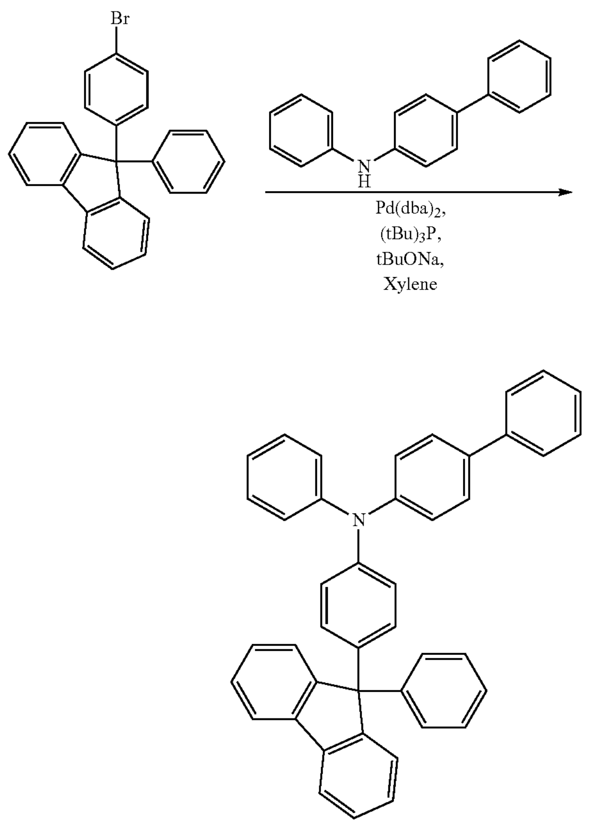

BPAFLP

The Rf values of the produced substance, 9-(4-bromophenyl)-9-phenylfluorene, and 4-phenyl-diphenylamine were respectively 0.41, 0.51, and 0.27, which were found by silica gel thin layer chromatography (TLC) (with a developing solvent of ethyl acetate and hexane in a ratio of 1:10).

The compound obtained through the above Step 2 was subjected to a nuclear magnetic resonance (NMR) method. The measurement data are shown below. The measurement results indicate that the obtained compound was BPAFLP, which is a fluorene derivative.

$^1$H NMR ($CDCl_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9 Hz, 2H).

Reference Example 2

A method of synthesizing (dipivaloylmethanato)bis(3,5-dimethyl-2-phenylpyrazinato)iridium(III) (abbreviation: [Ir(mppr-Me)$_2$(dpm)]) used in Example 13 and the like above will be specifically described. The structure of [Ir(mppr-Me)$_2$(dpm)] is illustrated below.

[Chemical Formula 112]

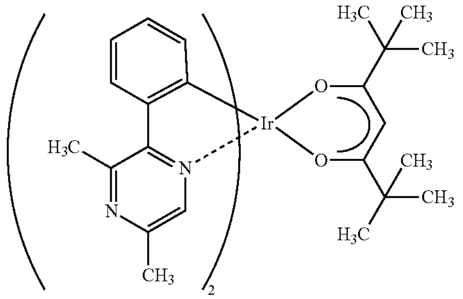

[Ir(mppr-Me)$_2$(dpm)]

First, 20 mL of 2-ethoxyethanol, 1.55 g of a binuclear complex di-μ-chloro-bis[bis(3,5-dimethyl-2-phenylpyrazinato)iridium(III)] (abbreviation: [Ir(mppr-Me)$_2$Cl]$_2$), 0.8 ml of dipivaloylmethane, and 1.38 g of sodium carbonate were mixed. The mixture was irradiated with microwaves under argon bubbling for 30 minutes, whereby the mixture was reacted. After reaction, the reaction solution was cooled down to room temperature, and water was added thereto. This mixture solution was separated into an organic layer and an aqueous layer, and organic substances were extracted from the aqueous layer with dichloromethane. The organic layer was combined with the solution of the extracted organic substances, the mixture was washed with water, followed by drying with anhydrous magnesium sulfate. After that, the mixture was gravity filtered, and the filtrate was concentrated to dry and harden. This solid was recrystallized from a mixed solvent of dichloromethane and ethanol to give a red powder in a yield of 67%. Note that the irradiation with microwaves was performed using a microwave synthesis system (Discover, manufactured by CEM Corporation). The synthesis scheme of this step is illustrate in the following (E-1).

[Chemical Formula 113]

(E-1)

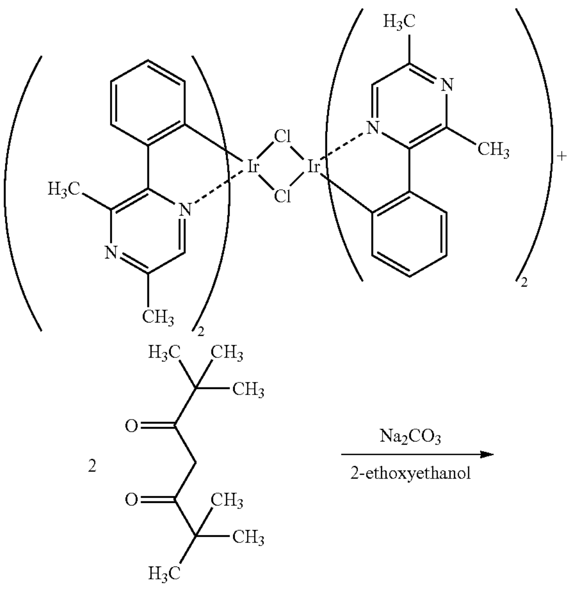

-continued

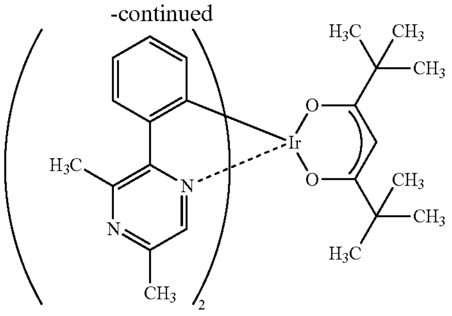

[Ir(mppr-Me)$_2$(dpm)]

Note that a nuclear magnetic resonance ($^1$H NMR) method identified this compound as an organometallic complex [Ir(mppr-Me)$_2$(dpm)], which was the substance to be produced. The obtained $^1$H NMR analysis results are shown below.

$^1$H NMR. δ ($CDCl_3$): 0.90 (s, 1H), 2.59 (s, 6H), 3.04 (s, 6H), 5.49 (s, 1H), 6.32 (dd, 2H), 6.70 (dt, 2H), 6.88 (dt, 2H), 7.86 (d, 2H), 8.19 (s, 2H).

Reference Example 3

A method of synthesizing 7-[3-(dibenzothiophen-4-yl)phenyl]dibenzo[f,h]quinoxaline (abbreviation: 7mDBTPDBq-II) used in Example 20 and the like will be specifically described. The structure of 7mDBTPDBq-II is illustrated below.

[Chemical Formula 114]

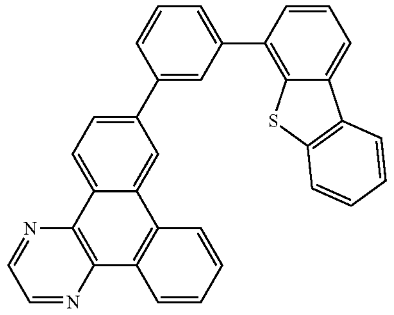

7mDBTPDBq-II

[Synthesis of 7mDBTPDBq-II]

A scheme for the synthesis of 7mDBTPDBq-II is illustrated in (F-1).

[Chemical Formula 115]

(F-1)

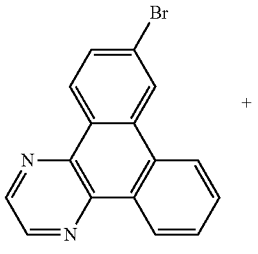

-continued

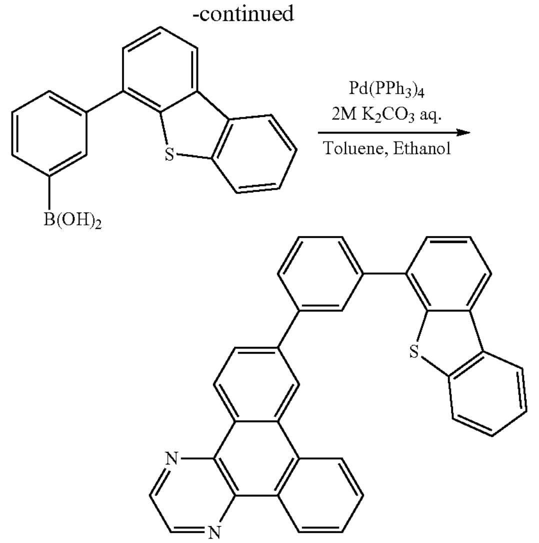

7mDBTPDBq-II

In a 50-mL three-neck flask were put 1.2 g (4.0 mmol) of 7-bromodibenzo[f,h]quinoxaline, 1.3 g (4.3 mmol) of 3-(dibenzothiophen-4-yl)phenylboronic acid, 20 mL of toluene, 4 mL of ethanol, and 4 mL of a 2M aqueous potassium carbonate solution. This mixture was degassed by stirring under reduced pressure. To this mixture was added 93 mg (81 μmol) of tetrakis(triphenylphosphine)palladium(0). This mixture was stirred under a nitrogen stream at 80° C. for 7 hours. After a predetermined time had elapsed, water was added to the obtained mixture, organic substances were extracted from the aqueous layer with toluene. The obtained solution of the extracted organic substances was combined with the organic layer, the mixture was washed with water and saturated brine, and the organic layer was dried with magnesium sulfate. This mixture was gravity filtered, and the filtrate was concentrated to give a solid. The obtained solid was purified by silica gel column chromatography (with a developing solvent of toluene) and recrystallized from toluene to give 1.4 g of a pale yellow powder in 61% yield, which was the substance to be produced.

By a train sublimation method, 1.4 g of the obtained pale yellow powder, which was the produced substance, was purified. In the purification, the produced substance was heated at 255° C. under a pressure of 2.5 Pa with a flow rate of argon gas of 5 mL/min. After the purification, 0.60 g of a pale yellow powder was obtained in a yield of 42%, which was the substance to be produced.

$^1$H NMR data of the obtained substance are as follows: $^1$H NMR ($CDCl_3$, 300 MHz): δ=7.47-7.51 (m, 2H), 7.62 (d, J=4.8 Hz, 2H), 7.68-7.92 (m, 6H), 8.08 (dd, J=8.4 Hz, 1.5 Hz, 1H), 8.19-8.24 (m, 3H), 8.74 (dd, J=7.8 Hz, 1.5 Hz, 1H), 8.91-8.93 (m, 3H), 9.24 (dd, J=7.2 Hz, 2.1 Hz, 1H), 9.31 (d, J=8.4 Hz, 1H).

This application is based on Japanese Patent Application serial no. 2010-044720 filed with the Japan Patent Office on Mar. 1, 2010, the entire contents of which are hereby incorporated by reference.

What is claimed is:

1. A compound including a dibenzo[f,h]quinoxaline ring and a hole-transport skeleton which are bonded to each other through an arylene group, wherein the hole-transport skeleton is a dibenzofuran ring or a dibenzothiophene ring.

2. The compound according to claim 1, wherein the arylene group has one or more substituents.

3. The compound according to claim 2, wherein the substituents are bonded to form a ring.

4. The compound according to claim 1, wherein the arylene group is any of a substituted or unsubstituted phenylene group, a substituted or unsubstituted biphenyldiyl group, and a substituted or unsubstituted m-phenylene group.

5. The compound according to claim 1, wherein:

the compound is represented by General Formula (G1):

(G1)

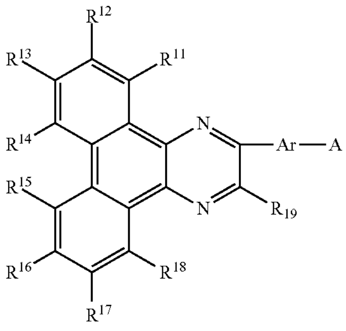

A represents any of a substituted or unsubstituted dibenzothiophenyl group, and a substituted or unsubstituted dibenzofuranyl group;

each of $R^{11}$ to $R^{19}$ independently represents any of hydrogen, an alkyl group having 1 to 4 carbon atoms, and a substituted or unsubstituted aryl group having 6 to 13 carbon atoms; and Ar represents the arylene group having 6 to 13 carbon atoms.

6. The compound according to claim 5, wherein the arylene group has one or more substituents.

7. The compound according to claim 6, wherein the substituents are bonded to form a ring.

8. The compound according to claim 5, wherein Ar is any of a substituted or unsubstituted phenylene group, a substituted or unsubstituted biphenyldiyl group, and a substituted or unsubstituted m-phenylene group.

9. The compound according to claim 5, wherein:

the compound is represented by General Formula (G2-1), (G2-1)

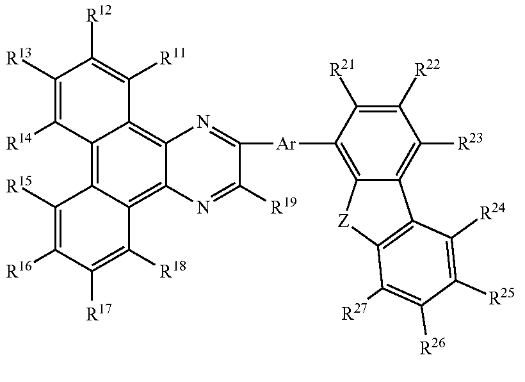

Z represents oxygen or sulfur; and each of $R^{21}$ to $R^{27}$ independently represents hydrogen, an alkyl group having 1 to 4 carbon atoms, or a substituted or unsubstituted aryl group having 6 to 13 carbon atoms.

10. The compound according to claim 9, wherein the arylene group has one of more substituents.

11. The compound according to claim 10, wherein the substituents are bonded to form a ring.

12. The compound according to claim 9, wherein Ar is any of a substituted or unsubstituted phenylene group, a substituted or unsubstituted biphenyldiyl group, and a substituted or unsubstituted m-phenylene group.

13. The compound according to claim 9, wherein:

the compound is represented by General Formula (G3-1), (G3-1)

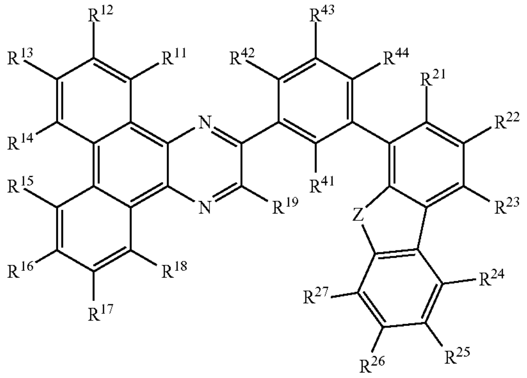

each of $R^{41}$ to $R^{44}$ independently represents hydrogen, an alkyl group having 1 to 4 carbon atoms, or a substituted or unsubstituted aryl group having 6 to 13 carbon atoms.

14. The compound according to claim 13, wherein $R^{42}$ and $R^{43}$ are bonded to $R^{43}$ and $R^{44}$ respectively to form a ring.

15. A light-emitting device comprising a light-emitting element, the light-emitting element comprising:

an electron-transport layer comprising an uncomplexed organic compound including a dibenzo[f,h]quinoxaline ring and a hole-transport skeleton which are bonded to each other through an arylene group.

16. The light-emitting device according to claim 15, wherein the hole-transport skeleton is a carbazole ring, a dibenzofuran ring, or a dibenzothiophene ring.

17. The light-emitting device according to claim 15, wherein the arylene group has one or more substituents.

18. The light-emitting device according to claim 17, wherein the substituents are bonded to form a ring.

19. The light-emitting device according to claim 15, wherein the arylene group is any of a substituted or unsubstituted phenylene group, a substituted or unsubstituted biphenyldiyl group, and a substituted or unsubstituted m-phenylene group.

20. An electronic device comprising the light-emitting device according to claim 15.

21. A lighting device comprising the light-emitting device according to claim 15.

22. A light-emitting device comprising a light-emitting element, the light-emitting element comprising:

a light-emitting layer comprising a light-emitting material and a compound including a dibenzo[f,h]quinoxaline ring and a hole-transport skeleton which are bonded to each other through an arylene group, wherein the compound is a host material.

23. The light-emitting device according to claim 22, wherein the hole-transport skeleton is a carbazole ring, a dibenzofuran ring, or a dibenzothiophene ring.

24. The light-emitting device according to claim 22, wherein the arylene group has one or more substituents.

25. The light-emitting device according to claim 24, wherein the substituents are bonded to form a ring.

26. The light-emitting device according to claim 22, wherein the arylene group is any of a substituted or unsubstituted phenylene group, a substituted or unsubstituted biphenyldiyl group, and a substituted or unsubstituted m-phenylene group.

27. An electronic device comprising the light-emitting device according to claim 22.

28. A lighting device comprising the light-emitting device according to claim 22.

29. A light-emitting device comprising a light-emitting element, the light-emitting element comprising:

a light-emitting layer comprising a light-emitting material and a first compound, the first compound being a host material; and an electron-transport layer over the light-emitting layer, the electron-transport layer comprising a second compound, wherein each of the first compound and the second compound includes a dibenzo[f,h]quinoxaline ring and a hole-transport skeleton which are bonded to each other through an arylene group.

30. The light-emitting device according to claim 29, wherein the hole-transport skeleton is a carbazole ring, a dibenzofuran ring, or a dibenzothiophene ring.

31. The light-emitting device according to claim 29, wherein the arylene group has one or more substituents.

32. The light-emitting device according to claim 31, wherein the substituents are bonded to form a ring.

33. The light-emitting device according to claim 29, wherein the arylene group is any of a substituted or unsubstituted phenylene group, a substituted or unsubstituted biphenyldiyl group, and a substituted or unsubstituted m-phenylene group.

34. An electronic device comprising the light-emitting device according to claim 29.

35. A lighting device comprising the light-emitting device according to claim 29.

36. The compound according to claim 5, wherein the compound is represented by any one of structural formulae (100), (101), (106), (107), (109), (116), (142), (201), and (515), (100)

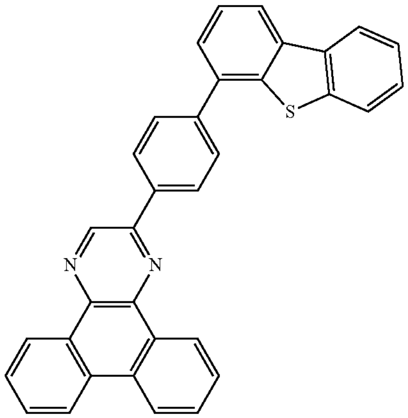

, (101)

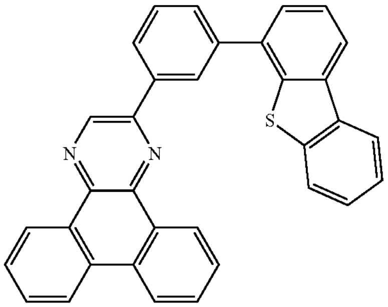

, (106)

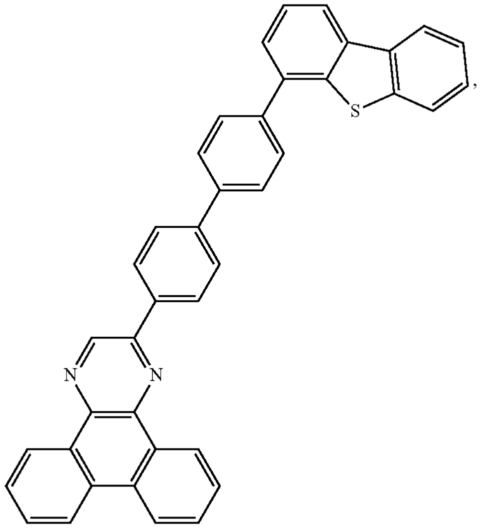

,

-continued
(107)
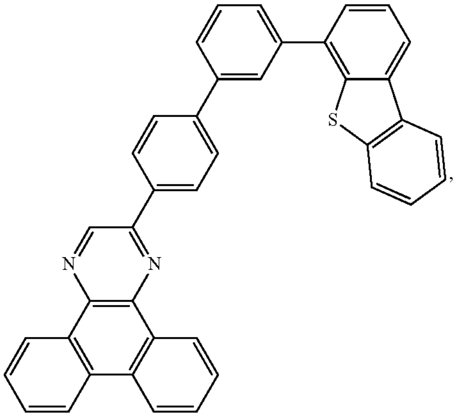
,
(109)
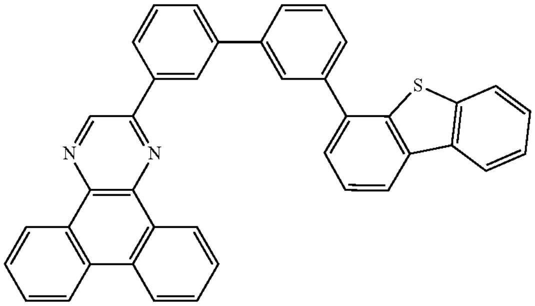
,
(116)
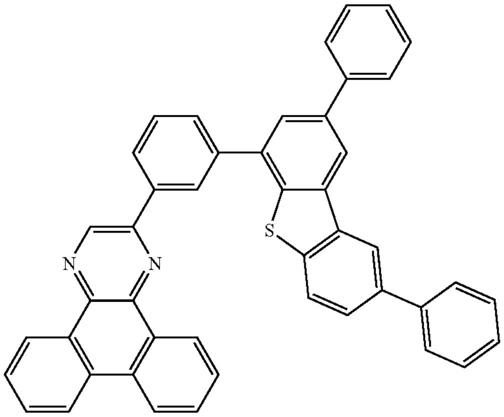
,
-continued
(142)
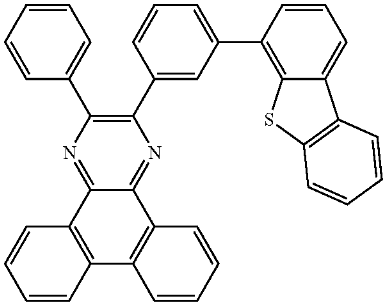
,
(201)
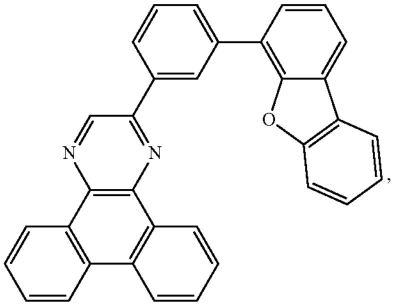
, and
(515)
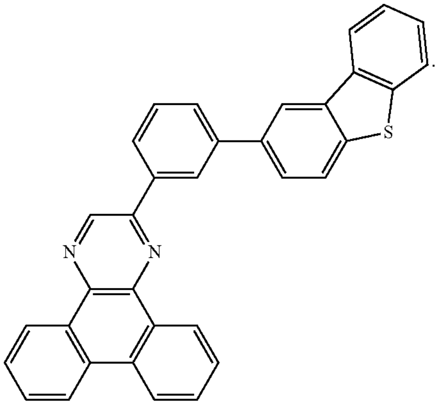
.
* * * * *

UNITED STATES PATENT AND TRADEMARK OFFICE

CERTIFICATE OF CORRECTION

PATENT NO. : 9,079,879 B2
APPLICATION NO. : 13/031734
DATED : July 14, 2015
INVENTOR(S) : Hiroshi Kadoma, Nobuharu Ohsawa and Satoshi Seo It is certified that error appears in the above-identified patent and that said Letters Patent is hereby corrected as shown below:

In the Specification

Column 7, line 55, replace “2 DBTPDBq-II” with --2DBTPDBq-II--;

Column 7, line 60, replace “2 DBTPDBq-II” with --2DBTPDBq-II--;

Column 12, line 20, after “to” replace “$R^{19}$” with --$R^{11}$--;

Column 12, line 26, after “Formulae” replace “(I-1)” with --(1-1)--;

Column 206, line 23 and 24, after “polycarbonate,” replace “polyaiylate” with --polyarylate--;

Column 207, line 37, after “phenyl-” replace “N=” with --N'- --;

Column 207, line 38, replace “methacryla mide” with --methacrylamide--;

Column 209, line 51, after “1, 2-” replace “a” with --α--;

Column 209, line 52, after “10-” replace “d iamine” with --diamine--;

Column 211, line 28, after “1,3-bis” replace “[5(p” with --[5-(p--;

Column 211, line 66, after “abbreviation:” replace “HF” with --TTF--;

Column 231, line 66, after “abbreviation:” replace “2 DBTPDBq-II” with --2DBTPDBq-II--;

Column 232, line 21, after “of” replace “2 DBTPDBq-II” with --2DBTPDBq-II--;

Column 232, line 22, after “of” replace “2 DBTPDBq-II” with --2DBTPDBq-II--;

Column 233, line 26, after “abbreviation:” replace “2 DBTPDBq-II” with --2DBTPDBq-II--;

Column 233, line 32, after “(m,” replace “21 I” with --2H--;

Column 233, line 33, after “illustrate the” insert --$^{1}$H--;

Column 233, line 37, after “of” replace “2 DBTPDBq-II” with --2DBTPDBq-II--;

Column 233, line 39, after “of” replace “2 DBTPDBq-II” with --2DBTPDBq-II--;

Column 235, line 20, after “as” replace “243'” with --2-[3'--;

Column 237, line 42, before “NMR” insert --$^{1}$H--;

Column 253, line 8, after “abbreviation:” replace “2 DBTPDBq-II” with --2DBTPDBq-II--;

Signed and Sealed this
Twenty-first Day of June, 2016

Michelle K. Lee
*Director of the United States Patent and Trademark Office*

Column 253, line 25, after “of” replace “2 DBTPDBq-II” with --2DBTPDBq-II--;

Column 253, line 27, after “(=” replace “2 DBTPDBq-II” with --2DBTPDBq-II--;

Column 253, line 30, after “a” replace “2 DBTPDBq-II” with --2DBTPDBq-II--;

Column 254, line 35, after “using” replace “2 DBTPDBq-II” with --2DBTPDBq-II--;

Column 254, line 64, after “of” replace “2 DBTPDBq-II” with --2DBTPDBq-II--;

Column 262, line 48, after “dibenzo” replace “[1 h]” with --[f, h]--;

Column 265, line 15, after “Element” insert --10--; and

Column 267, line 66, replace “inn” with --nm--.